US010787640B2

(12) United States Patent
Loh et al.

(10) Patent No.: US 10,787,640 B2
(45) Date of Patent: Sep. 29, 2020

(54) PRODUCING MESODERMAL CELL TYPES AND METHODS OF USING THE SAME

(71) Applicant: The Board of Trustees of the Leland Stanford Junior University, Stanford, CA (US)

(72) Inventors: Kyle Ming Loh, Stanford, CA (US); Irving L. Weissman, Stanford, CA (US); Lay Teng Ang, Singapore (SG); Angela Chen, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 49 days.

(21) Appl. No.: 15/553,438

(22) PCT Filed: Mar. 2, 2016

(86) PCT No.: PCT/US2016/020488
§ 371 (c)(1),
(2) Date: Aug. 24, 2017

(87) PCT Pub. No.: WO2016/141084
PCT Pub. Date: Sep. 9, 2016

(65) Prior Publication Data
US 2018/0030410 A1 Feb. 1, 2018

Related U.S. Application Data

(60) Provisional application No. 62/127,445, filed on Mar. 3, 2015.

(51) Int. Cl.
*C12N 5/0735* (2010.01)
*C12N 5/077* (2010.01)

(52) U.S. Cl.
CPC ......... *C12N 5/0606* (2013.01); *C12N 5/0657* (2013.01); *C12N 2501/115* (2013.01); *C12N 2501/15* (2013.01); *C12N 2501/155* (2013.01); *C12N 2501/415* (2013.01); *C12N 2501/727* (2013.01)

(58) Field of Classification Search
None
See application file for complete search history.

(56) References Cited

U.S. PATENT DOCUMENTS

| | | |
|---|---|---|
| 2002/0039522 A1 | 4/2002 | Hartmann et al. |
| 2012/0164731 A1 | 6/2012 | Sakurai et al. |
| 2012/0295347 A1* | 11/2012 | Kessler ............... C12N 5/0692 435/366 |
| 2014/0127173 A1 | 5/2014 | Sinha et al. |
| 2014/0273211 A1 | 9/2014 | Slukvin et al. |
| 2016/0244719 A1* | 8/2016 | Thomson ............... A61K 35/44 |

FOREIGN PATENT DOCUMENTS

WO 2014/062138 A1 4/2014

OTHER PUBLICATIONS

Lai et al., Development, vol. 130, pp. 6465-6474, 2003.*
Sturgeon et al., Nat Biotechnol. Jun. 2014; 32(6): 554-561.*
Sui et al., Proc. Natl. Acad. Sci. USA, vol. 92, pp. 2859-2863, Mar. 1995.*
Taguchi et al., Cell Stem Cell 14, 53-57, Jan. 2, 2014 (Year: 2014).*
Lam et al., J Am Soc Nephrol 25: 1211-1225, 2014 (Year: 2014).*
Beck et al., "Expression of Cdx-2 in the mouse embryo and placenta: possible role in patterning of the extra-embryonic membranes", Dev Dyn, Nov. 1995, pp. 219-227, vol. 204, Issue 3, Wiley, Hoboken, NJ.
Brunton et al., "Potent agonists of the Hedgehog signaling pathway", Bioorganic & Medicinal Chemistry Letters, Aug. 2009, pp. 4308-4311, vol. 19, Issue 15, Elsevier, Amsterdam, Netherlands.
Burridge et al., "Chemically Defined and Small Molecule-Based Generation of Human Cardiomyocytes", Nature Methods, Aug. 2014, pp. 855-860, 11(8), Macmillan Publishers, Basingstoke, United Kingdom.
Chapman et al., "Three neural tubes in mouse embryos with mutations in the T-box gene Tbx6", Nature, Feb. 12, 1998, pp. 695-697, 391, Macmillan Publishers, Basingstoke, United Kingdom.
Cheung et al., "Generation of human vascular smooth muscle subtypes provides insight into embryological origin-dependent disease susceptibility", Nat Biotechnol., 2012, pp. 165-173, 30(2), Macmillan Publishers, Basingstoke, United Kingdom.
Davis et al., "Targeting a GFP reporter gene to the MIXL1 locus of human embryonic stem cells identifies human primitive streak-like cells and enables isolation of primitive hematopoietic precursors", Blood, 2008, pp. 1876-1884, vol. 111, Issue 4, The American Society of Hematology, Washington, D.C.
Loh et al., "Efficient Endoderm Induction from Human Pluripotent Stem Cells by Logically Directing Signals Controlling Lineage Bifurcations", Cell Stem Cell, Feb. 6, 2014, pp. 237-252, vol. 14, Issue 2.

(Continued)

Primary Examiner — Scott Long
Assistant Examiner — Evelyn Y Pyla
(74) Attorney, Agent, or Firm — Pamela J. Sherwood; Bozicevic, Field & Francis LLP

(57) ABSTRACT

Methods are provided for the generation of mesodermal cell types and derivatives thereof. Also provided are methods for generating purified populations of mesodermal cell types and derivatives thereof. The instant disclosure also provides methods of screening for cellular responses of the generated mesodermal cell types and derivatives thereof. Also provide are methods for screening for organismal phenotypes induced by introduction of the generated mesodermal cell types and derivatives thereof. Treatment methods making use of the generated mesodermal cell types and derivatives thereof are also provided. The instant disclosure also provides systems, compositions, and kits for practicing the methods of the disclosure.

14 Claims, 52 Drawing Sheets
(46 of 52 Drawing Sheet(s) Filed in Color)
Specification includes a Sequence Listing.

(56) References Cited

OTHER PUBLICATIONS

Mendjan et al., "NANOG and CDX2 pattern distinct subtypes of human mesoderm during exit from pluripotency.", Cell Stem Cell, Sep. 4, 2014, pp. 310-325, 15(3), Elsevier, Amsterdam, Netherlands.
Proffitt et al., "Pharmacological Inhibition of the Wnt Acyltransferase PORCN Prevents Growth of WNT-Driven Mammary Cancer", Cancer Res., Jan. 15, 2013, pp. 502-507, 73(2), American Association for Cancer Research, Philadelphia, PA.
Robarage et al., "GDC-0449—a potent inhibitor of the hedgehog pathway" Bioorg Med Chem Lett, Oct. 1, 2009, pp. 5576-5581, vol. 19, Issue 19, Elsevier, Amsterdam, Netherlands.
Xu et al., "A zebrafish embryo culture system defines factors that promote vertebrate myogenesis across species", Cell, Nov. 7, 2013, pp. 909-921, vol. 155, Issue 4, Elsevier, Amsterdam, Netherlands.
Yamamizu et al., "PKA/CREB Signaling Triggers Initiation of Endothelial and Hematopoietic Cell Differentiation via Etv2 Induction", Stem Cells, Mar. 22, 2012, pp. 687-696, 30, AlphaMed Press, Durham, NC.
Zhang et al., "Short-term BMP-4 treatment initiates mesoderm induction in human embryonic stem cells", Blood, Feb. 15, 2008, pp. 1933-1941, vol. 111, No. 4, American Society of Hematology, Washington DC.
Loh et al., "Recreating Pluripotency?", Cell Press, Aug. 6, 2010, pp. 137-139, 7, Elsevier, Amsterdam, Netherlands.
Yu et al., "FGF2 Sustains NANOG and Switches the Outcome of BMP4-Induced Human Embryonic Stem Cell Differentiation", Cell Stem Cell, Mar. 4, 2011, pp. 326-334, 8, Elsevier, Amsterdam, Netherlands.

\* cited by examiner

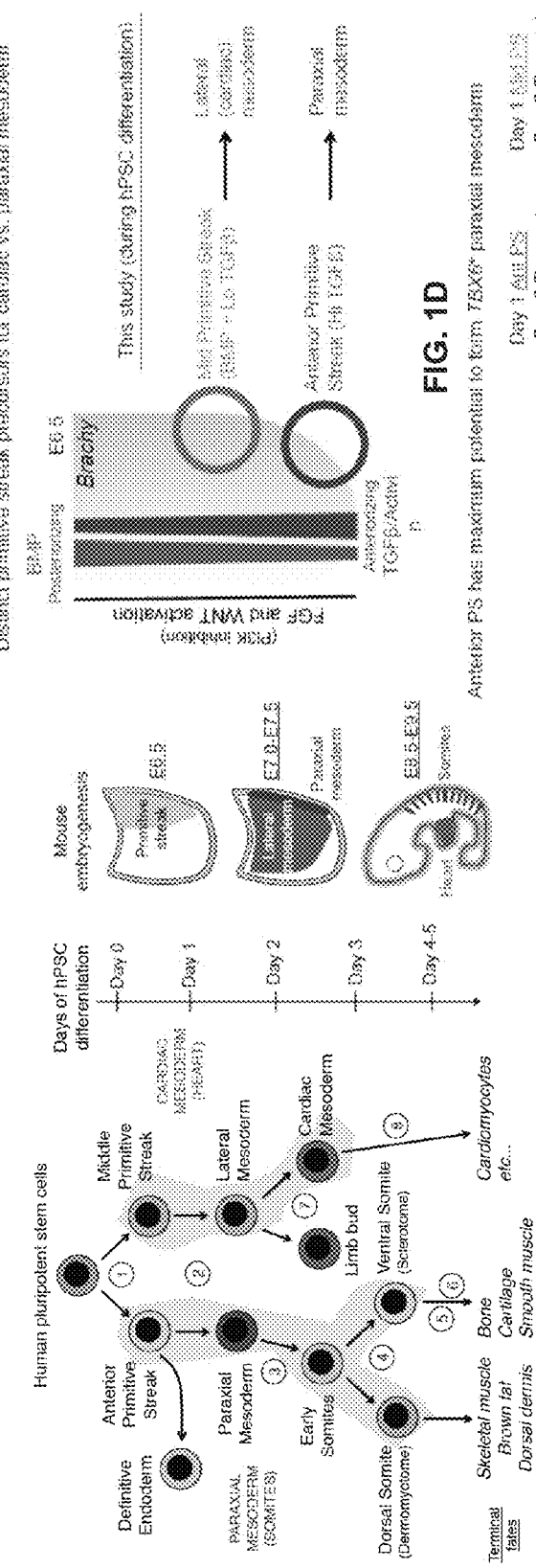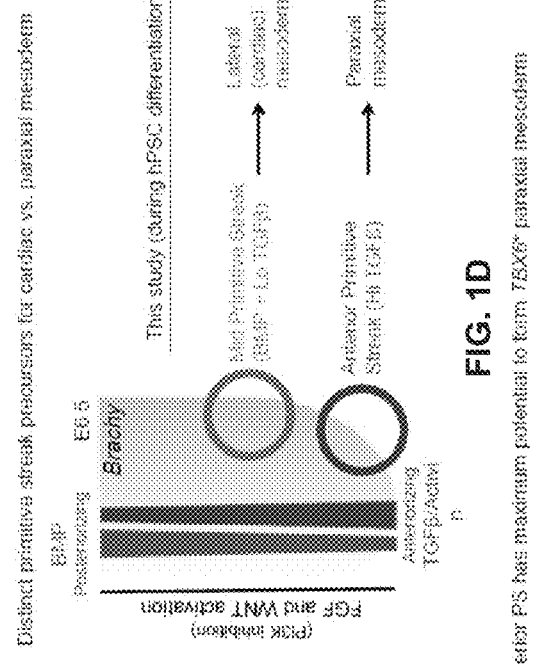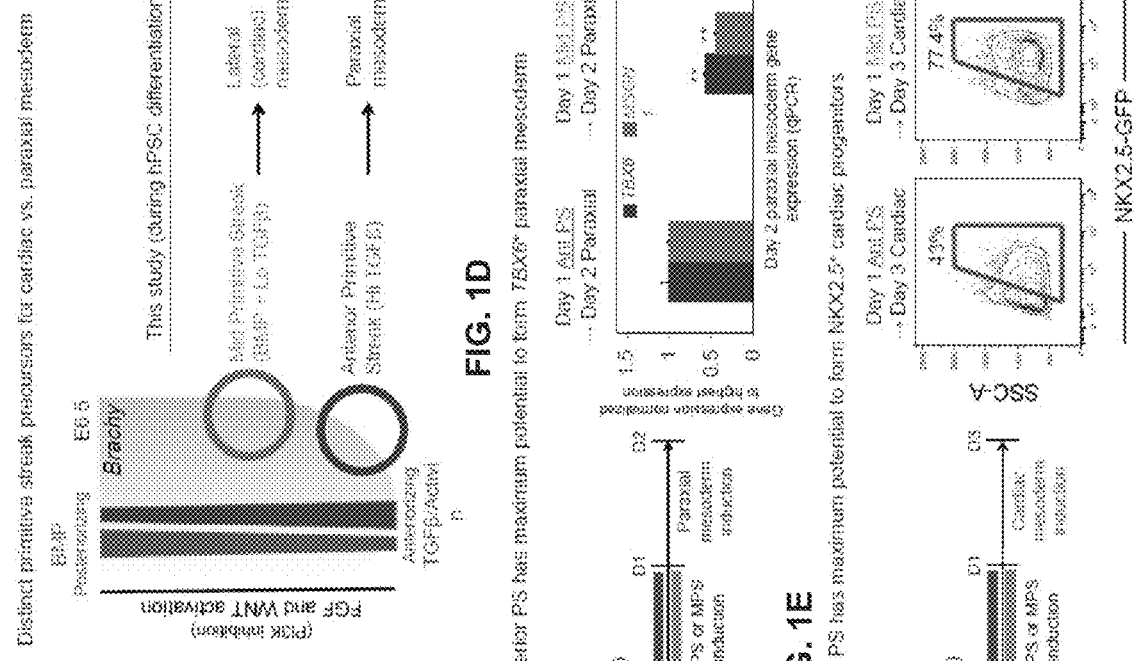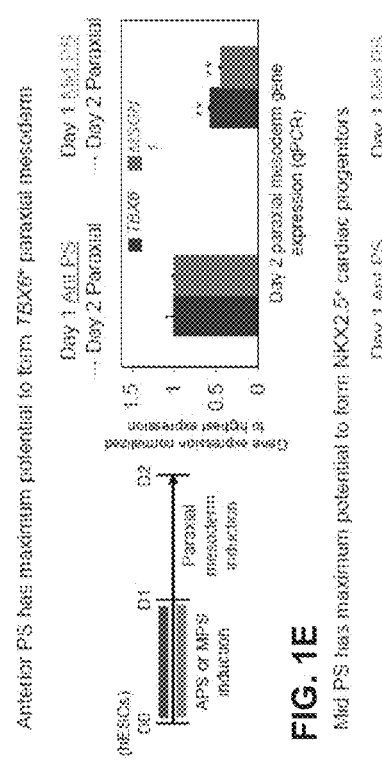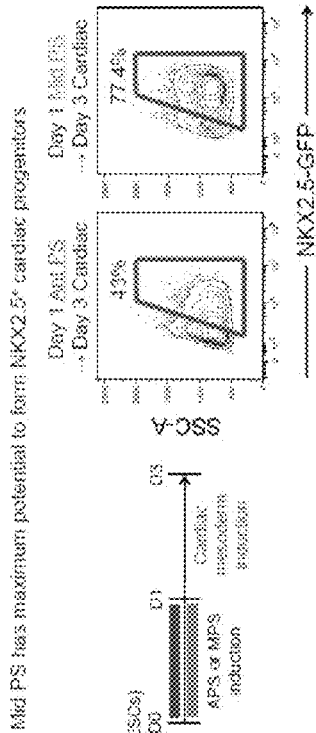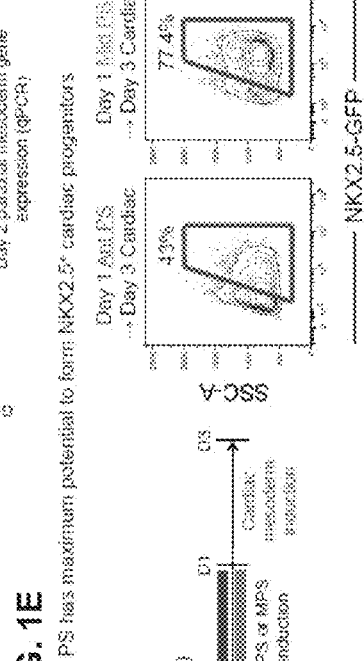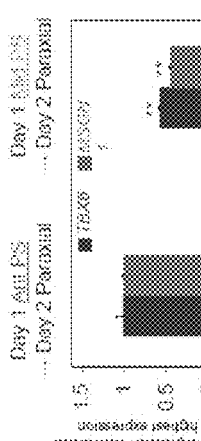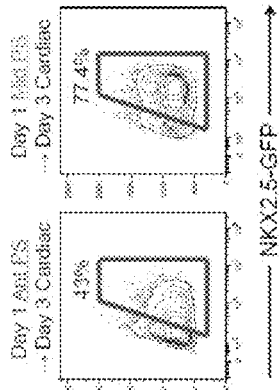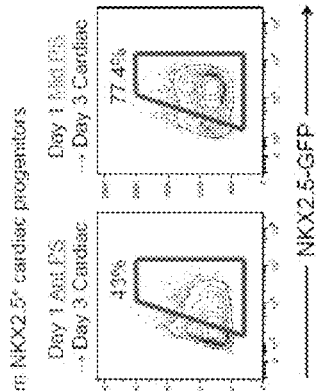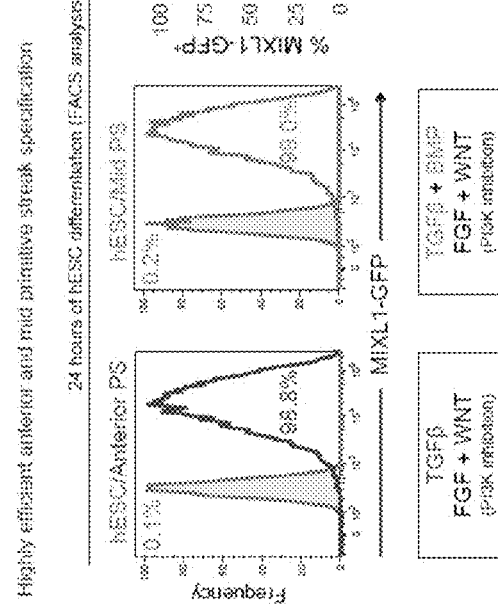

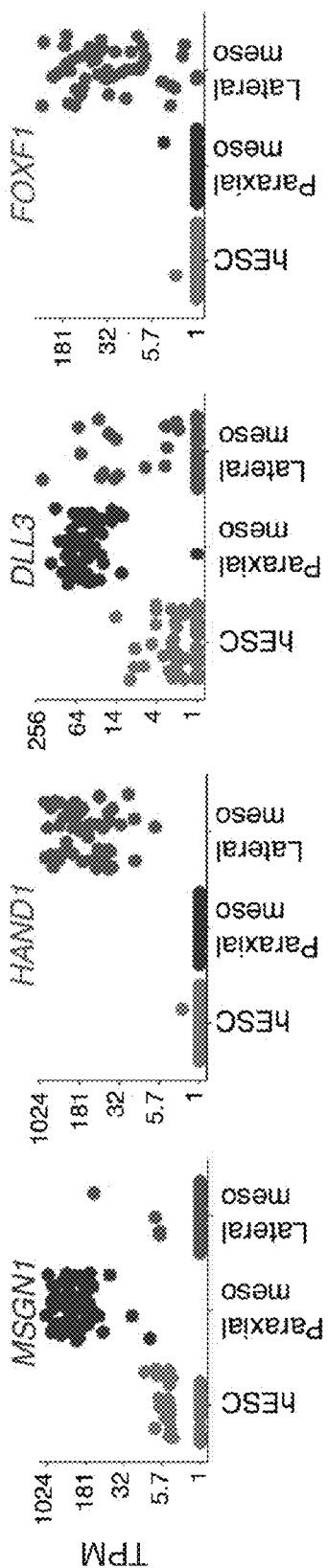
FIG. 1F
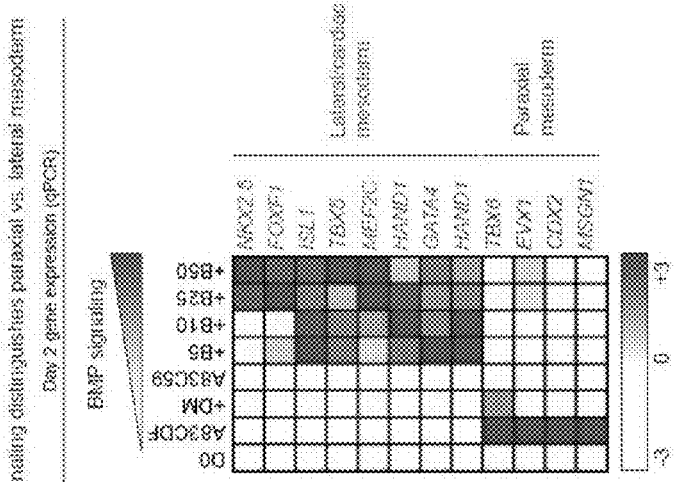
FIG. 2A
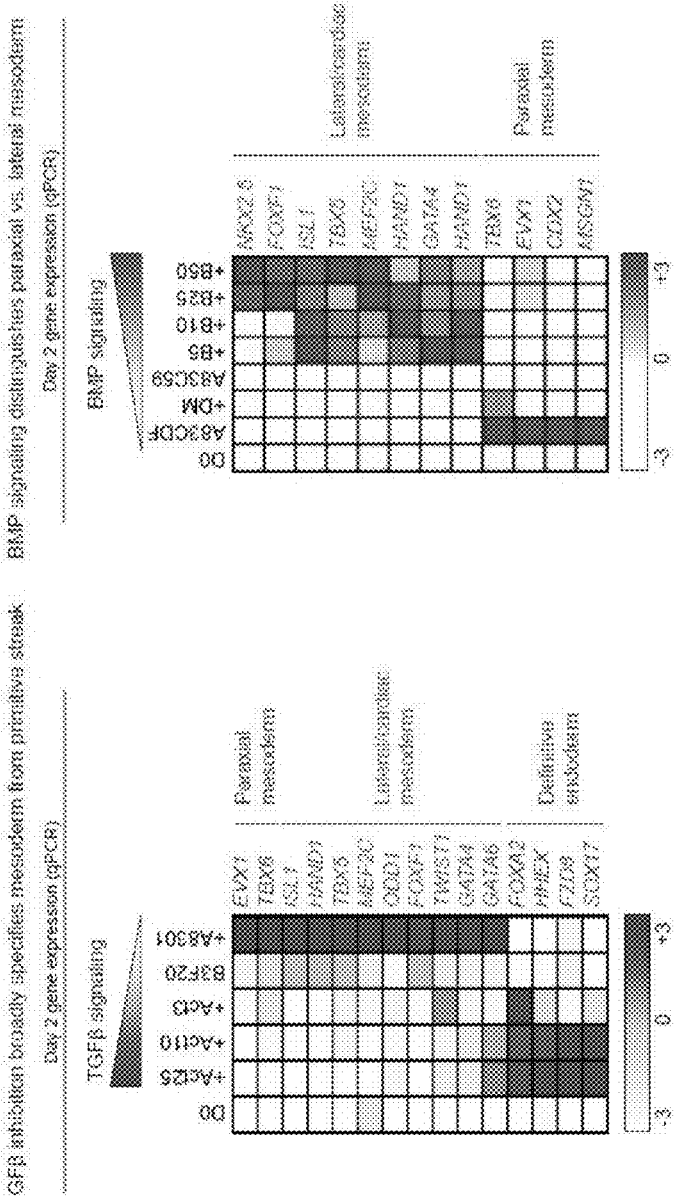
FIG. 2B
FIG. 2C

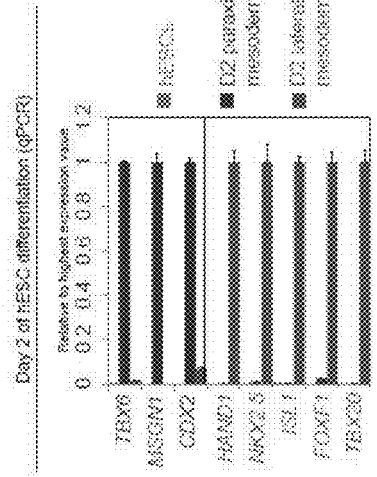
FIG. 2D
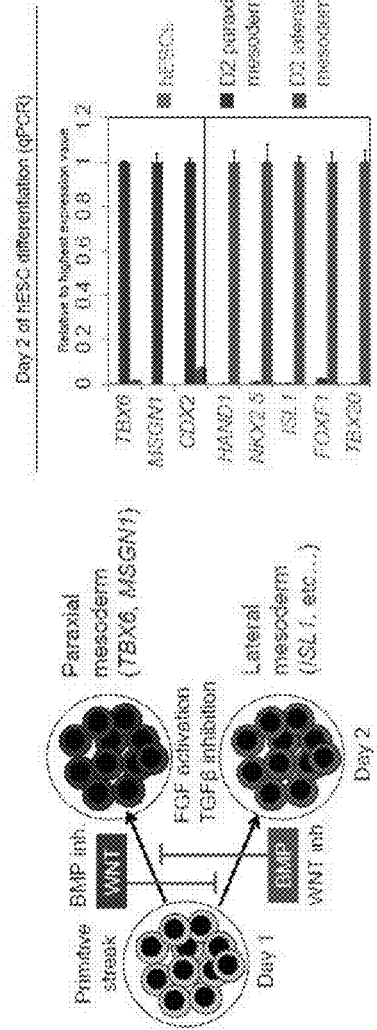
FIG. 2F
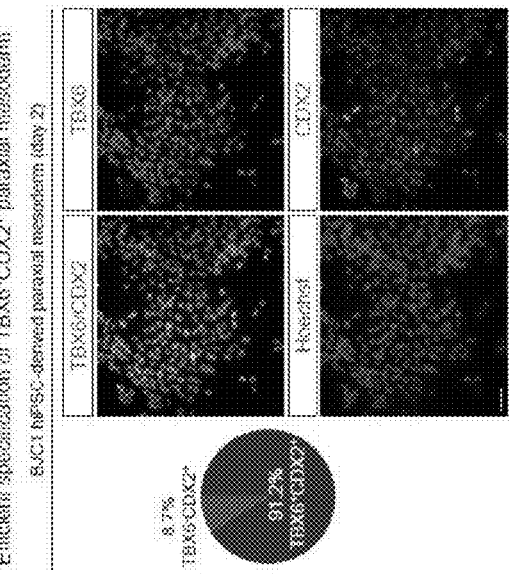
FIG. 2H
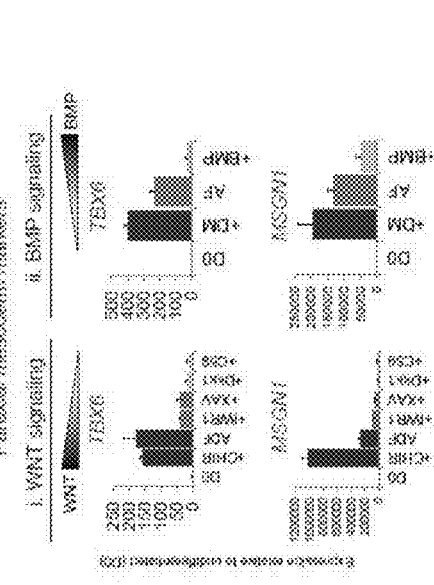
FIG. 2E
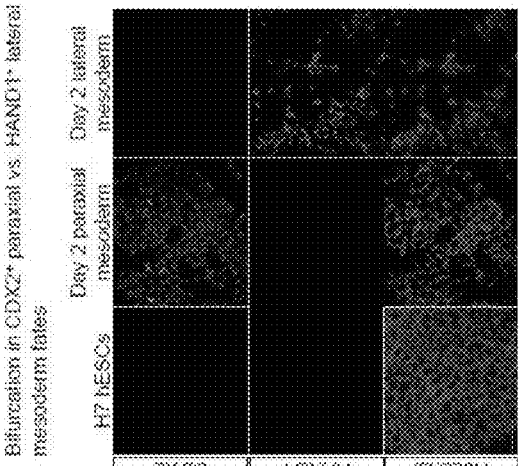
FIG. 2G
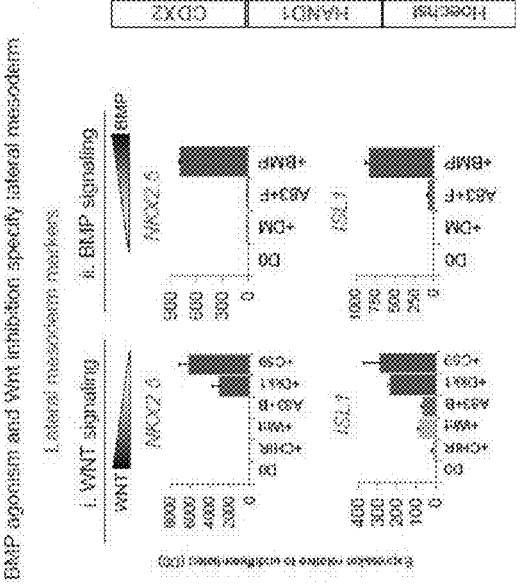

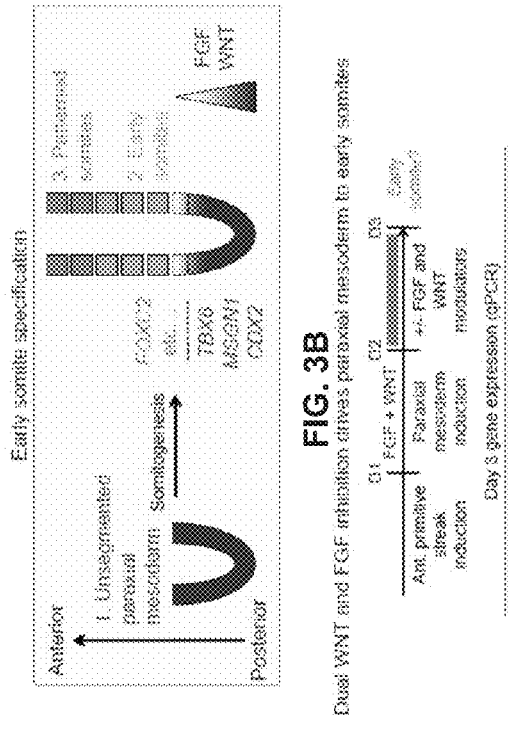
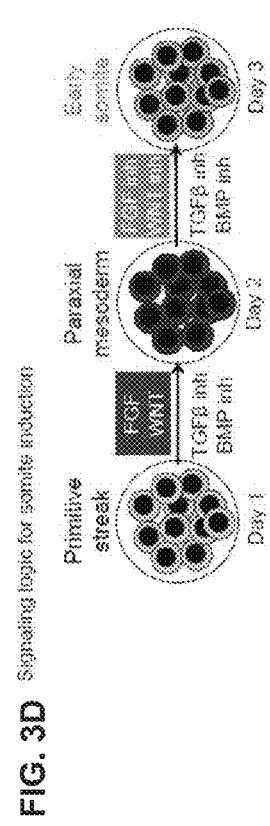
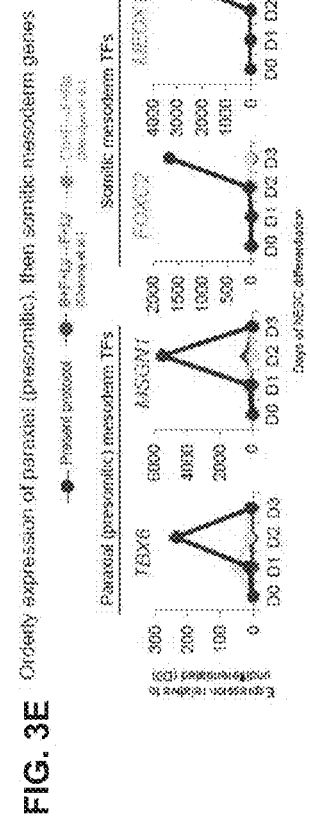
FIG. 3A
FIG. 3B
FIG. 3C
FIG. 3D
FIG. 3E

FIG. 4A Dorsal-ventral patterning of the somites
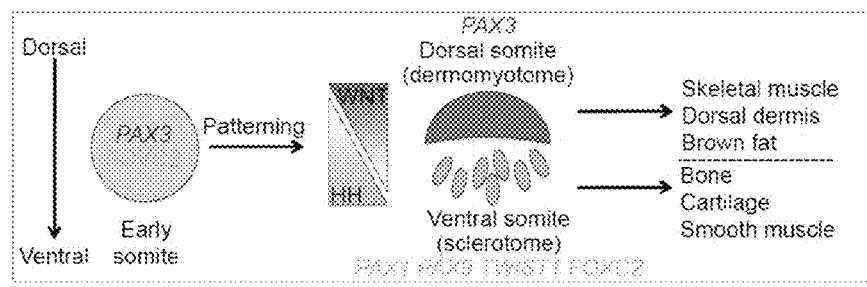
FIG. 4B Dorsal-ventral patterning of early somites by cross-repressive Wnt and Hh signals
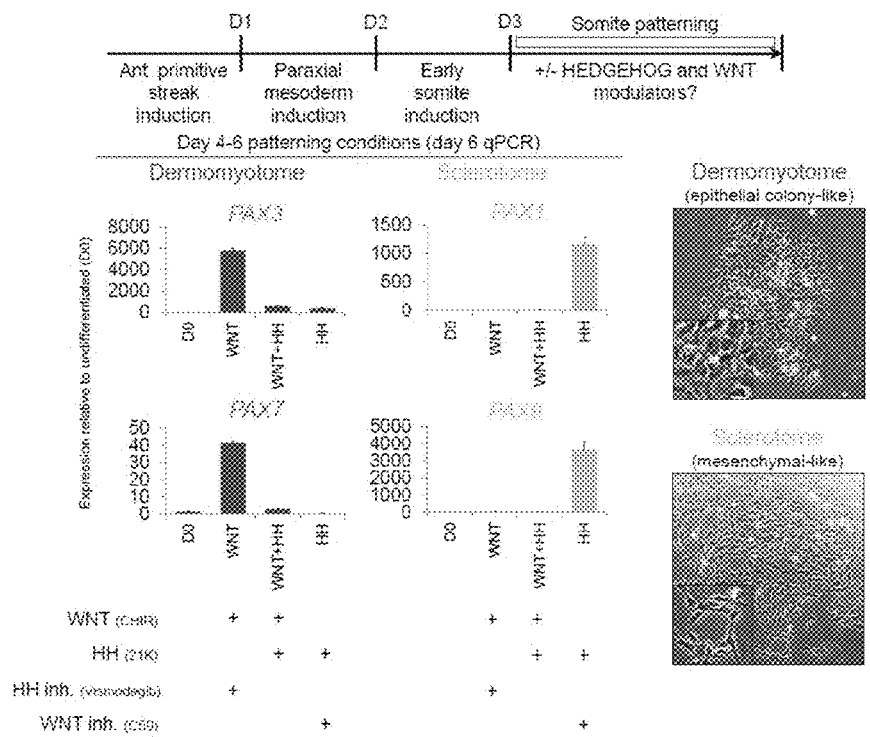
FIG. 4C Mutually-exclusive generation of sclerotome vs. dermomyotome
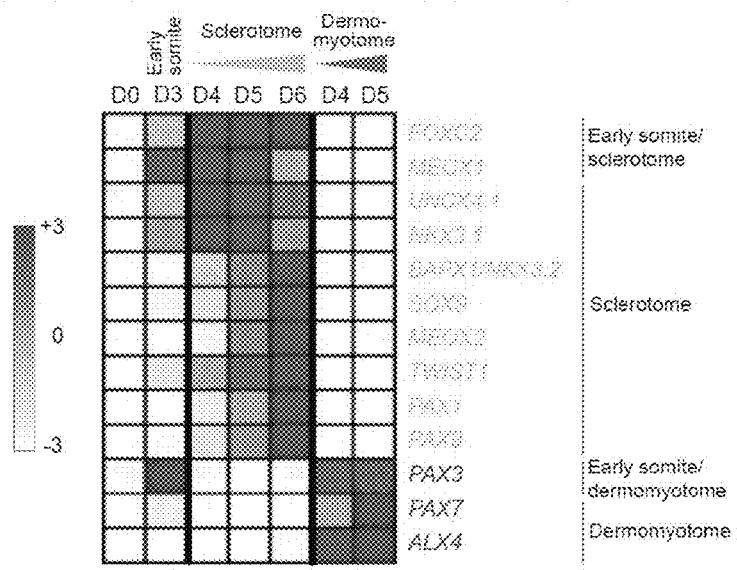

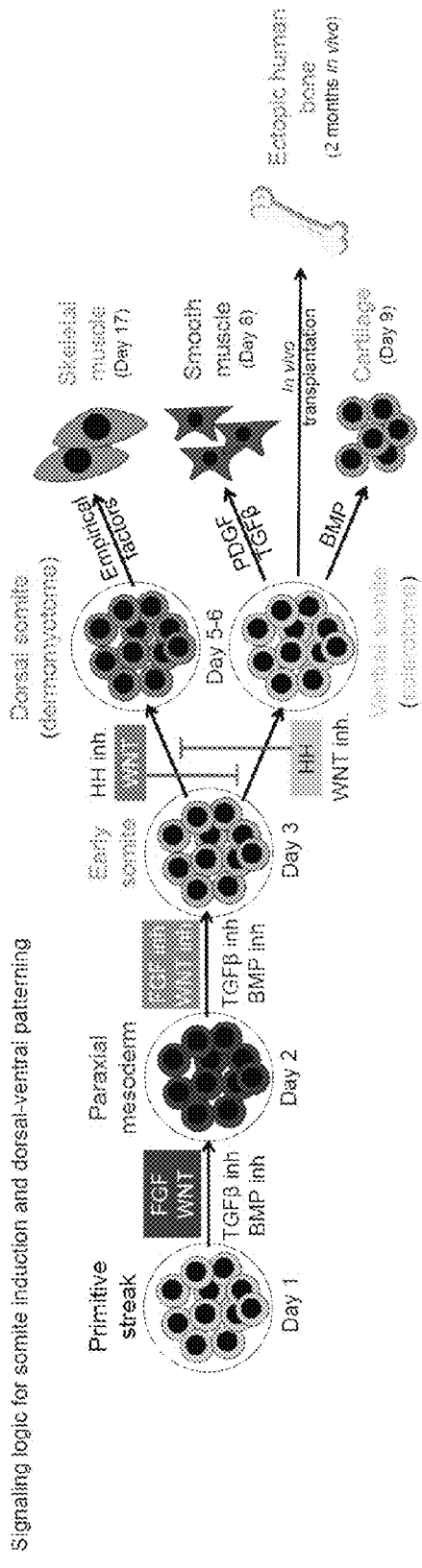
FIG. 4D
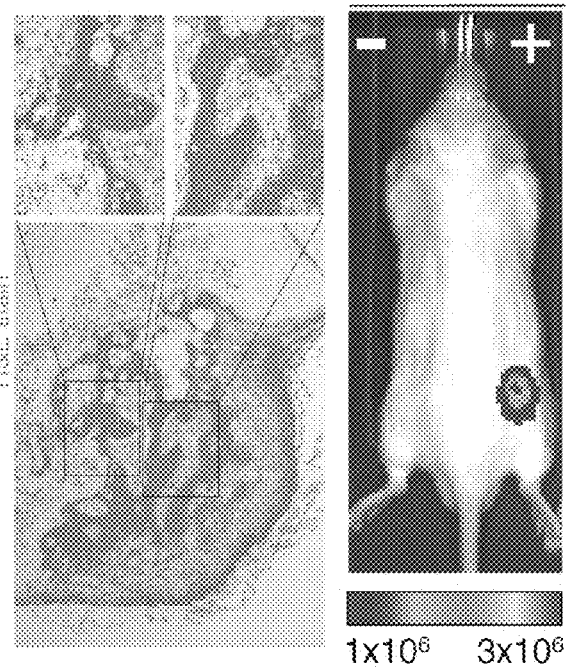
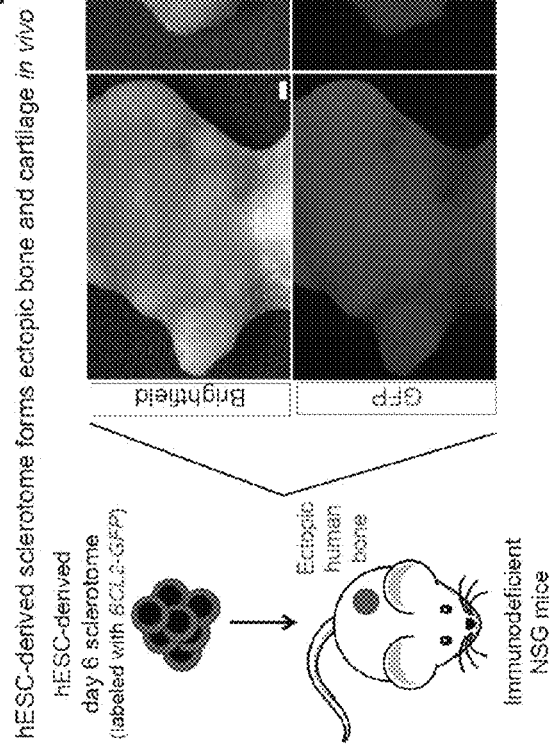
FIG. 4E

Human sclerotome purity

Trajectory of somite dorsal-ventral patterning

Self-organizing human bone formation *in vivo*

FIG. 5A Anterior-posterior patterning of lateral mesoderm
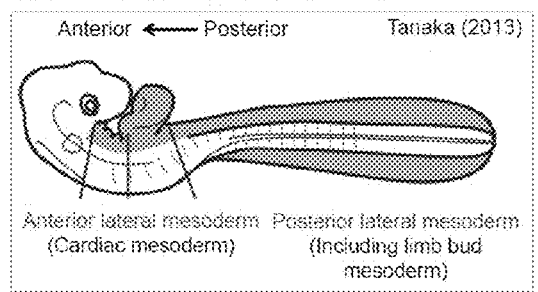
FIG. 5B WNT specifies anterior vs. posterior lateral mesoderm
FIG. 5C FGF anteriorly patterns lateral mesoderm
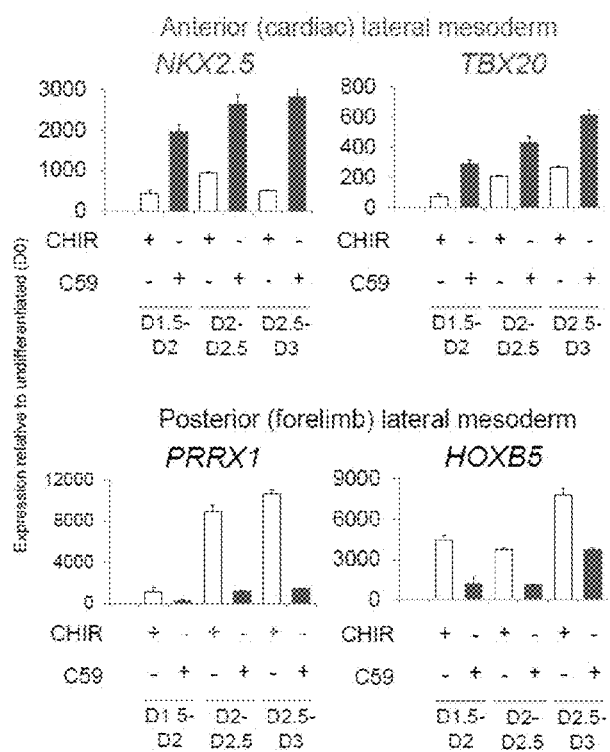
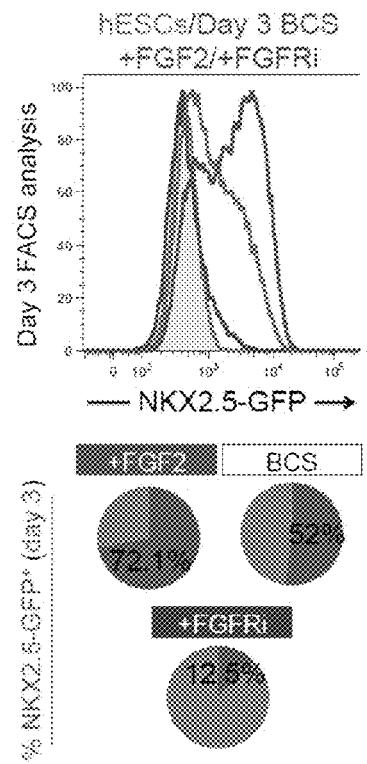
FIG. 5D Signaling logic for bifurcation in lateral mesoderm fates
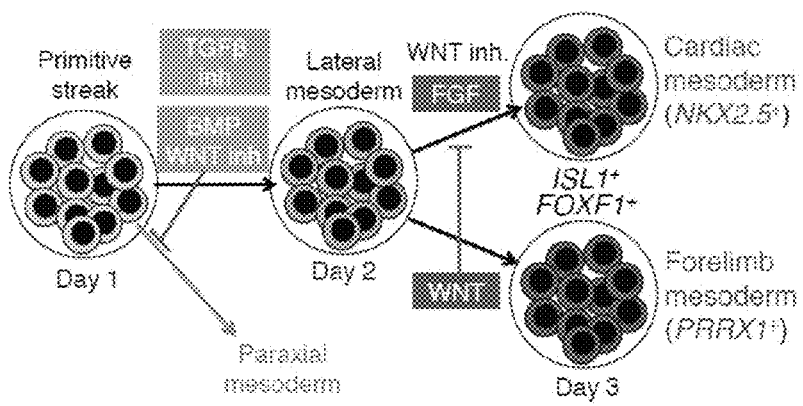

FIG. 5E NKX2.5+ cardiac mesoderm induction
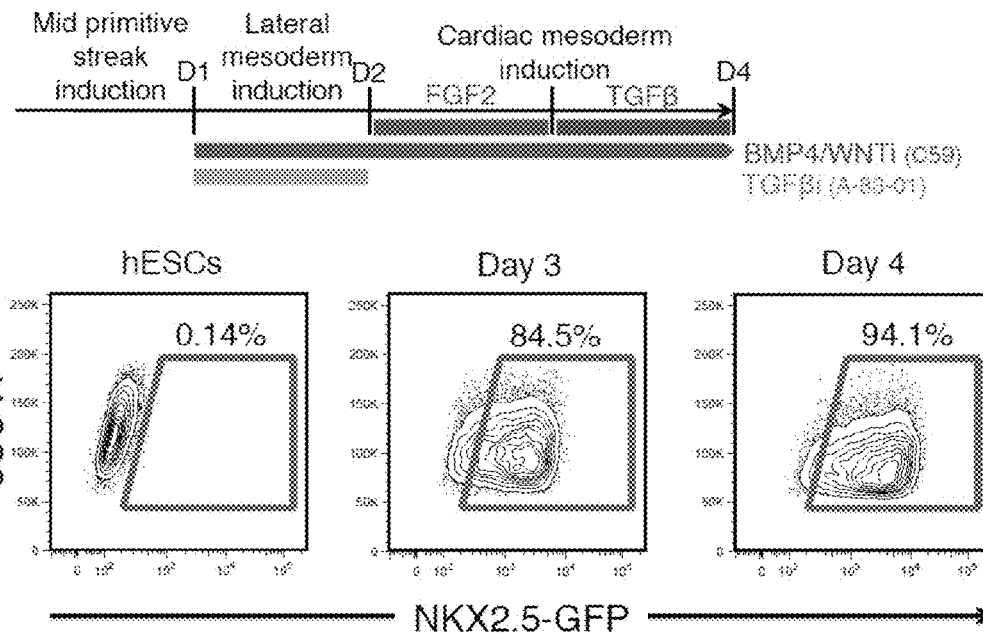
FIG. 5F Kinetics of cardiac mesoderm specification
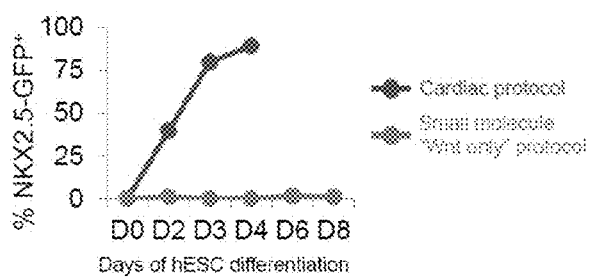
FIG. 5G Driving cardiac mesoderm to TROPONIN+ cardiomyocytes
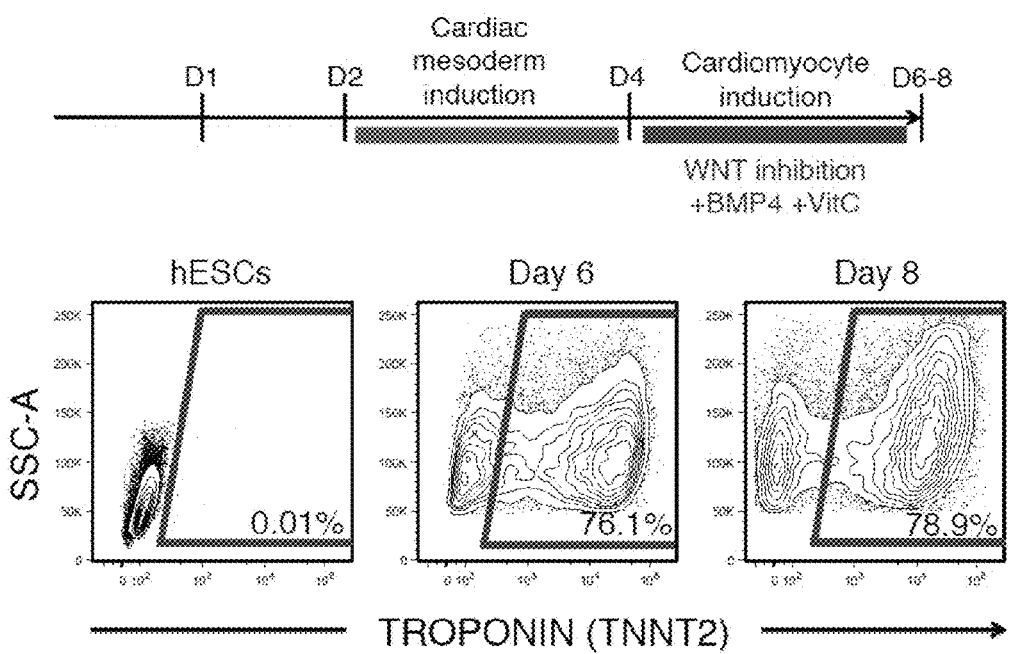

FIG. 5H Cardiomyocyte structural gene expression
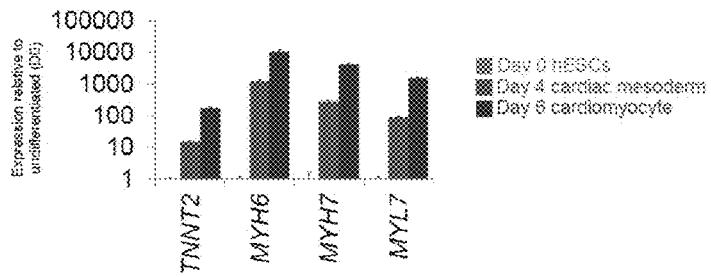
FIG. 5I Model for human fetal heart tissue engraftment
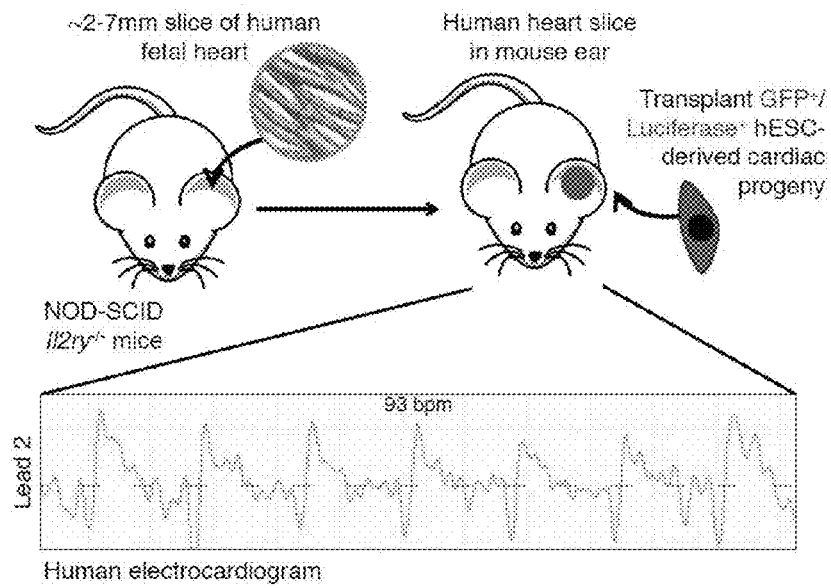
FIG. 5J
hESC-derived cardiomyocytes engraft in human fetal heart *in vivo*
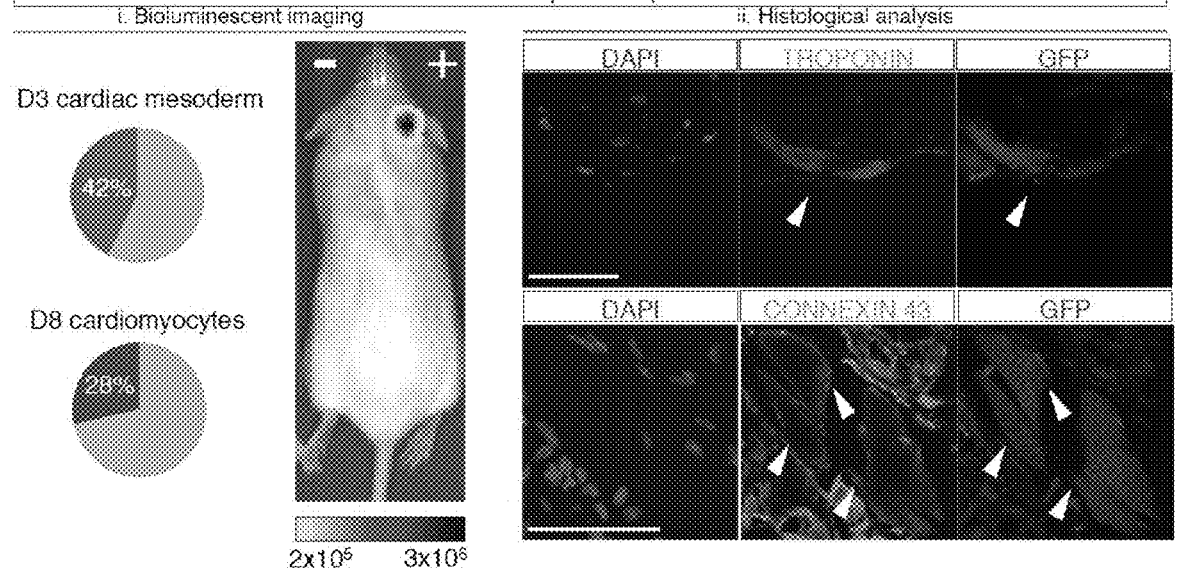

FIG. 6D DLL1 and GARP respectively identify paraxial vs. cardiac mesoderm
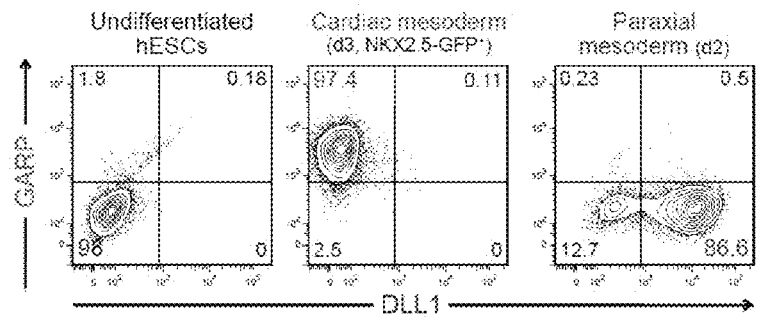
FIG. 6E lrrc32/garp marks the heart in zebrafish embryos
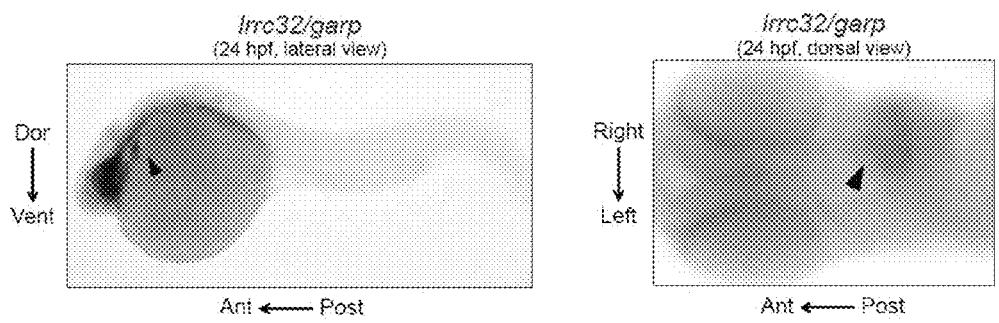
FIG. 6F DLL1 enables purification of hPSC-derived paraxial mesoderm
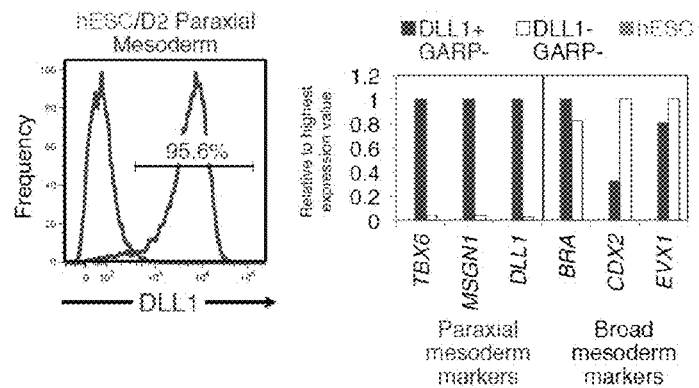
FIG. 6G PDGFRα enables purification of hPSC-derived sclerotome
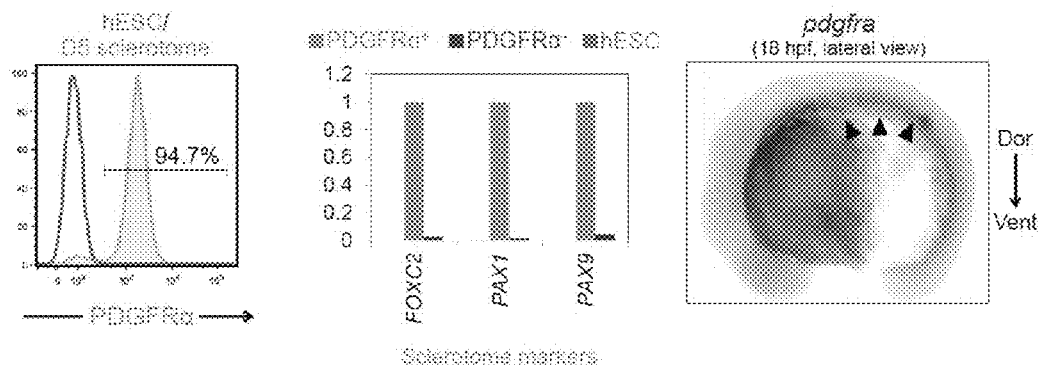

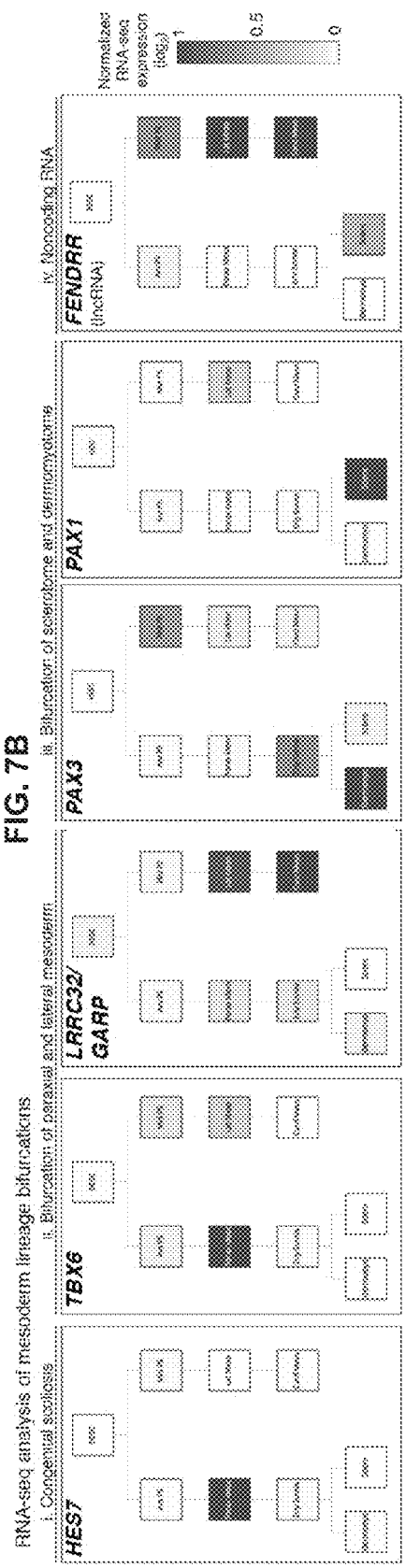
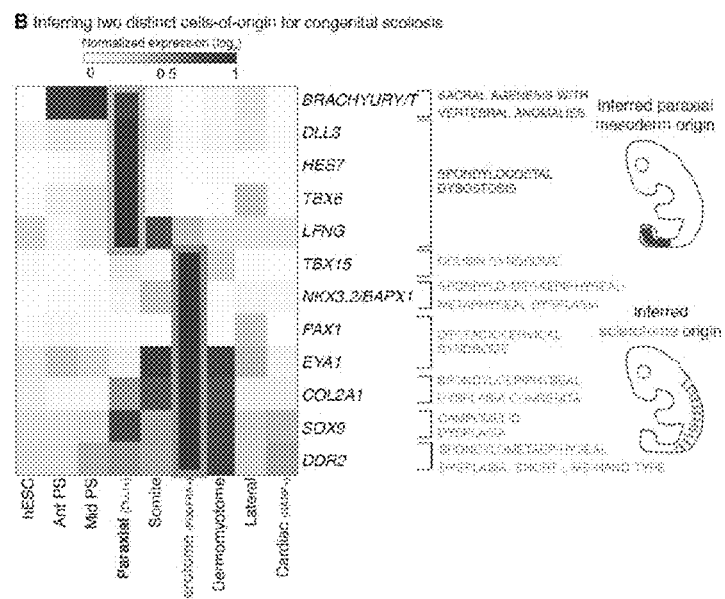
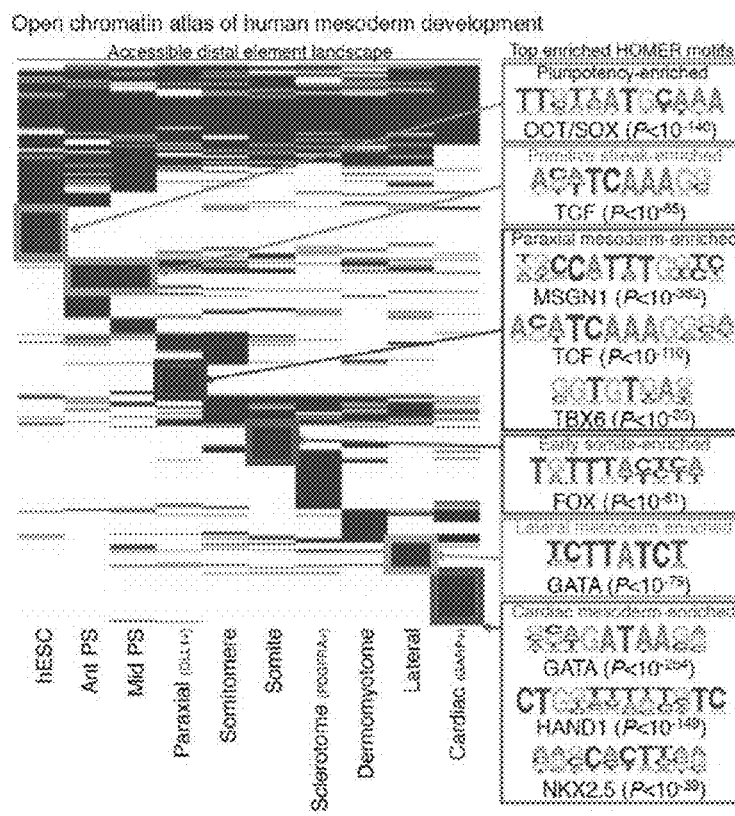
FIG. 7B
FIG. 7C
FIG. 7D

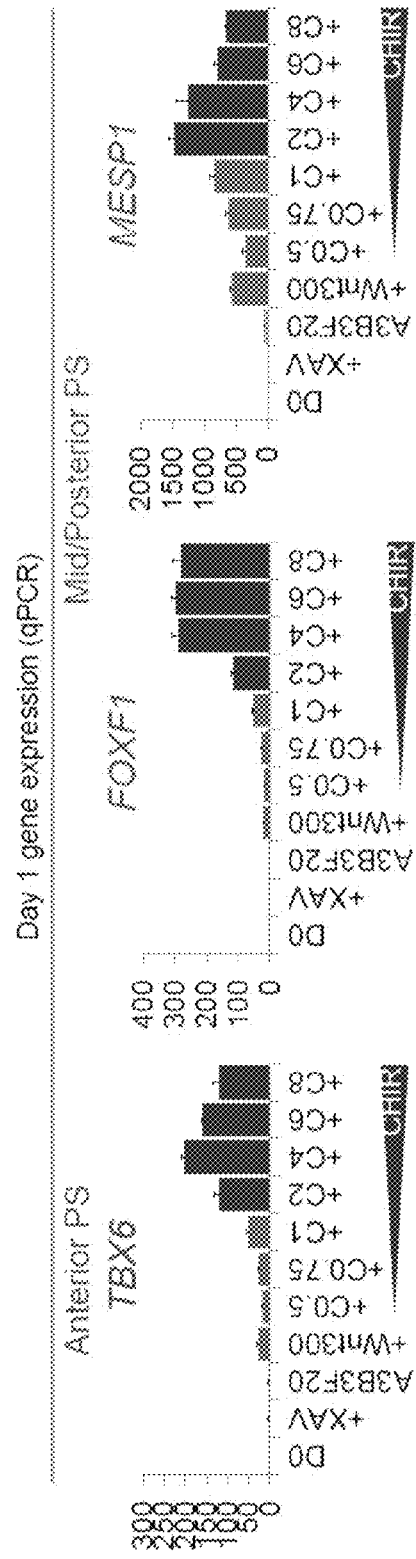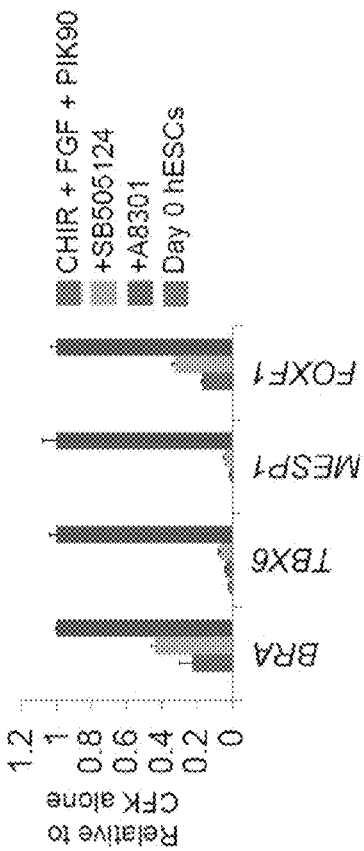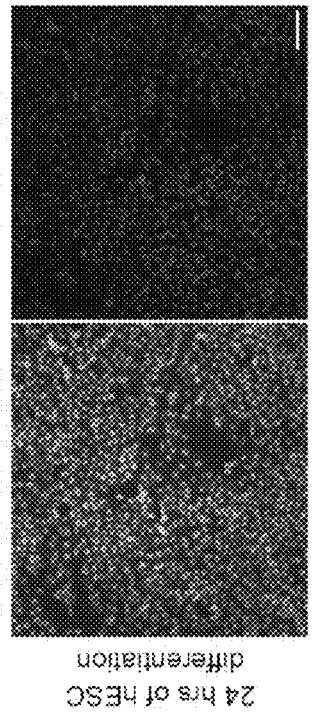
FIG. 8A
FIG. 8B
FIG. 8C

FIG. 8D BMP is critical for PS induction and high BMP posteriorizes the PS
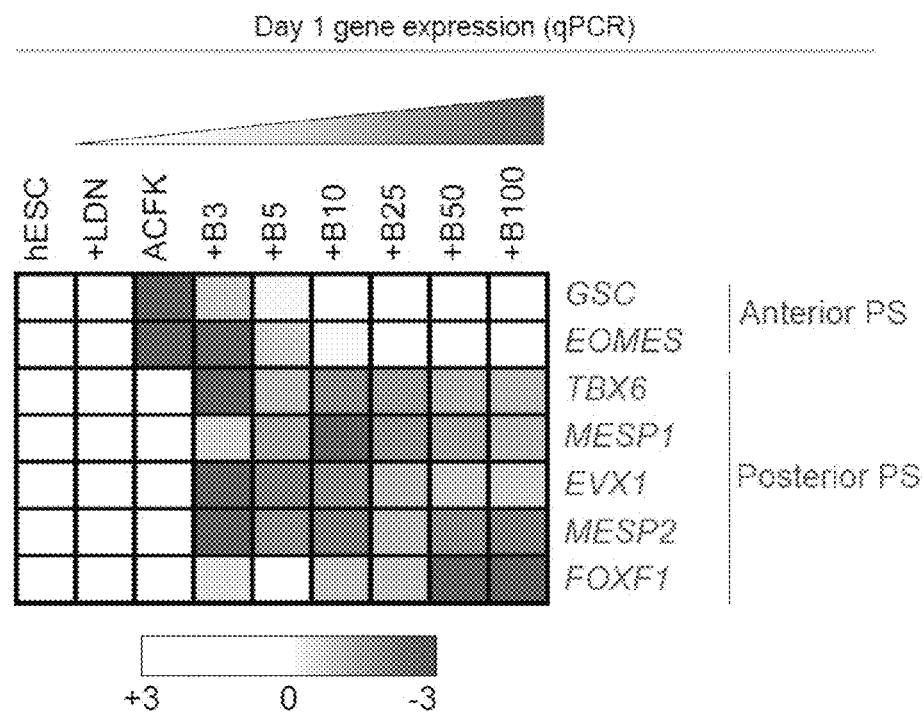
FIG. 8E
High TGFβ instills paraxial, whereas low TGFβ endows cardiac mesoderm potential
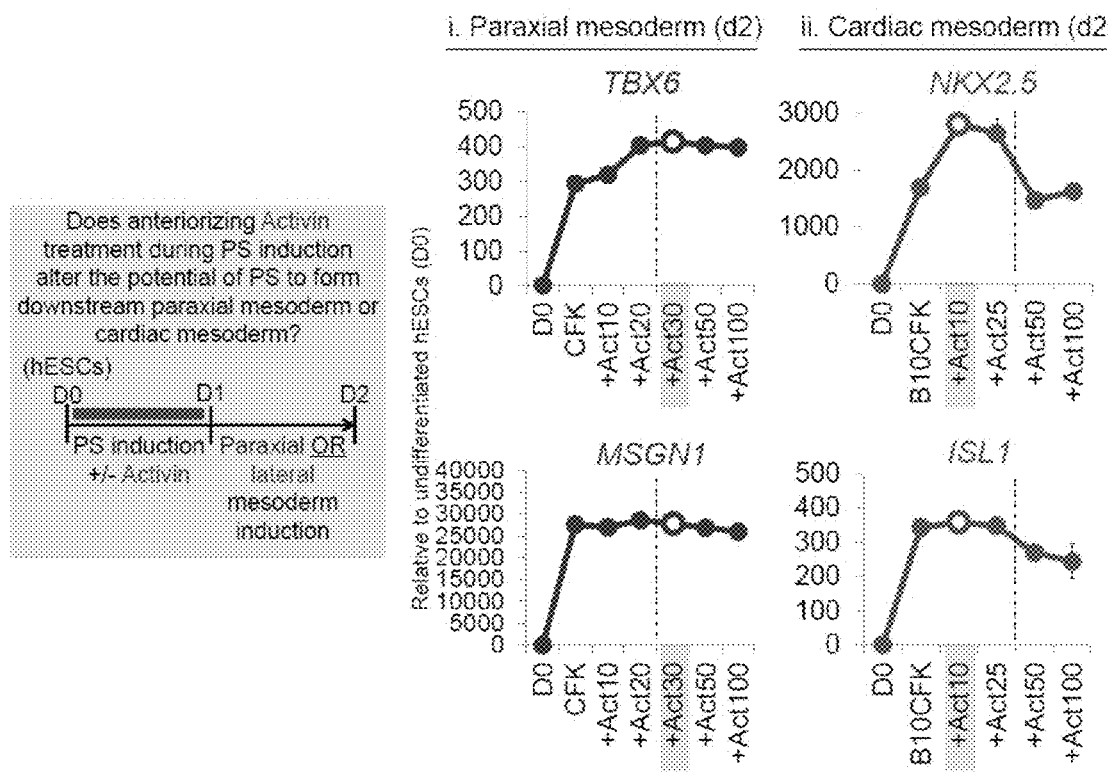

FIG. 8F Exogenous BMP endows cardiac, but inhibits paraxial mesoderm potential
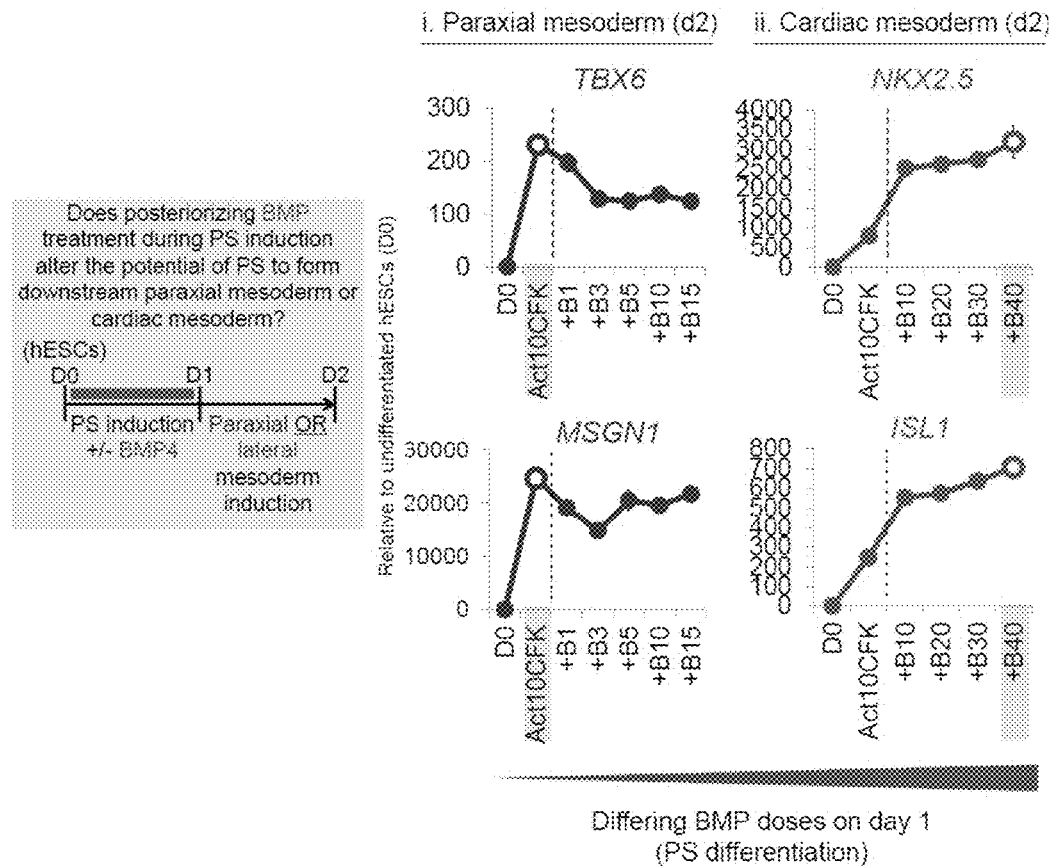
FIG. 8G Posteriorized (BMP-induced) PS has reduced paraxial potential
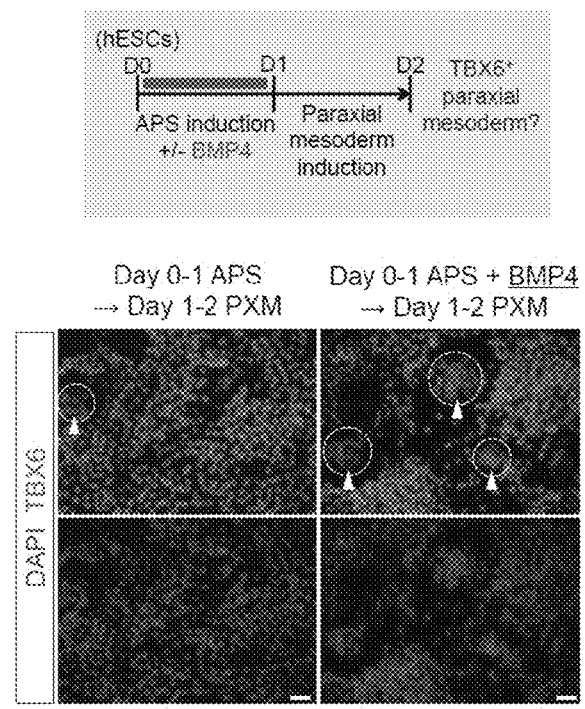

Mid TGFβ levels during PS induction enhance cardiac potential

Consistent primitive streak induction
24 hours of hESC differentiation (FACS analysis)

Differing potentials of anterior vs. mid primitive streak

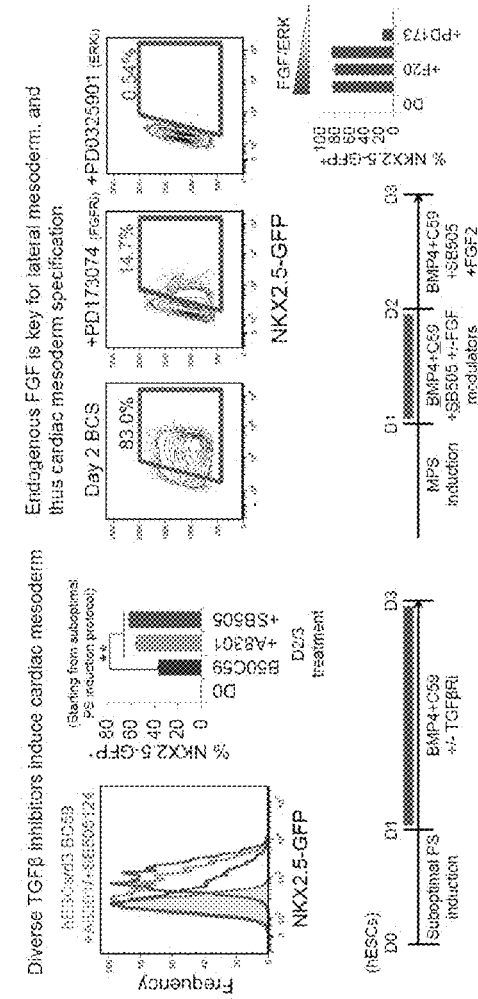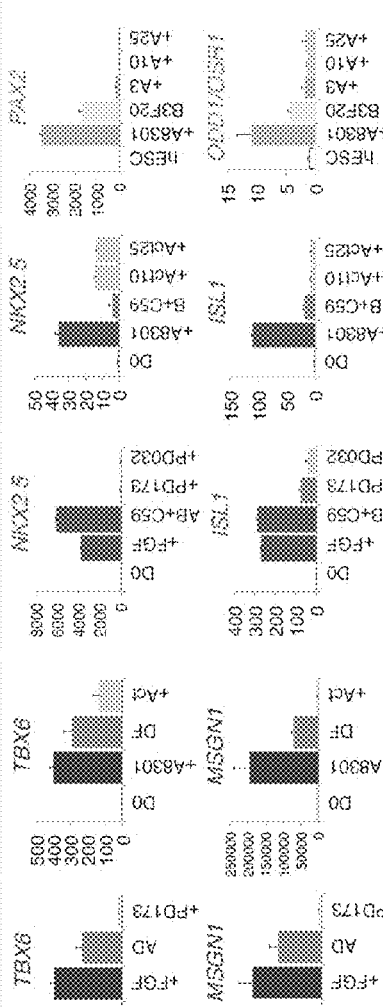
FIG. 9A · FIG. 9B · FIG. 9C · FIG. 9D · FIG. 9E · FIG. 9F

FIG. 10A
WNT and ERK inhibition specify early somites from hiPSCs
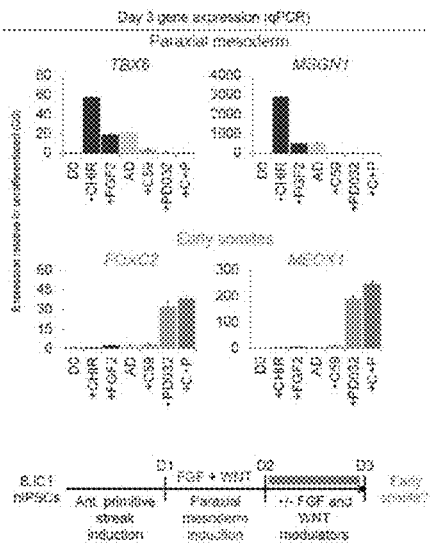
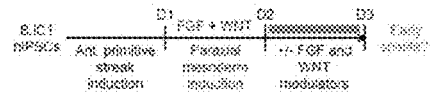
FIG. 10B
TGFβ blockade enhances early somite formation
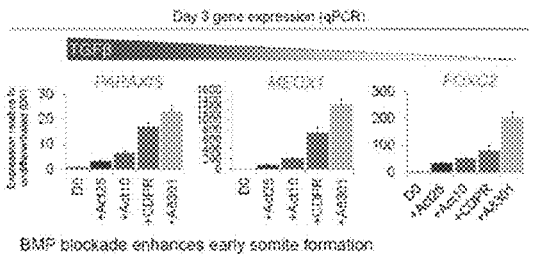
BMP blockade enhances early somite formation
FIG. 10C
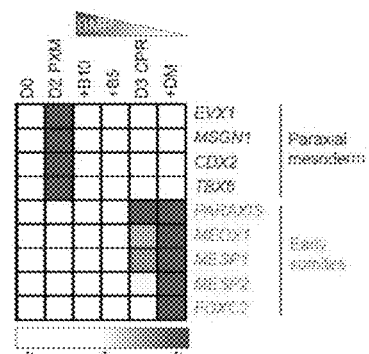
FIG. 10D
Exogenous RA is dispensable for early somite induction from paraxial mesoderm
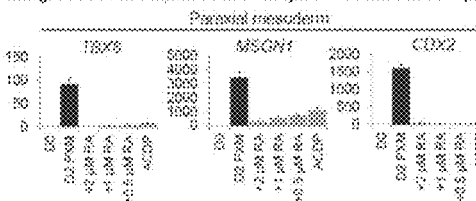
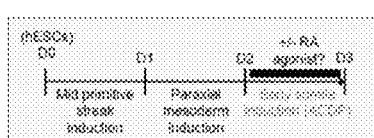
FIG. 10E
Transient *HEYL* expression in somitomeres
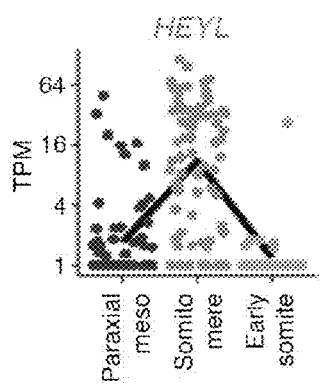
FIG. 10F
Principal component analysis of single-cell transcriptomes
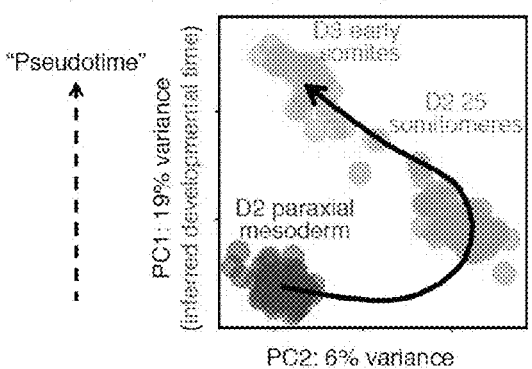

Generation of BCL2/GFP-expressing hESC line

Sclerotome-derived ectopic bone grafts *in vivo*

Late-stage Hedgehog activation upregulates *EN1* from dermomyotome

Prolonged BMP pre-treatment blocks *EN1* competence

Early transient BMP, followed by late Hh activation, is key for optimal *PAX3/PAX7/EN1* expression

FIG. 11K
BCL2 dispensable for bone graft formation
FIG. 11L
BCL2/GFP-expressing hESC line
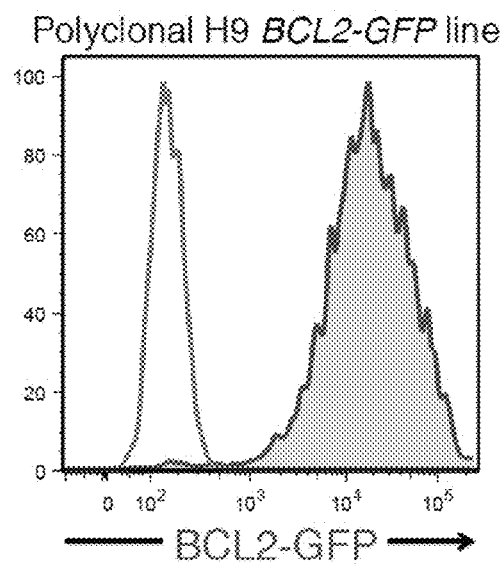
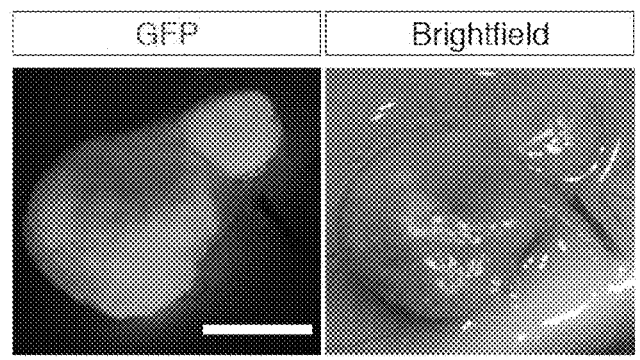
FIG. 11M
Luciferase-expressing hESC line
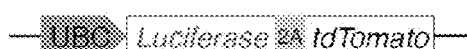
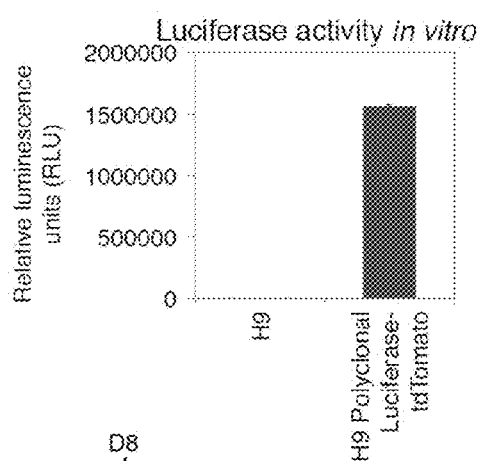
FIG. 11N
Fibroblast-like gene expression
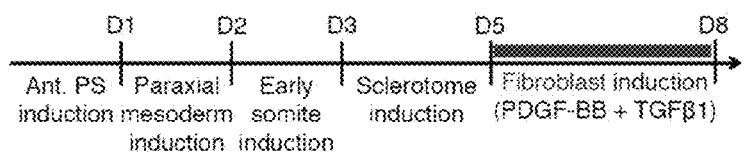

FIG. 12A
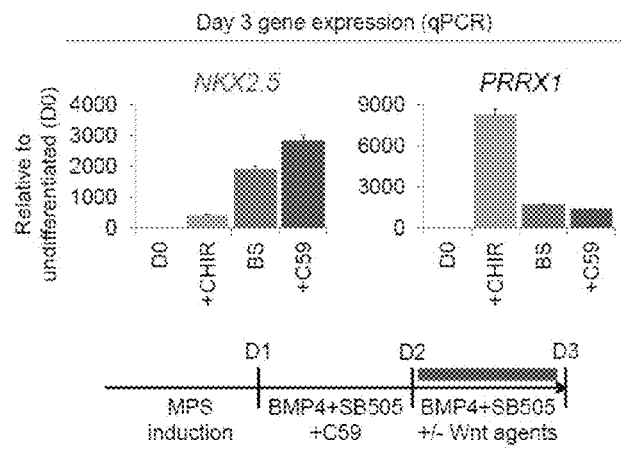
FIG. 12B
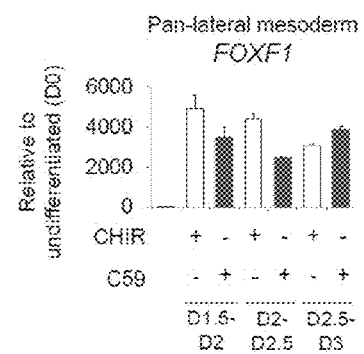
FIG. 12C
Limb progenitors in NKX2.5⁻ fraction
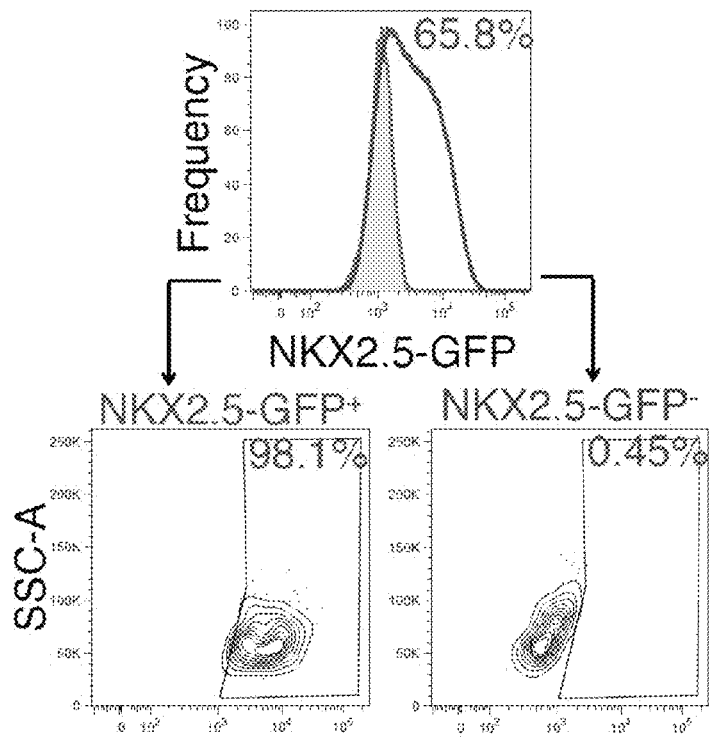
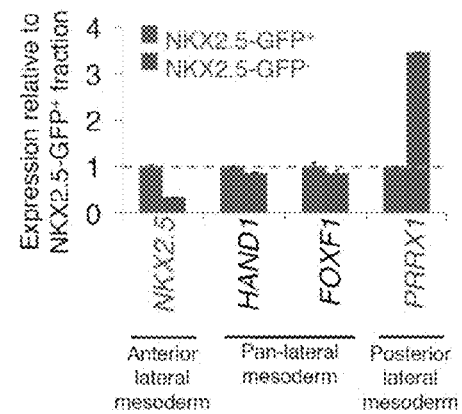

Timecourse of primitive streak and lateral/cardiac mesoderm markers

Days of hESC differentiation

BMP permissive for cardiomyocyte and endothelial differentiation from cardiac mesoderm WNT sustains cardiac progenitors and represses cardiomyocyte formation Vitamin C augments cardiomyocyte generation from cardiac mesoderm FIG. 12J Candidate human endocardium
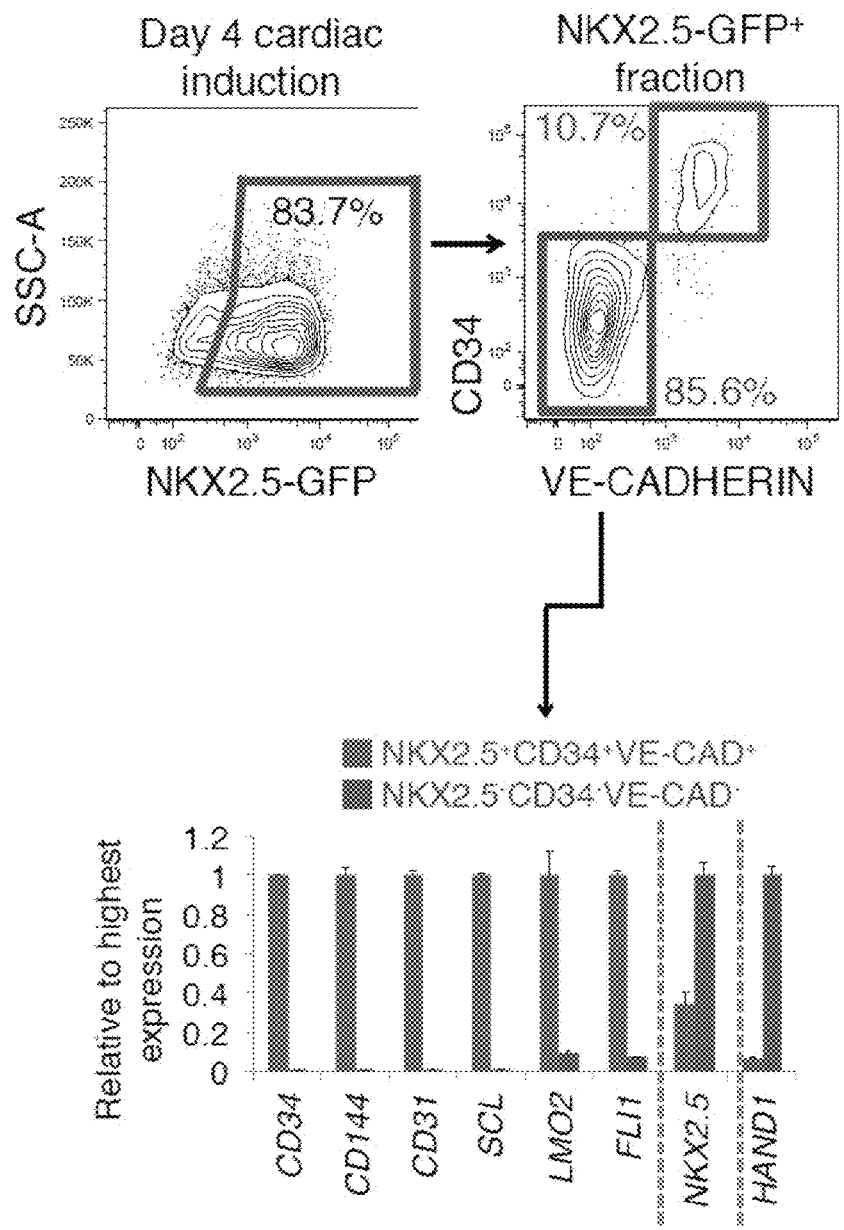
FIG. 12K
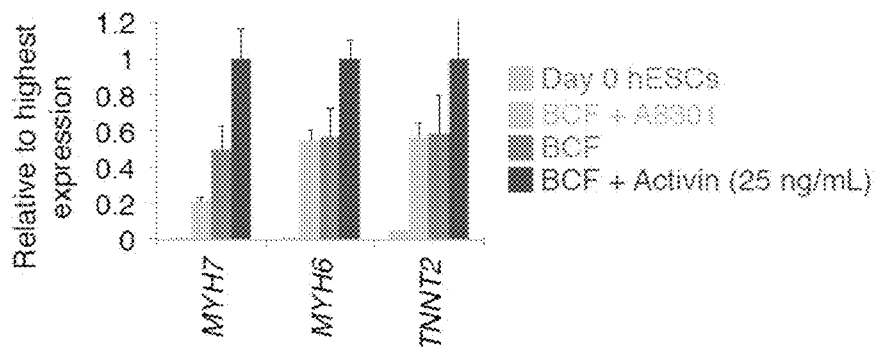

FIG. 13A CD13 and SIRPA are present on both hESCs and cardiac mesoderm
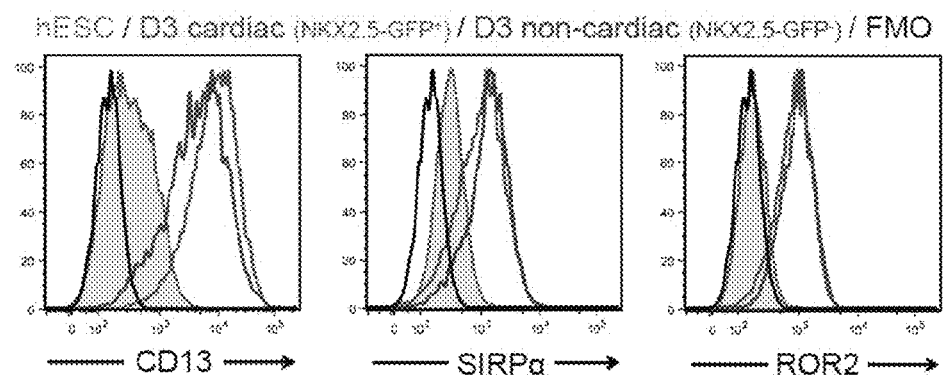
FIG. 13B Candidate cardiac/lateral markers from primary screen
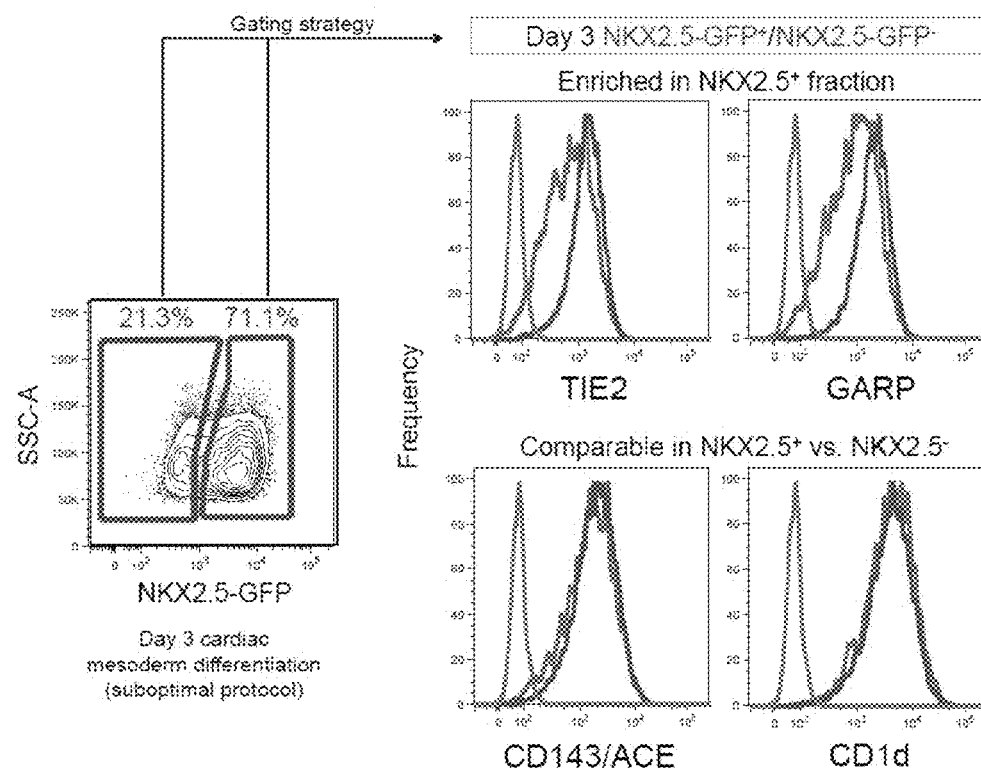
FIG. 13C DLL1 homolog *deltaC* is expressed in zebrafish paraxial mesoderm
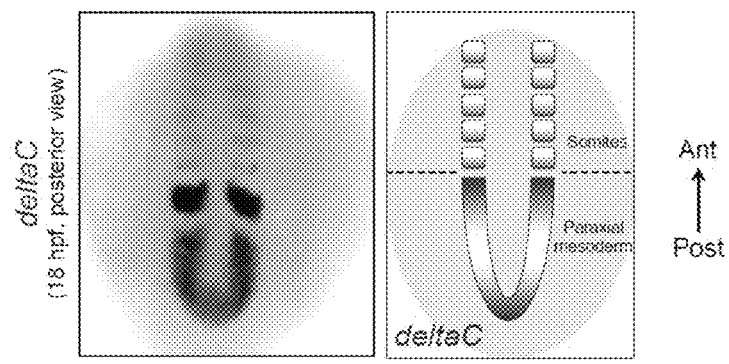

DLL1 in H7-derived paraxial mesoderm

DLL1 marks hiPSC-derived paraxial mesoderm

PDGFRα higher in sclerotome vs. dermomyotome

| | H7 hESC | Cardiac Mesoderm (NKX2.5-GFP+) | Dermomyotome | Sclerotome | Paraxial Mesoderm | Ant Primitive Streak (MIXL1-GFP+) | Early Somite |
|---|---|---|---|---|---|---|---|
| Blank | 0.0457 | 0 | 0 | 0 | 0.0153 | 0 | 0 |
| CD1a | 3.03 | 0.798 | 0.484 | 1.36 | 0.45 | 0.147 | 0.356 |
| CD1b | 14.6 | 3.68 | 0.63 | 1.58 | 0.389 | 0.136 | 0.504 |
| CD1c | 0.929 | 0.282 | 0.106 | 0.717 | 0.0464 | 0.0105 | 0.0948 |
| CD1d | 7.23 | 99.4 | 1.01 | 2.33 | 6.63 | 2.46 | 1.83 |
| CD2 | 0.146 | 0.0873 | 0.191 | 0.0223 | 0.0314 | 0 | 0.041 |
| CD3 | 0.227 | 0.191 | 0.223 | 0.808 | 0.0458 | 0.0418 | 0.0674 |
| CD4 | 10 | 23.7 | 4.73 | 0.761 | 6.36 | 0.138 | 0.165 |
| CD5 | 8.13 | 0.328 | 0.771 | 1.46 | 0.248 | 0.106 | 0.183 |
| CD6 | 30.9 | 0.433 | 0.203 | 1 | 0.0462 | 0.0106 | 0.0279 |
| CD7 | 30.6 | 67 | 19.8 | 10.3 | 37.3 | 12.8 | 59.9 |
| CD8a | 0.208 | 0.061 | 7.8 | 0.0303 | 0.377 | 0.0317 | 0.013 |
| CD9 | 100 | 99.7 | 37.4 | 8.41 | 99.9 | 99.9 | 99.7 |
| CD10 | 100 | 100 | 98.4 | 71.2 | 99.3 | 99.4 | 99.5 |
| CD11a | 0.441 | 1.49 | 0.447 | 0.844 | 0.0614 | 0.0849 | 0.122 |
| CD11b | 5.92 | 0.674 | 0.283 | 1.09 | 0.231 | 0.0742 | 0.228 |
| CD11b Activated | 1.14 | 0.65 | 0.388 | 1.2 | 0.419 | 0.0953 | 0.183 |
| CD11c | 27.4 | 1.63 | 0.471 | 1.26 | 0.373 | 0.0955 | 0.217 |
| CD13 | 62.1 | 99.9 | 79.1 | 96.3 | 85.6 | 54.2 | 92.3 |
| CD14 | 16.7 | 0.842 | 0.565 | 1.24 | 0.24 | 0.159 | 0.187 |
| CD15 | 4.69 | 0.566 | 3.31 | 1.18 | 0.402 | 1.66 | 0.194 |
| CD16 | 1.3 | 2.79 | 6.16 | 0.771 | 0.129 | 0.0425 | 0.127 |
| CD18 | 48.5 | 3.47 | 7.14 | 0.898 | 0.873 | 0.117 | 0.489 |
| CD19 | 0.239 | 0.147 | 0.0597 | 0.785 | 0.11 | 0 | 0.081 |
| CD20 | 0.119 | 0.716 | 0.0459 | 0.378 | 0.0154 | 0.0107 | 0.0411 |
| CD21 | 70.2 | 2.62 | 0.11 | 0.777 | 0.124 | 10.3 | 0.429 |
| CD22 | 0.344 | 0.334 | 0.215 | 0.888 | 0.137 | 0.0428 | 0.121 |
| CD23 | 0.316 | 0.262 | 0.194 | 0.898 | 0.139 | 0.0319 | 0.175 |
| CD24 | 100 | 100 | 99.6 | 99.9 | 99.9 | 100 | 100 |
| CD25 | 0.602 | 1.48 | 0.073 | 0.651 | 5.27 | 0.108 | 0.0841 |
| CD26 | 23.5 | 23.7 | 0.296 | 1.15 | 0.0758 | 0.83 | 0.184 |
| CD27 | 2.49 | 0.194 | 0.0949 | 0.931 | 0.0619 | 0.118 | 0.0528 |
| CD28 | 41.6 | 1.93 | 0.31 | 1.05 | 0.361 | 0.204 | 0.372 |
| CD29 | 100 | 100 | 99.6 | 99.9 | 99.9 | 99.9 | 100 |
| CD30 | 6.67 | 2.47 | 0.392 | 0.851 | 5.69 | 0.215 | 0.143 |
| CD31 | 0.517 | 24.6 | 0.313 | 0.93 | 0.687 | 0.138 | 0.961 |
| CD32 | 1.49 | 2.63 | 0.485 | 1.03 | 0.124 | 0.0754 | 0.134 |
| CD33 | 8.21 | 14.8 | 1.41 | 1.56 | 0.676 | 0.398 | 0.569 |
| CD34 | 1.63 | 41.9 | 4.09 | 25.8 | 2.85 | 0.129 | 7.51 |
| CD35 | 2.4 | 0.749 | 0.159 | 0.749 | 0.326 | 1 | 0.446 |
| CD36 | 9.08 | 0.272 | 1.86 | 2.34 | 0.0615 | 0.24 | 0.359 |
| CD38 | 9.32 | 1.83 | 0.771 | 3.67 | 0.371 | 0.388 | 0.958 |
| CD39 | 58.8 | 86.5 | 9.36 | 10.7 | 20.6 | 16.4 | 15.3 |
| CD40 | 98.1 | 94.8 | 9.13 | 36.2 | 39.3 | 27.3 | 68 |
| CD41 | 0.0837 | 0.0973 | 0.0382 | 0.119 | 0 | 0.0329 | 0.0131 |
| CD42b | 1.05 | 0.275 | 0.0909 | 0.504 | 0.0921 | 0.0218 | 0.0554 |
| CD43 | 1.21 | 3.26 | 0.801 | 2.97 | 1.28 | 0.836 | 0.636 |
| CD44 | 96.3 | 99.7 | 98.4 | 99.7 | 99.4 | 98.6 | 99.9 |
| CD45 | 0.0463 | 0.15 | 0.187 | 2.13 | 0.0469 | 0.152 | 0.242 |
| CD45RA | 0.102 | 0.124 | 0.152 | 0.875 | 0.19 | 0.0219 | 0.0791 |
| CD45RB | 0.14 | 0.105 | 0.0226 | 0.144 | 0.0469 | 0 | 0.0536 |
| CD45RO | 0.168 | 0.168 | 0.373 | 1.3 | 0.127 | 0.0329 | 0.223 |
| CD46 | 100 | 100 | 99.7 | 99.9 | 99.9 | 99.8 | 100 |
| CD47 | 100 | 100 | 99.8 | 99.3 | 100 | 100 | 99.9 |
| CD48 | 2.74 | 10.1 | 0.405 | 99.9 | 87.9 | 0.883 | 0.266 |
| CD49a | 99.9 | 100 | 98 | 99.9 | 97.3 | 97.5 | 98.3 |
| CD49c | 100 | 94.3 | 97.6 | 97.3 | 96.3 | 100 | 99.5 |
| CD49d | 80.8 | 81.7 | 12.8 | 8.57 | 49.5 | 13.9 | 24 |
| CD49e | 100 | 100 | 99.4 | 99.8 | 100 | 99.8 | 100 |
| CD49f | 100 | 92.8 | 42.5 | 79.9 | 82 | 99.9 | 92.8 |
| CD50 (ICAM-3) | 88.6 | 57.2 | 0.408 | 0.497 | 15.6 | 88.6 | 1.4 |
| CD51 | 100 | 100 | 99.1 | 99.8 | 99.8 | 100 | 99.9 |
| CD51/61 | 0.654 | 2.36 | 0.721 | 12.1 | 0.223 | 0.111 | 1.68 |
| CD52 | 0.207 | 12 | 0.184 | 0.622 | 30.9 | 0.0221 | 42.7 |
| CD53 | 1.03 | 1.56 | 0.523 | 1.1 | 0.484 | 0.785 | 0.408 |

FIG. 15 (cont. 1)

| | H7 hESC | Cardiac Mesoderm (NKX2.5-GFP+) | Dermomyotome | Sclerotome | Paraxial Mesoderm | Ant Primitive Streak (MIXL1-GFP+) | Early Somite |
|---|---|---|---|---|---|---|---|
| CD54 | 99.8 | 99.7 | 36.1 | 93.8 | 99.3 | 93.4 | 99.7 |
| CD55 | 100 | 100 | 64.2 | 12.1 | 98 | 100 | 99.5 |
| CD56(NCAM) | 99.3 | 99.9 | 99.5 | 99.9 | 95.6 | 66.5 | 99.5 |
| CD57 | 98.8 | 97.2 | 52.1 | 82 | 90.8 | 89.8 | 82.5 |
| CD58 | 100 | 100 | 99.7 | 100 | 100 | 99.9 | 100 |
| CD59 | 100 | 100 | 99.5 | 99.9 | 99.8 | 100 | 100 |
| CD61 | 12.5 | 1.71 | 0.855 | 5.21 | 0.0317 | 0.111 | 0.201 |
| CD62E | 0.365 | 0.812 | 0.553 | 0.822 | 0.319 | 0.0232 | 0.0956 |
| CD62L | 0.0755 | 0.141 | 0.633 | 0.259 | 0.0771 | 0 | 0.094 |
| CD62P-Selectin | 0.253 | 0.5 | 0.251 | 1.17 | 0.188 | 0.0111 | 0.0799 |
| CD63 | 100 | 100 | 99.8 | 99.9 | 99.9 | 99.9 | 100 |
| CD64 | 2.63 | 1 | 0.523 | 8.863 | 0.364 | 0.192 | 0.254 |
| CD66a/c/e | 11.4 | 2.45 | 0.512 | 0.885 | 0.445 | 0.0917 | 1.04 |
| CD66b | 0.643 | 0.899 | 0.0959 | 0.0289 | 0.0633 | 0 | 0.0791 |
| CD69 | 0.16 | 2.18 | 0.0912 | 0.214 | 0.0782 | 0 | 0.0421 |
| CD70 | 4.78 | 1.03 | 0.207 | 0.926 | 0.413 | 0.0784 | 0.159 |
| CD71 | 100 | 99.9 | 98 | 98.9 | 99.9 | 99.9 | 99.7 |
| CD73 | 55.4 | 13.5 | 0.943 | 52.2 | 1.15 | 0.619 | 2.87 |
| CD74 | 0.811 | 1.04 | 0.76 | 16.7 | 0.775 | 0.314 | 0.806 |
| CD79b | 2.18 | 3.73 | 2.02 | 15 | 1.41 | 0.621 | 3.6 |
| CD80 | 2.76 | 0.672 | 0.239 | 13.3 | 0.371 | 0.111 | 0.127 |
| CD81 | 100 | 100 | 99.8 | 99.9 | 99.9 | 99.7 | 100 |
| CD82 | 95.7 | 47.7 | 55.6 | 23.2 | 94.5 | 55.6 | 75.9 |
| CD83 | 32.7 | 2.15 | 0.573 | 3.41 | 0.857 | 0.28 | 0.492 |
| CD84 | 0.776 | 0.826 | 0.3 | 19.5 | 0.26 | 0.0909 | 0.217 |
| CD85a ILT5 | 1.07 | 8.24 | 0.0846 | 0.746 | 0.0486 | 0.0119 | 0.0541 |
| CD85d ILT4 | 3.55 | 1.13 | 0.199 | 13.8 | 0.164 | 0.0632 | 0.11 |
| CD85g ILT7 | 0.0941 | 0.257 | 0.181 | 0.867 | 0.129 | 0.0113 | 0.0822 |
| CD85h ILT1 | 3.71 | 0.988 | 0.233 | 1.15 | 0.181 | 0.0567 | 0.173 |
| CD85j ILT2 | 2.06 | 1.44 | 0.359 | 3.58 | 0.267 | 0.113 | 0.179 |
| CD85k ILT3 | 16.7 | 0.199 | 0.292 | 1.05 | 0.385 | 0.113 | 0.119 |
| Blank | 0.0578 | 0.0258 | 0 | 0.0394 | 0 | 0 | 0 |
| CD86 | 22.6 | 7.99 | 11.9 | 1.54 | 0.974 | 1.65 | 5.54 |
| CD87 | 2.53 | 1.34 | 1.02 | 3.78 | 0.34 | 0.38 | 0.638 |
| CD88 | 0.942 | 0.689 | 0.193 | 1.59 | 0.0932 | 0.138 | 0.559 |
| Cd89 | 1.39 | 0.593 | 0.551 | 0.655 | 0.101 | 0.161 | 0.154 |
| CD90 Thy1 | 100 | 100 | 99.5 | 99.9 | 99.9 | 99.9 | 100 |
| CD93 | 4.29 | 5.49 | 0.414 | 1.53 | 0.556 | 0.266 | 0.364 |
| CD94 | 0.615 | 0.247 | 0.465 | 1.33 | 0.133 | 0.0345 | 0.706 |
| CD95 | 98.8 | 97.3 | 93.8 | 93.6 | 82.3 | 85.9 | 96.7 |
| CD96 | 1.07 | 3.27 | 0.31 | 1.18 | 0.192 | 0.127 | 0.683 |
| CD97 | 45.7 | 55.1 | 7.68 | 4.5 | 76.3 | 3.13 | 16.3 |
| CD99 | 100 | 99.9 | 99.5 | 99.8 | 99.8 | 99.9 | 99.7 |
| CD100 | 99.4 | 74.5 | 5.21 | 20.8 | 94.2 | 21.7 | 61 |
| CD100 BB27 | 0.372 | 0.34 | 0.0992 | 0.486 | 0.0586 | 0.0211 | 0.194 |
| CD102 | 23 | 29.3 | 0.376 | 0.812 | 2.53 | 7.43 | 3.11 |
| CD103 | 0.134 | 0.0784 | 0.028 | 0.0184 | 0.0238 | 0 | 0.0128 |
| CD104 | 1.86 | 0.388 | 0.375 | 0.865 | 0.154 | 0.0693 | 0.513 |
| Cd105 | 2.44 | 42.5 | 0.283 | 2.74 | 1.24 | 0.116 | 0.478 |
| Cd106 | 0.19 | 2.96 | 1.95 | 24.2 | 0 | 0 | 1.73 |
| CD107a LAMP1 | 100 | 100 | 91 | 97.1 | 99.9 | 99.8 | 99.8 |
| CD108 | 59.9 | 78.3 | 13.8 | 49 | 98.1 | 93.9 | 93.2 |
| CD109 | 6.03 | 0.564 | 0.44 | 0.798 | 7.27 | 0.631 | 0.468 |
| CD111 | 99.3 | 96.2 | 97.1 | 98.9 | 97.3 | 99 | 94.9 |
| CD112 Nectin-2 | 100 | 100 | 99.4 | 99.8 | 99.7 | 99.9 | 99.9 |
| CD114 | 30 | 7.7 | 3.83 | 3.59 | 2.36 | 0.294 | 0.994 |
| CD115 | 29.4 | 0.671 | 0.696 | 1.9 | 0.153 | 0.32 | 0.658 |
| CD116 | 1.74 | 2.75 | 0.983 | 25.8 | 0.562 | 0.305 | 0.991 |
| CD117 c-Kit | 99.9 | 25.2 | 5.67 | 8.79 | 5.3 | 86.6 | 27.4 |
| CD119 IFNgralpha | 100 | 99.7 | 75 | 80 | 97.9 | 98.6 | 97.4 |
| CD122 | 0.236 | 0.322 | 0 | 0.118 | 0.0239 | 0.0423 | 0.0507 |
| CD123 | 0.633 | 0.768 | 0.0247 | 0.337 | 0.0651 | 0.0106 | 0.739 |
| CD124 | 26.3 | 0.8 | 0.431 | 1.49 | 0.268 | 0.105 | 0.242 |
| CD126 IL6RA | 4.66 | 0.347 | 0.246 | 0.833 | 0.88 | 0.0421 | 0.194 |
| CD127 IL7Ra | 1.24 | 0.278 | 0.0924 | 0.416 | 0.119 | 0.0316 | 0.0765 |

FIG. 15 (cont. 2)

| | H7 hESC | Cardiac Mesoderm (NKX2.5-GFP+) | Dermomyotome | Sclerotome | Paraxial Mesoderm | Ant Primitive Streak (MIXL1-GFP+) | Early Somite |
|---|---|---|---|---|---|---|---|
| CD129 IL9R | 14.3 | 2.58 | 0.661 | 5.76 | 0.31 | 0.126 | 0.536 |
| CD131 | 0.56 | 1.94 | 0.399 | 0.369 | 0.17 | 0.0635 | 0.229 |
| CD132 | 3.11 | 0.894 | 0.868 | 1.08 | 0.332 | 0.274 | 0.255 |
| CD134 | 1.54 | 0.96 | 0.738 | 4.1 | 0.532 | 0.114 | 3.7 |
| CD135 | 5.45 | 0.27 | 0.336 | 1.36 | 0.174 | 0.138 | 0.204 |
| CD137 41BB | 0.495 | 0.234 | 0.191 | 1.07 | 68.4 | 25.2 | 1.63 |
| CD137L 41BBL | 20.7 | 12.3 | 0.684 | 5.65 | 2.93 | 0.503 | 1.3 |
| CD138 | 21.9 | 25.1 | 0.756 | 2.92 | 0.816 | 0.305 | 1.38 |
| CD140a | 1.95 | 11.5 | 0.303 | 28.1 | 0.224 | 0.0552 | 0.334 |
| CD140b | 5.43 | 36.5 | 10.4 | 96.5 | 1.02 | 0.274 | 7.48 |
| CD141 | 2.97 | 19.1 | 4.71 | 84.6 | 1.99 | 3.42 | 1.3 |
| CD143 | 38.6 | 98.2 | 1.22 | 2.82 | 2.39 | 8.5 | 6.34 |
| CD144 | 44.4 | 29.1 | 0.343 | 0.999 | 0.149 | 0.149 | 0.488 |
| CD146 | 100 | 100 | 50.4 | 78.8 | 99.3 | 99.8 | 99.6 |
| CD148 | 99.4 | 98.6 | 72.3 | 92.6 | 96.2 | 98.1 | 99 |
| CD150 SLAM | 0.464 | 0.373 | 0.361 | 0.109 | 0.0451 | 0.0358 | 0.103 |
| CD152 | 3.77 | 20.1 | 0.386 | 1.28 | 0.273 | 0.106 | 0.309 |
| cd154 | 0.46 | 0.323 | 0.194 | 0.428 | 0.111 | 0.0232 | 0.115 |
| CD155 PVR | 100 | 100 | 99.7 | 99.3 | 99.9 | 99.8 | 99.9 |
| CD156c ADAM10 | 100 | 100 | 99.7 | 99.6 | 99.3 | 100 | 99.8 |
| CD158a/h | 2.98 | 0.695 | 1.13 | 2.1 | 1.48 | 0.868 | 1.16 |
| CD158b NKAT2 | 0.558 | 0.489 | 0.497 | 1.24 | 0.188 | 0.0699 | 0.216 |
| CD158d | 28.7 | 0.727 | 0.5 | 1.32 | 0.276 | 0.203 | 0.514 |
| CD158e1 NKB1 | 0.162 | 0.112 | 0.0728 | 0.198 | 0.0198 | 0.0107 | 0.0128 |
| CD158f | 0.931 | 3.83 | 0.334 | 0.979 | 0.275 | 0.0535 | 0.267 |
| CD161 | 5.06 | 0.776 | 0.14 | 0.294 | 0.124 | 0.0441 | 0.0776 |
| CD162 | 1.55 | 4.9 | 0.824 | 1.22 | 0.552 | 0.176 | 4.52 |
| CD163 | 1.06 | 0.426 | 0.345 | 1.45 | 0.97 | 0.0964 | 0.269 |
| CD164 | 99.5 | 100 | 93.1 | 99 | 99.7 | 99.7 | 98.9 |
| CD165 | 100 | 100 | 99.7 | 99.3 | 99.7 | 99.9 | 99.8 |
| CD166 | 100 | 100 | 99.7 | 99.7 | 95.8 | 99.9 | 99.4 |
| CD167a DDR1 | 6.41 | 84.2 | 15.9 | 14.3 | 53.1 | 1.8 | 67.8 |
| CD169 | 0.198 | 0.123 | 0.0356 | 0.26 | 0.0629 | 0 | 0.166 |
| CD170 SIGLEC-5 | 33.4 | 24.4 | 0.586 | 2.01 | 0.232 | 4.89 | 3.6 |
| CD172a SIRPa | 71.3 | 92.2 | 52.4 | 96.4 | 96.4 | 46.2 | 94.6 |
| CD172b SIRPb | 0.649 | 0.158 | 0.202 | 0.58 | 0.141 | 0.0541 | 0.206 |
| CD172g SIRPg | 0.886 | 0.505 | 0.327 | 1.06 | 0.0754 | 0.043 | 0.309 |
| CD178 FasL | 4.38 | 0.458 | 0.426 | 0.64 | 0.246 | 0.0323 | 0.342 |
| CD179a | 2.49 | 1.72 | 1.05 | 3.6 | 0.952 | 0.529 | 1.02 |
| CD179b | 18.2 | 0.325 | 0.234 | 0.51 | 0.227 | 0.118 | 0.131 |
| CD180 RP105 | 2 | 0.551 | 0.123 | 0.471 | 0.112 | 0.103 | 0.0815 |
| CD181 CXCR1 | 0.43 | 1.15 | 0.478 | 1.74 | 0.4 | 0.0951 | 0.678 |
| CD182 CXCR2 | 4.59 | 0.236 | 0.293 | 0.735 | 1.04 | 0.33 | 4.33 |
| CD183 | 20.4 | 3.86 | 6.28 | 17.6 | 2.79 | 0.921 | 3.02 |
| CD184 CXCR4 | 7.08 | 24.3 | 50.3 | 4.84 | 91.7 | 12.3 | 97.1 |
| CD193 CCR3 | 0.285 | 0.695 | 0.598 | 1.25 | 0.735 | 0.0902 | 0.696 |
| CD195 CCR5 | 5.59 | 1.05 | 0.727 | 2.02 | 1.49 | 0.362 | 1.3 |
| CD196 | 1.17 | 1.97 | 3.16 | 3.07 | 1.62 | 0.379 | 1.67 |
| CD197 CCR7 | 5.25 | 2.39 | 0.515 | 1.32 | 19.5 | 8.54 | 3.18 |
| CD200 OX2 | 100 | 99.9 | 97.7 | 99.1 | 99.9 | 99.4 | 99.9 |
| CD200R | 1.39 | 24.6 | 0.675 | 1.36 | 0.358 | 0.354 | 0.215 |
| CD201 EPCR | 98.6 | 89.3 | 9.91 | 6.3 | 31.8 | 27.8 | 9.8 |
| CD202b Tie2/Tek | 16.1 | 98 | 0.523 | 5.7 | 3.4 | 0.444 | 27.4 |
| CD203c ENPP3 | 1.16 | 2.27 | 8.8 | 0.938 | 0.371 | 0.0375 | 0.407 |
| CD205 Dec205 | 21.5 | 0.372 | 0.385 | 1.14 | 0.53 | 0.146 | 0.079 |
| CD206 MMR | 0.361 | 24.4 | 0.34 | 1.06 | 1.1 | 0.111 | 0.172 |
| CD207 Langerin | 0.344 | 0.0895 | 0.0635 | 0.539 | 0.0934 | 0.0124 | 0.0263 |
| CD209 DC-SIGN | 0.563 | 0.196 | 0.0935 | 0.355 | 0.0651 | 0.0111 | 0.131 |
| CD210 IL-10R | 6.3 | 1.15 | 0.676 | 1.38 | 0.733 | 0.166 | 0.829 |
| CD213a2 | 13.7 | 0.879 | 0.471 | 1 | 0.35 | 0.0891 | 0.312 |
| CD215 IL-15Ra | 0.717 | 0.601 | 0.698 | 2.05 | 0.691 | 0.244 | 0.48 |
| CD218a IL18-Ra | 9.63 | 19.7 | 0.298 | 3.69 | 0.345 | 0.0671 | 0.265 |
| Blank | 9.61E-03 | 0.0624 | 0 | 0 | 0 | 0 | 0.0127 |
| CD220 | 56 | 36.3 | 3.4 | 3.02 | 71.5 | 98 | 64.5 |
| CD221 IGF-1R | 100 | 100 | 98.9 | 99.7 | 99.3 | 100 | 99.9 |

FIG. 15 (cont. 3)

| | H7 hESC | Cardiac Mesoderm (NKX2.5-GFP+) | Dermomyotome | Sclerotome | Paraxial Mesoderm | Ant Primitive Streak (MIXL1-GFP+) | Early Somite |
|---|---|---|---|---|---|---|---|
| CD226 DNAM-1 | 0.384 | 1 | 0.507 | 1.29 | 13.7 | 0.301 | 8.17 |
| CD229 Ly-9 | 0.605 | 0.0975 | 0.0254 | 0.187 | 0.125 | 0.0106 | 0.0902 |
| CD231 TALLA | 39.8 | 0.945 | 1.17 | 3.29 | 0.484 | 0.125 | 9.77 |
| CD235ab | 0.124 | 1.18 | 0.689 | 2.06 | 0.493 | 0.323 | 1.57 |
| CD243 | 3.2 | 14.5 | 14.1 | 4.07 | 3.63 | 1.02 | 19.1 |
| CD244 2B4 | 0.235 | 0.496 | 0.0866 | 0.718 | 0.12 | 0.0216 | 0.445 |
| CD245 p220/240 | 97 | 47.9 | 4.06 | 12.5 | 93.2 | 47.2 | 15.4 |
| CD252 OX40L | 4.92 | 36.6 | 0.575 | 1.48 | 0.674 | 59.6 | 16 |
| CD253 TRAIL | 86.1 | 0.735 | 0.493 | 1.24 | 0.159 | 0.129 | 0.114 |
| CD254 | 0.515 | 1 | 4.3 | 0.966 | 0.426 | 0.125 | 0.367 |
| CD255 TWEAK | 33.7 | 37.2 | 33.7 | 19.5 | 1.83 | 4.81 | 2.69 |
| CD257 BAFF | 23.7 | 46.2 | 18.6 | 7.24 | 5.99 | 2.53 | 2.29 |
| CD258 LIGHT | 19.4 | 1.88 | 0.351 | 1.11 | 0.604 | 0.0832 | 0.318 |
| CD261 DR4 | 40.6 | 8.35 | 0.648 | 2.09 | 34.9 | 66.5 | 5.65 |
| CD262 DR5 | 100 | 99.7 | 99.7 | 99.8 | 99.4 | 99.9 | 99.4 |
| CD263 DcR1 | 80.6 | 38.9 | 30.3 | 1.48 | 0.317 | 0.256 | 2.96 |
| CD266 Fn14 | 98.2 | 34.4 | 39.7 | 21.2 | 84.8 | 95.5 | 86.5 |
| CD267 TACI | 28 | 0.539 | 0.312 | 1.38 | 0.149 | 0.572 | 0.229 |
| CD268 BAFF-R | 0.603 | 0.508 | 1.24 | 0 | 0.0933 | 0.0213 | 0.039 |
| CD270 HVEM | 0.492 | 1.02 | 0.727 | 2.24 | 0.988 | 0.127 | 0.912 |
| CD271 | 99.9 | 77.4 | 23.9 | 20.7 | 91.6 | 93.7 | 91.8 |
| CD273 B7-DC | 0.25 | 10.5 | 0.993 | 1 | 0.292 | 0.158 | 1.02 |
| CD274 B7-H1 | 51.4 | 3.42 | 5.62 | 7.06 | 1.83 | 0.325 | 5.75 |
| CD275 B7-H2 | 97.5 | 59.9 | 10.7 | 7.45 | 77.9 | 98.8 | 66.6 |
| CD276 | 100 | 100 | 99.7 | 99.8 | 100 | 100 | 100 |
| CD277 | 14.9 | 49.3 | 1.44 | 11.6 | 1.06 | 0.523 | 4.61 |
| CD278 ICOS | 0.135 | 0.145 | 0.244 | 0.368 | 0.0606 | 0 | 0.0789 |
| CD279 PD-1 | 4.01 | 0.186 | 0.0522 | 0.438 | 3.41 | 0.435 | 5.63 |
| CD282 TLR2 | 0.297 | 0.776 | 0.306 | 1.75 | 0.358 | 0.104 | 0.396 |
| CD284 TLR4 | 1.05 | 1.46 | 0.456 | 1.73 | 0.672 | 0.139 | 0.303 |
| CD286 TLR6 | 1.19 | 1.37 | 0.381 | 0.956 | 0.154 | 0.0246 | 0.164 |
| CD290 | 3.95 | 0.484 | 0.26 | 0.808 | 0.153 | 0.0129 | 0.126 |
| CD294 | 2.19 | 0.618 | 0.691 | 2.8 | 3.02 | 0.093 | 2.6 |
| CD298 | 100 | 100 | 99.8 | 99.9 | 99.9 | 99.8 | 100 |
| CD300e IREM-2 | 0.2 | 0.804 | 0.21 | 0.937 | 0.77 | 0.397 | 1.92 |
| CD300f | 51.7 | 0.728 | 0.383 | 0.677 | 0.244 | 0.0722 | 0.267 |
| CD301 | 0.645 | 1.78 | 0.632 | 21.6 | 1.83 | 0.14 | 1.08 |
| CD303 | 0.23 | 0.523 | 0.219 | 0.985 | 0.149 | 0.0405 | 0.264 |
| CD304 | 0.101 | 12.9 | 0.389 | 0.445 | 0.436 | 0.0134 | 0.0379 |
| CD307 | 0.35 | 0.365 | 0.113 | 1 | 0.0398 | 0.0143 | 0.113 |
| CD307d FcRL4 | 0.294 | 0.558 | 0.624 | 1.16 | 0.289 | 0.0536 | 0.277 |
| CD314 NKG2D | 35.7 | 0.479 | 0.464 | 1.03 | 0.325 | 0.0422 | 0.315 |
| CD317 | 99.8 | 88.1 | 14.9 | 24.1 | 56.2 | 85.6 | 35.1 |
| CD318 CDCP1 | 100 | 78.4 | 0.342 | 1.09 | 98.5 | 99.7 | 91 |
| CD319 CRACC | 30.7 | 1.45 | 20 | 0.936 | 0.347 | 0.917 | 0.301 |
| CD324 E-Cadherin | 99.9 | 98 | 66.2 | 43 | 97.1 | 99 | 95.4 |
| CD325 | 7.2 | 15.7 | 0.44 | 1.04 | 4.52 | 1.98 | 0.396 |
| CD326 EpCAM | 100 | 100 | 45.4 | 47.8 | 99.8 | 99.5 | 100 |
| CD328 Siglec-7 | 0.065 | 0.254 | 0.0777 | 0.243 | 0.136 | 0.179 | 0.175 |
| CD334 FGFR4 | 0.13 | 0.244 | 0.0537 | 0.183 | 0.0263 | 0.0289 | 0.238 |
| CD335 NKp46 | 0.102 | 0.567 | 0.051 | 0.123 | 0.0738 | 0.0157 | 0.15 |
| CD336 NKp44 | 0.205 | 27.2 | 0.0643 | 0.719 | 0.119 | 0.0119 | 0.19 |
| CD337 NKp30 | 0.112 | 0.146 | 0 | 0.325 | 0.717 | 0.0372 | 0.352 |
| CD338 ABCG2 | 2.58 | 97.6 | 65.3 | 20.1 | 70.1 | 26.7 | 97 |
| CD340 ErbB2 | 100 | 100 | 99.8 | 99.8 | 99.8 | 99.7 | 100 |
| CD344 Frizzled-4 | 57.3 | 88.3 | 6.1 | 16.8 | 26.2 | 7.38 | 91.8 |
| CD351 | 36.8 | 0.83 | 1.09 | 0.865 | 0.275 | 0.135 | 0.328 |
| CD352 NTB-A | 1.06 | 1.73 | 0.294 | 0.595 | 0.331 | 0.129 | 0.227 |
| CD354 TREM-1 | 3.68 | 1.12 | 0.363 | 1.08 | 0.566 | 0.0781 | 0.153 |
| CD355 CRTAM | 0.469 | 0.736 | 0.414 | 1.12 | 0.35 | 0.0484 | 0.281 |
| CD357 GITR | 4.87 | 3.16 | 0.681 | 5.86 | 1.59 | 0.156 | 0.901 |
| CD360 IL-21R | 4.42 | 6.7 | 0.411 | 1.88 | 1.22 | 0.0956 | 0.702 |
| B2-Microglobulin | 100 | 100 | 99.4 | 99.2 | 99.9 | 99.2 | 99.9 |
| BLTA | 1.83 | 1.55 | 0.369 | 1.39 | 0.425 | 0.938 | 0.193 |
| C3AR | 0.29 | 0.738 | 0.236 | 0.855 | 0.118 | 0.0666 | 0.219 |

FIG. 15 (cont. 4)

| | H7 hESC | Cardiac Mesoderm (NKX2.5-GFP+) | Dermomyotome | Sclerotome | Paraxial Mesoderm | Ant. Primitive Streak (MIXL1-GFP+) | Early Somite |
|---|---|---|---|---|---|---|---|
| C5L2 | 11.3 | 4.52 | 1.12 | 3.41 | 1.73 | 0.279 | 1.07 |
| CCR10 | 1.6 | 3.72 | 1.17 | 1.84 | 7.29 | 0.616 | 2.45 |
| CLEC-12A | 0.329 | 0.238 | 0.12 | 0.286 | 0 | 0 | 0.167 |
| CLEC9a | 12.5 | 0.343 | 0.195 | 0.919 | 0.0498 | 0.038 | 0.115 |
| CX3CR1 | 0.407 | 0.609 | 0.292 | 1.05 | 0.42 | 0.0736 | 0.182 |
| CXCR7 | 62.5 | 6.28 | 27.8 | 1.3 | 0.846 | 0.296 | 0.635 |
| opopid receptor | 0.291 | 1.04 | 0.388 | 1.19 | 0.129 | 2.14 | 0.155 |
| DLL1 | 0.5 | 0.241 | 0.0913 | 5.21 | 90.4 | 11.8 | 55.3 |
| DLL4 | 0.094 | 9.52 | 0.0536 | 0 | 0.0323 | 0.109 | 0.0512 |
| DR3 TRAMP | 0.18 | 0.989 | 1.08 | 6.03 | 0.304 | 0.191 | 0.446 |
| EGFR | 66.6 | 1.69 | 11.7 | 42.1 | 1.03 | 2.57 | 3.45 |
| ErbB3 | 99.4 | 49.2 | 2.45 | 1.45 | 35.5 | 95.1 | 4.11 |
| FcRR1a | 0.198 | 0.0577 | 0.27 | 0.531 | 0.136 | 1.91 | 0.0774 |
| FcRL6 | 4.34 | 2.3 | 0.721 | 1.39 | 0.933 | 0.252 | 0.647 |
| Galectin-9 | 5.85 | 1.04 | 0.381 | 1.58 | 1.13 | 0.159 | 0.61 |
| GARP | 0.264 | 99.3 | 2.56 | 4.72 | 0.508 | 0.0407 | 13.9 |
| HLA-ABC | 99.8 | 100 | 83.9 | 88.4 | 99.7 | 99.1 | 99.7 |
| HLA A2 | 98.3 | 2.24 | 55.4 | 59.7 | 86.8 | 0.64 | 79.9 |
| HLA DQ | 0.0189 | 0.592 | 0.0774 | 0.0573 | 0.0807 | 0.239 | 0.0129 |
| HLA DR | 0.443 | 19.9 | 0.106 | 0.163 | 0 | 5.82 | 0.0896 |
| HLA E | 1.9 | 45.4 | 0.504 | 1.63 | 0.796 | 0.171 | 0.245 |
| HLA G | 4.4 | 3.79 | 2.42 | 1.4 | 1.38 | 0.156 | 0.976 |
| IFNg R b chain | 34 | 2.4 | 0.897 | 4.77 | 2.47 | 0.259 | 1.32 |
| IG Light Chain K | 0.0756 | 0.0285 | 0 | 0.0951 | 0 | 0 | 0.0129 |
| Ig Light Chain L | 0.104 | 0.0536 | 0.0355 | 0.0432 | 0 | 0.0381 | 0 |
| IgD | 0.199 | 0.427 | 0.48 | 1.87 | 0.947 | 0.238 | 0.23 |
| IgM | 0.0853 | 0.0721 | 0.0105 | 0.065 | 0.0678 | 0 | 0.0256 |
| IL-28Ra | 2.68 | 1.29 | 0.371 | 0.616 | 0.234 | 0.0494 | 0.0779 |
| Blank | 0.0288 | 0.0354 | 85.6 | 0 | 0 | 0.0248 | 0 |
| Integrin a9b1 | 98.1 | 99.9 | 91.8 | 99.9 | 98.2 | 76.1 | 99.1 |
| Integrin b5 | 99.6 | 95.8 | 56.2 | 33.9 | 99.8 | 98.9 | 84.9 |
| Integrin b7 | 0.154 | 0.255 | 0.392 | 1.28 | 0.08 | 0.298 | 0.0388 |
| Jagged 2 | 0.977 | 3.95 | 0.447 | 1.72 | 0.414 | 0.0217 | 0.202 |
| LAP | 0.153 | 1.57 | 0.279 | 1.2 | 0.032 | 0.0305 | 0.0647 |
| LT-bR | 44 | 49.4 | 1.06 | 1.65 | 5.85 | 8.551 | 2.79 |
| Mac-2 Galectin-3 | 1.4 | 0.835 | 0.252 | 1.09 | 0.159 | 0 | 0.383 |
| MAIR-2 | 0.278 | 1.05 | 0.426 | 1.32 | 0.519 | 0.0552 | 0.355 |
| MICA/MICB | 29.4 | 72.2 | 0.239 | 2.55 | 70.2 | 26.2 | 0.378 |
| MSC W3D5 | 86.7 | 84.9 | 40.6 | 22.3 | 52.4 | 80.5 | 54.7 |
| MSC W5C5 | 93.4 | 89.1 | 43.5 | 28.1 | 53.7 | 84.2 | 58.1 |
| MSC W7C6 | 95.1 | 96.4 | 7.34 | 73.7 | 97.1 | 97.9 | 96 |
| MSC NPC W4A5 | 13.1 | 11.2 | 11.8 | 39.8 | 13.1 | 5.29 | 4.17 |
| MSCA-1 MSC | 99.9 | 99.9 | 99 | 93.8 | 99.9 | 99.6 | 100 |
| Nkp80 | 0.767 | 0.268 | 0.365 | 1.37 | 0.405 | 0.213 | 0.181 |
| Notch 1 | 1.93 | 0.868 | 0.392 | 1.23 | 86.3 | 0.131 | 0.155 |
| Notch 2 | 10.5 | 4.46 | 0.365 | 1.41 | 8.1 | 0.344 | 0.841 |
| Notch 3 | 20.8 | 2.96 | 0.181 | 1.63 | 0.249 | 0.0656 | 0.0534 |
| Notch 4 | 0.383 | 9.88 | 0.388 | 1.41 | 0.199 | 5.76 | 2.57 |
| NPC S7D2 | 6.09 | 6.25 | 1.41 | 23.3 | 8.33 | 5.44 | 4.47 |
| Podoplanin | 100 | 100 | 99.7 | 99.9 | 100 | 99.5 | 100 |
| Pre BCR | 1.67 | 0.645 | 0.314 | 1.04 | 0.304 | 0.373 | 0.14 |
| PSMA | 0.426 | 0.116 | 0.275 | 0.575 | 0.0853 | 0.0175 | 0.114 |
| Siglec 10 | 1.17 | 0.993 | 0.354 | 1.36 | 0.247 | 0.0647 | 0.0718 |
| Siglec 8 | 0.348 | 0.658 | 18.3 | 1.11 | 0.355 | 0.0674 | 0.122 |
| Siglec 9 | 0.776 | 0.432 | 0.315 | 0.982 | 0.185 | 0.069 | 0.209 |
| SSEA-1 | 0.61 | 0.645 | 1.53 | 0.147 | 0.184 | 0.191 | 0.0529 |
| SSEA-3 | 99 | 26.6 | 2.51 | 1.57 | 85.3 | 98.1 | 17.9 |
| SSEA-4 | 100 | 100 | 99.7 | 99.9 | 100 | 99.9 | 100 |
| SSEA-5 | 100 | 100 | 99.6 | 99.7 | 99.9 | 98.8 | 100 |
| TCR g/d | 27.2 | 4.68 | 0.706 | 2.91 | 2.61 | 0.165 | 0.842 |
| TCR vb13.2 | 0.388 | 0.512 | 0.213 | 0.936 | 0.107 | 0.0637 | 0.257 |
| TCR vb23 | 0.405 | 0.733 | 0.512 | 1.86 | 0.273 | 0.0802 | 0.184 |
| TCR vb8 | 0.128 | 0.201 | 19.1 | 0.735 | 0.0303 | 0.059 | 0.0843 |
| TCR vb9 | 0.298 | 0.301 | 0.307 | 1.13 | 0.0617 | 0.0303 | 0.0376 |
| TCR vd2 | 0.08 | 0.288 | 0.113 | 0.726 | 0.0616 | 0.0612 | 0.0655 |

FIG. 15 (cont. 5)

| | H7 hESC | Cardiac Mesoderm (NKX2.5-GFP+) | Dermomyotome | Sclerotome | Paraxial Mesoderm | Ant Primitive Streak (MIXL1-GFP+) | Early Somite |
|---|---|---|---|---|---|---|---|
| TCR vg9 | 0.314 | 0.516 | 0.309 | 1.12 | 0.1 | 0.0177 | 0.158 |
| TCR va24-ja18 | 0.491 | 0.641 | 0.249 | 0.732 | 0.0966 | 0.0535 | 0.216 |
| TCR va7p2 | 0.19 | 0.286 | 0.189 | 1 | 0.0776 | 0 | 0.122 |
| TCR a/b | 1.16 | 0.459 | 0.267 | 1.1 | 0.221 | 0.0198 | 0.377 |
| Tim-1 | 46.2 | 2.25 | 0.455 | 1.42 | 0.312 | 0.0994 | 0.658 |
| Tim-3 | 1.07 | 0.345 | 0.219 | 1.04 | 0.0476 | 0 | 0.254 |
| Tim-4 | 1.02 | 0.743 | 0.279 | 1.23 | 0.155 | 0.0687 | 0.254 |
| TLT-2 | 0.216 | 0.71 | 0.391 | 1.08 | 0.263 | 0.116 | 1.4 |
| TRA-1-60-R | 100 | 99.3 | 11.7 | 3.88 | 100 | 98.7 | 99 |
| TRA-1-81 | 96 | 24.1 | 10.7 | 1.77 | 97.6 | 100 | 72.9 |
| TSLPR | 0.476 | 0.448 | 0.376 | 0.672 | 0.0615 | 0.303 | 0.249 |
| Ms IgG1 | 0.369 | 0.896 | 0.757 | 0.606 | 0.729 | 2.41 | 1.49 |
| Ms IgG2a | 0.295 | 0.688 | 0.383 | 0.927 | 2.28 | 10.6 | 3.8 |
| Ms IgG2b | 0.341 | 0.639 | 0.433 | 1.16 | 0.255 | 0.179 | 0.262 |
| Ms IgG3 | 2.32 | 2.71 | 3.22 | 1.54 | 1.82 | 0.87 | 2.03 |
| Ms IgM | 0.989 | 1.36 | 0.494 | 0.962 | 0.24 | 0.0374 | 0.701 |
| Rat IgG1 | 78.9 | 3.6 | 0.334 | 0.956 | 0.296 | 0.0541 | 0.399 |
| Rat IgG2a | 1.09 | 0.629 | 0.784 | 2.95 | 0.325 | 0.0539 | 0.522 |
| Rat IgG2b | 0.619 | 0.127 | 0.12 | 0.0365 | 0 | 0 | 0.136 |
| Rat IgM | 3.42 | 2.3 | 0.504 | 0.428 | 0.015 | 0 | 0.418 |
| AH IgG | 5.26 | 0.546 | 0.416 | 0.729 | 0.224 | 0.0929 | 0.233 |
| Blank | 0.042 | 0 | 0 | 0.029 | 0.0151 | 0 | 0.0126 |
| Blank | 0.0526 | 0 | 0 | 0 | 0 | 0 | 0 |

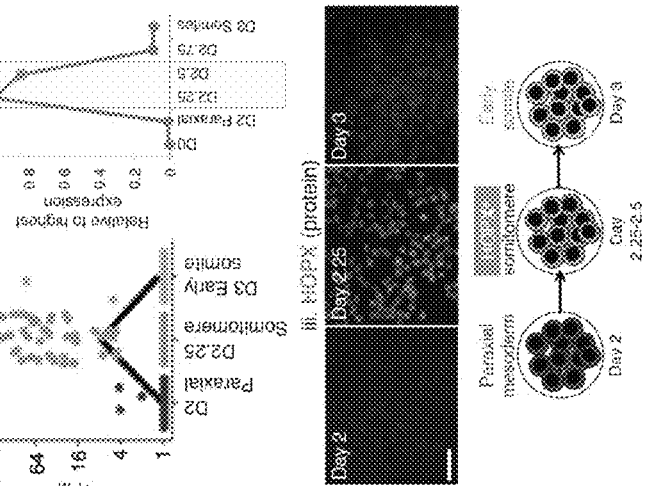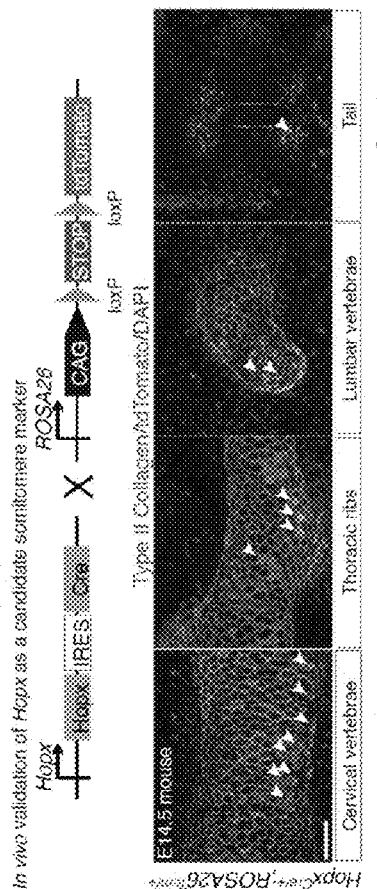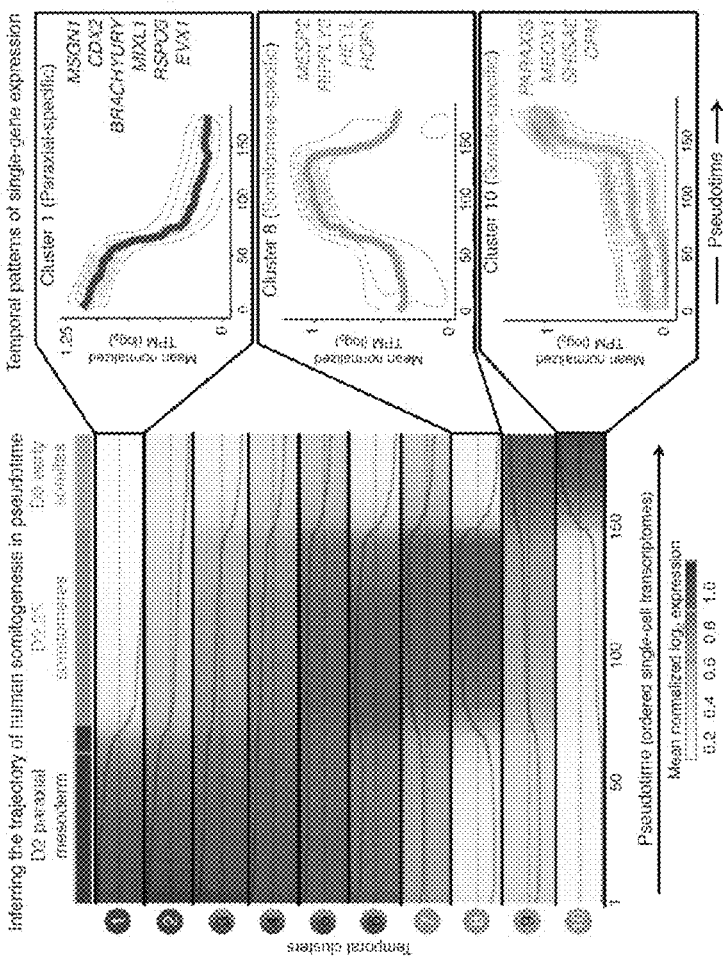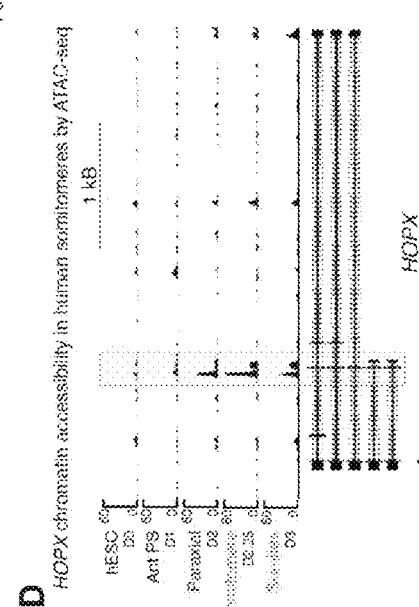

FIG. 17A Expression of congenital heart disease-related genes
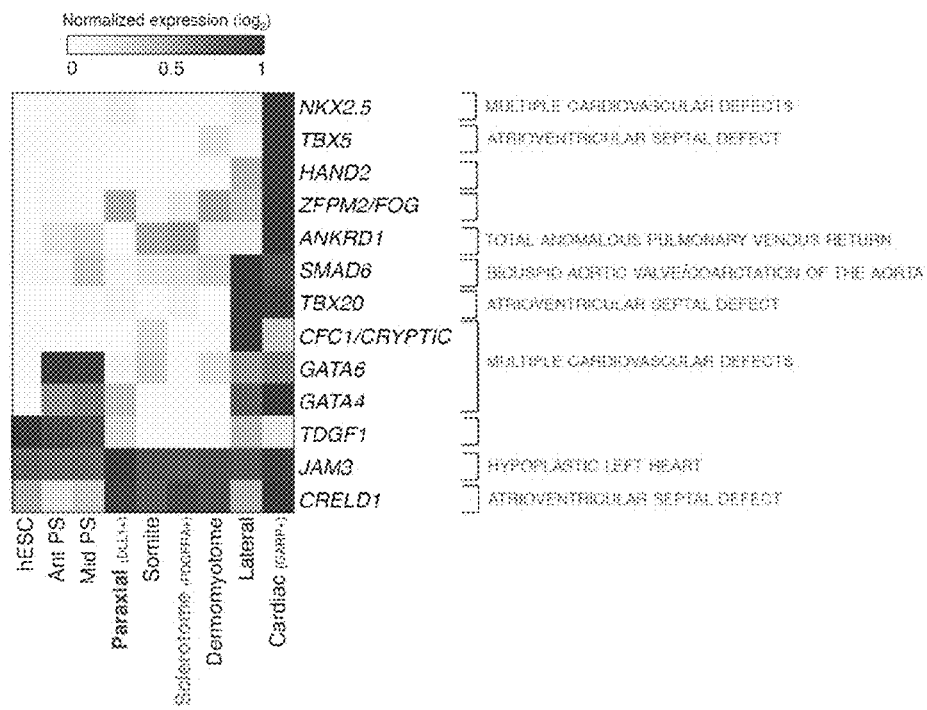
FIG. 17B Open chromatin atlas of human mesoderm development (non-binarized)
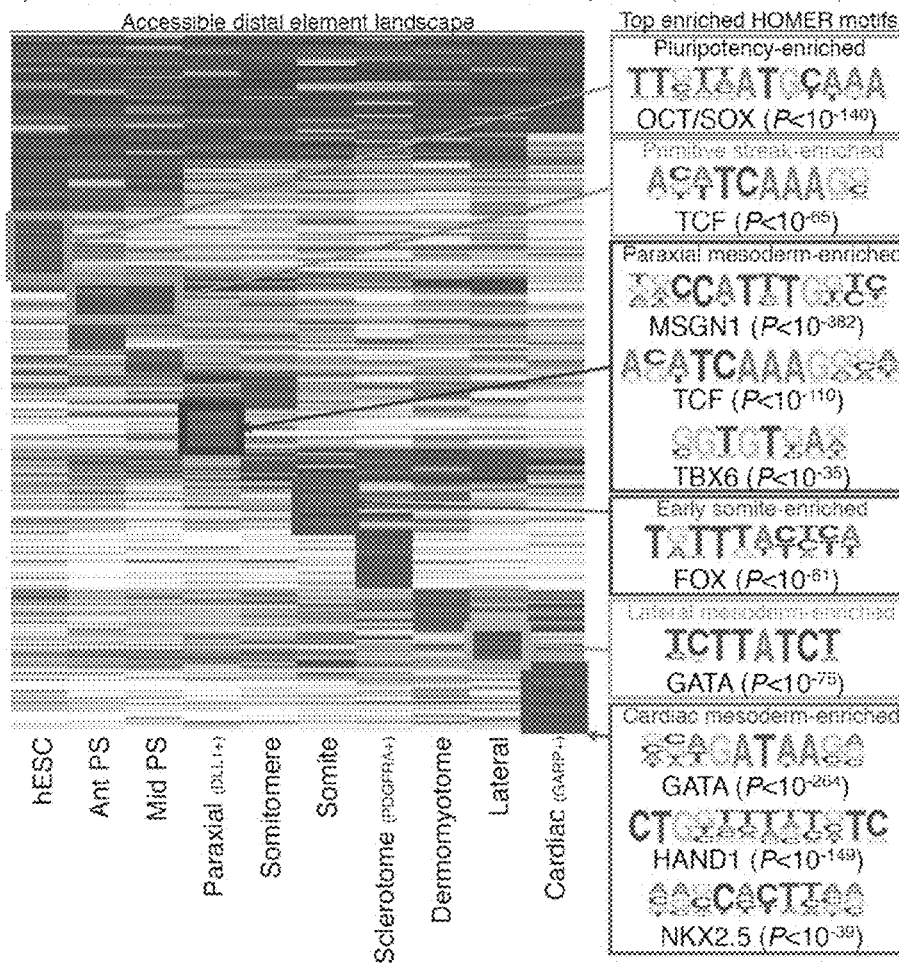

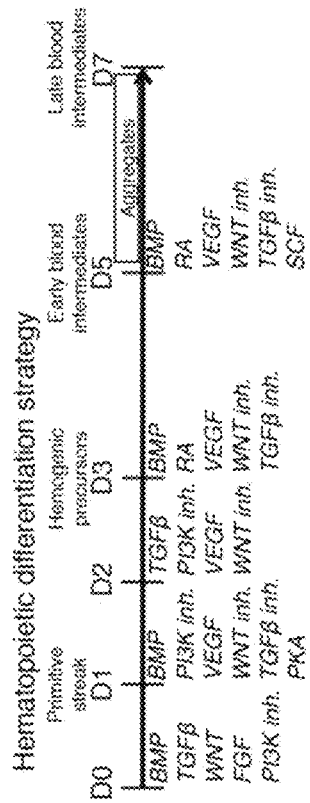
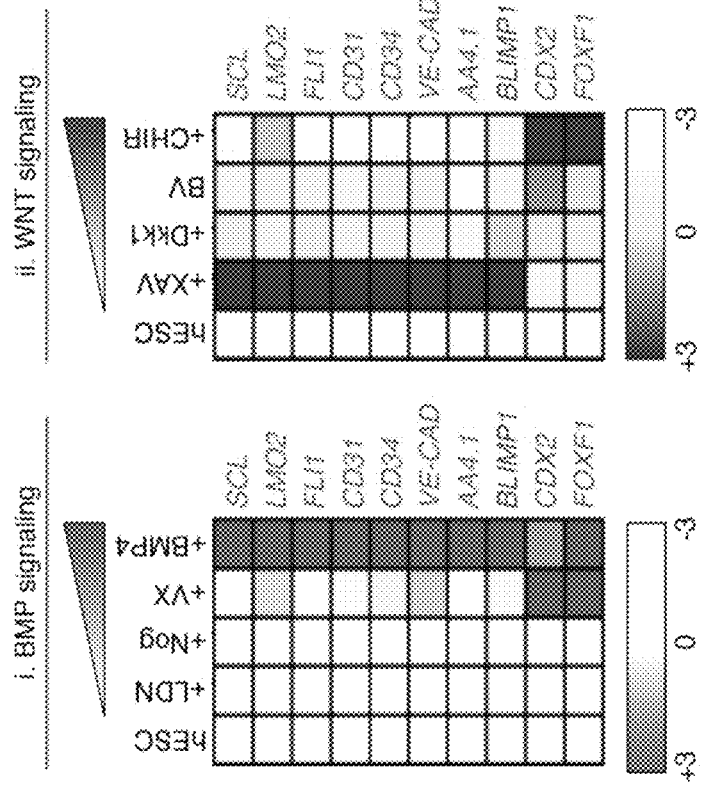
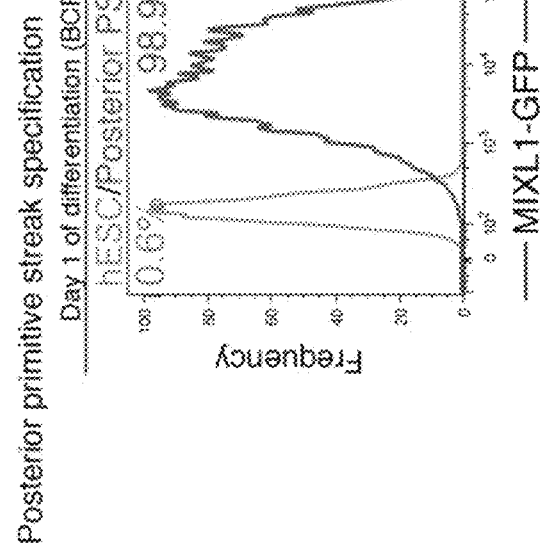
FIG. 18A
FIG. 18B
FIG. 18C

TGFβ agonism and Wnt blockade specify a definitive hematopoietic fate on day 3

Efficient generation of SOX17+CD34+ definitive hematopoietic progenitors

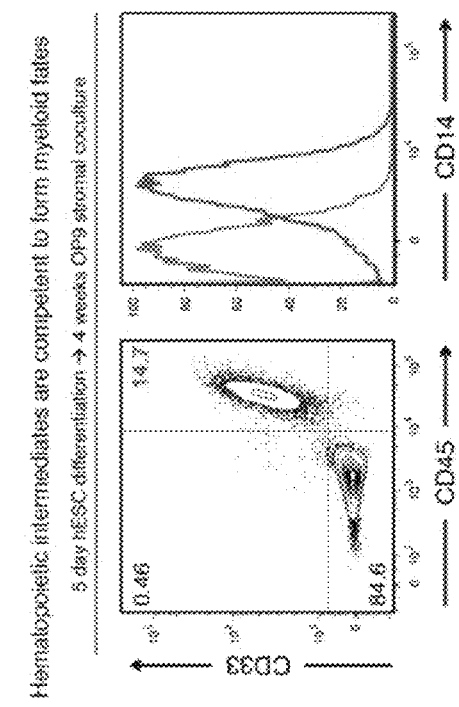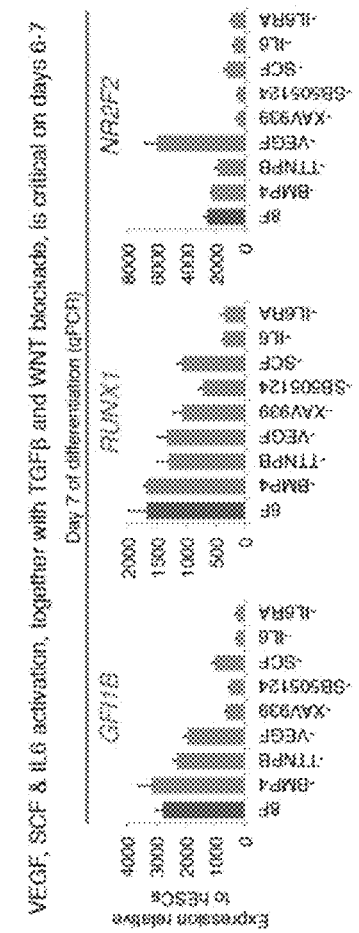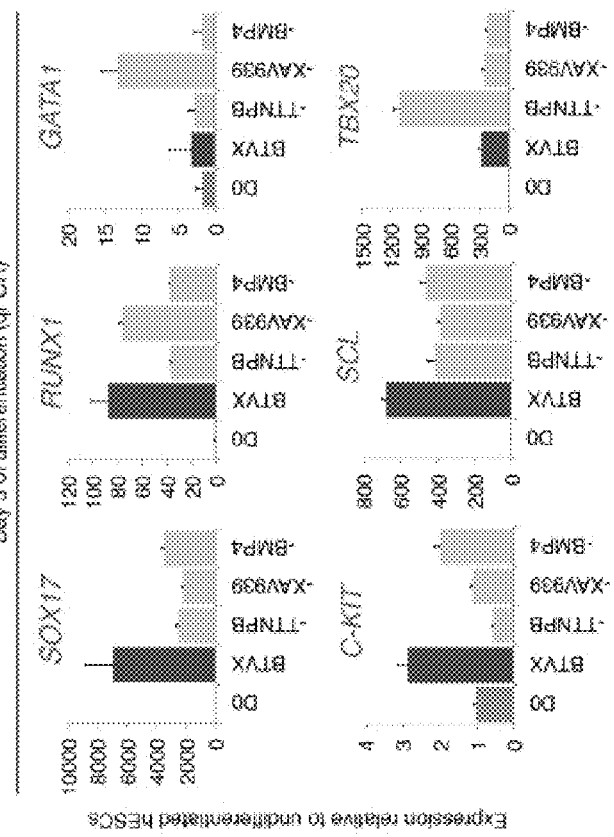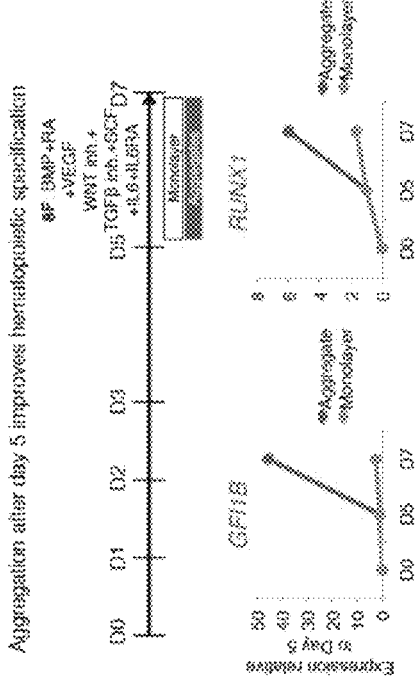
FIG. 19A
FIG. 19B
FIG. 19C
FIG. 19D

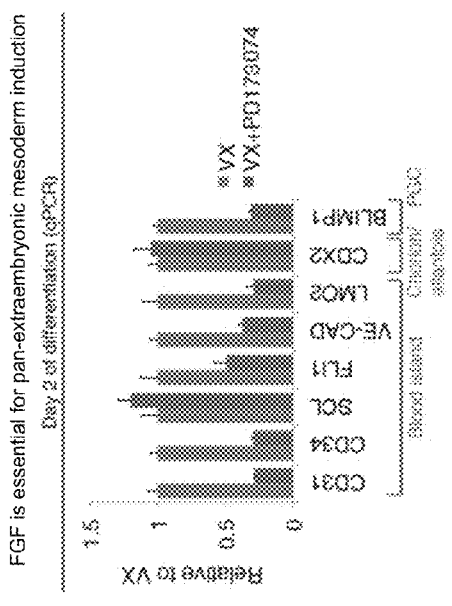
FIG. 20A
FIG. 20B
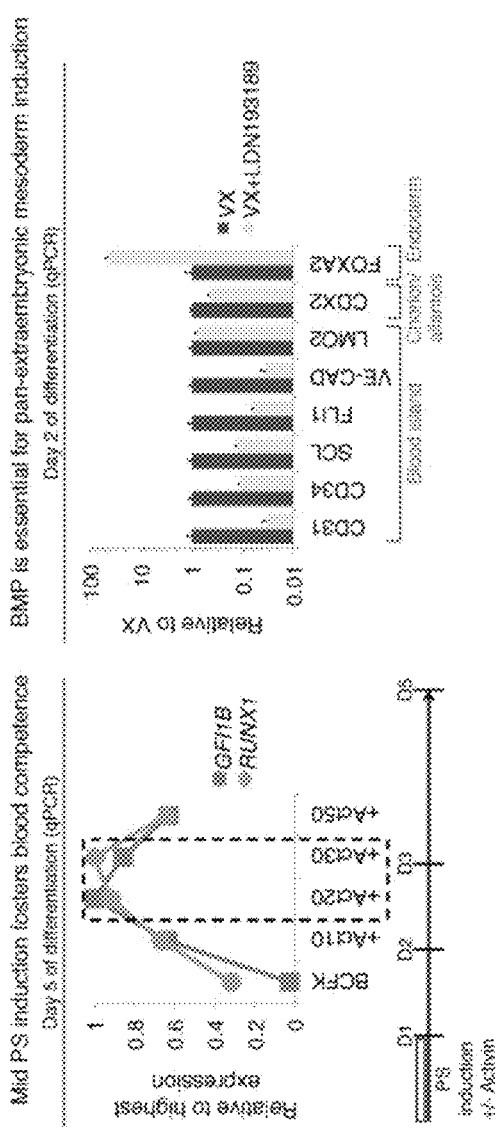
FIG. 20C
FIG. 20D
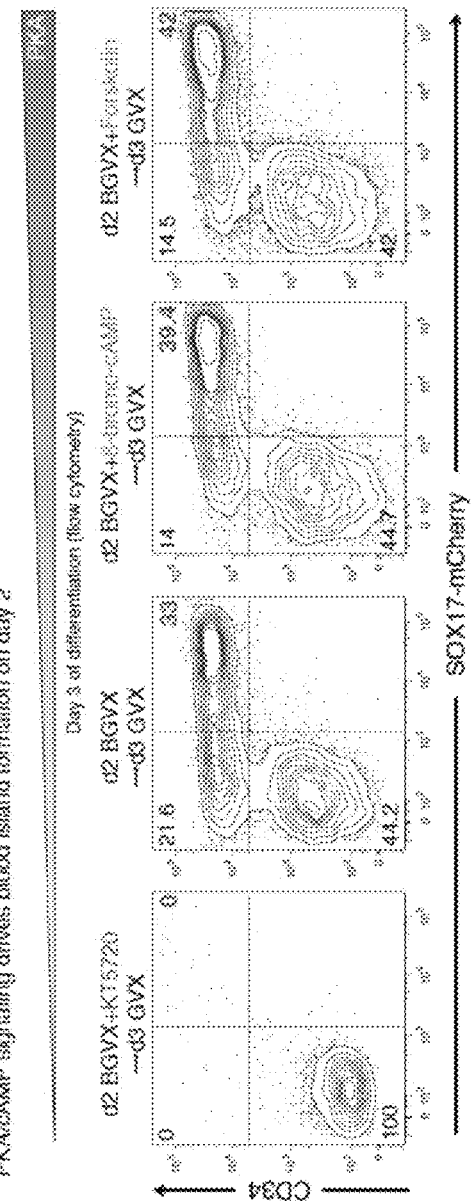

FIG. 22C
TGFβ inhibition on day 4-5 further enhances hematopoietic markers
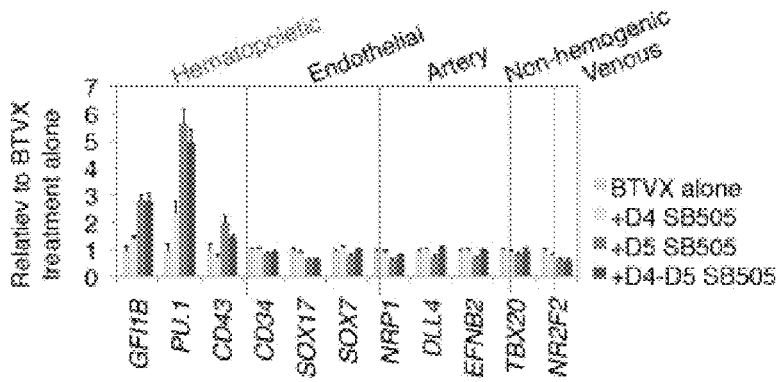
FIG. 23A
Chronology of limb bud progenitor reconstitution
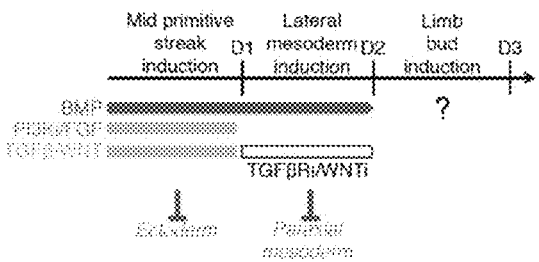
FIG. 23B
Lateral mesoderm induced with retinoids can subsequently form forelimb
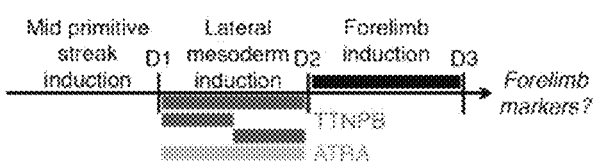
FIG. 23C
Early retinoid blockade abolishes future forelimb potential
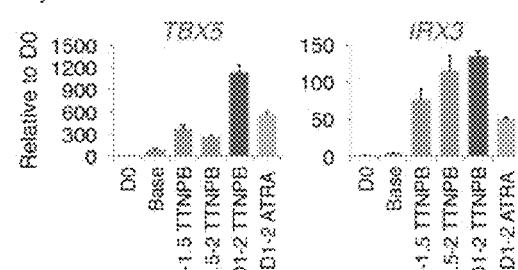
FIG. 23D
Retinoid activation decreases future hindlimb potential
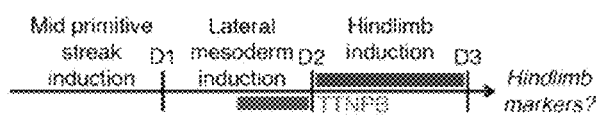
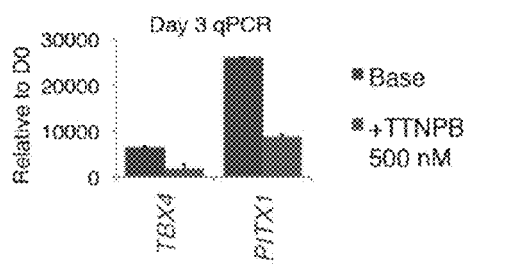

WNT activation promotes limb fate from lateral mesoderm

TGFβ/GDF signaling specifies a hindlimb fate in limb bud

PRODUCING MESODERMAL CELL TYPES AND METHODS OF USING THE SAME

CROSS REFERENCE

This application is a 371 application and claims the benefit of PCT Application No. PCT/US2016/020488, filed Mar. 2, 2016, which claims the benefit of U.S. Provisional Patent Application No. 62/127,445, filed Mar. 3, 2015, which applications are incorporated herein by reference in their entirety.

BACKGROUND

During embryogenesis, pluripotent cells form all bodily cell-types through a complex series of developmental steps, which include the generation of the endoderm, mesoderm and ectoderm germ layers. In particular, the mesoderm germ layer is the embryonic precursor to diverse adult tissues, including bone, cartilage, skeletal muscle and a subset of smooth muscle (which originate from paraxial mesoderm), kidney and gonads (intermediate mesoderm), heart and limb tissues (lateral mesoderm) and blood and blood vessels (extraembryonic mesoderm).

Within the mouse embryo, the pluripotent epiblast (~E5.5 of mouse embryogenesis) gives rise to the primitive streak ("PS", ~E6.5), which harbors the progenitors to the endoderm and mesoderm germ layers. Lineage tracing and cell grafting studies have revealed that endoderm arises from the anterior-most tip of the PS. The paraxial mesoderm emanates from the anterior third of the PS, whereas lateral and extraembryonic mesoderm respectively emerge from mid and posterior PS.

After emerging from the anterior PS, the unsegmented sheet of paraxial mesoderm (~E7.0-E7.5) begins undergoing progressive segmentation to generate the somites (beginning at ~E8.0), which are fundamental building blocks of trunk tissue (FIG. 1a). Subsequently, somites become patterned along the dorsal-ventral axis, such that the ventral somite (sclerotome) generates a subset of smooth muscle cells as well as bone and cartilage of the axial skeleton, whereas the dorsal somite (dermomyotome) yields brown fat, skeletal muscle and dorsal dermis. Separately, lateral mesoderm (FIG. 1a) gives rise to cardiac mesoderm (~E7.5) of the first and second heart fields as well as limb bud mesoderm. Cardiac mesoderm subsequently generates cardiomyocytes and other tissues of the heart.

There is a need for a unified mesoderm germ layer developmental roadmap and improved methods for the efficient in vitro patterning of mesoderm cells from pluripotent progenitors. Also of interest is rapid and efficient induction and purification of highly homogeneous populations of mesoderm lineages from pluripotent progenitors.

PUBLICATIONS

Beck, F., et al. (1995). Dev Dyn 204, 219-227.
Brunton, S. A., et al. (2009). Bioorganic & Medicinal Chemistry Letters 19, 4308-4311.
Burridge, P. W., et al. (2014). Chemically defined generation of human cardiomyocytes. Nature Methods.
Chapman, D. L., and Papaioannou, V. E. (1998). Nature 391, 695-697.
Cheung, C., et al. (2012). Nat Biotechnol.
Davis, R. P., et al. (2008). Blood 111, 1876-1884.
Loh, K M., et al. (2014). Cell Stem Cell 14, 237-252.
Mendjan, S., et al. (2014). Cell Stem Cell.
Proffitt, K. D., et al. (2012). Cancer Res.
Robarge, K. D., et al. (2009). Bioorg Med Chem Lett 19, 5576-5581.
Xu, C., et al. (2013). Cell 155, 909-921.

SUMMARY

Methods are provided for producing mesodermal cell types, populations of mesodermal cell types, and terminally differentiated cells and tissues. Also provided are methods of screening for cellular responses and treating a subject for a condition using the produced mesodermal cell types, populations of mesodermal cell types, and/or terminally differentiated cells and tissues. The instant disclosure also provides systems and kits for producing mesodermal cell types and/or screening for cellular responses and/or treating subjects with such mesodermal cell type.

Aspects of the method relate to producing mesodermal cell types and populations of mesodermal cell types and tissues thereof from pluripotent progenitors cells. In some embodiments, pluripotent progenitor cells or intermediate cell populations, e.g., intermediate mesodermal progenitors, may be contacted with one or more induction compositions to produce a lineage restricted mesodermal progenitor population or a differentiated mesodermal cell type or population of cells thereof. Any of the herein described induction compositions may be used independently or in combination with any of the other herein described induction compositions. Accordingly, the described methods, and individual steps thereof, for producing mesodermal progenitors and/or differentiated mesodermal cell types may be performed independently or in an combination with and of the other described methods, and individual steps thereof.

Aspects of the disclosure relate to producing anterior primitive streak cells through contacting a population of pluripotent progenitor cells with an anterior primitive streak induction composition. As described herein, anterior primitive streak induction compositions may vary and may generally include effective amounts of a TGF-beta pathway activator and/or a Wnt pathway activator and/or a FGF pathway activator and/or a PI3K pathway inhibitor.

Aspects of the disclosure relate to producing paraxial mesodermal cells through contacting anterior primitive streak cells with a paraxial mesodermal induction composition. As described herein, a paraxial mesodermal induction composition may vary and may generally include effective amounts of a TGF-beta pathway inhibitor and/or FGF pathway activator and/or a BMP pathway inhibitor and/or a Wnt pathway activator.

Aspects of the disclosure relate to deriving early somite cells through contacting paraxial mesodermal cells with an early somite induction composition. As described herein, early somite induction compositions may vary and may generally include effective amounts of a Wnt pathway inhibitor and/or a FGF pathway inhibitor and/or a TGF-beta pathway inhibitor and/or a BMP pathway inhibitor and/or a retinoic acid pathway activator.

Aspects of the disclosure relate to deriving sclerotome cells through contacting early somite cells with a sclerotome induction composition. As described herein, sclerotome induction compositions may vary and may generally include effective amounts of a hedgehog pathway activator and/or a Wnt pathway inhibitor.

Aspects of the disclosure relate to deriving early (i.e. first) dermomyotome cells through contacting early somite cells with a first dermomyotome induction composition. As described herein, first dermomyotome induction compositions may vary and may generally include effective amounts of a BMP pathway activator and/or a Wnt pathway activator and/or a hedgehog pathway inhibitor.

Aspects of the disclosure relate to deriving late (i.e. second) dermomyotome cells through contacting early dermomyotome cells with a second dermomyotome induction composition. As described herein, second dermomyotome induction compositions may vary and may generally include effective amounts of a hedgehog pathway activator and/or a Wnt pathway activator.

Aspects of the disclosure relate to deriving cartilage through contacting sclerotome cells with a cartilage induction composition. As described herein, cartilage induction compositions may vary and may generally include effective amounts of a BMP pathway activator and/or a FGF pathway activator and/or a TGFβ pathway inhibitor.

Aspects of the disclosure relate to deriving bone through transplanting sclerotome cells into a host under conditions sufficient to generate bone. As described herein, methods of transplantation and conditions sufficient to generate bone may vary. In some aspects, methods of deriving bone may include co-administering sclerotome cells with at least one pro-engraftment factor.

Aspects of the disclosure relate to deriving smooth muscles and/or smooth muscle cells through contacting sclerotome cells with a smooth muscle induction composition. As described herein, smooth muscle induction compositions may vary and may generally include effective amounts of a TGF-beta pathway activator and/or a PDGF pathway activator.

Aspects of the disclosure relate to producing mid primitive streak cells through contacting a population of pluripotent progenitor cells with a mid primitive streak induction composition. As described herein, mid primitive streak induction compositions may vary and may generally include effective amounts of a TGF-beta pathway activator and/or a Wnt pathway activator and/or and a BMP pathway activator and/or a FGF pathway activator and/or a PI3K pathway inhibitor.

Aspects of the disclosure relate to producing lateral mesodermal cells through contacting mid primitive streak cells with a lateral mesodermal induction composition. As described herein, lateral mesodermal induction compositions may vary and may generally include effective amounts of a BMP pathway activator and/or a Wnt pathway inhibitor and/or a TGF-beta pathway inhibitor.

Aspects of the disclosure relate to producing cardiac mesodermal cells through contacting lateral mesodermal cells with a cardiac mesodermal induction composition. As described herein, cardiac mesodermal induction compositions may vary and may generally include effective amounts of a BMP pathway activator and/or a WNT pathway inhibitor and/or a FGF pathway activator and/or a TGFβ pathway modulator.

Aspects of the disclosure relate to deriving cardiomyocytes through contacting cardiac mesodermal cells with a cardiomyocyte induction composition. As described herein, cardiomyocyte induction compositions may vary and may generally include effective amounts of a BMP pathway activator and/or a WNT pathway inhibitor and/or vitamin C/ascorbic acid or an analog thereof.

Aspects of the disclosure relate to deriving endocardium cells through contacting cardiac mesodermal cells with a endocardium cell induction composition. As described herein, endocardium cell induction compositions may vary and may generally include effective amounts of a FGF pathway activator and/or vitamin C/ascorbic acid or an analog thereof.

Aspects of the disclosure relate to deriving (pro)epicardium cells through contacting cardiac mesodermal cells with a (pro)epicardium cell induction composition. As described herein, (pro)epicardium cell induction compositions may vary and may generally include effective amounts of a PKA/cAMP pathway activator and/or FGF/ERK pathway inhibitor.

Aspects of the disclosure relate to deriving early hematopoietic mesoderm cells through contacting mid primitive streak cells with a early hematopoietic mesoderm cell induction composition. As described herein, early hematopoietic mesoderm cell induction compositions may vary and may generally include effective amounts of a BMP pathway activator and/or a PI3K pathway inhibitor and/or a VEGF activator and/or a WNT pathway inhibitor and/or a TGFβ pathway inhibitor and/or a PKA/cAMP pathway activator and/or vitamin C/ascorbic acid or an analog thereof.

Aspects of the disclosure relate to deriving late hematopoietic mesoderm cells through contacting early hematopoietic mesoderm cells with a late hematopoietic mesoderm cell induction composition. As described herein, late hematopoietic mesoderm cell induction compositions may vary and may generally include effective amounts of a TGFβ pathway activator and/or a PI3K pathway inhibitor and/or a VEGF pathway activator and/or a WNT pathway inhibitor and/or vitamin C/ascorbic acid or an analog thereof.

Aspects of the disclosure relate to deriving arterial endothelial cells through contacting hematopoietic mesoderm cells with an arterial endothelial cell induction composition. As described herein, Day 3 arterial endothelial cell induction compositions may vary and may generally include effective amounts of a BMP pathway activator and/or a retinoic acid pathway activator and/or VEGF pathway activator and/or a WNT pathway inhibitor and/or a TGFβ pathway inhibitor.

Aspects of the disclosure relate to deriving hematopoietic intermediate cells through contacting arterial endothelial cells with a hematopoietic intermediate cell induction composition. As described herein, hematopoietic intermediate cell induction compositions may vary and may generally include effective amounts of a WNT pathway inhibitor and/or a TGFβ pathway inhibitor and/or a SCF agonist and/or a gp130/IL6 superfamily agonist. Hematopoietic intermediate cell induction compositions may further include effective amounts of a BMP pathway activator and/or a retinoic acid pathway activator and/or VEGF pathway activator. In some instances, derivation of hematopoietic intermediate cells may further include culturing hematopoietic mesoderm cells under conditions permissive for cell aggregate formation including but not limited to e.g., (3D culture, suspension culture, adherent aggregate culture, and the like).

Aspects of the disclosure relate to deriving forelimb-forming lateral plate mesodermal cells through contacting mid primitive streak cells with a forelimb-forming lateral plate mesodermal cell induction composition. As described herein, forelimb-forming lateral plate mesodermal cell induction compositions may vary and may generally include effective amounts of a retinoic acid pathway activator and/or BMP pathway activator and/or a WNT pathway inhibitor and/or a TGFβ pathway inhibitor.

Aspects of the disclosure relate to deriving forelimb progenitor cells through contacting forelimb-forming lateral plate mesodermal cells with a forelimb progenitor cell induction composition. As described herein, forelimb progenitor cell induction compositions may vary and may generally include effective amounts of a retinoic acid pathway activator and/or a WNT pathway activator and/or a TGFβ pathway inhibitor and/or a BMP pathway inhibitor.

Aspects of the disclosure relate to deriving hindlimb progenitor cells through contacting lateral plate mesodermal cells with a hindlimb progenitor cell induction composition. As described herein, hindlimb progenitor cell induction compositions may vary and may generally include effective amounts of a TGFβ pathway activator and/or a WNT pathway activator and/or a BMP pathway inhibitor.

Aspects of the disclosure relate to deriving or producing desired mesodermal cell types through contacting pluripotent cells and/or progenitor cells with one or more induction compositions wherein the contacting is performed for a specified time period sufficient to produce the desired cell type or a desired intermediate. As described herein, time periods produce a desired cell type or a desired intermediate will vary depending on the desired cell type or desired intermediate and/or the induction composition being used. In certain aspects of the disclosure the time period consists essentially 24 hours. In certain aspects of the disclosure the time period consists essentially 24 hours to 72 hours. In certain aspects of the disclosure the time period consists essentially 48 hours. In certain aspects of the disclosure the time period includes at least 72 hours. In certain aspects of the disclosure the time period consists essentially 24 hours to 48 hours.

Aspects of the disclosure relate to producing purified populations of mesodermal progenitors and/or differentiated mesodermal cell types. As described herein, the level of purity of a particular purified population of mesoderm progenitors and/or differentiated mesodermal cell types will vary depending on various factors and may be achieved through use of the cell derivation methods described herein including or excluding the use of one or more binding agents used to isolate particular mesodermal progenitors and/or differentiated mesodermal cell types.

In certain aspects, methods may include producing a purified population of paraxial mesodermal cells through contacting the paraxial mesodermal cells with a DLL1 binding agent and isolating the paraxial mesodermal cells based on binding of the DLL1 binding agent to the paraxial mesodermal cells.

In certain aspects, methods may include producing a purified population of sclerotome cells through contacting the sclerotome cells with a PDGFR binding agent and isolating the sclerotome cells based on binding of the PDGFR binding agent to the sclerotome cells.

In certain aspects, methods may include producing a purified population of dermomyotome cells through contacting the dermomyotome cells with a PDGFR binding agent and isolating the dermomyotome cells based on binding of the PDGFR binding agent to the dermomyotome cells.

In certain aspects, methods may include producing a purified population of cardiac mesodermal cells through contacting the cardiac mesodermal cells with a GARP binding agent and isolating the cardiac mesodermal cells based on binding of the GARP binding agent to the cardiac mesodermal cells.

Aspects of the disclosure relate to screening mesoderm progenitors and/or differentiated mesoderm cell types derived or produced according to the methods described herein for a cellular response. In certain aspects, a method of screening mesoderm progenitors and/or differentiated mesoderm cell types for a cellular response may include contacting a population of mesoderm progenitors and/or differentiated mesoderm cell types with a pharmacological agent and evaluating the population of cells for a cellular response induced by the pharmacological agent. In certain aspects, the screening may be in vitro screening and the contacting may be performed in vitro. In certain aspects, the screening may be in vivo screening and the contacting may be performed by administering the pharmacological agent to a host animal that contains the population of cells.

Aspects of the disclosure relate to screening an animal for a phenotype wherein the host animal has been administered a genetically modified population of mesoderm progenitors and/or differentiated mesoderm cell types derived or produced according to the methods described herein. In certain aspects, the genetically modified population of mesoderm progenitors and/or differentiated mesoderm cell types derived or produced according to the methods described herein may include a genetic modification in at least one genetic locus. In certain aspects, the genetically modified population of mesoderm progenitors and/or differentiated mesoderm cell types derived or produced according to the methods described herein may include a genetic modification in at least one genetic locus resulting in disruption or deletion of at least one gene. In certain aspects, the host animal may be evaluated or a detectable phenotype induced by the administered population of cells.

Aspects of the disclosure relate to methods of treating a subject for a condition through the administration of mesoderm progenitors and/or differentiated mesoderm cell types derived or produced according to the methods described herein. In certain aspects, the method of eating a subject for a condition through administration of cells derived according to the methods as described herein may further include co-administration with at least one pro-survival or pro-engraftment factor. In certain aspects, the cells administered to a subject may be genetically modified at least one genetic locus.

Aspects of the disclosure include kits for the production, derivation, purification, and use of mesoderm progenitors and/or differentiated mesoderm cell types that include one or more induction compositions and/or one or more specific binding agents and/or combinations thereof. In certain aspects, such kits may or may not include one or more cell types described herein.

Aspects of the disclosure include systems for the production, derivation, purification, and use of mesoderm progenitors and/or differentiated mesoderm cell types that include one or more components configured to administer one or more induction compositions and/or one or more specific inducing agents and/or one or more specific binding agents and/or combinations thereof. In certain aspects, such systems are configured to administer such compositions and/or agents at specific amounts or for specific periods of time according to the methods described herein.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1A-1F, describe primitive streak differentiation. (FIG. 1A) Summary of mesoderm induction. (FIG. 1B) FACS of MIXL1-GFP hESC differentiated for 24 hrs in anterior or mid PS conditions (left); consistency across 4 experiments (right). (FIG. 1C) Summary of primitive streak (PS) patterning in vivo in the E6.5 mouse embryo. (FIG. 1D) qPCR of H7 hESC differentiated initially into anterior or mid PS, followed by D1-2 paraxial mesoderm induction; qPCR reveals that paraxial mesoderm gene expression is markedly higher in the APS-derived population (**p<0.01). (FIG. 1E) Day 3 FACS of NKX2.5-GFP hESC differentiated into anterior or mid PS (D0-1), followed by D1-3 lateral/cardiac mesoderm induction; MPS is markedly more competent at generating cardiac progenitors. (FIG. 1F) Tracking the bifurcation of day 1 PS into day 2 lateral mesoderm or DLL1+ sorted paraxial mesoderm at the single-cell level shows mutually-exclusive partitioning in marker expression by single-cell RNA-seq, where each dot depicts expression in a single cell.

FIG. 2A-2H, describe cross-antagonism between WNT and BMP respectively induces paraxial versus lateral mesoderm from primitive streak. (FIG. 2A) How endoderm, paraxial mesoderm and lateral mesoderm fates were segregated from the PS was previously unclear. (FIG. 2B) TGFβ inhibition on D1-2 specifies endoderm from PS. qPCR of D1 PS treated with 3 ng/mL BMP4+20 ng/mL FGF2 ("B3F20") in the presence or absence of TGFβ agonists (3-25 ng/mL Activin; "Act") or a TGFβR inhibitor (1 μM A8301) for 24 hrs. (FIG. 2C) BMP on D1-2 specifies lateral mesoderm, and inhibits paraxial mesoderm from PS. qPCR of D1 PS treated with 1 μM A8301+1 μM C59 ("A83C59") in the presence or absence of BMP4 (5-50 ng/mL) or BMP inhibitor (250 nM DM3189) for 24 hrs; also included is another BMP inhibitor-containing condition (A83CDF containing DM3189). (FIG. 2D) WNT induces, whereas BMP inhibits, paraxial mesoderm from the PS on D1-2. (i) qPCR of D1 PS treated with WNT agonist (CHIR99021, 3 μM) or WNT inhibitors (2 μM IWR1, 1 μM XAV939 or C59 or 300 ng/mL Dkk1) for 24 hrs (in the context of A8301+DM3189+FGF2 [ADF]); (ii) qPCR of D1 PS treated with BMP4 or a BMP inhibitor (DM3189) for 24 hrs (in the context of A8301+FGF2 [AF]). (FIG. 2E) WNT inhibits, whereas BMP induces, lateral mesoderm from the PS on D1-2. (i) qPCR of D1 PS treated with WNT agonists (CHIR99021 or WNT3A) or WNT inhibitors (300 ng/mL Dkk1 or 1 μM C59) for 24 hrs (in the context of A8301+BMP [AB]); (ii) qPCR of D1 PS treated with BMP4 or a BMP inhibitor (DM3189) for 24 hours (in the context of A8301+FGF2). (FIG. 2F) Cartoon of signaling switch for lateral versus paraxial mesoderm bifurcation (left); qPCR of day 2 H7 hESC-derived paraxial mesoderm or lateral mesoderm populations (as well as undifferentiated hESCs); gene expression normalized to the highest value=1.0 (right). (FIG. 2G) CDX2 and HAND1 immunostaining of day 2 H7-derived paraxial or lateral mesoderm populations or undifferentiated hESCs shows mutually-exclusive expression of CDX2 and HAND1 (scale bar=100 μm), with nuclear counterstaining (Hoescht dye). (FIG. 2H) TBX6 and CDX2 immunostaining of day 2 BJC1-derived paraxial mesoderm populations shows >90% of cells co-express TBX6 and CDX2 (scale bar=100 μm).

FIG. 3A-3I, describe paraxial mesoderm differentiation into early somites in vivo. (FIG. 3A) Cartoon of paraxial mesoderm segmentation leading to early somites. (FIG. 3B) Day 2 H7-derived paraxial mesoderm treated with retinoic acid (RA, 2 μM) for 24 hours, in combination with a WNT agonist (CHIR, 3 μM), a WNT inhibitor (C59, 1 μM), FGF2 (20 ng/mL), a ERK inhibitor (PD0325901, 500 nM), or combined WNT/ERK inhibition (CPR: C59+PD0325901+RA) and qPCR (*p<0.05, **p<0.01), showing WNT/ERK blockade is beneficial for early somite specification (it was subsequently found that exogenous RA was dispensable for early somite formation; see FIG. 10D) revealed how WNT and FGF/ERK control paraxial mesoderm progression to early somites. (FIG. 3C) CDX2 and FOXC2 immunostaining of BJC1-derived paraxial mesoderm (day 2) and early somite (day 3) populations (left) and quantification (right). (FIG. 3D) Cartoon of FGF and WNT activation, which followed by inhibition, leads to specification of paraxial mesoderm and then early somite progenitors. (FIG. 3E) Side-by-side qPCR timecourse comparison of H7 hESCs differentiated into somitic mesoderm using previously-described differentiation protocols or the herein described method. (FIG. 3F) Differentially expressed genes in day 2 paraxial mesoderm vs. day 3 early somites, as shown by bulk-population RNA-seq (FIG. 3G) Single cells progress along a continuous trajectory during human somitogenesis as shown by principal component analysis of single-cell RNA-seq data; different colors designate distinct cell populations harvested for single-cell RNA-seq at different time-points; individual dots indicate single cells. (FIG. 3H) Comparison of single-cell gene expression in day 2, day 2.25 and day 3 hESC-derived populations by single-cell RNA-seq (TPM=transcripts per million); individual dots depict expression in a single cell and bolded line indicates mean gene expression in all single cells harvested from each population. (FIG. 3I) Quantitative PCR (qPCR) analysis of H7-derived cells at different timepoints.

FIG. 4A-4J, describe dorsal-ventral patterning of somite precursors into sclerotome & dermomyotome and downstream progeny. (FIG. 4A) Cartoon of somite patterning in vivo. (FIG. 4B) D3 early somite populations were treated with either ventralizing conditions ("HH"; HH agonist/WNT inhibitor), dorsalizing conditions ("WNT"; HH inhibitor/WNT agonist) or a hybrid of these ("WNT+HH"; HH agonist/WNT agonist) for 48 hrs, and qPCR was conducted (left); morphology of cell populations after 24 hours of either sclerotome or dermomyotome differentiation (right). (FIG. 4C) qPCR heatmap of hESCs (D0), early somite progenitors (D3) or those differentiated into sclerotome (D4, D5 or D6, using 21K+C59) or dermomyotome (D4 or D5, using BMP4+CHIR+Vismodegib). (FIG. 4D) Signaling logic for early somite patterning into dermomyotome or sclerotome and subsequent differentiation into downstream fates. (FIG. 4E) BCL2-GFP expressing H9 hESC-derived sclerotome was subcutaneously transplanted into NSG mice; 2 months later, an ectopic GFP+ human bone-like structure was formed (scale bar=1 mm; top), which was sectioned and stained with H&E; bioluminescent imaging of mice after 1 month of transplantation by UBC-Luciferase-2A-tdTomato H9-derived sclerotome reveals engraftment on the injected side of the mouse ("+"; right). (FIG. 4F) SMAα intracellular FACS of hESCs or D8 smooth muscle-like populations. (FIG. 4G) qPCR (left) and Safranin-O staining (right) of D9 or D12 hESC-derived cartilage, respectively; scale bar=1 mm. (FIG. 4H) SOX9 and TWIST1 staining of day 6 H7-derived sclerotome (scale bar=100 μm). (FIG. 4I) Principal Component Analysis (PCA) of single-cell RNA-seq data from indicated populations; each dot indicates a single cell. (FIG. 4J) Sectioning and staining of 2-month-old sclerotome grafts with Russell-Movat's Pentachrome revealed zones of progressive chondrogenesis and ossification, with cartilage stained blue; black line denotes the edge of the graft and white line denotes boundary of the ossifying region (scale bar=1 mm).

FIG. 5A-5J, describe lateral mesoderm patterning into cardiac vs. limb mesoderm fates. (FIG. 5A) Cartoon of lateral mesoderm patterning into anterior vs. posterior lateral mesoderm fates. (FIG. 5B) To determine the effects of WNT on lateral mesoderm patterning, D1 PS was differentiated to lateral mesoderm (30 ng/mL BMP4+1 µM C59+2 µM SB505124) for varying lengths of time (until D2, D2.5 or D3) and for the last 12 hrs was treated with C59 or 3 µM CHIR (in addition to BS) and qPCR was conducted. (FIG. 5C) To determine the effects of FGF on lateral mesoderm patterning, day 2 NKX2.5-GFP lateral mesoderm was treated with BMP4+C59+SB505124 with or without FGF2 (20 ng/mL) or FGF inhibitor PD173074 (100 nM) for 24 hrs and FACS was conducted on day 3. (FIG. 5D) Bifurcation of cardiac vs. forelimb mesoderm fates from lateral mesoderm. (FIG. 5E) Schema for cardiac mesoderm specification described (top); timepoint FACS of NKX2.5-GFP hESC differentiation using cardiac mesoderm protocol (bottom). (FIG. 5F) Side-by-side comparison of NKX2.5-GFP$^+$ cell percentages (determined by FACS) present on various days of hESC differentiation, using the current protocol or a previous method solely using Wnt small-molecule modulators. (FIG. 5G) Schema for cardiomyocyte induction (top); intracellular FACS for TNNT2 protein expression in NKX2.5-GFP hESCs differentiated towards cardiomyocytes in this system (bottom) (FIG. 5H). qPCR of undifferentiated, D4 or D6 populations during cardiac induction (see induction schema in preceding subpanel). (FIG. 5I) Electrocardiogram signal shows that human fetal heart grafts implanted into the mouse ear remain viable and continue contracting >1 month post-implantation. (FIG. 5J) 2.5 months post-transplantation of EF1A-BCL2-2A-GFP; UBC-tdTomato-Luciferase H9 hESC-derived cardiac lineages into human fetal heart grafts, luciferase$^+$ donor cells were detected in 28-42% of recipients (i; sections showed engrafted hESC-derived cardiomyocytes survived in human fetal heart tissue and expressed TROPONIN and CONNEXIN 43 (scale bar=40 µm) (ii).

FIG. 6A-6I, describe high-throughput screen for lineage-specific mesoderm surface markers. (FIG. 6A) Screening strategy. (FIG. 6B) Heatmap of surface marker expression in hESCs and six mesoderm derivatives. Each row represents an individual surface marker and color denotes the percentage of cells positive for a given marker. Heatmap was clustered using AutoSOME to reveal lineage-specific markers. For PS and cardiac mesoderm analyses, marker expression was analyzed after pre-gating on the MIXL1-GFP$^+$ and NKX2.5-GFP$^+$ fractions of those populations, respectively. (FIG. 6C) Heatmap of surface marker expression on indicated lineages (PS and cardiac mesoderm populations were first pre-gated on MIXL1-GFP$^+$ and NKX2.5-GFP$^+$ fractions, as above). (FIG. 6D) FACS of GARP and DLL1 expression in undifferentiated hESCs or after 2 days of paraxial mesoderm differentiation or 3 days of cardiac mesoderm differentiation (the latter of which was pre-gated on NKX2.5-GFP$^+$ cells). (FIG. 6E) In situ hybridization for Irrc32 expression in 24 hpf (hpf: hours post-fertilization) zebrafish embryos; arrows indicate heart. (FIG. 6F) DLL1 FACS of day 2 paraxial mesoderm population (left); qPCR of sorted DLL1$^+$GARP$^-$ and DLL1$^-$GARP$^-$ populations (right). (FIG. 6G) PDGFRα FACS of day 5 sclerotome population (left); qPCR of sorted PDGFRα$^+$ and PDGFRα$^-$ populations (center); in situ hybridization for pdgfra expression (right) in 18 hpf zebrafish embryos (arrowheads denote ventral staining in sclerotome). (FIG. 6H) mRNA expression in sorted DLL1$^+$ day 2 human paraxial mesoderm as shown by single-cell RNA-seq; each dot depicts a single cell. (FIG. 6I) mRNA expression in sorted PDGFRα$^+$ human sclerotome as shown by single-cell RNA-seq; each dot depicts a single cell.

FIG. 7A-7E, describe a developmental and transcriptional roadmap for mesoderm development. (FIG. 7A) Summary of lineage bifurcations, including lineage-specifying signals and surface markers enabling prospective isolation of desired mesoderm intermediates. (FIG. 7B) RNA-seq profiling of mesoderm hierarchy; color intensity depicts gene expression ($\log_2$ TPM) normalized to the expression of that gene in all populations profiled, with the highest-expressing population assigned the most intense color value. (FIG. 7C) RNA-seq expression of genes linked to various forms of human congenital scoliosis across varying human mesoderm lineages. (FIG. 7D). Heatmap of changing chromatin accessibility across different lineages as shown by ATAC-seq; each horizontal line depicts a single chromatin element (left, non-binarized form in FIG. 17B), with transcription motifs representative of the top 4 motifs enriched in each lineage-specific group of elements shown (right). (FIG. 7E) Cartoon of inferred trans-regulatory states in different lineages (left) and heatmap of the 4 FOX transcription factors most highly expressed in hESC-derived somites, as shown by RNA-seq (right) and ATAC-seq signal at the MEOX1 locus across different cell-types, with FOX motifs centered in two somitic enhancer elements show.

FIG. 8A-8J, show that establishing the anterior or mid primitive streak is crucial for subsequent respective generation of paraxial mesoderm or cardiac mesoderm. Figure descriptions are provided in the Examples section.

FIG. 9A-9F, depict the signaling logic for specification of paraxial mesoderm or cardiac mesoderm from primitive streak. Figure descriptions are provided in the Examples section.

FIG. 10A-10F, depict the signaling logic for specification of early somite progenitors from paraxial mesoderm. Figure descriptions are provided in the Examples section.

FIG. 12A-12K, depict the signaling logic for sequential production of lateral mesoderm, cardiac mesoderm and finally cardiomyocytes. Figure descriptions are provided in the Examples section.

FIG. 13A-13G, depict the cell-surface marker profiling of the mesoderm hierarchy. Figure descriptions are provided in the Examples section.

FIG. 14A-14E, provide a summary of the extended RNA-seq data analysis. Figure descriptions are provided in the Examples section.

FIG. 15, provides Table 1, which contains the results of high-throughput cell-surface marker screening which include the percentages of cells in each lineage that stained positive for a given marker; each column denotes a distinct cellular lineage whereas each row denotes a different cell-surface marker. For the cardiac mesoderm and anterior primitive streak populations, cells were respectively pre-gated on the NKX2.5-GFP$^+$ and MIXL1-GFP$^+$ fractions prior to analysis of surface markers.

FIG. 16A-16E, show that single-cell analysis captures a transient HOPX+ human somitomere progenitor state. (FIG. 16A) Heatmap of normalized single-cell RNA-seq gene expression across the inferred trajectory of human somitogenesis. Each column reflects expression in a single cell, with individual single-cell paraxial mesoderm, somitomere and early somite transcriptomes (denoted by colored blocks) ordered in pseudotime along the y-axis. Genes were clustered into 10 clusters (rows) by virtue of their expression kinetics across this pseudotime timecourse; line indicates mean expression of all genes in the cluster across pseudotime. (FIG. 16B) Average expression (bold line) of all genes in each temporal cluster across pseudotime (with contours representing standard deviation), with representative genes in each cluster noted. (FIG. 16C) Single-cell RNA-seq shows HOPX is transiently expressed at the single-cell level in the human somitogenesis time series (i), as confirmed by qPCR (ii) and immunostaining (iii) of different timepoints in H7 hESC differentiation towards somites (scale bar=50 µm). (FIG. 16D) ATAC-seq shows the HOPX locus is accessible in D2.25 hESC-derived somitomeres (signal track represents P values). (FIG. 16E) Fate mapping the progeny of Hopx$^+$ cells in E14.5 Hopx-IRES-Cre; ROSA26-LSL-tdTomato embryos reveals contribution to the spine and ribs (themselves labeled by type II collagen) (scale bar=50 µm).

FIG. 17A-17B provide an extended transcriptional and chromatin state analysis of human mesoderm development. (FIG. 17A) Bulk-population RNA-seq shows that a subset of genes associated with various human congenital heart defects are expressed in human lateral and/or cardiac mesoderm progenitors. (FIG. 17B) Non-binarized version of ATAC-seq heatmap shown in FIG. 7D with corresponding transcription factor motif enrichments as determined by HOMER.

FIG. 18A-18E demonstrate aspects of sequential specification of primitive streak, blood-island mesoderm and hemogenic precursors according to an embodiment of the instant disclosure.

FIG. 19A-19D demonstrate aspects of further hematopoietic specification of hemogenic precursors according to an embodiment of the instant disclosure.

FIG. 20A-20E provide further aspects of sequential specification of primitive streak, blood-island mesoderm and hemogenic precursors according to an embodiment of the instant disclosure.

FIG. 22A-22C provide further analysis of the involvement of BMP, PI3K, and TGFβ signaling in hematopoietic specification.

FIG. 23A-23G demonstrate the reconstitution of early human limb bud progenitors according to an embodiment of the instant disclosure.

DETAILED DESCRIPTION OF THE EMBODIMENTS

Figure 3F:
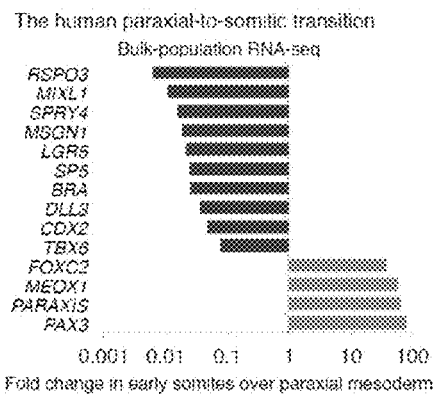

Methods are provided for the generation of mesodermal cell types and derivatives thereof. Also provided are methods for generating purified populations of mesodermal cell types and derivatives thereof. The instant disclosure also provides methods of screening for cellular responses of the generated mesodermal cell types and derivatives thereof. Also provide are methods for screening for organismal phenotypes induced by introduction of the generated mesodermal cell types and derivatives thereof. Treatment methods making use of the generated mesodermal cell types and derivatives thereof are also provided. The instant disclosure also provides systems, compositions, and kits for practicing the methods of the disclosure.

Before the present methods and compositions are described, it is to be understood that this invention is not limited to particular method or composition described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom(s) but has not yet been diagnosed as having it; (b) inhibiting the disease and/or symptom(s), i.e., arresting development of a disease and/or the associated symptoms; or (c) relieving the disease and the associated symptom(s), i.e., causing regression of the disease and/or symptom(s). Those in need of treatment can include those already inflicted (e.g., those with mesodermal cell type dysfunction or deficiency, e.g. those having skeletal muscle dysfunction or deficiency, brown fat dysfunction or deficiency, dorsal dermis dysfunction or deficiency, cartilage dysfunction or deficiency, bone dysfunction or deficiency, smooth muscle dysfunction or deficiency, cardiomyocyte dysfunction or deficiency, etc.) as well as those in which prevention is desired (e.g., those with increased susceptibility to a mesodermal cell type dysfunction or deficiency; those suspected of having a mesodermal cell type dysfunction or deficiency; those having one or more risk factors for a mesodermal cell type, etc.).

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, camels, etc. In some embodiments, the mammal is human.

The terms "pluripotent progenitor cells", "pluripotent progenitors", "pluripotent stem cells", "multipotent progenitor cells" and the like, as used herein refer to cells that are capable of differentiating into two or more different cell types and proliferating. Non limiting examples of pluripotent precursor cells include but are not limited to embryonic stem cells, blastocyst derived stem cells, fetal stem cells, induced pluripotent stem cells, ectodermal derived stem cells, endodermal derived stem cells, mesodermal derived stem cells, neural crest cells, amniotic stem cells, cord blood stem cells, adult or somatic stem cells, neural stem cells, bone marrow stem cells, bone marrow stromal stem cells, hematopoietic stem cells, lymphoid progenitor cell, myeloid progenitor cell, mesenchymal stem cells, epithelial stem cells, adipose derived stem cells, skeletal muscle stem cells, muscle satellite cells, side population cells, intestinal stem cells, pancreatic stem cells, liver stem cells, hepatocyte stem cells, endothelial progenitor cells, hemangioblasts, gonadal stem cells, germline stem cells, and the like. Pluripotent progenitor cells may be acquired from public or commercial sources or may be newly derived. As described herein, in some instances, pluripotent progenitor cells of the subject disclosure are those cells capable of giving rise to mesodermal cell types or derivatives.

Of interest herein are pluripotent progenitors having the capacity to generate mesodermal cell types or derivatives thereof. Pluripotent progenitors not naturally having the capacity to generate mesodermal cell types or derivatives thereof may be dedifferentiated to a cell type having such capacity by methods well-known in the art, including, e.g., those described below for the production of induced pluripotent cells. For example, a cell may be naturally capable of giving rise to mesodermal cell types or derivatives thereof or may be artificially made (e.g., reprogrammed, dedifferentiated, transdifferentiated, etc.) to be capable of giving rise to mesodermal cell types or derivatives thereof. By "naturally capable" is meant that giving rise to mesodermal cell types or derivatives thereof represents part of the natural developmental lineage or the natural differentiation potential of the cell. As such, cells artificially made capable of giving rise to mesodermal cell types or derivatives thereof are generally cells that do not have such capability naturally.

The term "mesodermal cell types" as used herein refers to cells of the entire mesodermal lineage and thus encompasses cells of the developing embryo that are non-ectodermal, non-endodermal, and non-germline. Mesodermal cell types, as used herein may refer to mesodermal progenitors and/or differentiated mesodermal cell types.

The terms "mesodermal progenitors" and "mesoderm progenitors" are used interchangeably herein and generally refer to precursor and/or progenitor cells capable of giving rise to one or more mesodermal cell types and proliferating. As used herein mesodermal progenitors include but are not limited to, e.g., anterior primitive streak cells, mid primitive streak cells, paraxial mesoderm cells, lateral mesoderm cells, forelimb-forming lateral mesoderm cells, early somite cells, anterior lateral mesoderm cells, cardiac mesoderm cells, early and late dermomyotome cells, sclerotome cells, muscle precursor cells, brown fat precursor cells, dorsal dermis precursor cells, cartilage precursor cells, smooth muscle precursor cells, cardiomyocyte precursor cells, endocardium, (pro)epicardium, hematopoietic mesoderm, arterial endothelial cells and hematopoietic intermediates (e.g., those cells marked by transcription factors SOX17, SCL, LMO2, RUNX1, GFI1, GFI1B, PU.1, FOS, IKZF1/HELIOS or IKZF2/IKAROS and combinations there). Such terms have well-known equivalents in the art and, in some instances, equivalent terms may be interchanged, e.g., in some instances paraxial mesoderm may be referred to as presomitic mesoderm, and the like. Both mesodermal progenitors and differentiated mesodermal cell types, as described below, may be identified according to a variety of factors and combinations thereof. For examples, mesodermal progenitors and differentiated mesodermal cell types by be identified by the expression or lack of expression of one or more markers including but not limited to gene expression markers or protein expression markers. In some instances, identification of a particular mesodermal progenitor and differentiated mesodermal cell type is based on the location of the particular progenitor or cell within an organism, e.g., a developing or developed organism or within a tissue within such an organism. In other instances, identification of a particular mesodermal progenitor and differentiated mesodermal cell type is based on a particular cellular phenotype including but not limited to physical characteristics (e.g., size, shape, granularity, morphology, etc.), behavioral characteristics (e.g., movement, motility, adherence, non-adherence, etc.). Such characteristics of mesodermal progenitors and differentiated mesodermal cell types are described in, e.g., Gilbert (2006) *Developmental Biology*, 8th Ed. Sunderland (Mass.): Sinauer Associates, the disclosure of which is incorporated herein by reference in its entirety.

The terms "differentiated mesodermal cell types" and "differentiated mesodermal cells" are used interchangeably herein and refer to mesodermally derived cells that have terminally differentiated and are readily identifiable as such. Such differentiated mesodermal cell types may or may not be proliferative. As described herein, differentiated mesodermal cell types include those adult cell types and cells of adult tissues derived from mesoderm that are well-known to the ordinary skilled artisan, including but not limited to, e.g., cells of the bone, osteocytes, cells of the cartilage, chondrocytes, cells of tendons, tenocytes, cells of the muscle, cells of skeletal muscle, cells of cardiac muscle, cells of smooth muscle, myocytes, cardiomyocytes, cells of fat, cells of brown fat, adipocytes, cells of the dermis, cells of the dorsal dermis, fibroblasts, fibrocytes, cells of the blood vessels, endothelial cells, mesangial cells, cells of the kidneys, juxtaglomerular cells, macula densa cells, podocytes, interstitial cells, cells of the blood, lymphocytes, myeloid cells, pericytes, mural cells, and the like.

The term "lineage bifurcation" and "lineage segregation" are used interchangeably herein and refer to a cell-fate decision where a stem cell and/or progenitor cell has the ability to differentiate into two or more cell-types.

The term "population", e.g., "cell population" or "population of cells", as used herein means a grouping (i.e., a population) of two or more cells that are separated (i.e., isolated) from other cells and/or cell groupings. For example, a 6-well culture dish can contain 6 cell populations, each population residing in an individual well. The cells of a cell population can be, but need not be, clonal derivatives of one another. A cell population can be derived from one individual cell. For example, if individual cells are each placed in a single well of a 6-well culture dish and each cell divides one time, then the dish will contain 6 cell populations. The cells of a cell population can be, but need not be, derived from more than one cell, i.e. non-clonal. The cells from which a non-clonal cell population may be derived may be related or unrelated and include but are not limited to, e.g., cells of a particular tissue, cells of a particular sample, cells of a particular lineage, cells having a particular morphological, physical, behavioral, or other characteristic, etc. A cell population can be any desired size and contain any number of cells greater than one cell. For example, a cell population can be 2 or more, 10 or more, 100 or more, 1,000 or more, 5,000 or more, $10^4$ or more, $10^5$ or more, $10^6$ or more, $10^7$ or more, $10^8$ or more, $10^9$ or more, $10^{10}$ or more, $10^{11}$ or more, $10^{12}$ or more, $10^{13}$ or more, $10^{14}$ or more, $10^{15}$ or more, $10^{16}$ or more, $10^{17}$ or more, $10^{18}$ or more, $10^{19}$ or more, or $10^{20}$ or more cells.

The terms "homogenous population", as it relates to cell populations, refers to a cell population that is essentially pure and does not consist of a significant amount of undesired or contaminating cell types. By significant amount, in this context, is meant an amount of undesired or contaminating cell types that negatively impacts the use of the isolated desired cell population. As such, the actual amount of undesired or contaminating cells that defines a significant amount will vary and depend on the particular type of undesired or contaminating cells and/or the particular use of the desired cell type. For example, in a population of differentiated mesodermal cells used in the treatment of a subject, a significant amount of improperly differentiated contaminating cell types will be small as such cells may a high capacity to negatively impact the use of the generated desired cell population. In comparison, e.g., in a population of differentiated mesodermal cells used in the treatment of a subject, a significant amount of contaminating progenitor cells may be relatively large as such cells may have a low capacity to negatively impact the use of the generated desired cell population. In some instances, a homogenous population may refer to a highly enriched population. Levels of homogeneity will vary, as described, and may, in some instances, be greater than 60% pure, including e.g., more than 65%, more than 70%, more than 75%, more than 80%, more than 85%, more than 90%, more than 95%, more than 96%, more than 97%, more than 98%, more than 99%, more than 99.5%, more than 99.6%, more than 99.7%, more than 99.8%, and more than 99.9%.

The term "heterologous", as it refers to a "heterologous sequence" or "heterologous nucleic acid", means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter.

Methods

Cell Derivation

Aspects of the disclosure include methods for deriving mesodermal cell types from pluripotent progenitor cells. What is meant by pluripotent progenitors is described herein. Pluripotent progenitors of the instant disclosure may be acquired from any convenient source, including but not limited to newly derived from a subject of interest or tissue specimen or other cellular sample, obtained from a public repository, obtained from a commercial vendor, and the like. In some instances, pluripotent cells of interest include human cells including but not limited to, e.g., human embryonic stem cells, human induced pluripotent stem cells, human fetal stem cells, and the like.

In some instances, pluripotent progenitor cells of the subject disclosure may be unmodified such that the cells have not been genetically or otherwise modified from their natural state prior to modification according the methods described herein. In other instances, pluripotent progenitor cells of the subject disclosure may be unmodified such that the cells have been genetically or otherwise modified from their natural state prior to modification according the methods described herein. Modification of pluripotent progenitors and derived mesodermal cell type is described in further detail elsewhere herein.

Generation of mesodermal cell types from pluripotent progenitors as described herein generally involves one or more lineage restriction events in which cultured pluripotent progenitor cells are subjected to one or more treatments causing the cultured cells or a population thereof to take on the features of one mesodermal cell type or intermediate over another. Such lineage restrictions, in some instances, may be referred to as developmental bifurcations. In some instances, a desired mesodermal cell type may be achieved through inducing a single lineage restriction event. In other instances, two or more lineage restriction events may be required to achieve a desired mesodermal cell type of interest. In certain instances, lineage restriction events may be performed successively such that a first mesodermal cell type may be achieved by a first linage restriction event and the first cell type may be subjected to a second lineage restriction event to achieve a desired second mesodermal cell type. The number of lineage restriction events required to achieve a particular mesodermal cell type of interest will vary depending on the particular desired mesodermal cell type and the starting progenitor or pluripotent cell type. In some instances, the number of lineage restriction events required to achieve a particular mesodermal cell type of interest may be one or more events, including but not limited to, e.g., 1 lineage restriction event, 2 lineage restriction events, 3 lineage restriction events, 4 lineage restriction events, 5 lineage restriction events, 6 lineage restriction events, etc.

In many instances, homogeneous populations of specific mesodermal cell-types are produced by contacting cells with various signaling pathway modulators that promote the formation of a desired cell type and various signaling pathway modulators that block the formation of other cell-types that emerge at relevant lineage bifurcations or lineage segregations.

Lineage restriction events as described herein may be induced by induction compositions wherein an induction composition is a composition that contains one or more induction agents useful in guiding cellular development or lineage restricting a cell along a particular lineage. Induction agents include those agents that activate or inhibit particular developmental signaling pathways that drive development. Such signaling pathways that may be activated or inhibited by induction agents include but are not limited to those signaling pathways that upon activation and inhibition generally promote mesodermal differentiation. In some instances, signaling pathways of interest also include those pathways that generally inhibit ectodermal differentiation or those signaling pathways that generally inhibit endodermal differentiation. As will be clear from the instant disclosure, whether activation or inhibition of a particular signaling pathway is necessary to generate a particular mesodermal cell type of interest will depend on a number of factors including but not limited to, e.g., the particular desired mesodermal cell type, the timing of use of the particular inductive agent and/or induction composition, the starting cell type to be induced, etc.

In some instances, an inducing agent useful in a particular induction composition may include an activator or inhibitor of the TGF-beta (transforming growth factor β (TGF-β)) pathway. Activators and inhibitors of the TGF-beta pathway include small molecule activators, small molecule inhibitors, peptide activators, peptide inhibitors, antibodies, nucleic acid activators, nucleic acid inhibitors, and the like that activate or inhibit at least one component of the TGF-beta pathway resulting in a corresponding activation or inhibition in cellular TGF-beta signaling. Components and downstream effectors of the TGF-beta pathway include but are not limited to, e.g., 14-3-3 e (UniProtID P62258), ark (UniProtID Q6ZNA4), axin1 (UniProtID O15169), bambi (UniProtID Q13145), beta arrestin 2 (UniProtID P32121), beta catenin (UniProtID P35222), beta glycan (UniProtID Q03167), camkiia (UniProtID Q9UQM7), caveolin-1 (UniProtID Q03135), ctgf (UniProtID P29279), dab2 (UniProtID P98082), dapper2 (UniProtID Q5SW24), daxx (UniProtID Q9UER7), eif2a (UniProtID Q9BY44), elf (UniProtID Q01082), endofin (UniProtID Q7Z3T8), fkbp12 (UniProtID P62942), gadd34 (UniProtID O75807), grb2 (UniProtID P62993), itch (UniProtID Q96J02), km23-1 (UniProtID Q9NP97), nedd4-2 (UniProtID Q96PU5), ocln (UniProtID Q16625), p70s6k (UniProtID P23443), par6 (UniProtID Q9NPB6), pdk1 (UniProtID O15530), pml (UniProtID P29590), ppp1ca (UniProtID P62136), ppp2ca (UniProtID P67775), ppp2cb (UniProtID P62714), ppp2r2a (UniProtID P63151), rhoa (UniProtID P61586), sara (UniProtID O95405), she (UniProtID P29353), smad2 (UniProtID Q15796), smad3 (UniProtID P84022), smad4 (UniProtID Q13485), smad7 (UniProtID O15105), smurf1 (UniProtID Q9HCE7), smurf2 (UniProtID Q9HAU4), snon (UniProtID P12757), sos1 (UniProtID Q07889), strap (UniProtID Q9Y3F4), tab1 (UniProtID Q15750), tab2 (UniProtID Q9NYJ8), tak1 (UniProtID O43318), TGFB1 (UniProtID P01137), TGFB2 (UniProtID P61812), TGFB3 (UniProtID P10600), tgfbr1 (UniProtID P36897), tgfbr2 (UniProtID P37173), trap-1 (UniProtID O60466), wwp1 (UniProtID Q9HOMO), xiap (UniProtID P98170), yap65 (UniProtID P46937), and the like.

Activators of the TGF-beta pathway include but are not limited to, e.g., TGF-beta family ligands (e.g., TGF-beta proteins and other activators of TGF-beta receptors) and portions thereof, Activin A, TGF-beta1, TGF-beta2, TGF-beta3, IDE1/2 (IDE1 (1-[2-[(2-Carboxyphenyl)methylene]hydrazide]heptanoic acid), IDE2 (Heptanedioic acid-1-(2-cyclopentylidenehydrazide)), Nodal, and the like. In some instances, activation of the TGF-beta pathway may be achieved through repression of the a TGF-beta pathway inhibitor, e.g., including but not limited to the use of an inhibitory nucleic acid targeting an inhibitor of the TGF-beta pathway or an antibody or small molecule directed to a TGF-beta pathway inhibitor.

Inhibitors of the TGF-beta pathway include but are not limited to, e.g., A-83-01 (3-(6-Methyl-2-pyridinyl)-N-phenyl-4-(4-quinolinyl)-1H-pyrazole-1-carbothioamide), D4476 (4-[4-(2,3-Dihydro-1,4-benzodioxin-6-yl)-5-(2-pyridinyl)-1H-imidazol-2-yl]benzamide), GW 788388 (4-[4-[3-(2-Pyridinyl)-1H-pyrazol-4-yl]-2-pyridinyl]-N-(tetrahydro-2H-pyran-4-yl)-benzamide), LY 364947 (4-[3-(2-Pyridinyl)-1H-pyrazol-4-yl]-quinoline), RepSox (2-(3-(6-Methylpyridine-2-yl)-1H-pyrazol-4-yl)-1,5-naphthyridine), SB431542 (4-[4-(1,3-benzodioxol-5-yl)-5-(2-pyridinyl)-1H-imidazol-2-yl]benzamide), SB-505124 (2-[4-(1,3-Benzodioxol-5-yl)-2-(1,1-dimethylethyl)-1H-imidazol-5-yl]-6-methyl-pyridine), SB 525334 (6-[2-(1,1-Dimethylethyl)-5-(6-methyl-2-pyridinyl)-1H-imidazol-4-yl]quinoxaline), SD208 (2-(5-Chloro-2-fluorophenyl)-4-[(4-pyridyl)amino]pteridine), ITD1 (4-[1,1'-Biphenyl]-4-yl-1,4,5,6,7,8-hexahydro-2,7,7-trimethyl-5-oxo-3-quinolinecarboxylic acid ethyl ester), DAN/Fc, antibodies to TGF-beta and TGF-beta receptors, TGF-beta inhibitory nucleic acids, and the like.

In some instances, an inducing agent useful in a particular induction composition may include an activator or inhibitor of the Wnt pathway. Activators and inhibitors of the Wnt pathway include small molecule activators, small molecule inhibitors, peptide activators, peptide inhibitors, antibodies, nucleic acid activators, nucleic acid inhibitors, and the like that activate or inhibit at least one component of the Wnt pathway resulting in a corresponding activation or inhibition in cellular Wnt signaling. Components and downstream effectors of the Wnt pathway include but are not limited to, e.g., cthrc1 (UniProtID Q96CG8), dkk1 (UniProtID O94907), fzd1 (UniProtID Q9UP38), fzd10 (UniProtID Q9ULW2), fzd2 (UniProtID Q14332), fzd4 (UniProtID Q9ULV1), fzd5 (UniProtID Q13467), fzd6 (UniProtID O60353), fzd7 (UniProtID O75084), fzd8 (UniProtID Q9H461), fzd9 (UniProtID O00144), igfbp4 (UniProtID P22692), kremen 1 (UniProtID Q96MU8), kremen 2 (UniProtID Q8NCW0), lrp5 (UniProtID O75197), lrp6 (UniProtID O75581), prr (UniProtID O75787), ror2 (UniProtID Q01974), rspo1 (UniProtID Q2MKA7), ryk (UniProtID P34925), wnt inhibitory 1 (UniProtID Q9Y5W5), wnt1 (UniProtID P04628), wnt2 (UniProtID P09544), wnt3 (UniProtID P56703), wnt3a (UniProtID P56704), wnt5a (UniProtID P41221), wnt7a (UniProtID O00755), wnt7b (UniProtID P56706), CTNNB1 (UniProtID P35222), GSK3A (UniProtID P49840), GSK3B (UniProtID P49841), TNKS1 (UniProtID O95271), TNKS2 (UniProtID Q9H2K2) and the like.

Activators of the WNT pathway include but are not limited to, e.g., CHIR99021 (6-[[2-[[4-(2,4-Dichlorophenyl)-5-(5-methyl-1H-imidazol-2-yl)-2-pyrimidinyl]amino]ethyl]amino]-3-pyridinecarbonitrile), WNT family ligands (e.g., including but not limited to Wnt-1, Wnt-2, Wnt-2b, Wnt-3a, Wnt-4, Wnt-5a, Wnt-5b, Wnt-6, Wnt-7a, Wnt-7a/b, Wnt-7b, Wnt-8a, Wnt-8b, Wnt-9a, Wnt-9b, Wnt-10a, Wnt-10b, Wnt-11, Wnt-16b, etc.), RSPO co-agonists (e.g., RSPO2), lithium chloride, TDZD8 (4-Benzyl-2-methyl-1,2,4-thiadiazolidine-3,5-dione), BIO-Acetoxime ((2'Z,3'E)-6-Bromoindirubin-3'-acetoxime), A1070722 (1-(7-Methoxyquinolin-4-yl)-3-[6-(trifluoromethyl)pyridin-2-yl]urea), HLY78 (4-Ethyl-5,6-Dihydro-5-methyl-[1,3]dioxolo[4,5-j]phenanthridine), CID 11210285 hydrochloride (2-Amino-4-(3,4-(methylenedioxy)benzylamino)-6-(3-methoxyphenyl)pyrimidine hydrochloride), WAY-316606, (hetero)arylpyrimidines, IQ1, QS11, SB-216763, DCA, and the like. In some instances, activation of the Wnt pathway may be achieved through repression of the a Wnt pathway inhibitor, e.g., including but not limited to the use of an inhibitory nucleic acid targeting an inhibitor of the Wnt pathway or an antibody or small molecule directed to a Wnt pathway inhibitor.

Inhibitors of the WNT pathway include but are not limited to, e.g., C59 (4-(2-Methyl-4-pyridinyl)-N-[4-(3-pyridinyl)phenyl]benzeneacetamide), DKK1, IWP-2 (N-(6-Methyl-2-benzothiazolyl)-2-[(3,4,6,7-tetrahydro-4-oxo-3-phenylthieno[3,2-d]pyrimidin-2-yl)thio]-acetamide), Ant1.4Br, Ant 1.4CI, Niclosamide, apicularen, bafilomycin, XAV939 (3,5,7,8-Tetrahydro-2-[4-(trifluoromethyl)phenyl]-4H-thiopyrano[4,3-d]pyrimidin-4-one), IWR-1 (4-(1,3,3a,4,7,7a-Hexahydro-1,3-dioxo-4,7-methano-2H-isoindol-2-yl)-N-8-quinolinyl-Benzamide), NSC668036 (N-[(1,1-Dimethylethoxy)carbonyl]-L-alanyl-(2S)-2-hydroxy-3-methylbutanoyl-L-Alanine-(1S)-1-carboxy-2-methylpropyl ester hydrate), 2,4-diamino-quinazoline, Quercetin, ICG-001 ((6S,9aS)-Hexahydro-6-[(4-hydroxyphenyl)methyl]-8-(1-naphthalenylmethyl)-4,7-dioxo-N-(phenylmethyl)-2H-pyrazino[1,2-a]pyrimidine-1(6H)-carboxamide), PKF115-584, BML-284 (2-Amino-4-[3,4-(methylenedioxy)benzylamino]-6-(3-methoxyphenyl)pyrimidine), FH-535, iCRT-14, JW-55, JW-67, antibodies to Wnts and Wnt receptors, Wnt inhibitory nucleic acids, and the like.

In some instances, a specific WNT inhibitor may be administered in such a manner as to result in a decrease in PAX3 expression and a promotion of FOXC2 expression.

In some instances, a Wnt activator or inhibitor useful in the methods described herein may include those described in, e.g., Dodge and Lum et al. Annu Rev Pharmacol Toxicol. 2011; 51:289-310; Chen et al. Am J Physiol Gastrointest Liver Physiol. 2010 August; 299(2):G293-300; Baker and Clevers, Nat Rev Drug Discov. 2006 December; 5(12):997-1014; Meijer et al. Trends Pharmacol Sci. 2004 September; 25(9):471-80; and Lepourcelet et al. Cancer Cell. 2004 January; 5(1):91-102, the disclosures of which are incorporated herein by reference in their entirety.

In some instances, an inducing agent useful in a particular induction composition may include an activator or inhibitor of the FGF pathway. In some instances, an activator or inhibitor of the FGF pathway may also include activators or inhibitors of related signal transduction pathways including but not limited to, e.g., the MAPK/ERK signal transduction pathway. Activators and inhibitors of the FGF pathway include small molecule activators, small molecule inhibitors, peptide activators, peptide inhibitors, antibodies, nucleic acid activators, nucleic acid inhibitors, and the like that activate or inhibit at least one component of the FGF pathway resulting in a corresponding activation or inhibition in cellular FGF signaling. Components and downstream effectors of the FGF pathway include but are not limited to, e.g., akt1 (UniProtID P31749), beta-klotho (UniProtID Q86Z14), camkiia (UniProtID Q9UQM7), cb1 (UniProtID P22681), cortactin (UniProtID Q14247), e-cadherin (UniProtID P12830), erk1 (UniProtID P27361), erk2 (UniProtID P28482), FGF1 (UniProtID P05230), FGF16 (UniProtID O60258), FGF17 (UniProtID O60258), FGF18 (UniProtID 076093), FGF19 (UniProtID O95750), FGF2 (UniProtID P09038), fgf23 (UniProtID Q9GZV9), FGF4 (UniProtID P08620), FGF6 (UniProtID P10767), FGF8 (UniProtID P55075), FGF9 (UniProtID P31371), fgfr1 (UniProtID P11362), fgfr2 (UniProtID P21802), fgfr2b (UniProtID P21802-18), FGFR2c (UniProtID P21802-5), FGFR3c (UniProtID P22607-1), FGFR4 (UniProtID P22455), fos (UniProtID P01100), frs2 (UniProtID Q8WU20), gab1 (UniProtID Q13480), grb2 (UniProtID P62993), hgf (UniProtID P14210), jun (UniProtID P05412), klotho (UniProtID Q9UEF7), mapk 14 (UniProtID Q16539), met (UniProtID P08581), mkp-3 (UniProtID Q16828), mmp9 (UniProtID P14780), n-cad-ctfl (UniProtID P19022), n-cad-ctf2 (UniProtID P19022), n-cadherin (UniProtID P19022), ncam (UniProtID P13591), osteocalcin (UniProtID P02818), osteopontin (UniProtID P10451), p110-alpha (UniProtID P42336), p120ctn (UniProtID O60716), p90-rsk 1 (UniProtID Q15418), pak4 (UniProtID Q8WYL5), pak4 (UniProtID O96013), pdk1 (UniProtID O15530), pik3r1 (UniProtID P27986), plcgamma1 (UniProtID P19174), pro-e-cadherin (UniProtID P12830), pro-mmp9 (UniProtID P14780), ps1 (UniProtID gamma), pyk2 (UniProtID Q14289), runx2 (UniProtID Q13950), se-cad (UniProtID P12830), secad-ntf2 (UniProtID P12830), sef (UniProtID Q8NFM7), shc (UniProtID P29353), shp2 (UniProtID Q06124), sn-cad (UniProtID P19022), sos1 (UniProtID Q07889), sprouty2 (UniProtID O43597), src (UniProtID P12931), stat1 (UniProtID P42224), stat3 (UniProtID P40763), stat5b (UniProtID P51692), syndecan-2 (UniProtID P34741), syndecan-4 (UniProtID P31431), upa (UniProtID P00749), upar (UniProtID Q03405), and the like.

Activators and inhibitors of the MAPK/ERK pathway include small molecule activators, small molecule inhibitors, peptide activators, peptide inhibitors, antibodies, nucleic acid activators, nucleic acid inhibitors, and the like that activate or inhibit at least one component of the MAPK/ERK pathway resulting in a corresponding activation or inhibition in cellular MAPK/ERK signaling. Components and downstream effectors of the MAPK/ERK pathway MAPK/ERK signaling include but are not limited to, e.g., a-raf (EntrezGeneID 369), ask1 (EntrezGeneID 4217), atf2 (EntrezGeneID 1386), cebpa (EntrezGeneID 1050), c-myc (EntrezGeneID 4609), creb (EntrezGeneID 1385), elk1 (EntrezGeneID 2002), erk5 (EntrezGeneID 5598), fos (EntrezGeneID 2353), grb2 (EntrezGeneID 2885), hexokinase type iv glucokinase (EntrezGeneID 2645), ikk-alpha (EntrezGeneID 1147), ikk-beta (EntrezGeneID 3551), jnk (EntrezGeneID 5599), jun (EntrezGeneID 3725), map2k1 (EntrezGeneID 5604), map2k2 (EntrezGeneID 5605), map2k4 (EntrezGeneID 6416), map2k5 (EntrezGeneID 5607), map2k6 (EntrezGeneID 5608), map2k7 (EntrezGeneID 5609), map3k1 (EntrezGeneID 4214), map3k11 (EntrezGeneID 4296), map3k12 (EntrezGeneID 7786), map3k13 (EntrezGeneID 9175), map3k14 (EntrezGeneID 9020), map3k2 (EntrezGeneID 10746), map3k3 (EntrezGeneID 4215), map3k4 (EntrezGeneID 4216), map3k7 (EntrezGeneID 6885), map3k8 (EntrezGeneID 1326), map4k1 (EntrezGeneID 11184), map4k3 (EntrezGeneID 8491), map4k5 (EntrezGeneID 11183), mapk1 (EntrezGeneID 5594), mapk10 (EntrezGeneID 5602), mapk11 (EntrezGeneID 5600), mapk12 (EntrezGeneID 6300), mapk13 (EntrezGeneID 5603), mapk14 (EntrezGeneID 1432), mapk3 (EntrezGeneID 5595), mapk9 (EntrezGeneID 5601), max (EntrezGeneID 4149), mef2 polypeptide a (EntrezGeneID 4205), mef2 polypeptide c (EntrezGeneID 4208), mef2b (EntrezGeneID 4207), mef2 polypeptide d (EntrezGeneID 4209), mek3 (EntrezGeneID 5606), mknk2 (EntrezGeneID 2872), mnk1 (EntrezGeneID 8569), msk1 (EntrezGeneID 9252), ngf r (EntrezGeneID 4804), ngfb (EntrezGeneID 4803), nik (EntrezGeneID 9448), pak1 (EntrezGeneID 5058), pak2 (EntrezGeneID 5062), pp2a (EntrezGeneID 5528), ptprr (EntrezGeneID 5801), rac1 (EntrezGeneID 5879), raf1 (EntrezGeneID 5894), ras (EntrezGeneID 3265), rps6ka1 (EntrezGeneID 6195), shc (EntrezGeneID 6464), sos1 (EntrezGeneID 6654), sp1 (EntrezGeneID 6667), src (EntrezGeneID 6714), stat1 (EntrezGeneID 6772), stat3 (EntrezGeneID 6774), tert (EntrezGeneID 7015), and the like.

Activators of the FGF pathway and/or the MAPK/ERK pathway include but are not limited to, e.g., FGF family ligands (e.g., FGF1, FGF2, FGF-3, FGF-4, FGF-5, FGF-6, KGF/FGF-7, FGF-8, FGF-9, FGF-10, FGF-11, FGF-12, FGF-13, FGF-15, FGF-16, FGF-17, FGF-19, FGF-20, FGF-21, FGF-22, FGF-23, etc.), SUN 11602 (4-[[4-[[2-[(4-Amino-2,3,5,6-tetramethylphenyl)amino]acetyl]methylamino]-1-piperidinyl]methypenzamide), t-Butylhydroquinone, U-46619, C2 Ceramide, Lactosyl Ceramide, Angiotensin II, Baicalin, and the like. In some instances, activation of the FGF pathway and/or the MAPK/ERK pathway may be achieved through repression of the a FGF pathway and/or the MAPK/ERK pathway inhibitor, e.g., including but not limited to the use of an inhibitory nucleic acid targeting an inhibitor of the FGF pathway and/or the MAPK/ERK pathway or an antibody or small molecule directed to a FGF pathway inhibitor and/or MAPK/ERK pathway inhibitor.

Inhibitors of the FGF pathway and/or the MAPK/ERK pathway and or the p38/JNK/MAPK cascade include but are not limited to, e.g., AP 24534 (3-(2-Imidazo[1,2-b]pyridazin-3-ylethynyl)-4-methyl-N-[4-[(4-methyl-1-piperazinyl)methyl]-3-(trifluoromethyl)phenyl]-benzamide), PD173074 (N-[2-[[4-(Diethylamino)butyl]amino]-6-(3,5-dimethoxyphenyl)pyrido[2,3-d]pyrimidin-7-yl]-N'-(1,1-dimethylethyl)urea), FIIN 1 hydrochloride (N-(3-((3-(2,6-dichloro-3,5-dimethoxyphenyl)-7-(4-(diethylamino) butylamino)-2-oxo-3,4-dihydropyrimido[4,5-d]pyrimidin-1(2H)-yl)methyl)acrylamide), PD 161570 (N-[6-(2,6-Dichlorophenyl)-2-[[4-(diethylamino)butyl]amino]pyrido [2,3-d]pyrimidin-7-yl]-N'-(1,1-dimethylethyl)urea), SU 5402 (2-[(1,2-Dihydro-2-oxo-3H-indol-3-ylidene)methyl]-4-methyl-1H-pyrrole-3-propanoic acid), SU 6668 (5-[1,2-Dihydro-2-oxo-3H-indol-3-ylidene)methyl]-2,4-dimethyl-1H-pyrrole-3-propanoic acid), PD0325901 (N-[(2R)-2,3-Dihydroxypropoxy]-3,4-difluoro-2-[(2-fluoro-4-iodophenyl)amino]-benzamide), BIX 02189 ((3Z)-3-[[[3-[(Dimethylamino)methyl]phenyl]amino]phenylmethylene]-2,3-dihydro-N,N-dimethyl-2-oxo-1H-indole-6-carboxamide), FR 180204 (5-(2-Phenyl-pyrazolo[1,5-a]pyridin-3-yl)-1H-pyrazolo[3,4-c]pyridazin-3-ylamine), Pluripotin (N-[3-[7-[(1,3-Dimethyl-1H-pyrazol-5-yl) amino]-1,4-dihydro-1-methyl-2-oxopyrimido[4,5-d]pyrimidin-3(2H)-yl]-4-methylphenyl]-3-(trifluoromethyl)benzamide), TCS ERK 11e (4-[2-[(2-Chloro-4-fluorophenyl) amino]-5-methyl-4-pyrimidinyl]-N-[(1S)-1-(3-chlorophenyl)-2-hydroxyethyl]-1H-pyrrole-2-carboxamide), TMCB (2-(4,5,6,7-Tetrabromo-2-(dimethylamino)-1H-benzo[d]imidazol-1-yl)acetic acid), XMD 8-92 (2-[[2-Ethoxy-4-(4-hydroxy-1-piperidinyl)phenyl]amino]-5,11-dihydro-5,11-dimethyl-6H-pyrimido[4,5-b][1,4]benzodiazepin-6-one), SU5402, AZD4547, BGJ398, AL 8697, AMG 548, CMPD-1, DBM 1285 dihydrochloride, EO 1428, JX 401, ML 3403, RWJ 67657, SB 202190, SB-203580, SB 239063, SB 706504, Scio-469, SKF 86002 dihydrochloride, SX 011, TA 01 (4-(2-(2,6-Difluorophenyl)-4-(fluorophenyl)-1H-imidazol-5-yl)pyridine), TA 02 (4-(2-(2-Fluorophenyl)-4-(fluorophenyl)-1H-imidazol-5-yl)pyridine), TAK 715, VX-702, VX-745, antibodies to FGF and/or MAPK pathway components including ligands and receptors, FGF and/or MAPK inhibitory nucleic acids, and the like.

In some instances, a FGF or MAPK activator or inhibitor useful in the methods described herein may include those described in, e.g., English and Cobb, Trends Pharmacol Sci. 2002 January; 23(1):40-5, the disclosure of which is incorporated herein by reference in its entirety.

In some instances, an inducing agent useful in a particular induction composition may include an activator or inhibitor of the BMP pathway. Activators and inhibitors of the BMP pathway include small molecule activators, small molecule inhibitors, peptide activators, peptide inhibitors, antibodies, nucleic acid activators, nucleic acid inhibitors, and the like that activate or inhibit at least one component of the BMP pathway resulting in a corresponding activation or inhibition in cellular BMP signaling. Components and downstream effectors of the BMP pathway include but are not limited to, e.g., bambi (UniProtID Q13145), bmp2 (UniProtID P12643), bmp4 (UniProtID P12644), bmp6 (UniProtID P22004), bmp7 (UniProtID P18075), bmpr1a (UniProtID P36894), bmpr1b (UniProtID O00238), bmpr2 (UniProtID Q13873), cer1 (UniProtID O95813), chrd (UniProtID Q9H2X0), chrdl1 (UniProtID Q9BU40), endofin (UniProtID Q7Z3T8), erk2 (UniProtID P28482), fetua (UniProtID P02765), fs (UniProtID P19883), gadd34 (UniProtID O75807), grem1 (UniProtID O60565), gsk3beta (UniProtID P49841), nog (UniProtID Q13253), nup214 (UniProtID P35658), ppm1a (UniProtID P35813), ppp1ca (UniProtID P62136), rgma (UniProtID Q96B86), rgmb (UniProtID Q6NW40), rgmc (UniProtID Q6ZVN8), scp1 (UniProtID Q9GZU7), scp2 (UniProtID O14595), scp3 (UniProtID O15194), ski (UniProtID P12755), smad1 (UniProtID Q15797), smad4 (UniProtID Q13485), smad5 (UniProtID Q99717), smad6 (UniProtID O43541), smad7 (UniProtID O15105), smad8a (UniProtID O15198), smurf1 (UniProtID Q9HCE7), smurf2 (UniProtID Q9HAU4), tab1 (UniProtID Q15750), tab2 (UniProtID Q9NYJ8), tak1 (UniProtID O43318), usag1 (UniProtID Q6X4U4), xiap (UniProtID P98170), and the like.

Activators of the BMP pathway include but are not limited to, e.g., BMP family ligands (e.g., BMP2, BMP4, BMP7, etc.), Alantolactone, FK506, isoliquiritigenin, 4'-hydroxychalcone, and the like. In some instances, activation of the BMP pathway may be achieved through repression of the a BMP pathway inhibitor, e.g., including but not limited to the use of an inhibitory nucleic acid targeting an inhibitor of the BMP pathway or an antibody or small molecule directed to a BMP pathway inhibitor.

Inhibitors of the BMP pathway include but are not limited to, e.g., NOGGIN, CHORDIN, LDN-193189 (4-[6-[4-(1-Piperazinyl)phenyl]pyrazolo[1,5-a]pyrimidin-3-yl]-quinoline hydrochloride), DMH1 (4-[6-[4-(1-Methylethoxy)phenyl]pyrazolo[1,5-a]pyrimidin-3-yl]-quinoline), Dorsomorphin (6-[4-[2-(1-Piperidinyl)ethoxy]phenyl]-3-(4-pyridinyl)-pyrazolo[1,5-a]pyrimidine dihydrochloride), K 02288 (3-[(6-Amino-5-(3,4,5-trimethoxyphenyl)-3-pyridinyl]phenol), ML 347 (5-[6-(4-Methoxyphenyl)pyrazolo[1, 5-a]pyrimidin-3-yl]quinoline), DMH-1, antibodies to BMPs and BMP receptors, BMP inhibitory nucleic acids, and the like.

In some instances, an inducing agent useful in a particular induction composition may include an activator or inhibitor of the retinoic acid signaling pathway. Activators and inhibitors of the retinoic acid signaling pathway include small molecule activators, small molecule inhibitors, peptide activators, peptide inhibitors, antibodies, nucleic acid activators, nucleic acid inhibitors, and the like that activate or inhibit at least one component of the retinoic acid signaling pathway resulting in a corresponding activation or inhibition in cellular retinoic acid signaling. Components and downstream effectors of the retinoic acid signaling pathway include but are not limited to, e.g., CRABP (e.g., Accession: NP_004369), TRAIL (e.g., Accession: NP_003801), TRAILR1 (e.g., Accession: NP_003835), TRAILR2 (e.g., Accession: NP_003833), DAP3 (e.g., Accession: NP_001186780), FADD (e.g., Accession: CAG33019), FLIP (e.g., Accession: NP_001294972), Caspase 8 (e.g., Accession: AAD24962), BID (e.g., Accession: NP_001304162), tBID (e.g., Accession: P55957), APAF1 (e.g., Accession: ABQ59028), Caspase 9 (e.g., Accession: P55211), PARPs (e.g., Accession: AAH14206), RAR (e.g., Accession: NP_001138773 and components thereof e.g., AF2 domain, AF1 domain, DBD domain, and the like. Activators and inhibitors of the retinoic acid signaling include but are not limited to e.g., Tretinoin, Retinol palmitate, Etretinate, Isotretinoin, Adapalene, Tazarotene, Tamibarotene, Retinol acetate, Acitretin, Alitretinoin, Bexarotene, Isotretinoin anisatil, Motretinide, Vitamin A, Retinol propionate, and the like. In some instances, useful modulators of the retinoic acid signaling pathway include retinoid agonist, including but not limited to e.g., all-trans retinoic acid, TTNPB, AM580 and the like. In some instances, an inducing agent useful in a particular induction composition may include an activator or inhibitor of the Hedgehog pathway. Activators and inhibitors of the Hedgehog pathway include small molecule activators, small molecule inhibitors, peptide activators, peptide inhibitors, antibodies, nucleic acid activators, nucleic acid inhibitors, and the like that activate or inhibit at least one component of the Hedgehog pathway resulting in a corresponding activation or inhibition in cellular Hedgehog signaling. Components and downstream effectors of the Hedgehog pathway include but are not limited to, e.g., akt1 (UniProtID P31749), beta arrestin2 (UniProtID P32121), boc (UniProtID Q9BWV1), cdo (UniProtID Q4KMG0), dhh (UniProtID O43323), gas1 (UniProtID P54826), gli2 (UniProtID P10070), grk2 (UniProtID P25098), hhat (UniProtID Q5VTY9), hhip (UniProtID Q96QV1), ihh (UniProtID Q14623), lrpap1 (UniProtID P30533), megalin (UniProtID P98164), p110-alpha (UniProtID P42336), pik3r1 (UniProtID P27986), ptch1 (UniProtID Q13635), ptch2 (UniProtID Q9Y6C5), pthrp (UniProtID P12272), shh (UniProtID Q15465), sil (UniProtID Q15468), smo (UniProtID Q99835), tgf-beta2 (UniProtID P61812), and the like.

Activators of the Hedgehog pathway include but are not limited to, e.g., Hedgehog family ligands (Hh, Shh, Ihh, Dhh, etc.) and fragments thereof, benzothiophene smoothened agonists, SAG (Hh-Ag1.3), SAG21k (3-chloro-4,7-difluoro-N-(4-methoxy-3-(pyridin-4-yl)benzyl)-N-((1r,4r)-4-(methylamino)cyclohexyl)benzo[b]thiophene-2-carboxamide), Hh-Ag1.1, Hh-Ag1.5, purmorphamine, and the like. In some instances, activation of the Hedgehog pathway may be achieved through repression of the a Hedgehog pathway inhibitor, e.g., including but not limited to the use of an inhibitory nucleic acid targeting an inhibitor of the Hedgehog pathway or an antibody or small molecule directed to a Hedgehog pathway inhibitor.

Inhibitors of the Hedgehog pathway include but are not limited to, e.g., Hedgehog antagonists that target smoothened (SMO), Hedgehog antagonists that target patched (PTCH), Hedgehog antagonists that target Gli, cyclopamine and analogs and derivatives thereof, cyclopamine-competitive antagonists, IPI-926 (Saridegib), LDE225 (sonidegib), itraconazole, GDC-0449 (vismodegib), SANT1, KAAD-cyclopamine, LEQ506, PF-04449913, TAK-441, BMS833923 (XL-139), LY2940680, and inhibitory nucleic acids targeting SMO, inhibitory nucleic acids targeting a Hedgehog, inhibitory nucleic acids targeting PTCH, inhibitory nucleic acids targeting Gli (e.g., siRNA targeting Gli1), arsenic trioxide, and the like.

In some instances, Hedgehog pathway activators and Hedgehog pathway inhibitors include those agents described in, e.g., Chen et al. (2002) PNAS. 99(22):14071-14076; Frank-Kamenetsky, et al. (2002) J Biol. 1(2):10; Paladini et al. (2005) J Invest Dermatol. 125(4):638-46; Nakamura et al. (2014) J Cell. Physiol. ePub, Yun et al., Arch Pharm Res. 2012 August; 35(8):1317-33; the disclosures of which are incorporated herein by reference in their entirety.

In some instances, an inducing agent useful in a particular induction composition may include an activator or inhibitor of the PI3K pathway. Activators and inhibitors of the PI3K pathway include small molecule activators, small molecule inhibitors, peptide activators, peptide inhibitors, antibodies, nucleic acid activators, nucleic acid inhibitors, and the like that activate or inhibit at least one component of the PI3K pathway resulting in a corresponding activation or inhibition in cellular PI3K signaling. Components and downstream effectors of the PI3K pathway include but are not limited to, e.g., arap3 (UniProtID Q8WWN8), arf1 (UniProtID P84077), arf5 (UniProtID P84085), arf6 (UniProtID P62330), arno (UniProtID Q99418), bam32 (UniProtID Q9UN19), blk (UniProtID P51451), bink (UniProtID Q8WV28), btk (UniProtID Q06187), centa1 (UniProtID O75689), cytohesin-1 (UniProtID Q15438), fgr (UniProtID P09769), foxo3a (UniProtID O43524), fyn (UniProtID P06241), grp1 (UniProtID O43739), hck (UniProtID P08631), h-ras isoform 1 (UniProtID P01112), h-ras isoform 2 (UniProtID P01112), hsp90 (UniProtID P07900), itk (UniProtID Q08881), k-ras isoform 2a (UniProtID P01116-1), k-ras isoform 2b (UniProtID P01116-2), lat (UniProtID O43561-2), lck (UniProtID P06239), lyn (UniProtID P07948), n-ras (UniProtID P01111), p101 (UniProtID Q8WYR1), p110-alpha (UniProtID P42336), p110-beta (UniProtID P42338), p110D (UniProtID O00329), p55-gamma (UniProtID Q92569), p84 (UniProtID Q5UE93), p85-beta (UniProtID O00459), pdk1 (UniProtID O15530), PI3Kgamma (UniProtID P48736), PIK3R1 (UniProtID P27986), plcgamma1 (UniProtID P19174), plcgamma2 (UniProtID P16885), pten (UniProtID P60484), rac1 (UniProtID P63000), rap1a (UniProtID P62834), rhoa (UniProtID P61586), sgk1 (UniProtID O00141), ship (UniProtID O00145), ship2 (UniProtID O15357), src (UniProtID P12931), syk (UniProtID P43405), tapp1 (UniProtID Q9HB19), tapp2 (UniProtID Q9HB21), yes (UniProtID P07947), zap-70 (UniProtID P43403), and the like.

Activators of the PI3K pathway include but are not limited to, e.g., PI3K family ligands, 740 Y-P, Insulin receptor substrate (Tyr608) peptide (KKHTDDGYMPMSPGVA, SEQ ID NO:1), and the like. In some instances, an FGF signaling protein may serve as an activator of the PI3K pathway. In some instances, activation of the PI3K pathway may be achieved through repression of the a PI3K pathway inhibitor, e.g., including but not limited to the use of an inhibitory nucleic acid targeting an inhibitor of the PI3K pathway or an antibody or small molecule directed to a PI3K pathway inhibitor.

Inhibitors of the PI3K pathway include but are not limited to, e.g., AS 252424 (5-[[5-(4-Fluoro-2-hydroxyphenyl)-2-furanyl]methylene]-2,4-thiazolidinedione), AS 605240 (5-(6-Quinoxalinylmethylene)-2,4-thiazolidine-2,4-dione), AZD 6482 ((−)-2-[[(1R)-1-[7-Methyl-2-(4-morpholinyl)-4-oxo-4H-pyrido[1,2-a]pyrimidin-9-yl]ethyl]amino]benzoic acid), BAG 956 (α,α,-Dimethyl-4-[2-methyl-8-[2-(3-pyridinyl)ethynyl]-1H-imidazo[4,5-c]quinolin-1-yl]-benzeneacetonitrile), CZC 24832 (5-(2-Amino-8-fluoro[1,2,4]triazolo[1,5-a]pyridin-6-yl)-N-(1,1-dimethylethyl)-3-pyridinesulfonamide), GSK 1059615 (5-[[4-(4-Pyridinyl)-6-quinolinyl]methylene]-2,4-thiazolidenedione), KU 0060648 (4-Ethyl-N-[4-[2-(4-morpholinyl)-4-oxo-4H-1-benzopyran-8-yl]-1-dibenzothienyl]-1-piperazineacetamide), LY 294002 hydrochloride (2-(4-Morpholinyl)-8-phenyl-4H-1-benzopyran-4-one hydrochloride), 3-Methyladenine (3-Methyl-3H-purin-6-amine), PF 04691502 (2-Amino-8-[trans-4-(2-hydroxyethoxy)cyclohexyl]-6-(6-methoxy-3-pyridinyl)-4-methyl-pyrido[2,3-d]pyrimidin-7(8H)-one), PF 05212384 (N-[4-[[4-(Dimethylamino)-1-piperidinyl]carbonyl]phenyl]-N'-[4-(4,6-di-4-morpholinyl-1,3,5-triazin-2-yl)phenyl]urea), PI 103 hydrochloride (3-[4-(4-Morpholinylpyrido[3',2':4,5]furo[3,2-d]pyrimidin-2-yl]phenol hydrochloride), PI 828 (2-(4-Morpholinyl)-8-(4-aminophenyl)-4H-1-benzopyran-4-one), PP 121 (1-Cyclopentyl-3-(1H-pyrrolo[2,3-b]pyridin-5-yl)-1H-pyrazolo[3,4-d]pyrimidin-4-amine), Quercetin, TG 100713 (3-(2,4-Diamino-6-pteridinyl)-phenol), Wortmannin, PIK90, GDC-0941, antibodies to PI3K and PI3K receptors, PI3K inhibitory nucleic acids, and the like.

In some instances, an inducing agent useful in a particular induction composition may include an activator or inhibitor of the PDGF pathway. Activators and inhibitors of the PDGF pathway include small molecule activators, small molecule inhibitors, peptide activators, peptide inhibitors, antibodies, nucleic acid activators, nucleic acid inhibitors, and the like that activate or inhibit at least one component of the PDGF pathway resulting in a corresponding activation or inhibition in cellular PDGF signaling. Components and downstream effectors of the PDGF pathway include but are not limited to, e.g., 14-3-3 e (UniProtID P62258), abi1 (UniProtID Q8IZP0), acta2 (UniProtID P62736), afadin (UniProtID P55196), alpha actinin 4 (UniProtID O43707), alphav integrin (UniProtID P06756), arap1 (UniProtID Q96P48), arp2 (UniProtID P61160), arp3 (UniProtID P61158), arpc1b (UniProtID O15143), arpc2 (UniProtID O15144), arpc3 (UniProtID O15145), arpc4 (UniProtID P59998), arpc5 (UniProtID O15511), beta3 integrin (UniProtID P05106), blk (UniProtID P51451), braf (UniProtID P15056), c3g (UniProtID Q13905), c-abl (UniProtID P00519), caveolin-1 (UniProtID Q03135), caveolin-3 (UniProtID P56539), cbl (UniProtID P22681), ck2a1 (UniProtID P68400), cortactin (UniProtID Q14247), crk (UniProtID P46108), crk1 (UniProtID P46109), csk (UniProtID P41240), dep1 (UniProtID Q12913), dock4 (UniProtID Q8N1I0), dynamin 2 (UniProtID P50570), elk1 (UniProtID P19419), eps8 (UniProtID Q12929), erk1 (UniProtID P27361), erk2 (UniProtID P28482), fgr (UniProtID P09769), fos (UniProtID P01100), fyn (UniProtID P06241), gab1 (UniProtID Q13480), grb10 (UniProtID Q13322), grb2 (UniProtID P62993), hck (UniProtID P08631), h-ras isoform 1 (UniProtID P01112), h-ras isoform 2 (UniProtID P01112), hspc300 (UniProtID Q8WUW1), ifn-gamma (UniProtID P01579), idgap1 (UniProtID P46940), irsp53 (UniProtID Q9UQB8), jak1 (UniProtID P23458), jak2 (UniProtID O60674), jnk1 (UniProtID P45983), jnk2 (UniProtID P45984), jnk3 (UniProtID P53779), jun (UniProtID P05412), jund (UniProtID P17535), k-ras isoform 2a (UniProtID P01116-1), k-ras isoform 2b (UniProtID P01116-2), ksr (UniProtID Q8IVT5), lck (UniProtID P06239), lrp1 (UniProtID Q07954), lyn (UniProtID P07948), mek1 (UniProtID Q02750), mek2 (UniProtID P36507), mkk4 (UniProtID P45985), mkk7 (UniProtID O14733), myc (UniProtID P01106), myocardin (UniProtID Q8IZQ8), nap1 (UniProtID Q9Y2A7), nck1 (UniProtID P16333), nck2 (UniProtID O43639), nherf1 (UniProtID O14745), nherf2 (UniProtID Q15599), n-ras (UniProtID P01111), n-wasp (UniProtID O00401), p101 (UniProtID Q8WYR1), p110-alpha (UniProtID P42336), p110-beta (UniProtID P42338), p110D (UniProtID O00329), p130 cas (UniProtID P56945), p190rhogap (UniProtID Q9NRY4), p52 shc (UniProtID P29353-2), p55-gamma (UniProtID Q92569), p62dok (UniProtID Q99704), p84 (UniProtID Q5UE93), p85-beta (UniProtID O00459), pag1 (UniProtID Q9NWQ8), pak1 (UniProtID Q13153), pdgfa (UniProtID P04085), pdgfb (UniProtID P01127), pdgfc (UniProtID Q9NRA1), pdgfd (UniProtID Q9GZP0), pdgfra (UniProtID P16234), pdgfrb (UniProtID P09619), PI3Kgamma (UniProtID P48736), pik3r1 (UniProtID P27986), pin1 (UniProtID Q13526), pkc alpha (UniProtID P17252), pkc delta (UniProtID Q05655), pkc epsilon (UniProtID Q02156), pkr (UniProtID P19525), pla2g4a (UniProtID P47712), plcgamma1 (UniProtID P19174), ppp2ca (UniProtID P67775), ppp2r1a (UniProtID P30153), ppp2r2b (UniProtID Q00005), pten (UniProtID P60484), ptp1b (UniProtID P18031), rab4a (UniProtID P20338), rab5 (UniProtID P20339), rac1 (UniProtID P63000), raf1 (UniProtID P04049), rap1a (UniProtID P62834), rap1b (UniProtID P61224), rasgap (UniProtID P20936), rhoa (UniProtID P61586), rhogdi (UniProtID P52565), rntre (UniProtID Q92738), rsk2 (UniProtID P51812), s1p1 (UniProtID P21453), shb (UniProtID Q15464), shc (UniProtID P29353), shf (UniProtID Q7M4L6), shp2 (UniProtID Q06124), slap (UniProtID Q13239), sm22 (UniProtID Q01995), sos1 (UniProtID Q07889), spa-1 (UniProtID Q96FS4), sphk1 (UniProtID Q9NYA1), sra1 (UniProtID Q96F07), src (UniProtID P12931), srf (UniProtID P11831), stat1 (UniProtID P42224), stat3 (UniProtID P40763), STATSA (UniProtID P42229), STATSB (UniProtID P51692), tcptp p45 (UniProtID P17706-1), vav2 (UniProtID P52735), wave2 (UniProtID Q9Y6W5), yes (UniProtID P07947), ywhab (UniProtID P31946), ywhag (UniProtID P61981), ywhah (UniProtID Q04917), ywhaq (UniProtID P27348), ywhas (UniProtID P31947), ywhaz (UniProtID P63104), and the like.

Activators of the PDGF pathway include but are not limited to, e.g., PDGF family ligands (e.g., PDGF, PDGF A, PDGF B, PDGF C, PDGF D, etc.) and fragments thereof and/or dimers thereof (e.g., PDGF-AA, PDGF-BB, PDGF-CC, PDGF-DD, PDGF-AB, etc.), and the like. In some instances, activation of the PDGF pathway may be achieved through repression of the a PDGF pathway inhibitor, e.g., including but not limited to the use of an inhibitory nucleic acid targeting an inhibitor of the PDGF pathway or an antibody or small molecule directed to a PDGF pathway inhibitor.

Inhibitors of the PDGF pathway include but are not limited to, e.g., AG 18 ([(3,4-Dihydroxyphenyl)methylene]-propenedinitrile), AG1295, AG1296, AGL2043, AP 24534 (3-(2-Imidazo[1,2-b]pyridazin-3-ylethynyl)-4-methyl-N-[4-

[(4-methyl-1-piperazinyl)methyl]-3-(trifluoromethyl)phenyl]-benzamide), CDP860, DMPQ dihydrochloride (5,7-Dimethoxy-3-(4-pyridinyl)quinoline dihydrochloride), Imatinib, PD 166285 dihydrochloride (6-(2,6-Dichlorophenyl)-2-[[4-[2-(diethylamino)ethoxy]phenyl]amino]-8-methylpyrido[2,3-d]pyrimidin-7(8H)-one dihydrochloride), SU 16f (5-[1,2-Dihydro-2-oxo-6-phenyl-3H-indol-3-ylidene)methyl]-2,4-dimethyl-1H-pyrrole-3-propanoic acid), SU 6668 (5-[1,2-Dihydro-2-oxo-3H-indol-3-ylidene)methyl]-2,4-dimethyl-1 H-pyrrole-3-propanoic acid), SU11248, Sunitinib malate (N-[2-(Diethylamino)ethyl]-5-[(Z)-(5-fluoro-1,2-dihydro-2-oxo-3H-indol-3-ylidine)methyl]-2,4-dimethyl-1H-pyrrole-3-carboxamide (2S)-2-hydroxybutanedioate salt), Toceranib (5-[(Z)-(5-Fluoro-1,2-dihydro-2-oxo-3H-indol-3-ylidene)methyl]-2,4-dimethyl-N-[2-(1-pyrrolidinyl)ethyl]-1H-pyrrole-3-carboxamide), antibodies targeting PDGF and/or PDGF receptor, PDGF inhibitory nucleic acids, and the like.

In some instances, an inducing agent useful in a particular induction composition may include an activator of the NOTCH pathway. Activators of the NOTCH pathway include small molecule activators, peptide activators, antibodies against NOTCH repressors, nucleic acid activators, nucleic acid inhibitors of NOTCH repressors, and the like that activate at least one component of the NOTCH pathway resulting in a corresponding activation in cellular NOTCH signaling.

Activators of the NOTCH pathway include but are not limited to, e.g., NOTCH family ligands, including both canonical and non-canonical NOTCH family ligands, and portions or fragments thereof. Canonical and non-canonical NOTCH family ligands include but are not limited to, e.g., Delta-like ligands, Jagged ligands, homologous vertebrate proteins and polypeptides to invertebrate NOTCH ligands (e.g., delta, serrate, LAG-2, APX-1, ARG-1, DSL-1, and the like), and the like. NOTCH ligands and methods of activating NOTCH signaling are known in the art and include, e.g., those described in D'Souza et al. (Curr Top Dev Biol. 2010; 92:73-129) Li et al. (J Biol Chem. 2008; 283(12):8046-54), the disclosures of which is incorporated herein by reference in their entirety. In some instances, activation of the NOTCH pathway may be achieved through repression of the a NOTCH pathway inhibitor, e.g., including but not limited to the use of an inhibitory nucleic acid targeting an inhibitor of the NOTCH pathway or an antibody or small molecule directed to a NOTCH pathway inhibitor.

In some instances, an inducing agent useful in a particular induction composition may include an activator or inhibitor of the PKA/cAMP pathway (i.e., the cAMP-dependent pathway, adenylyl cyclase pathway, PAK signaling, etc.). Activators and inhibitors of the PKA/cAMP pathway include small molecule activators, small molecule inhibitors, peptide activators, peptide inhibitors, antibodies, nucleic acid activators, nucleic acid inhibitors, and the like that activate or inhibit at least one component of the PKA/cAMP pathway resulting in a corresponding activation or inhibition in cellular PKA/cAMP signaling. Components and downstream effectors of the PKA/cAMP pathway include but are not limited to, e.g., G-protein alpha-12 family, WASF1 (WAVE1), LBC, G-protein alpha-i family, AKAP2, ATP cytosol, PDE3B, SMAD3, Androgen receptor, KDELR, AKAP7 gamma, PCTK1, 4.6.1.1, AKAP12, SMAD4, Anaphase-promoting complex (APC), GABA-A receptor beta-2 subunit, Ryanodine receptor 1, Troponin I, cardiac, AKAP8, 3.1.4.17, AKAP11, PHK beta, GABA-A receptor beta-3 subunit, PKA-cat alpha, CREB1, cAMP, G-protein alpha-s, GSK3 alpha/beta, AKAP3, Adenylate cyclase, PDK (PDPK1), GABA-A receptor beta-1 subunit, PKA-reg (cAMP-dependent), PDE4D, PKA-cat (cAMP-dependent), DARPP-32, PKA-reg type II (cAMP-dependent), NFKBIA, Meprin A, beta, AKAP82, AMP, PDE3A, PKI, PHK gamma, PDE4A, NFKBIB, PP2A regulatory, BAD, p90RSK1, G-protein alpha-13, Phospholamban, G-protein alpha-i family, RAP-1A, Adenylate cyclase type II, cAMP, G-protein beta/gamma, Calcineurin A (catalytic), PKC, Calmodulin, GSK3 alpha/beta, Adenylate cyclase type VII, Adenylate cyclase type IV, Adenylate cyclase type VIII, CREB1, ATP cytosol, Ca('2+) cytosol, 4.6.1.1, Ryanodine receptor 1, G-protein alpha-s, PKC-alpha, RAP-2A, CaMK IV, PHK alpha, PKA-reg (cAMP-dependent), Adenylate cyclase type III, cAMP-GEFII, Adenylate cyclase type V, LIPS, KDELR, cAMP-GEFI, Adenylate cyclase type VI, PKA-cat (cAMP-dependent), PHK gamma, CaMK II, PKC-zeta, PKC-delta, Adenylate cyclase type I, Adenylate cyclase type IX, and the like.

Activators of the PKA/cAMP pathway include but are not limited to, e.g., forskolin, dibutyryl-cAMP (bucladesine), 8-bromo-cAMP, 8-CPT-cAMP, taxol, Adenosine 3',5'-cyclic Monophosphate, N6-Benzoyl, Adenosine 3',5'-cyclic monophosphate, belinostat, 8-Chloroadenosine 3',5'-Cyclic Monophosphate, (S)-Adenosine, cyclic 3',5'-(hydrogen-phosphorothioate), Sp-Adenosine 3',5'-cyclic monophosphorothioate, Sp-5,6-DCl-cBiMPS, Adenosine 3',5'-cyclic Monophosphorothioate,8-Bromo-, Sp-Isomer, Sp-8-pCPT-cyclic GMPS Sodium, N6-Monobutyryladenosine 3':5'-cyclic monophosphate, 8-PIP-cAMP, Sp-cAMPS caffeine, theophylline, pertussis toxin and the like. In some instances, activation of the PKA/cAMP pathway may be achieved through repression of the a PKA/cAMP pathway inhibitor, e.g., including but not limited to the use of an inhibitory nucleic acid targeting an inhibitor of the PKA/cAMP pathway or an antibody or small molecule directed to a PKA/cAMP pathway inhibitor.

In some instances, an inducing agent useful in a particular induction composition may include an activator or inhibitor of the VEGF pathway. Activators and inhibitors of the VEGF pathway include small molecule activators, small molecule inhibitors, peptide activators, peptide inhibitors, antibodies, nucleic acid activators, nucleic acid inhibitors, and the like that activate or inhibit at least one component of the VEGF pathway resulting in a corresponding activation or inhibition in cellular VEGF signaling. Components and downstream effectors of the VEGF pathway include but are not limited to, e.g., VEGFA, KDR, SH2D2A, PLCG1, PLCG2, PRKCA, PRKCB, PRKCG, SPHK1, SPHK2, HRAS, KRAS, NRAS, RAF1, MAP2K1, MAP2K2, MAPK1, MAPK3, PLA2G4E, PLA2G4A, JMJD7-PLA2G4B, PLA2G4B, PLA2G4C, PLA2G4D, PLA2G4F, PPP3CA, PPP3CB, PPP3CC, PPP3R1, PPP3R2, NFATC2, PTGS2, PTK2, SHC2, PXN, CDC42, MAPK11, MAPK12, MAPK13, MAPK14, MAPKAPK2, MAPKAPK3, HSPB1, SRC, PIK3CA, PIK3CD, PIK3CB, PIK3CG, PIK3R1, PIK3R5, PIK3R2, PIK3R3, RAC1, RAC2, RAC3, AKT1, AKT2, AKT3, NOS3, CASP9, BAD, and the like.

Modulators of the VEGF signaling pathway include but are not limited to e.g., Aspirin, Naproxen, Sulindac, Ibuprofen, Piroxicam, Diflunisal, Ketoprofen, Indometacin, Mefenamic acid, Tolmetin sodium, Meclofenamate sodium, Etodolac, Flurbiprofen, Nabumetone, Sasapyrine, Oxaprozin, Phenylbutazone, Sodium salicylate, Celecoxib, Rofecoxib, Axitinib, Bosutinib, Dasatinib, Doramapimod, Pegaptanib sodium, Ranibizumab, Semaxanib, Sorafenib tosilate, Vatalanib, Sunitinib malate, Vandetanib, Bevacizumab, Dasatinib hydrate, Motesanib, Dexketoprofen, Ketoprofen sodium, Meclofenamate sodium, Piketoprofen, Piketoprofen hydrochloride, Toceranib, Sorafenib, Toceranib phosphate, Sunitinib, Bevasiranib sodium, Brivanib alaninate, Cediranib, Cediranib maleate, Motesanib phosphate, Pamapimod, Ramucirumab, Talmapimod, Aflibercept, Dilmapimod, Dilmapimod tosylate, Foretinib, Linifanib, Losmapimod, Saracatinib, Saracatinib difumarate, Tivozanib, Bosutinib hydrate, Pegdinetanib, Naproxen etemesil, Cabozantinib, Tivozanib hydrochloride, Golvatinib, Pimasertib, Pimasertib hydrochloride, and the like. In some instances, VEGF activators useful in the subject methods include but are not limited to e.g., a VEGF polypeptide and/or a nucleic acid encoding a VEGF polypeptide.

In some instances, activation of the PKA/cAMP pathway may be achieved through repression of the a PKA/cAMP pathway inhibitor, e.g., including but not limited to the use of an inhibitory nucleic acid targeting an inhibitor of the PKA/cAMP pathway or an antibody or small molecule directed to a PKA/cAMP pathway inhibitor.

In some instances, an inducing agent useful in a particular induction composition may include a SCF agonist. SCF activators (i.e., SCF agonists) with vary and may include small molecule activators, peptide activators, agonist antibodies, nucleic acid activators, and the like that activate a molecule that responds to SCF or promotes the expression or functional bioactivity of SCF. In some instances, activation of SCF may be achieved through repression of a SCF inhibitor, e.g., including but not limited to the use of an inhibitory nucleic acid targeting an inhibitor of SCF or an antibody or small molecule directed to a SCF inhibitor. SCF agonists include but are not limited to, e.g., a SCF protein or polypeptide, an agonistic SCF peptide, a nucleic acid encoding a SCF protein or polypeptide, a nucleic acid encoding an agonistic SCF peptide, and the like.

In some instances, an inducing agent useful in a particular induction composition may include a gp130/IL6 superfamily agonist. Gp130/IL6 superfamily agonists will vary and may include small molecules, peptides, nucleic acids, and the like that activate Gp130/IL6 signaling or promotes the functional bioactivity of Gp130/IL6. In some instances, activation of Gp130/IL6 may be achieved through repression of a Gp130/IL6 inhibitor, e.g., including but not limited to the use of an inhibitory nucleic acid targeting an inhibitor of Gp130/IL6 or an antibody or small molecule directed to a Gp130/IL6 inhibitor.

Gp130/IL6 agonists will include a gp130/IL6 agonist binding-pair where such a binding-pair includes a first binding partner and a second binding partner that, when both binding partners are present in the culture medium function as a gp130/IL6 agonist. In some instances, one or more component of the gp130/IL6 agonist binding-pair may be added to the culture media. In other instances, one or more component of the gp130/IL6 agonist binding-pair may be expressed from a cell of the culture. The first and second binding partners of the a gp130/IL6 agonist binding-pair may be ligand receptor pairs, including soluble ligand and soluble receptor pairs that are capable of functioning as a gp130/IL6 agonist including extracellularly activating gp130/IL6.

Exemplary gp130/IL6 agonist binding-pairs include but are not limited to e.g., soluble IL6 and soluble IL6 receptor or a portion thereof (including e.g., soluble IL6 receptor alpha (IL6RA) ectodomain), soluble IL11 and soluble IL11 receptor (IL11R) or a portion thereof, soluble LIF and soluble LIF receptor (LIFR) or a portion thereof, soluble OSM and soluble OSM receptor (OSMR) or a portion thereof, soluble CNTF and soluble CNTF receptor (CNTFR) or a portion thereof, soluble CT1 and soluble CT1 receptor (i.e., LIF receptor (LIFR)) or a portion thereof. In some instances, gp130/IL6 agonist binding-pairs include those pairs containing component parts selected from those described in Taga & Kishimoto (Annu Rev Immunol. 1997; 15:797-81), the disclosure of which is incorporated herein by reference in its entirety.

In some instances, pathway modulating agents, as described above and including pathway activators and pathway inhibitors include, e.g., those that are commercially available, e.g., from such suppliers such as Tocris Bioscience (Bristol, UK), Sigma-Aldrich (St. Louis, Mo.), Santa Cruz Biotechnology (Santa Cruz, Calif.), and the like.

Pluripotent progenitors and derivatives thereof may be contacted with induction agents by any convenient means. Generally an induction agent is added to culture media, as described herein, within which cells of the instant disclosure are grown or maintained, such that the induction agent is present, in contact with the cells, at an effective concentration to produce the desired effect, e.g., induce a desired lineage restriction event. In other instances, e.g., where the existing culture media is not compatible with a particular induction agent, the culture media in which the cells are being grown is replaced with fresh culture media containing the particular induction agent present in the fresh media at an effective concentration to produce the desired effect. In instances where fresh or specific culture media is provided with a particular induction agent the culture agent may, in some instances, be specifically formulated for the particular induction agent, e.g., containing one or more specific additional reagents to, e.g., aid in the delivery of the induction agent, aid in the solubility of the induction agent, aid in the stability of the induction agent, etc.

In instances where a particular induction agent may consists of two or more parts, e.g., in the instance of a specific binding pair including but not limited to e.g., a gp130/IL6 agonist binding pair, both components may be administered simultaneously or the components may be added sequentially provided both components are present together in an effective concentration in the culture medium at the time necessary to perform the desired induction.

The effective concentration of a particular induction agent will vary and will depend on the agent. In addition, in some instances, the effective concentration may also depend on the cells being induced, the culture condition of the cells, other induction agents co-present in the culture media, etc. As such, the effective concentration of induction agents will vary and may range from 1 ng/mL to 10 μg/mL or more, including but not limited to, e.g., 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 11 ng/mL, 12 ng/mL, 13 ng/mL, 14 ng/mL, 15 ng/mL, 16 ng/mL, 17 ng/mL, 18 ng/mL, 19 ng/mL, 20 ng/mL, 21 ng/mL, 22 ng/mL, 23 ng/mL, 24 ng/mL, 25 ng/mL, 26 ng/mL, 27 ng/mL, 28 ng/mL, 29 ng/mL, 30 ng/mL, 31 ng/mL, 32 ng/mL, 33 ng/mL, 34 ng/mL, 35 ng/mL, 36 ng/mL, 37 ng/mL, 38 ng/mL, 39 ng/mL, 40 ng/mL, 41 ng/mL, 42 ng/mL, 43 ng/mL, 44 ng/mL, 45 ng/mL, 46 ng/mL, 47 ng/mL, 48 ng/mL, 49 ng/mL, 50 ng/mL, 1-5 ng/mL, 1-10 ng/mL, 1-20 ng/mL, 1-30 ng/mL, 1-40 ng/mL, 1-50 ng/mL, 5-10 ng/mL, 5-20 ng/mL, 10-20 ng/mL, 10-30 ng/mL, 10-40 ng/mL, 10-50 ng/mL, 20-30 ng/mL, 20-40 ng/mL, 20-50 ng/mL, 30-40 ng/mL, 30-50 ng/mL, 40-50 ng/mL, 1-100 ng/mL, 50-100 ng/mL, 60-100 ng/mL, 70-100 ng/mL, 80-100 ng/mL, 90-100 ng/mL, 10-100 ng/mL, 50-200 ng/mL, 100-200 ng/mL, 50-300 ng/mL, 100-300 ng/mL, 200-300 ng/mL, 50-400 ng/mL, 100-400 ng/mL, 200-400 ng/mL, 300-400 ng/mL, 50-500 ng/mL, 100-500 ng/mL, 200-500 ng/mL, 300-500 ng/mL, 400 to 500 ng/mL, 0.001-1 µg/mL, 0.001-2 µg/mL, 0.001-3 µg/mL, 0.001-4 µg/mL, 0.001-5 µg/mL, 0.001-6 µg/mL, 0.001-7 µg/mL, 0.001-8 µg/mL, 0.001-9 µg/mL, 0.001-10 µg/mL, 0.01-1 µg/mL, 0.01-2 µg/mL, 0.01-3 µg/mL, 0.01-4 µg/mL, 0.01-5 µg/mL, 0.01-6 µg/mL, 0.01-7 µg/mL, 0.01-8 µg/mL, 0.01-9 µg/mL, 0.01-10 µg/mL, 0.1-1 µg/mL, 0.1-2 µg/mL, 0.1-3 µg/mL, 0.1-4 µg/mL, 0.1-5 µg/mL, 0.1-6 µg/mL, 0.1-7 µg/mL, 0.1-8 µg/mL, 0.1-9 µg/mL, 0.1-10 µg/mL, 0.5-1 µg/mL, 0.5-2 µg/mL, 0.5-3 µg/mL, 0.5-4 µg/mL, 0.5-5 µg/mL, 0.5-6 µg/mL, 0.5-7 µg/mL, 0.5-8 µg/mL, 0.5-9 µg/mL, 0.5-10 µg/mL, and the like.

In some instances, the effective concentration of an induction agent in solution, e.g., cell culture media, may range from 1 nM to 100 µM or more, including but not limited to, e.g., 1 nM, 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, 25 nM, 26 nM, 27 nM, 28 nM, 29 nM, 30 nM, 31 nM, 32 nM, 33 nM, 34 nM, 35 nM, 36 nM, 37 nM, 38 nM, 39 nM, 40 nM, 41 nM, 42 nM, 43 nM, 44 nM, 45 nM, 46 nM, 47 nM, 48 nM, 49 nM, 50 nM, 1-2 nM, 1-3 nM, 1-4 nM, 1-5 nM, 1-6 nM, 1-7 nM, 1-8 nM, 1-9 nM, 1-10 nM, 1.5 nM, 1.5-2 nM, 1.5-3 nM, 1.5-4 nM, 1.5-5 nM, 1.5-6 nM, 1.5-7 nM, 1.5-8 nM, 1.5-9 nM, 1.5-10 nM, 2-3 nM, 2-4 nM, 2-5 nM, 2-6 nM, 2-7 nM, 2-8 nM, 2-9 nM, 2-10 nM, 3-4 nM, 3-5 nM, 3-6 nM, 3-7 nM, 3-8 nM, 3-9 nM, 3-10 nM, 4-5 nM, 4-6 nM, 4-7 nM, 4-8 nM, 4-9 nM, 4-10 nM, 5-6 nM, 5-7 nM, 5-8 nM, 5-9 nM, 5-10 nM, 6-7 nM, 6-8 nM, 6-9 nM, 6-10 nM, 7-8 nM, 7-9 nM, 7-10 nM, 8-9 nM, 8-10 nM, 9-10 nM, 5-15 nM, 5-20 nM, 5-25 nM, 5-30 nM, 5-35 nM, 5-40 nM, 5-45 nM, 5-50 nM, 10-15 nM, 10-20 nM, 10-25 nM, 10-30 nM, 10-35 nM, 10-40 nM, 10-50 nM, 15-20 nM, 15-25 nM, 15-30 nM, 15-35 nM, 15-40 nM, 15-45 nM, 15-50 nM, 20-25 nM, 20-30 nM, 20-35 nM, 20-40 nM, 20-45 nM, 20-50 nM, 25-30 nM, 25-35 nM, 25-40 nM, 25-45 nM, 25-50 nM, 30-35 nM, 30-40 nM, 30-45 nM, 30-50 nM, 35-40 nM, 35-45 nM, 35-50 nM, 40-45 nM, 40-50 nM, 45-50 nM, 10-100 nM, 20-100 nM, 30-100 nM, 40-100 nM, 50-100 nM, 60-100 nM, 70-100 nM, 80-100 nM, 90-100 nM, 50-150 nM, 50-200 nM, 50-250 nM, 50-300 nM, 50-350 nM, 50-400 nM, 50-450 nM, 50-500 nM, 10-150 nM, 10-200 nM, 10-250 nM, 10-300 nM, 10-350 nM, 10-400 nM, 10-450 nM, 10-500 nM, 100-150 nM, 100-200 nM, 100-250 nM, 100-300 nM, 100-350 nM, 100-400 nM, 100-450 nM, 100-500 nM, 200-500 nM, 300-500 nM, 400-500 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 200-400 nM, 300-500 nM, 400-600 nM, 500-700 nM, 600-800 nM, 700-900 nM, 800 nM to 1 µM, 0.5-1 µM, 0.5-1.5 µM, 0.5-2 µM, 0.5-2.5 µM, 0.5-3 µM, 0.5-3.5 µM, 0.5-4 µM, 0.5-4.5 µM, 0.5-5 µM, 1 µM, 2 µM, 3 µM, 4 µM, 5 µM, 6 µM, 7 µM, 8 µM, 9 µM, 10 µM, 11 µM, 12 µM, 13 µM, 14 µM, 15 µM, 16 µM, 17 µM, 18 µM, 19 µM, 20 µM, 21 µM, 22 µM, 23 µM, 24 µM, 25 µM, 26 µM, 27 µM, 28 µM, 29 µM, 30 µM, 31 µM, 32 µM, 33 µM, 34 µM, 35 µM, 36 µM, 37 µM, 38 µM, 39 µM, 40 µM, 41 µM, 42 µM, 43 µM, 44 µM, 45 µM, 46 µM, 47 µM, 48 µM, 49 µM, 50 µM, 1-2 µM, 1-3 µM, 1-4 µM, 1-5 µM, 1-6 µM, 1-7 µM, 1-8 µM, 1-9 µM, 1-10 µM, 1.5 µM, 1.5-2 µM, 1.5-3 µM, 1.5-4 µM, 1.5-5 µM, 1.5-6 µM, 1.5-7 µM, 1.5-8 µM, 1.5-9 µM, 1.5-10 µM, 2-3 µM, 2-4 µM, 2-5 µM, 2-6 µM, 2-7 µM, 2-8 µM, 2-9 µM, 2-10 µM, 3-4 µM, 3-5 µM, 3-6 µM, 3-7 µM, 3-8 µM, 3-9 µM, 3-10 µM, 4-5 µM, 4-6 µM, 4-7 µM, 4-8 µM, 4-9 µM, 4-10 µM, 5-6 µM, 5-7 µM, 5-8 µM, 5-9 µM, 5-10 µM, 6-7 µM, 6-8 µM, 6-9 µM, 6-10 µM, 7-8 µM, 7-9 µM, 7-10 µM, 8-9 µM, 8-10 µM, 9-10 µM, 5-15 µM, 5-20 µM, 5-25 µM, 5-30 µM, 5-35 µM, 5-40 µM, 5-45 µM, 5-50 µM, 10-15 µM, 10-20 µM, 10-25 µM, 10-30 µM, 10-35 µM, 10-40 µM, 10-50 µM, 15-20 µM, 15-25 µM, 15-30 µM, 15-35 µM, 15-40 µM, 15-45 µM, 15-50 µM, 20-25 µM, 20-30 µM, 20-35 µM, 20-40 µM, 20-45 µM, 20-50 µM, 25-30 µM, 25-35 µM, 25-40 µM, 25-45 µM, 25-50 µM, 30-35 µM, 30-40 µM, 30-45 µM, 30-50 µM, 35-40 µM, 35-45 µM, 35-50 µM, 40-45 µM, 40-50 µM, 45-50 µM, 10-100 µM, 20-100 µM, 30-100 µM, 40-100 µM, 50-100 µM, 60-100 µM, 70-100 µM, 80-100 µM, 90-100 µM, and the like.

In some instances, the effective concentration of an induction agent will be below a critical concentration such that the induction produces the desired effect essentially without undesirable effects. As used herein, the term "critical concentration" refers to a concentration of induction agent above which undesirable effects are produced. Undesirable effects that may be the result of a concentration exceeding the critical concentration include but are not limited to, e.g., off-target effects (off-target activation of signaling, off-target inhibition of signaling), reduction or loss of function (e.g., loss of desired activator function, loss of desired inhibitor function) reduction of cell viability, increase in cell mortality, lineage restriction towards an undesired cell type, differentiation into an undesired cell type, loss of expression of a particular desired marker, etc. Whether a particular induction agent will have a critical concentration and what the critical concentrations of those agents having a critical concentration are will depend on the agent and the specific conditions in which the agent is used. In one non-limiting example, during induction of paraxial mesoderm the Wnt pathway activator CHIR99021 results in an undesired decrease in marker expression at 4 µM and thus, in the particular context of this embodiment, CHIR99021 has a critical concentration of less than 4 µM.

In some instances, cells of the instant disclosure may be contacted with multiple induction agents and/or multiple induction compositions in order achieve a desired mesodermal cell type of derivative thereof. In some instances, a particular induction composition will contain two or more induction agents such that a particular cell culture is simultaneously contacted with multiple induction agents. In some instances, a particular series of induction compositions may be used, one at a time, in generating a desired mesodermal cell type such that a particular cell culture is successively contacted with multiple induction agents.

The duration of contact of a particular induction composition with a particular cell type will vary and will depend, e.g., on the desired mesodermal cell type, the cell type being induced, and the components of the induction composition. In some instances, a particular induction composition may be introduced for different exposure times depending on the context of use, e.g., cell type X may be contacted with induction composition Y for time Z whereas cell type A may be contacted with induction composition Y for time B, wherein cell type X is different than cell type A and time Z is different than time B. As such, the time cells are contacted with a particular induction composition may vary, e.g., when being used on different cells, when being used to generate different cells, or when being used at different steps of a differentiation process.

The duration of contact of a particular induction composition with a particular cell type, in some instances, may be referred to as the "exposure time" and exposure times may range from a day to weeks or more, including but not limited to e.g., 1 day, 1.5 days, 2 days, 2.5 days, 3 days, 3.5 days, 4 days, 4.5 days, 5 days, 5.5 days, 6 days, 6.5 days, 7 days, 7.5 days, 8 days, 8.5 days, 9 days, 9.5 days, 10 days, 11 days, 12, days, 13, days, 14 days, 15, days, etc. As used herein, exposure times are, in some instances, referred as consisting essentially of, e.g., 24 hours, indicating that the exposure time may be longer or shorter than that specified including those exposure times that are longer or shorter but do not materially affect the basic outcome of the particular exposure. As such, in some instances where a particular exposure is more time sensitive such that under or over exposure, e.g., of more or less than 1 hour, materially affects the outcome of the exposure, a time period consisting essentially of, e.g., 24 hours, will be interpreted to refer to a time period ranging from about 23 hours to about 25 hours. In some other instances where a particular exposure is less time sensitive such that under or over exposure, e.g., of more than 12 hours, does not materially affect the outcome of the exposure, a time period consisting essentially of, e.g., 24 hours will mean a time period ranging from about 12 hours or less to about 36 hours or more. In some instances, depending on the context, an exposure period consisting essentially of 24 hours may refer to an exposure time of 22-26 hours, 21-27 hours, 20-28 hours, 19-29 hours, 18-30 hours, etc.

In some instances, time periods of exposure may be pre-determined such that cells are contacted with an induction composition according to a schedule set forth prior to the contacting. In some instances, the time period of exposure, whether pre-determined or otherwise, may be modulated according to some feature or characteristic of the cells and/or cell culture, including but not limited to, e.g., cell morphology, cell viability, cell appearance, cellular behaviors, cell number, culture confluence, marker expression, etc.

Markers

Aspects of the present disclosure include identifying cells based on the presence or absence or relative amount of one or more markers. In some instances, markers of interest include cell surface markers that may be detected, e.g., on live cells. In other instances, markers of interest include expression markers, e.g., cellular expression markers indicative of cell type.

Markers may be detected or measured by any convenient means as such marker detection is well-known in the art and may make use of one or more detection reagents including but not limited to, e.g., antibodies, antibody fragments, binding partners (e.g., ligands, binding pairs, etc), hybridizable nucleic acids, aptamers, etc. In some instances, a marker may be a cell surface marker and detection of the marker may be performed based on the use of one or more detection reagents that specifically bind to the marker. Detection reagents, e.g., antibodies, may be detectably labeled (e.g., fluorescently labeled through the attachment of a fluorescent molecule, fluorescent bead, or other fluorescent label) or may be detected through the use of a second detectably labeled detection reagent that specifically binds to the first detection reagent (e.g., a fluorescently labeled secondary antibody). In some instances, a detection agent, e.g., having a detectable label or having been bound by a second agent having a detectable label, can be visualized or otherwise observed or detected based on the visual characteristics of the label, including e.g., fluorescent detection, colorimetric detection, and the like. Detectable labels useful in detection reagents need not be visually detectable and may, in some instances, be detected by a detection device configured to detect a non-visual detectable label including but not limited to, e.g., a magnetic label, a radioactive label, etc. In some instances, detectable labels may be detected through the use of one or more detection reactions, including but not limited to, e.g., enzymatic detection reactions (enzymatic reactions generating a detectable substrate, e.g., a fluorescent or colorimetric substrate), amplification reactions (PCR amplification, fluorescent signal amplification (e.g., tyramide signal amplification, etc.), etc.)

In certain aspects of the instant disclosure, methods described make use of cell surface markers detectable on the surface of cells using one or more appropriate detection reagents. Cell surface markers of interest may vary and depend on the type of cell to be detected or the desired cell type being derived. In some instances, a cell surface marker or combination thereof useful in detecting and/or isolating a cell type of interest or a derived mesodermal progenitor cell type is one provided in Table 1, provided in FIG. 15.

In certain embodiments, derived paraxial mesodermal cells may be identified or isolated based on the detection or measurement of the cell surface marker DLL, e.g., identified or isolated based on being positive for DLL, having a high level of DLL or having a level of DLL above a threshold level. As used herein DLL may refer to any DLL protein including but not limited to, e.g., DLL1.

In certain embodiments, derived paraxial mesodermal cells may be identified or isolated based on the detection or measurement of the cell surface marker CXCR4, e.g., identified or isolated based on being positive for CXCR4, having a high level of CXCR4 or having a level of CXCR4 above a threshold level.

In certain embodiments, derived sclerotome cells may be identified or isolated based on the detection or measurement of the cell surface marker PDGFR and various family members of PDGFR including but not limited to, e.g., PDGFRA (i.e., PDGFRα), PDGFRB (i.e., PDGFRβ). In some instances, derived sclerotome cells may be identified or isolated based on the detection or measurement of the cell surface marker PDGFRA, e.g., identified or isolated based on having a high level of PDGFRA or having a level of PDGFRA above a threshold level. In some instances, derived sclerotome cells may be identified or isolated based on the detection or measurement of the cell surface marker PDGFRB, e.g., identified or isolated based on having a high level of PDGFRB or having a level of PDGFRB above a threshold level.

In certain embodiments, derived dermomyotome cells may be identified or isolated based on the detection or measurement of the cell surface marker PDGFR and various isoforms of PDGFR including but not limited to, e.g., PDGFRA (i.e., PDGFRα), PDGFRB (i.e., PDGFRβ). In some instances, derived dermomyotome cells may be identified or isolated based on the detection or measurement of the cell surface marker PDGFRA, e.g., identified or isolated based on having a low level of PDGFRA or having a level of PDGFRA below a threshold level. In some instances, derived dermomyotome cells may be identified or isolated based on the detection or measurement of the cell surface marker PDGFRB, e.g., identified or isolated based on having a low level of PDGFRB or having a level of PDGFRB below a threshold level.

In certain embodiments, derived cardiac mesoderm cells may be identified or isolated based on the detection or measurement of the cell surface marker GARP (i.e. LRRC32), e.g., identified or isolated based on being positive for GARP, having a high level of GARP or having a level of GARP above a threshold level.

In certain embodiments, derived cardiac mesoderm cells may be identified or isolated based on the detection or measurement of the cell surface marker CD143, e.g., identified or isolated based on being positive for CD143, having a high level of CD143 or having a level of CD143 above a threshold level.

In certain embodiments, derived cardiac mesoderm cells may be identified or isolated based on the detection or measurement of the cell surface marker TIE2, e.g., identified or isolated based on being positive for TIE2, having a high level of TIE2 having a level of TIE2 above a threshold level.

In certain embodiments, derived cardiac mesoderm cells may be identified or isolated based on the detection or measurement of the cell surface marker CD1d, e.g., identified or isolated based on being positive for CD1d, having a high level of CD1d having a level of CD1d above a threshold level.

In some instances, identification and/or selection for sorting of cells may be performed using a combination of markers. Such combinations may include but combinations of positive selection markers, combinations of negative selection markers or mixed combinations of positive and negative selection markers.

In certain embodiments marker detection and/or measurement of marker level is performed using flow cytometry. Flow cytometry is a technique for counting, examining, and sorting microscopic particles suspended in a stream of fluid. It allows simultaneous multi-parametric analysis of the physical and/or chemical characteristics of single cells flowing through an optical and/or electronic detection apparatus. Fluorescence-activated cell sorting (FACS) is a specialized type of flow cytometry. FACS provides a method for sorting a heterogeneous mixture of biological cells into two or more containers, generally one cell at a time, based upon the specific light scattering and fluorescent characteristics of each cell. The flow cytometer and the FACS machine are useful scientific instruments as they provide fast, objective and quantitative recording of signals, e.g., fluorescent signals, and/or detection of cellular characteristics, e.g., size, granularity, viability, etc., from individual cells as well as physical separation of cells of particular interest. Fluorescent signals used in flow cytometry, for instance when quantifying and/or sorting cells by any marker present on or in the cell, typically are fluorescently-tagged antibody preparations or fluorescently-tagged ligands for binding to antibodies or other antigen-, epitope- or ligand-specific agent, such as with biotin/avidin binding systems or fluorescently-labeled and optionally addressable beads (e.g. microspheres or microbeads). The markers or combinations of markers detected by the optics and/or electronics of a flow cytometer vary and in some cases include but are not limited to: cell surface markers, intracellular and nuclear antigens, DNA, RNA, cell pigments, cell metabolites, protein modifications, transgenic proteins, enzymatic activity, apoptosis indicators, cell viability, cell oxidative state, etc.

In certain instances, flow cytometry is performed using a detection reagent, e.g., a fluorochrome-labeled antibody, e.g., a monoclonal antibody, with specific avidity against a cell surface maker of interest. A cellular sample is contacted with a detection reagent under conditions sufficient to allow the detection reagent to bind the cell surface maker and the cells of the sample are loaded into the flow cytometer, e.g., by first harvesting the cells from a cell culture using methods known in the art or described herein and re-suspending the isolated cells in a suitable buffer, e.g., running buffer. The cells loaded into the flow cytometer are run through the flow cytometer, e.g., by flowing cell containing buffer or liquid sample through the flow cell of the flow cytometer. The flow cytometer detects events as the cell passes one or more detection areas of the flow cytometer. For example, the flow cytometer may detect fluorescence emitted from a fluorochrome of a detection reagent upon excitation of the fluorochrome with a particular wavelength of light. In some instances, the flow cytometer detects the relative intensity of a particular signal, e.g., fluorescence of a particular detection reagent, of a particular cell, e.g., to quantify the level of a marker present on the surface of the cell and/or to qualitatively categorize the cell, e.g., as a cell that is positive for a particular marker or a cell that is negative for a particular marker. Detected events are counted or otherwise evaluated by the flow cytometer with or without input from an operator and used to determine, e.g., the total number of cells, the number or proportion of cells bound to a particular detection reagent, etc. In instances where FACS is utilized cells may be sorted, e.g., into separate containers, based on the detection or measurement of a particular marker. In some instances, cell sorting, e.g., by FACS, may be utilized to generate a purified population of a desired cell type.

In some instances, a threshold level of a particular detectable marker is used to categorize cells for sorting by FACS. Threshold levels may be used to categorize cells as "positive", "negative, "high", "low", etc. for a particular marker based on the level of detection of the marker. In some instances, a marker threshold level is determined by making a comparison of the levels of marker within a population of cells, e.g., a population of cells of unknown expression levels of Marker X or a population of cells suspected of containing subpopulations of cells having different expression levels of Marker X. For example, the expression level of Marker X is measured on a flow cytometer of at least a sufficient number of cells such that the measurements may be plotted, e.g., on a histogram, and separation between two or more subpopulations of cells is revealed based on individual cell expression levels of Marker X. Accordingly, the flow cytometer operator may then determine a threshold level between the subpopulations that may be used to categorize cells as belonging to a particular subpopulation, e.g., a subpopulation having a low level of expression of Marker X or a subpopulation having high level of expression of Marker X.

In other instances, a threshold is predetermined based on a known or expected difference in marker level between cells of different populations. In some instances, a threshold is pre-calibrated or saved, e.g., in computer readable form, in a device, e.g., a flow cytometer, used in detecting or measuring a marker and/or sorting cells based on marker detection and/or measurement.

In some instances, the marker threshold is based on the limit of detection of the flow cytometer. For example, cells of a population of cells may be identified as expressing a particular marker (i.e. being positive for a particular marker) if the cells have any detectable level of a particular marker. Likewise, cells of a population of cells may be identified as not expressing a particular marker (i.e. being negative for a particular marker) if the cells do not have a detectable level of a particular biomarker. Accordingly, the detection level of the flow cytometer may be used to determine the biomarker threshold.

Expression markers of interest may be used to identify a particular cell type or verify that a derived cell type expresses a characteristic component of the derived cell type. In some instances, detection of expression markers may allow for optimization of a particular differentiation protocol, e.g., to optimize production of a desired cell type based on detection of one or more expression markers. Expression markers will vary depending on the type of cell to be identified or verified and/or desired downstream uses of the cell following identification or verification with the expression marker. Types of expression markers will include but are not limited to, e.g., gene expression marker, protein expression markers, expressed reporters, and the like. Expression marker detection and/or measurement may be detrimental to cell viability (e.g., wherein detection requires lysing or fixing a cell of interest) or may be essentially neutral to cell viability (e.g., wherein detection does not require lysing or fixing a cell of interest and may be performed on live cells).

Gene expression markers include but are not limited to the presence, absence, and/or relative amounts of a particular gene transcript that is indicative of particular cell type. Protein expression markers include but are not limited to the presence, absence, and/or relative amounts of a particular expression product that is indicative of particular cell type. Protein expression markers may be intercellular proteins, intracellular proteins or cell surface proteins. In some instances, a gene expression marker and a protein expression marker derived from the same gene may be indicative of a particular cell type.

Methods of detecting and/or measuring gene expression and/or protein expression are well-known in the art and include but are not limited to, e.g., Northern blot, Western blot, ELISA, PCR, quantitative PCR, in situ hybridization, fluorescent in situ hybridization, immunohistochemistry, immunofluorescence, microarray, quantitative sequencing, RNAseq, quantitative mass spectrometry, and the like.

Gene and protein expression markers useful in characterizing and/or identifying anterior primitive streak cells, e.g., derived as described herein, include but are not limited to, e.g., MIXL1, BRACHYURY, GSC, EOMES, TBX6 (posterior primitive streak cell markers include but are not limited to e.g., MESP1, EVX1, MESP2, FOXF1), and the like. In some instances, the measurement of one or more such anterior primitive streak markers above a particular threshold is indicative of an increased likelihood that an analyzed cell or cell population is an anterior primitive streak cell or are anterior primitive streak cells. Generally, the detection and/or measurement of more such markers increases confidence in such determinations. In certain instances, measurement of one or more anterior primitive streak markers above a particular threshold indicates that a cell is an anterior primitive streak cell or a population of cells are anterior primitive streak cells.

One of skill in the art will readily understand that, in some instances, a marker used in determining a portion of the primitive streak, e.g., the anterior primitive streak, may find use as a marker for other sections of the primitive streak, e.g., mid primitive streak, particularly considering the continuous nature of fate specification along the anterior-to-posterior axis of the primitive streak. As such, use of particular markers and combinations of markers useful in determining a particular cell type along the primitive streak or derived from cells of the primitive streak may vary and selection of markers and/or combinations of, depending on the particular cell type to be identified, is within the skill of the ordinary skilled artisan. The use of a particular marker for more than one cell type, either alone or in combination with other markers, is not limited to cells of the primitive streak and may, in some instances, occur for other related or unrelated cell types. The selection of such markers which may be used in more than one cell type is with within the skill of the ordinary artisan.

Gene and protein expression markers useful in characterizing and/or identifying paraxial mesoderm cells, e.g., derived as described herein, include but are not limited to, e.g., TBX6, MESOGENIN1, CDX2, EVX1, WNT3, WNT5A, FGF4, FGF8, DLL1, CXCR4, and the like. In some instances, the measurement of one or more such paraxial mesoderm markers above a particular threshold is indicative of an increased likelihood that an analyzed cell or cell population is a paraxial mesoderm cell or are paraxial mesoderm cells. Generally, the detection and/or measurement of more such markers increases confidence in such determinations. In certain instances, measurement of one or more paraxial mesoderm markers above a particular threshold indicates that a cell is a paraxial mesoderm cell or a population of cells are paraxial mesoderm cells.

Gene and protein expression markers useful in characterizing and/or identifying early somite cells, e.g., derived as described herein, include but are not limited to, e.g., FOXC2, PARAXIS/TCF15, PAX3, FOXC2, MEOX1, and the like. In some instances, the measurement of one or more such early somite markers above a particular threshold is indicative of an increased likelihood that an analyzed cell or cell population is an early somite cell or are early somite cells. Generally, the detection and/or measurement of more such markers increases confidence in such determinations. In certain instances, measurement of one or more early somite markers above a particular threshold indicates that a cell is an early somite cell or a population of cells are early somite cells. In some instances, gene or protein expression below a particular threshold may be indicative of a cell or cell population being early somite cells or having an increased likelihood of being early somite cells. Such markers wherein expression in early somites may be below a particular threshold include but are not limited to, e.g., TBX6, MESOGENIN1, CDX2, and the like.

Gene and protein expression markers useful in characterizing and/or identifying sclerotome cells, e.g., derived as described herein, include but are not limited to, e.g., FOXC2, MEOX1, UNCX4.1, BAPX1, SOX9, MEOX2, TWIST1, PAX1, PAX9, and the like. In some instances, the measurement of one or more such sclerotome markers above a particular threshold is indicative of an increased likelihood that an analyzed cell or cell population is a sclerotome cell or are sclerotome cells. Generally, the detection and/or measurement of more such markers increases confidence in such determinations. In certain instances, measurement of one or more sclerotome markers above a particular threshold indicates that a cell is a sclerotome cell or a population of cells are sclerotome cells.

Gene and protein expression markers useful in characterizing and/or identifying dermomyotome cells, e.g., derived as described herein, include but are not limited to, e.g., PAX3, PAX7, ALX4, EN1, and the like. In some instances, the measurement of one or more such dermomyotome markers above a particular threshold is indicative of an increased likelihood that an analyzed cell or cell population is a dermomyotome cell or are dermomyotome cells. Generally, the detection and/or measurement of more such markers increases confidence in such determinations. In certain instances, measurement of one or more dermomyotome markers above a particular threshold indicates that a cell is a dermomyotome cell or a population of cells are dermomyotome cells.

Gene and protein expression markers useful in characterizing and/or identifying cartilage cells, e.g., derived as described herein, include but are not limited to, e.g., COL2A1, AGGRECAN, EPIPHYCAN, COMP, and the like. In some instances, the measurement of one or more such cartilage markers above a particular threshold is indicative of an increased likelihood that an analyzed cell or cell population is a cartilage cell or are cartilage cells. Generally, the detection and/or measurement of more such markers increases confidence in such determinations. In certain instances, measurement of one or more cartilage markers above a particular threshold indicates that a cell is a cartilage cell or a population of cells are cartilage cells.

Gene and protein expression markers useful in characterizing and/or identifying mid primitive streak cells, e.g., derived as described herein, include but are not limited to, e.g., MIXL1, BRACHYURY, GSC, EOMES, TBX6, MESP1, EVX1, MESP2, FOXF1, and the like. In some instances, the measurement of one or more such mid primitive streak markers above a particular threshold is indicative of an increased likelihood that an analyzed cell or cell population is a mid primitive streak cell or are mid primitive streak cells. Generally, the detection and/or measurement of more such markers increases confidence in such determinations. In certain instances, measurement of one or more mid primitive streak markers above a particular threshold indicates that a cell is a mid primitive streak cell or a population of cells are mid primitive streak cells.

Gene and protein expression markers useful in characterizing and/or identifying lateral mesoderm cells, e.g., derived as described herein, include but are not limited to, e.g., HAND1, ISL1, FOXF1, NKX2.5, TBX20, and the like. In some instances, the measurement of one or more such lateral mesoderm markers above a particular threshold is indicative of an increased likelihood that an analyzed cell or cell population is a lateral mesoderm cell or are lateral mesoderm cells. Generally, the detection and/or measurement of more such markers increases confidence in such determinations. In certain instances, measurement of one or more lateral mesoderm markers above a particular threshold indicates that a cell is a lateral mesoderm cell or a population of cells are lateral mesoderm cells.

Gene and protein expression markers useful in characterizing and/or identifying lateral mesoderm cells, e.g., derived as described herein, include but are not limited to, e.g., HAND1, ISL1, TBX5, and the like. In some instances, the measurement of one or more such lateral mesoderm markers above a particular threshold is indicative of an increased likelihood that an analyzed cell or cell population is a lateral mesoderm cell or are lateral mesoderm cells. Generally, the detection and/or measurement of more such markers increases confidence in such determinations. In certain instances, measurement of one or more lateral mesoderm markers above a particular threshold indicates that a cell is a lateral mesoderm cell or a population of cells are lateral mesoderm cells.

Gene and protein expression markers useful in characterizing and/or identifying cardiac mesoderm cells, e.g., derived as described herein, include but are not limited to, e.g., NKX2.5, TBX20, HAND1, ISL1, FOXF1, and the like. In some instances, the measurement of one or more such cardiac mesoderm markers above a particular threshold is indicative of an increased likelihood that an analyzed cell or cell population is a cardiac mesoderm cell or are cardiac mesoderm cells. Generally, the detection and/or measurement of more such markers increases confidence in such determinations. In certain instances, measurement of one or more cardiac mesoderm markers above a particular threshold indicates that a cell is a cardiac mesoderm cell or a population of cells are cardiac mesoderm cells.

Gene and protein expression markers useful in characterizing and/or identifying cardiomyocyte cells, e.g., derived as described herein, include but are not limited to, e.g., CARDIAC TROPONIN (TNNT2), MYL2, MYH6, MYH7, MYL7, and the like. In some instances, the measurement of one or more such cardiomyocyte markers above a particular threshold is indicative of an increased likelihood that an analyzed cell or cell population is a cardiomyocyte cell or are cardiomyocyte cells. Generally, the detection and/or measurement of more such markers increases confidence in such determinations. In certain instances, measurement of one or more cardiomyocyte markers above a particular threshold indicates that a cell is a cardiomyocyte cell or a population of cells are cardiomyocyte cells.

Gene and protein expression markers useful in characterizing and/or identifying endocardium cells, e.g., derived as described herein, include but are not limited to, e.g., CD31, CD34, CD144, and the like. In some instances, the measurement of one or more such endocardium markers above a particular threshold is indicative of an increased likelihood that an analyzed cell or cell population is an endocardium cell or are endocardium cells. Generally, the detection and/or measurement of more such markers increases confidence in such determinations. In certain instances, measurement of one or more endocardium markers above a particular threshold indicates that a cell is an endocardium cell or a population of cells are endocardium cells.

Gene and protein expression markers useful in characterizing and/or identifying (pro)epicardium cells, e.g., derived as described herein, include but are not limited to, e.g., WT1, TBX18, and the like. In some instances, the measurement of one or more such (pro)epicardium markers above a particular threshold is indicative of an increased likelihood that an analyzed cell or cell population is a (pro)epicardium cell or are (pro)epicardium cells. Generally, the detection and/or measurement of more such markers increases confidence in such determinations. In certain instances, measurement of one or more (pro)epicardium markers above a particular threshold indicates that a cell is a (pro)epicardium cell or a population of cells are (pro)epicardium cells.

Gene and protein expression markers useful in characterizing and/or identifying early hematopoietic mesoderm cells, e.g., derived as described herein, include but are not limited to, e.g., CD31, CD34, CD144 (VE-cadherin), SCL, LMO2, FLI1, AA4.1, ESAM1, artery markers (SOX17, DLL4, JAG1, EFNB2), and the like. In some instances, the measurement of one or more such early hematopoietic mesoderm markers above a particular threshold is indicative of an increased likelihood that an analyzed cell or cell population is a early hematopoietic mesoderm cell or are early hematopoietic mesoderm cells. Generally, the detection and/or measurement of more such markers increases confidence in such determinations. In certain instances, measurement of one or more early hematopoietic mesoderm markers above a particular threshold indicates that a cell is a early hematopoietic mesoderm cell or a population of cells are early hematopoietic mesoderm cells. Gene and protein expression markers useful in characterizing and/or identifying late hematopoietic mesoderm cells, e.g., derived as described herein, include but are not limited to, e.g., CD31, CD34, CD144 (VE-cadherin), SCL, LMO2, FLI1, AA4.1, ESAM1, artery markers (SOX17, DLL4, JAG1, EFNB2), and the like. In some instances, the measurement of one or more such late hematopoietic mesoderm markers above a particular threshold is indicative of an increased likelihood that an analyzed cell or cell population is a late hematopoietic mesoderm cell or are late hematopoietic mesoderm cells. Generally, the detection and/or measurement of more such markers increases confidence in such determinations. In certain instances, measurement of one or more late hematopoietic mesoderm markers above a particular threshold indicates that a cell is a late hematopoietic mesoderm cell or a population of cells are late hematopoietic mesoderm cells. late hematopoietic mesoderm cells may also be differentiated on the basis of morphological characteristics including e.g., a rudimentary network appearance. In some instances, late hematopoietic mesoderm cells may also be differentiated on the basis of population characteristics including e.g., where the population of cells express a combination of markers above a particular threshold including but not limited to e.g., more than 90% of cell are CD34(+)SOX17(+).

Gene and protein expression markers useful in characterizing and/or identifying arterial endothelial cells, e.g., derived as described herein, include but are not limited to, e.g., CD31, CD34, CD144 (VE-cadherin), SCL, LMO2, FLI1, AA4.1, ESAM1, artery markers (SOX17, DLL4, JAG1, EFNB2), hemogenic markers (RUNX1, MYB), and the like. In some instances, the measurement of one or more such arterial endothelial markers above a particular threshold is indicative of an increased likelihood that an analyzed cell or cell population is an arterial endothelial cell or are arterial endothelial mesoderm cells. Generally, the detection and/or measurement of more such markers increases confidence in such determinations. In certain instances, measurement of one or more arterial endothelial markers above a particular threshold indicates that a cell is an arterial endothelial cell or a population of cells are arterial endothelial cells.

Arterial endothelial cells may also be differentiated on the basis of morphological characteristics including e.g., a distinctive network appearance. In some instances, arterial endothelial cells may also be differentiated on the basis of functional characteristics including e.g., the ability to subsequently form monocytes, the ability to subsequently form macrophages, the ability to subsequently form monocytes and macrophages, etc.

Gene and protein expression markers useful in characterizing and/or identifying hematopoietic intermediate cells, e.g., derived as described herein, include but are not limited to, an elevated expression of conventional hematopoietic stem cell markers including but not limited to e.g., SOX17, SCL, LMO2, RUNX1, GFI1, GFI1B, PU.1, FOS, IKZF1/HELIOS and IKZF2/IKAROS.

Gene and protein expression markers useful in characterizing and/or identifying forelimb-forming lateral plate mesoderm cells, e.g., derived as described herein, include but are not limited to, an elevated expression of TBXS, elevated expression of HOXB4, elevated expression of HOXBS and/or a combination thereof.

Gene and protein expression markers useful in characterizing and/or identifying forelimb progenitor cells, e.g., derived as described herein, include but are not limited to, an elevated expression of TBXS, elevated expression of HOXB4, elevated expression of HOXBS, elevated expression of PRRX1, a decrease in TBX4 expression and/or a combination thereof.

Gene and protein expression markers useful in characterizing and/or identifying hindlimb progenitor cells, e.g., derived as described herein, include but are not limited to, an elevated expression of TBX4, elevated expression of PITX1, elevated expression of PRRX1 and/or a combination thereof.

Expressed markers useful in identifying the above cell types as well as other cell types described herein are not limited to those specifically disclosed as other markers are known in the art may be deployed either independently to identify or characterize a particular cell type or in combination with one or more markers described herein. Furthermore, expressed markers are not limited to those gene products that produce a polypeptide and may include e.g., non-coding RNAs, non-coding transcripts, microRNAs, and the like. For example, in some instances identification and/or characterization of a cell type of interest may make use of one or more differentially expressed long noncoding RNAs as described herein.

In some instances, cells may be identified based on an expressed reporter wherein the expressed reporter may be heterologous sequence introduced into a cell. For example, in some instances, heterologous sequence encoding a detectable reporter may be introduced into a cell such that upon differentiation and/or lineage restriction to a mesodermal cell type of interest the reporter, e.g., a fluorescent molecule, becomes alternatively active or inactive. As describe herein, heterologous sequence may be stably or transiently introduced. Such introduced heterologous sequence may be configured to be responsive to activation of a marker, e.g., a marker of a particular cell type as described herein or known in the art, such that upon expression of the marker the reporter is activated. Alternatively, such introduced heterologous sequence may be configured to be responsive to activation of a marker, e.g., a marker of a particular cell type as described herein or known in the art, such that the reporter is active independent of expression of the marker but upon expression of the marker the reporter is deactivated. Methods of creating and using expression reporters are well-known in art.

Cell Modification

Methods of modification of cells, including modification of pluripotent cells and modification of mesodermal cell types are well-known in the art and include but are not limited to e.g., genetic modification (e.g., through deletion mutagenesis, through substitution mutagenesis), through insertional mutagenesis (e.g., through the introduction of heterologous nucleic acid into the pluripotent cell, etc.), non-mutagenic genetic modification (e.g., the non-mutagenic insertion of heterologous nucleic acid, etc.), epigenetic modification (e.g., through the treatment with one or more specific or general epigenetic modifying agents (e.g., methylation inhibitors, methylation activators, demethylases, etc.), other modifications (e.g., non-genetic labeling, etc.).

Modifications of cells may be transient or stable. In some instances, a modification of a particular pluripotent cell or mesodermal progenitor cell may be stable such that the modification persists through derivation of a desired mesodermal cell type from the pluripotent cell or progenitor cell as described herein. In some instances, stable modifications may persist through introduction of a mesodermally derived cell type into a host. In some instances, stable modifications may persist through proliferation of the cell such that all progenitors of a particular modified cell also contain the subject modification. In some instances, a modification of a particular pluripotent cell or progenitor cell may be transient such that the modification is lost after derivation of a mesodermal cell type of interest from the transiently modified pluripotent cell. In certain instances, transient modifications may persist through one or more rounds of proliferation of the modified cell such that some but not all of the progeny of the modified cell contain the subject modification. In some instances, a transient modification will not persist during proliferation such that none of the progeny of a modified cell will contain the subject modification. In some instances, a transiently modified cell may be configured such that the modification persists through certain aspects of derivation of the cell type of interest, e.g., through derivation of a particular mesodermal cell type of interest, but is lost prior to introduction of the derived cell into a host.
Screening Aspects of the instant disclosure include method of screening pharmacological agents using mesodermal cell types derived according to the methods described herein. In some instances, a plurality cell populations derived according to the methods as described herein are contacted with a plurality of pharmacological agents in order to screen for agents producing a cellular response of interest. A cellular response of interest may be any cellular response including but not limited to, e.g., cell death, cell survival, cell self-renewal, proliferation, differentiation, expression of one or more markers, loss of expression of one or more markers, change in morphology, change in cellular physiology, cellular engraftment, change in cell motility, change in cell migration, production of a particular cellular component, cease of production of a particular cellular component, change in metabolic output, response to stress, and the like.

Screening pharmacological agents using cells described herein may be performed in vitro, e.g., in a tissue culture chamber, on a slide, etc., or may be performed in vivo, e.g., in an animal host, etc. Cells used in such screening assays may be genetically altered or may an unaltered. In some instances, cells generated according to the methods as described herein are used in multiplexed in vitro pharmacological screening. Methods for evaluating cellular responses during in vitro screening are well-known in the art and include but are not limited to, e.g., microscopic methods (e.g., light microscopy, electron microscopy, etc.), expression assays, enzymatic assays, cytological assays (e.g., cellular staining), genomics, transcriptomics, metabolomics, and the like.

In some instances, cells generated according to the methods as described herein are introduced into a host animal and the host animal may be administered a pharmacological agent in order to screen for a response from the introduced cells. In some instances, the cells of the in vivo assay may be directly evaluated, e.g., for an intrinsic response to a pharmacological agent. In some instances, the host animal of the in vivo assay may be evaluated as an indirect measurement of the response of the cells to the pharmacological agent.

In certain embodiments, the subject disclosure includes screening cells derived according to the methods described herein as a method of therapy of an animal model of disease and/or a human disease. Methods of screening cells derived according to the methods described herein as a method of therapy may be, in some instances, performed according to those methods described below regarding using such cells in therapeutic protocols.

In certain embodiments, the subject disclosure includes screening cells derived according to the methods described herein introduced to a host animal as a method of directly evaluating the cells or particular cellular behaviors, e.g., due to an introduced genetic modification or a naturally derived mutation. In one embodiment, genetically modified cells, e.g., having at least one modified genomic locus, derived according to the methods described herein may be introduced into a host animal and the ability of the cells to differentiate into a particular tissue or cell type may be evaluated. In another embodiment, genetically modified cells derived according to the methods described herein may be introduced into a host animal and the behavior of the cells within the host animal and/or within a tissue of the host animal may be evaluated. In another embodiment, cells derived from a donor organism having a particular mutation or phenotype and lineage restricted according to the methods described herein may be introduced into a host animal and the behavior of the cells within the host animal and/or within a tissue of the host animal may be evaluated, including, e.g., the ability of the cells to differentiate into one or more tissue or cell types. The cells may introduced into the host animal in a autologous graft, an allograft, or a xenograft such that the introduced cells may be derived from the host animal, a separate donor of the same species as the host animal, or a separate donor of a different species as compared to the host animal, respectively.

Therapy

Aspects of the disclosure include methods for lessening the symptoms of and/or ameliorating a dysfunction in a mesodermal cell type or a disease of mesodermal origin, herein referred to as mesodermal dysfunction or disorder. Non-limiting examples of mesodermal cell types and/or tissues of mesoderm origin that may be subject to disease or dysfunction that may be treated according to the method described herein include but are not limited to, e.g., muscle precursor or progenitor cells, cells of the muscle, fat precursor or progenitor cells, cells of the fat, dorsal dermis precursor or progenitor cell cells, cells of the dorsal dermis, cartilage precursor or progenitor cells, cells of the cartilage, smooth muscle precursor or progenitor cells, cells of the smooth muscle, cardiomyocyte precursor or progenitor cells, cells of the heart, bone precursor or progenitor cells, cells of the bone, osteocytes, chrondrocytes, cells of tendons, tenocytes, cells of skeletal muscle, cells of cardiac muscle, cells of smooth muscle, myocytes, cardiomyocytes, cells of fat, cells of brown fat, adipocytes, cells of the dermis, fibroblasts, fibrocytes, cells of the blood vessels, endothelial cells, mesangial cells, cells of the kidneys, juxtaglomerular cells, macula densa cells, podocytes, interstitial cells, cells of the blood, lymphocytes, myeloid cells, pericytes, mural cells, and the like.

Treatment methods described herein include therapeutic treatments, in which the subject is inflicted prior to administration, and prophylactic treatments, in which the subject is not inflicted prior to administration. In some embodiments, the subject has an increased likelihood of becoming inflicted or is suspected of having an increased likelihood of becoming inflicted (e.g., relative to a standard, e.g., relative to the average individual, e.g., a subject may have a genetic predisposition to mesodermal dysfunction or disorder and/or a family history indicating increased risk of mesodermal dysfunction or disorder), in which case the treatment can be a prophylactic treatment. In some embodiments, the individual to be treated is an individual with mesodermal dysfunction or disorder. As used herein "mesodermal dysfunction or disorder" includes any form of dysfunction of a mesodermal derived tissue or cell type (including, e.g., bone disease or dysfunction, cartilage disease or dysfunction, muscle disease or dysfunction, etc.). Any and all forms of mesodermal dysfunction, whether treated or untreated, or resulting from any primary condition, whether treated or untreated, are suitable mesodermal dysfunctions or disorders to be treated by the subject methods described herein.

In some instances, the treatment methods described herein include the alleviation or reduction or prevention of one or more symptoms of mesodermal dysfunction or disorder. Symptoms of mesodermal dysfunction or disorder will vary, may be infrequent, occasional, frequent, or constant.

The methods of treatment described herein include administering a therapeutically effective amount of a population, e.g., an essentially homogenous population, of mesodermal cell types to a subject in need thereof in order to treat the subject for a mesodermal dysfunction or deficiency. In some instances the mesodermal dysfunction or deficiency is bone disease and the effective amount is a dose effective (i.e. a therapeutically effective dose) to obtain a desired pharmacologic and/or physiologic effect in the subject with bone disease including, e.g., reducing the symptoms of bone disease.

The effective amount administered varies depending upon the goal of the administration, the health and physical condition of the individual to be treated, age, the taxonomic group of individual to be treated (e.g., human, non-human primate, primate, etc.), the degree of resolution desired (e.g., the amount of alleviation or reduction of symptoms), the formulation of the cell composition, the treating clinician's assessment of the medical situation, and other relevant factors.

A "therapeutically effective dose" or "therapeutic dose" is an amount sufficient to effect desired clinical results (i.e., achieve therapeutic efficacy) or reduce, alleviate, or prevent symptoms to a desired extent as determined by the patient or the clinician. A therapeutically effective dose can be administered in one or more administrations. For purposes of this disclosure, a therapeutically effective dose of cells (e.g., cartilage cells, bone cells, muscle cells, dermomyotome cells, sclerotome cells, cardiac mesodermal cells, cardiomyocytes, paraxial mesodermal cells, lateral mesodermal cells, and the like) and/or compositions (e.g., cartilage cell compositions, bone cell compositions, muscle cell compositions, dermomyotome cell compositions, sclerotome cell compositions, cardiac mesodermal cell compositions, cardiomyocyte compositions, paraxial mesodermal cell compositions, lateral mesodermal cell compositions, and the like) is an amount that is sufficient, when administered to (e.g., transplanted into) the individual, to palliate, ameliorate, stabilize, reverse, prevent, slow or delay the progression of the disease state (e.g., cartilage cell dysfunction, bone cell dysfunction, muscle cell dysfunction, cartilage cell deficiency, bone cell deficiency, muscle cell deficiency, etc.) by, for example, inducing stabilization, repair, or regeneration of existing mesodermally derived tissues, e.g., cartilage, bone, muscle.

In some embodiments, a therapeutically effective dose of cells (e.g., derived mesodermal cell types, etc.) is one cell or more (e.g., $1 \times 10^2$ or more, $5 \times 10^2$ or more, $1 \times 10^3$ or more, $5 \times 10^3$ or more, $1 \times 10^4$ cells, $5 \times 10^4$ or more, $1 \times 10^5$ or more, $5 \times 10^5$ or more, $1 \times 10^6$ or more, $2 \times 10^6$ or more, $5 \times 10^6$ or more, $1 \times 10^7$ cells, $5 \times 10^7$ or more, $1 \times 10^9$ or more, $5 \times 10^9$ or more, $1 \times 10^9$ or more, $5 \times 10^9$ or more, or $1 \times 10^{10}$ or more).

In some embodiments, a therapeutically effective dose of cells is in a range of from $1 \times 10^3$ cells to $1 \times 10^{10}$ cells (e.g., from $5 \times 10^3$ cells to $1 \times 10^{10}$ cells, from $1 \times 10^4$ cells to $1 \times 10^{10}$ cells, from $5 \times 10^4$ cells to $1 \times 10^{10}$ cells, from $1 \times 10^5$ cells to $1 \times 10^{10}$ cells, from $5 \times 10^5$ cells to $1 \times 10^{10}$ cells, from $1 \times 10^6$ cells to $1 \times 10^{10}$ cells, from $5 \times 10^6$ cells to $1 \times 10^{10}$ cells, from $1 \times 10^7$ cells to $1 \times 10^{10}$ cells, from $5 \times 10^7$ cells to $1 \times 10^{10}$ cells, from $1 \times 10^8$ cells to $1 \times 10^{10}$ cells, from $5 \times 10^8$ cells to $1 \times 10^{10}$, from $5 \times 10^3$ cells to $5 \times 10^9$ cells, from $1 \times 10^4$ cells to $5 \times 10^9$ cells, from $5 \times 10^4$ cells to $5 \times 10^9$ cells, from $1 \times 10^5$ cells to $5 \times 10^9$ cells, from $5 \times 10^5$ cells to $5 \times 10^9$ cells, from $1 \times 10^6$ cells to $5 \times 10^9$ cells, from $5 \times 10^6$ cells to $5 \times 10^9$ cells, from $1 \times 10^7$ cells to $5 \times 10^9$ cells, from $5 \times 10^7$ cells to $5 \times 10^9$ cells, from $1 \times 10^8$ cells to $5 \times 10^9$ cells, from $5 \times 10^8$ cells to $5 \times 10^9$, from $5 \times 10^3$ cells to $1 \times 10^9$ cells, from $1 \times 10^4$ cells to $1 \times 10^9$ cells, from $5 \times 10^4$ cells to $1 \times 10^9$ cells, from $1 \times 10^5$ cells to $1 \times 10^9$ cells, from $5 \times 10^5$ cells to $1 \times 10^9$ cells, from $1 \times 10^6$ cells to $1 \times 10^9$ cells, from $5 \times 10^6$ cells to $1 \times 10^9$ cells, from $1 \times 10^7$ cells to $1 \times 10^9$ cells, from $5 \times 10^7$ cells to $1 \times 10^9$ cells, from $1 \times 10^8$ cells to $1 \times 10^9$ cells, from $5 \times 10^8$ cells to $1 \times 10^9$, from $5 \times 10^3$ cells to $5 \times 10^8$ cells, from $1 \times 10^4$ cells to $5 \times 10^8$ cells, from $5 \times 10^4$ cells to $5 \times 10^8$ cells, from $1 \times 10^5$ cells to $5 \times 10^8$ cells, from $5 \times 10^5$ cells to $5 \times 10^8$ cells, from $1 \times 10^6$ cells to $5 \times 10^8$ cells, from $5 \times 10^6$ cells to $5 \times 10^8$ cells, from $1 \times 10^7$ cells to $5 \times 10^8$ cells, from $5 \times 10^7$ cells to $5 \times 10^8$ cells, or from $1 \times 10^8$ cells to $5 \times 10^8$ cells).

In some embodiments, the concentration of cells (e.g., derived mesodermal cell types, etc.) to be administered is in a range of from $1 \times 10^5$ cells/ml to $1 \times 10^9$ cells/ml (e.g., from $1 \times 10^5$ cells/ml to $1 \times 10^8$ cells/ml, from $5 \times 10^5$ cells/ml to $1 \times 10^8$ cells/ml, from $5 \times 10^5$ cells/ml to $5 \times 10^7$ cells/ml, from $1 \times 10^6$ cells/ml to $1 \times 10^8$ cells/ml, from $1 \times 10^6$ cells/ml to $5 \times 10^7$ cells/ml, from $1 \times 10^6$ cells/ml to $1 \times 10^7$ cells/ml, from $1 \times 10^6$ cells/ml to $6 \times 10^6$ cells/ml, or from $2 \times 10^6$ cells/ml to $8 \times 10^6$ cells/ml).

In some embodiments, the concentration of cells to be administered is $1 \times 10^5$ cells/ml or more (e.g., $1 \times 10^5$ cells/ml or more, $2 \times 10^5$ cells/ml or more, $3 \times 10^5$ cells/ml or more, $4 \times 10^5$ cells/ml or more, $5 \times 10^5$ cells/ml or more, $6 \times 10^5$ cells/ml or more, $7 \times 10^5$ cells/ml or more, $8 \times 10^5$ cells/ml or more, $9 \times 10^5$ cells/ml or more, $1 \times 10^6$ cells/ml or more, $2 \times 10^6$ cells/ml or more, $3 \times 10^6$ cells/ml or more, $4 \times 10^6$ cells/ml or more, $5 \times 10^6$ cells/ml or more, $6 \times 10^6$ cells/ml or more, $7 \times 10^6$ cells/ml or more, or $8 \times 10^6$ cells/ml or more).

A therapeutically effective dose of cells may be delivered or prepared and any suitable medium, including but not limited to, e.g., those described herein. Suitable medium for the delivery of a therapeutically effective dose of cells will vary and may depend on, e.g., the type of pluripotent cells from which the effective dose of cells is derived or the type of derived cells of the effective dose. In some instances, a suitable medium may be a basal medium. "Cell medium" as used herein are not limited to liquid media may, in some instances, include non-liquid components or combinations of liquid media and non-liquid components. Non-liquid components that may find use a delivery or preparation medium include those described herein and those known in the art. In some instances, non-liquid components include natural or synthetic extra cellular matric components including but not limited to, e.g., basement membrane matrix components and the like.

In some instances, an effective dose of the cells described herein may be co-administered with one or more additional agents (e.g., prepared in a suitable medium). For example, an effective dose of derived mesodermal cell types from a homogenous population of cells derived according to the methods described herein may be co-administered with one or more additional agents. Additional agents useful in such co-administration include agents that improve the overall effectiveness of the effective dose of cells or decrease the dose of cells necessary to achieve an effect essentially equal to administration of an effective dose of the cells without the additional agent. Non-limiting examples of additional agents that may be co-administered with derived mesodermal cell types derived according to the methods described herein include: conventional agents for treating diseases of the mesodermally derived tissues, non-mesodermally derived cell types, pro-survival factors, pro-engraftment factors, functional mobilization agents, and the like. Additional agents useful in co-administration also include agents useful in treating or preventing conditions associated with mesodermally derived tissue dysfunction (e.g., agents useful in treating or preventing bone disease, cartilage disease, muscle disease, etc.).

By conventional agents for treating diseases or dysfunction of mesodermally derived tissue is meant agents known in the art that prevent or inhibit disease or dysfunction of mesodermally derived tissues including but not limited to, e.g., bone disease, cartilage disease, muscle disease or symptoms of bone disease, cartilage disease, muscle disease or conditions or symptoms of conditions related to bone disease, cartilage disease, muscle disease.

By non-mesodermally derived cell types is meant a progenitor cell that has not been lineage restricted to the mesodermal cell lineage or a fate-restricted cell that is of a lineage other than that of the mesodermal cell lineage. Encompassed within the term non-mesodermally derived cell types are other stem cells or pluripotent or totipotent progenitors including but not limited to e.g., endodermal cell types, ectodermal cell types, embryonic stem cells, undifferentiated induced pluripotent stem (iPS) cells, and the like.

By pro-survival factors is meant a factor or agent that may be added to the medium, culture media, delivery excipient, or storage solution that promotes the survival of a desired cell type. Such pro-survival factors may be general pro-survival factors that generally promote the survival of most cell types or may be specific pro-survival factors that only promote the survival of certain specific cell types. In some instances, pro-survival factors of the subject disclosure include but are not limited to, e.g., Rho-associated kinase (ROCK) inhibitor, pinacidil, allopurinol, uricase, cyclosporine (e.g., low does, i.e., sub-immunosuppressive dose, cyclosporine), ZVAD-fmk, pro-survival cytokines (e.g., insulin-like growth factor-1 (IGF-1)), extra cellular matrix (ECM) components, hydrogels, matrigel, collagen, gelatin, agarose, alginate, poly(ethylene glycol), hyaluronic acid, etc.

By pro-engraftment factors is meant a factor or agent that may be added to the administered dose or the delivery excipient or the cell storage solution that, upon delivery of the cells into a subject for treatment, increase the engraftment of the administered cells into the tissue targeted for engraftment and therapy. In some instances, pro-engraftment factors include factors that physically retain the administered cells at the delivery site, e.g., the injection site in the case of direct injection to the affected area, including but not limited to, e.g., gels, polymers, and highly viscous liquids that have physical properties that prevent the administered cells from freely diffusing. Such gels, polymers, and highly viscous liquids include but are not limited to e.g., ECM components, hydrogels, matrigel, collagen, gelatin, agarose, alginate, poly(ethylene glycol), and the like.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

The cells may be introduced by injection, catheter, intravenous perfusion, or the like. The cells may be frozen at liquid nitrogen temperatures and stored for long periods of time, being capable of use upon thawing. Once thawed, the cells may be expanded by use of growth factors and/or feeder cells or in feeder-free conditions associated with progenitor cell proliferation and differentiation. In some instances, the cells may be administered fresh such that the cells are expanded and differentiated and administer without being frozen.

The cells (e.g., derived mesodermal cell types, etc.) and/or compositions (e.g., derived mesodermal cell type compositions) of this disclosure can be supplied in the form of a pharmaceutical composition, comprising an isotonic excipient or buffer or media prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition will be adapted in accordance with the route and device used for administration. The composition may also comprise or be accompanied with one or more other ingredients that facilitate the engraftment or functional mobilization of the cells. Suitable ingredients include matrix proteins that support or promote adhesion of the cells, or complementary cell types.

Cells of the subject methods (e.g., derived mesodermal cell types, differentiated mesodermal cell types, etc.) may be autologously derived. By autologously derived it is meant that the cells are derived from the subject that is to be treated with the cells. The cells may be derived from a tissue sample obtained from the subject including but not limited to, e.g., a blood sample (e.g., a peripheral blood sample), a skin sample, a bone marrow sample, and the like. In some instances, the sample from which cells are derived may be a biopsy or swab, e.g., a biopsy or swab collected to diagnose, monitor, or otherwise evaluate the subject, e.g., diagnose the subject for a mesodermal dysfunction or deficiency, e.g., bone disease or a muscle disease or a cartilage disease or a related condition, or for cell collection. In some instances, the autologous sample from which the cells are derived may be a previously collected and stored sample, e.g., a banked tissue sample, from the subject to be treated, including but not limited to e.g., banked cardiac tissue or cells, banked musculoskeletal tissue or cells, banked reproductive tissue or cells, banked skin tissue or cells, banked bone tissue or cells, banked bone marrow tissue or cells, banked vascular tissue or cells, banked umbilical cord blood tissue or cells, and the like.

In some instances, cells of the subject methods (e.g., derived mesodermal cell types, differentiated mesodermal cell types, etc.) may be non-autologously derived. By non-autologously derived it is meant that the cells are not derived from the subject that is to be treated with the cells. In some instances, non-autologously derived cells may be xeno-derived (i.e., derived from a non-human animal) or allo-derived (i.e. derived from a human donor other than the subject to be treated). Non-autologously derived cells or tissue may be derived from any convenient source of cells or tissue collected by any convenient means.

Whether to use autologously derived or non-autologously derived cells may be determined according to the discretion of the subject's clinician and may depend on, e.g., the health, age, genetic predisposition or other physical state of the subject. In some instances, autologous cells may be preferred, including, e.g., to decrease the risk or immune rejection of the transplanted cells. In some instances, non-autologous cells may be preferred, including, e.g., when the subject has a genetic defect that affects mesodermally derived tissues.

Methods of derivation of pluripotent progenitor cells from an autologous or non-autologous tissue useful in the methods described herein include but are not limited to, e.g., methods of embryonic stem cell derivation and methods of induced pluripotent stem cell derivation. In some instances, methods as described herein may be performed using non-autologous pluripotent progenitor cells previously derived including, e.g., those publically or available or commercially available (e.g., from Biotime, Inc., Alameda, Calif.). In some instances, methods as described herein may be performed using newly derived non-autologous pluripotent progenitor cells or newly derived autologous pluripotent progenitor cells including but not limited to, e.g., newly derived embryonic stem cells (ESC) (including, e.g., those derived under xeno-free conditions as described in, e.g., Lei et al. (2007) *Cell Research,* 17:682-688) and newly derived induced pluripotent stem cells (iPS). General methods of inducing pluripotency to derive pluripotent progenitor cells are described in, e.g., Rodolfa K T, (2008) *Inducing pluripotency*, StemBook, ed. The Stem Cell Research Community, doi/10.3824/stembook.1.22.1 and Selvaraj et al. (2010) *Trends Biotechnol,* 28(4)214-23, the disclosures of which are incorporated herein by reference. In some instances, pluripotent progenitor cells, e.g., iPS cells, useful in the methods described herein are derived by reprogramming and are genetically unmodified, including e.g., those derived by integration-free reprogramming methods, including but not limited to those described in Goh et al. (2013) *PLoS ONE* 8(11): e81622; Awe et al (2013) *Stem Cell Research & Therapy,* 4:87; Varga (2014) *Exp Cell Res,* 322(2)335-44; Jia et al. (2010) *Nat Methods,* 7(3):197-9; Fusaki et al. (2009) *Proc Jpn Acad Ser B Phys Biol Sc.* 85(8):348-62; Shao & Wu, (2010) *Expert Opin Biol Ther.* 10(2):231-42; the disclosures of which are incorporated herein by reference.

In some instances, the derived or obtained pluripotent progenitor cells are prepared, dissociated, maintained and/or expanded in culture prior to being differentiated and/or lineage restricted as described herein.

In some instances, before differentiation or lineage restriction of the pluripotent progenitor cells the pluripotent progenitor cells are dissociated, e.g., to generate a single-cell suspension. In some instances, the dissociation of the pluripotent progenitors is chemical, molecular (e.g., enzyme mediated), or mechanical dissociation. Methods of chemical, molecular, and/or enzyme mediated dissociation will vary and in some instances may include but are not limited to the use of, e.g., trypsin, TrypLE Express™, TrypLE Select™ Accutase®, StemPro® (Life Technologies, Inc., Grand Island, N.Y.), calcium and magnesium free media, low calcium and magnesium medium, and the like. In some instances the dissociation media may further include pro-survival factors including but not limited to, e.g., Rho-associated kinase (ROCK) inhibitor, pinacidil, allopurinol, uricase, cyclosporine (e.g., low does, i.e., sub-immunosuppressive dose, cyclosporine), ZVAD-fmk, pro-survival cytokines (e.g., insulin-like growth factor-1 (IGF-1)), Thiazovivin, etc.

In some instances, methods of culturing pluripotent stem cells include xeno-free culture conditions wherein, e.g., human cells are not cultured with any reagents derived from non-human animals. In some instances, methods culturing of pluripotent stem cells include feeder-free culture conditions, wherein the pluripotent stem cells are cultured under conditions that do not require feeder cells and/or in feeder cell free medium, including e.g., commercially available feeder-free mediums, such as, e.g., those available from STEM-CELL Technologies, Inc. (Vancouver, BC). In some instances, methods culturing of pluripotent stem cells include culture conditions that include supplemental serum, including e.g. supplement of autologously derived serum, e.g., as described in Stute et al. (2004) *Exp Hematol,* 32(12):1212-25. In some instances, methods of culturing of pluripotent cells or derivatives thereof include culture conditions that are serum-free, meaning the culture media does not contain animal, mammal, or human derived serum. Serum-free culture conditions may be performed for only a portion of the life of the culture or may performed for the entire life of the culture. In some instances, serum-free culture conditions are used for a particular method step or procedure, e.g., during differentiation, during lineage restriction, prior to or during harvesting, etc. As is known in the art, in some instances, cells may be cultured in two dimensional or three dimensional formats (e.g., on non-coated or coated surfaces or within a solid or semi-solid matrix). Instances where two dimensional or three dimensional culture is appropriate for use in the methods as described herein, e.g., to promote survival or differentiation of a desired cell type, will be readily apparent to the ordinary skilled artisan. In some instance the pluripotent progenitor cell media includes one or more pro-survival factors, e.g., including those described herein. General methods of culturing human pluripotent progenitor cells are described in, e.g., Freshney et al. (2007) *Culture of human stem cells*, Wiley-Interscience, Hoboken, N.J. and Borowski et al. (2012) *Basic pluripotent stem cell culture protocols*, StemBook, ed. The Stem Cell Research Community, StemBook, doi/10.3824/stembook, the disclosures of which are incorporated herein by reference.

In some instances, the pluripotent progenitor cells used according to the methods described herein may be genetically unmodified. By "genetically unmodified" is meant that essentially no modification of the genome of the cells transplanted into the subject has been performed. Encompassed within the term genetically unmodified are instances wherein transient genetic modification is performed at some point during the derivation of the cells but essentially no genetic modification persists in the cells that are eventually transplanted into the subject (i.e. the cells are essentially indistinguishable before the transient genetic modification and after the course of the transient modification). Also encompassed within the term genetically unmodified are instances wherein the genome of the cells is not transiently or stably modified, e.g., where the cells are manipulated, e.g., pluripotent progenitors are derived or cells are transformed, without genetic modification (e.g., modification of the nucleotide sequence of the genome) of the cells.

In some instances, the cells (e.g., derived mesodermal cell types, differentiated mesodermal cell types, etc.) used according to the methods described herein may be genetically modified. By "genetically modified" is meant that at least one nucleotide is added to, changed within, or deleted from of the genome of the cell. In some instances, the genetic modification may be an insertion of a heterologous sequence, e.g., a sequence that encodes a tag, a label sequence, a reporter, a selectable marker, a gene encoding a protein from a species different from that of the host cell, etc. In some instances, the genetic modification corrects a defect or a mutation within the cell, e.g., corrects an anomalous mutation that confers a mesodermally derived tissue dysfunction or deficiency. In some instances, the genetic modification deletes or renders inoperable an endogenous gene of the host cell. In some instances, the genetic modification enhances an endogenous gene of the host cell. In some instances, the genetic modification represents a change that enhances survival, control of proliferation, and the like. Cells may be genetically altered by transfection or transduction with a suitable vector, homologous recombination, or other appropriate technique, so that they express a heterologous sequence or have altered expression of an endogenous gene.

For further elaboration of general techniques useful in the practice of this disclosure, the practitioner can refer to standard textbooks and reviews in cell biology, tissue culture, and embryology. With respect to tissue culture and stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998).

Systems

Also provided are systems for use in practicing the subject methods. Systems of the subject disclosure may include a cell production system, e.g., for the production of a homogenous or highly pure population of derived mesodermal cell types from pluripotent progenitor cells.

In some instances, the cell production system includes a cell culture chamber or cell culture vessel for the culture of desired cell types. Such cell culture chambers may be configured for the expansion of pluripotent progenitor cells and for the differentiation and/or lineage restriction of such pluripotent progenitor cells into desired cell types, e.g., derived mesodermal cell types and/or differentiated mesodermal cell types. In some instances, the cell culture chamber is also configured for the expansion of mesodermal cell types and/or differentiated mesodermal cell types. In certain embodiments, the cell culture chamber or cell culture vessel may be an open culture system, including but not limited to e.g., tissue culture dishes, tissue culture plates, tissue culture multi-well plates, tissue culture flasks, etc. In certain embodiments, the cell culture chamber or cell culture vessel may be a closed culture system, including e.g., a bioreactor, a stacked tissue culture vessel (e.g., CellSTACK Culture Chambers available from Corning, Inc. Corning, N.Y.). In some instances, culture media and or other factors or agents may be exchanged in and out of the cell culture chamber through the use of one or more pumps (e.g., syringe pumps, peristaltic pumps, etc.) or gravity flow devices. In instances where the cells are cultured under sterile conditions the culture system may allow for the sterile exchange of culture media, e.g., through the use of sterile tubing connected, sealed, and reconnected through the use of a sterile devices, including but not limited to, e.g., a sterile tube welder and/or a sterile tube sealer. The cell culture system may be configured to control certain environmental conditions, including but not limited to e.g., temperature, humidity, light exposure, air composition (e.g., oxygen levels, carbon dioxide levels, etc.) to achieve the conditions necessary for expansion and/or differentiation of desired cell types. In some instances, the cell culture chamber may include a cell culture vessel that includes one or more patterned cell culture substrates or one or more arrays of patterned cell culture substrates as described herein.

The cell culture chamber may be configured for the production of cells for clinical use, e.g., according to current good manufacturing practice (cGMP) compliant cell culture practices, including the methods and configurations described in e.g., Fekete et al. *PLoS ONE* (2012) 7(8): e43255; Pham et al. (2014) *J Trans Med* 12:56; Gastens et al. (2007) *Cell Transplant* 16(7):685-96; Fernandes et al. (2013) *Stem Cell Bioprocessing: For Cellular Therapy, Diagnostics and Drug Development*, Burlington, Oxford: Elsevier Science: Woodhead Publishing, the disclosures of which are incorporated herein by reference.

The cell production system may, in some instances, by computer controlled and/or automated. Automated and/or computer controlled cell production systems may include a "memory" that is capable of storing information such that it is accessible and retrievable at a later time or date by a computer. Any convenient data storage structure may be chosen, based on the means used to access the stored information. In certain aspects, the information may be stored in a "permanent memory" (i.e. memory that is not erased by termination of the electrical supply to a computer or processor) or "non-permanent memory". Computer harddrive, CD-ROM, floppy disk, portable flash drive and DVD are all examples of permanent memory. Random Access Memory (RAM) is an example of non-permanent memory. A file in permanent memory may be editable and re-writable.

In in certain instances, a computer controlled and/or automated cell culture system may include a module or program stored in memory for production of cells according to the methods described herein. Such a module may include instructions for the administration of induction agent and/or induction compositions, e.g., at particular timing intervals or according to a particular schedule, in order to generate a desired mesodermally derived cell type. In some instances, such a computer module may further include additional modules for routine cell culture tasks including but not limited to, e.g., monitoring and record keeping, media changes, environmental monitoring, etc.

Systems of the present disclosure include components and/or devices for delivering cells produced according to the methods described herein to a subject in need thereof. For example, in some instances a system for treating a subject with a mesodermal derived tissue dysfunction or deficiency includes a cell injection system for delivering cells in a carrier, with or without optional adjuvants, to a desired injection site, including diseased tissue, adjacent to diseased tissue, and/or within, on or near a dysfunctioning organ. Such systems utilize known injection devices (e.g., including but not limited to needles, bent needles, cannulas, syringes, pumps, infusion devices, diffusion devices, etc.) and techniques (e.g., including but not limited to intramuscular injection, subcutaneous injection, device-guided injection, etc.). In some instances, a device or technique used for the delivery of a cell scaffold or other bioengineered device may be configured or adapted for use in a cell delivery system for use in delivering cells derived according to the methods described herein In addition to the above described components systems of the subject disclosure may include a number of additional components, such as data output devices, e.g., monitors and/or speakers, data input devices, e.g., interface ports, keyboards, etc., fluid handling components, power sources, controllers, etc.

Compositions and Kits

Also provided are compositions and kits for use in the subject methods. The subject compositions and kits include any combination of components for performing the subject methods. In some embodiments, a composition can include, but is not limited to and does not require, the following: cell dissociation agents and/or media, cell reprogramming agents and/or media, pluripotent progenitor cells, cell culture agents and/or media, cell differentiation agents and/or media; lineage restriction agents (e.g., induction agents) and/or media; conventional agents for treating diseases and/or dysfunctions of mesodermally derived tissues, non-mesodermally derived cell types, pro-survival factors, pro-engraftment factors, functional mobilization agents and any combination thereof.

In some embodiments, a kit can include, but is not limited to and does not require, the following: any of the above described composition components, a sample collection container, a sample collection device (e.g., a sample collection container that includes a sample enrichment mechanism including, e.g., a filter), a tissue collection device (e.g., a biopsy device), a tissue dissociation device, a cell culture vessel, a cell production system; and any combination thereof.

In some embodiments, a kit can include, but is not limited to and does not require, a cell delivery system and/or a cell injection system configured for delivery of cells derived according to the methods described herein. For example, a kit may include a cell injection system configured for injection or delivery of cells into a desired area of the subject in order to effectively treat the subject for a mesodermally derived tissue dysfunction or deficiency, e.g., through delivery of cells to the mesodermally derived tissue. Such kits may include a cell delivery or injection system, as described herein, including individual components of such systems in assembled or unassembled form. In some instances, cells derived according to the methods described herein may be "preloaded" into a cell injection or delivery system such that the system is provided in a "ready-to-use" configuration. In other instances, a cell injection or delivery system may be provided in an "unloaded" configuration such that cells derived according to the methods described herein must be loaded into the system, with any desired carrier or vehicle, prior to use.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is electronic, e.g., a website address which may be used via the internet to access the information at a removed site.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., room temperature (RT); base pairs (bp); kilobases (kb); picoliters (ph; seconds (s or sec); minutes (m or min); hours (h or hr); days (d); weeks (wk or wks); nanoliters (nl); microliters (ul); milliliters (ml); liters (L); nanograms (ng); micrograms (ug); milligrams (mg); grams ((g), in the context of mass); kilograms (kg); equivalents of the force of gravity ((g), in the context of centrifugation); nanomolar (nM); micromolar (uM), millimolar (mM); molar (M); amino acids (aa); kilobases (kb); base pairs (bp); nucleotides (nt); intramuscular (i.m.); intraperitoneal (i.p.); subcutaneous (s.c.); and the like.

Materials and Methods

Unless specifically designated otherwise, the examples provided below make use of the materials and methods described here.

Primitive Streak and Mesoderm Subtype Induction

All differentiation was conducted in serum-free CDM2 basal medium in monolayer feeder-free conditions. hPSCs were sparsely passaged ~1:15-1:20 as fine clumps (using Accutase) onto Geltrex (Gibco)-coated cell culture wells and cultured overnight in mTeSR1+1 µM thiazovivin. The following morning, hPSCs were differentiated towards anterior PS (30 ng/mL Activin+4 µM CHIR+20 ng/mL FGF2+100 nM PIK90; for subsequent paraxial differentiation) or mid PS (30 ng/mL Activin+40 ng/mL BMP4+6 µM CHIR+20 ng/mL FGF2+100 nM; for subsequent lateral differentiation) for 24 hrs. D1 anterior PS→D2 paraxial mesoderm (1 µM A8301+3 µM CHIR+250 nM LDN193189+20 ng/mL FGF2) for 24 hrs. D1 mid PS→D2 lateral mesoderm (1 µM A8301+30 ng/mL BMP4+1 µM C59) for 24 hrs.

Differentiation to Somitic Progeny

D2 paraxial mesoderm→D3 early somites (1 µM A8301+1 µM C59+250 nM LDN193189+500 nM PD0325901) for 24 hrs. D3 early somites→either D5-6 sclerotome (5 nM 21K+1 µM C59) or D5 dermomyotome (3 µM CHIR+150 nM Vismodegib, sometimes with 50 ng/mL BMP4) for 48-72 hrs. D5 sclerotome→D8 smooth muscle-like cells (10 ng/mL TGFβ1+2 ng/mL PDGF-BB (Cheung et al., 2012)) for 72 hrs. D6 sclerotome→D9-D12 cartilage-like cells (20 ng/mL BMP4) for 3-6 days. For skeletal muscle differentiation, see below.

Ectopic Human Bone Formation

BCL2-2A-GFP H9 hESCs were differentiated into D6 sclerotome as above, and $1.5 \times 10^7$ cells were mixed 1:1 in CDM2 and Matrigel (BD) and subcutaneously transplanted into NOD-SCID Il2rg-/- mice, which were sacrificed ~2 months later.

Differentiation to Cardiac Mesoderm and Cardiac Fates

D2 lateral mesoderm→D4 cardiac mesoderm (1 µM A8301+30 ng/mL BMP4+1 µM C59+20 ng/mL FGF2) for 48 hrs. D4 cardiac mesoderm→D6-8 cardiomyocyte populations (30 ng/mL BMP4+1 µM XAV939+200 µg/mL 2-phospho-ascorbic acid) for 48-96 hrs.

High-Throughput Surface Marker Screen hESCs or their mesodermal progeny were dissociated (TrypLE Express) and plated into individual wells of a 96-well plate, each well containing a distinct antibody against a human cell-surface antigen, altogether 332 unique cell-surface markers across 4×96-well plates (LEGEND-Screen PE-Conjugated Human Antibody Plates; Biolegend, 700001), stained per the manufacturers' instructions and analyzed on an LSR Fortessa. In follow up experiments, DLL1, GARP and PDGFRα antibodies were used to purify hPSC-derived paraxial mesoderm, cardiac mesoderm and sclerotome, respectively (see below for further detail).

RNA-Seq Profiling of the Mesodermal Hierarchy

RNA was purified from hESCs or their mesodermal progeny and sequencing libraries were prepared (TruSeq RNA Library Preparation Kit, Illumina) per the manufacturer's instructions. Libraries were sequenced on a Next-Seq 2000 to obtain 150 bp paired-end reads, aligned to hg19 using BWA and CuffDiff analysis was performed to identify differentially-expressed genes across the mesodermal lineage hierarchy (see below for further detail).

Human Pluripotent Stem Cell Culture

H7, MIXL1-GFP HES3, NKX2.5-GFP HES3, SOX17-mCherry H9, pCAG-GFP H7, EF1A-BCL2-2A-GFP H9 and UBC-Luciferase-2A-tdTomato; EF1A-BCL2-2A-GFP H9 hESCs and BJC1 hiPSCs were routinely propagated feeder-free in mTeSR1 medium (StemCell Technologies) on cell culture plastics coated with Geltrex basement membrane matrix (Gibco). Undifferentiated hPSCs were maintained at high quality with particular care to avoid any spontaneous differentiation, which would confound downstream differentiation. Unless otherwise indicated, the majority of experiments performed in this study were conducted using H7 hESCs, including all bulk-population RNA-seq, single-cell RNA-seq and ATAC-seq experiments.

Directed Differentiation in Defined Medium

Partially-confluent wells of undifferentiated hPSCs were dissociated into very fine clumps using Accutase (Gibco) and sparsely passaged ~1:12-1:20 onto new Geltrex-coated cell culture plates in mTeSR1 supplemented with 1 µM thiazovivin (Tocris; a ROCK inhibitor to prevent cell death after dissociation) overnight. Seeding hPSCs sparsely prior to differentiation was critical to prevent cellular overgrowth during differentiation, especially during long-duration differentiation. hPSCs were allowed to plate overnight, and the following morning, were briefly washed (in DMEM/F12) before addition of differentiation medium. All differentiation was conducted in serum-free, feeder-free and monolayer conditions in chemically-defined CDM2 basal medium.

The composition of CDM2 basal medium, which has been previously described in, Loh et al., 2014, the disclosure of which is incorporated herein by reference in its entirety, is as follows: 50% IMDM (+GlutaMAX, +HEPES, +Sodium Bicarbonate; Gibco, 31980-097)+50% F12 (+GlutaMAX; Gibco, 31765-092)+1 mg/mL polyvinyl alcohol (Sigma, P8136-250G)+1% v/v concentrated lipids (Gibco)+450 µM monothioglycerol (Sigma)+0.7 µg/mL insulin+transferrin+1% v/v penicillin/streptomycin (Gibco). Polyvinyl alcohol was brought into solution by gentle warming and magnetic stirring in IMDM/F12 media before addition of additional culture supplements.

Primitive Streak Induction

As aforementioned, after overnight plating, hPSCs were briefly washed (with DMEM/F12) and then differentiated into either anterior primitive streak (30 ng/mL Activin A+4 µM CHIR99021+20 ng/mL FGF2+100 nM PIK90; for subsequent paraxial mesoderm induction) or mid primitive streak (30 mg/mL Activin A+40 ng/mL BMP4+6 µM CHIR99021+20 ng/mL FGF2+100 nM PIK90; for subsequent cardiac mesoderm induction) for 24 hrs.

Subsequently, day 1 anterior primitive streak was briefly washed (DMEM/F12) and differentiated towards day 2 paraxial mesoderm for 24 hours (1 µM A-83-01+3 µM CHIR99021+250 nM LDN-193189+20 ng/mL FGF2). Separately, day 1 mid primitive streak was differentiated towards day 2 lateral mesoderm for 24 hours (1 µM A-83-01+30 ng/mL BMP4+1 µM C59; with 2 µM SB-505124 sometimes used instead of A-83-01).

Paraxial Mesoderm Downstream Differentiation

Day 2 paraxial mesoderm was briefly washed (DMEM/F12) and further differentiated into day 3 early somite/somitomere precursors for 24 hours (1 µM A-83-01+250 nM LDN-193189+1 µM C59+500 nM PD0325901). Subsequently, day 3 early somites were dorsoventrally patterned into either ventral somites/sclerotome (5 nM 21K+1 µM C59) or dorsal somites/dermomyotome (3 µM CHIR99021+150 nM Vismodegib). Sclerotome induction was conducted for 48-72 hours (leading to day 5-6 ventral somite progenitors). For dermomyotome induction, sometimes dermomyotome was induced in the presence of 50 ng/mL BMP4 to upregulate PAX7 after 48 hours of BMP4+CHIR99021+Vismodegib differentiation (leading to day 5 dermomyotome progenitors). Media was changed 24 hours for all steps. The Hedgehog agonist 21K, which has been previously described in, e.g., Brunton et al., 2009 the disclosure of which is incorporated herein by reference in its entirety, was commercially synthesized.

Differentiation into Downstream Somitic Fates

Cartilage:

Day 6 sclerotome was briefly washed (DMEM/F12) and treated with BMP4 (20 ng/mL) for 72-144 hours, leading to day 9 or day 12 cartilage-like progeny. Media was changed every 24 hours.

Smooth Muscle:

Day 5 sclerotome was briefly washed (DMEM/F12) and treated with TGFβ1 (2 ng/mL)+PDGF-BB (10 ng/mL), which has been previously described in, e.g., Cheung et al. 2012, the disclosure of which is incorporated herein by reference in its entirety, for 72 hours, leading to day 8 smooth muscle-like progeny. Media was changed every 24 hours.

Skeletal Muscle:

For myogenic differentiation, dermomyotome was initially induced via a modified approach. Day 3 early somites were briefly washed (DMEM/F12), treated with BMP4+CHIR99021+Vismodegib for 24 hours, washed again (DMEM/F12) and subsequently treated with CHIR99021 (3 µM)+21K (5 nM) for 24 hours. This day 5 dermomyotome was further empirically differentiated towards skeletal muscle-like progeny (using medium containing 2% horse serum, which has been previously described in, e.g., Xu et al. 2013, the disclosure of which is incorporated herein by reference in its entirety) for 12 days, yielding day 17 skeletal muscle-containing populations.

Lateral/Cardiac Downstream Differentiation

Figure 12D:
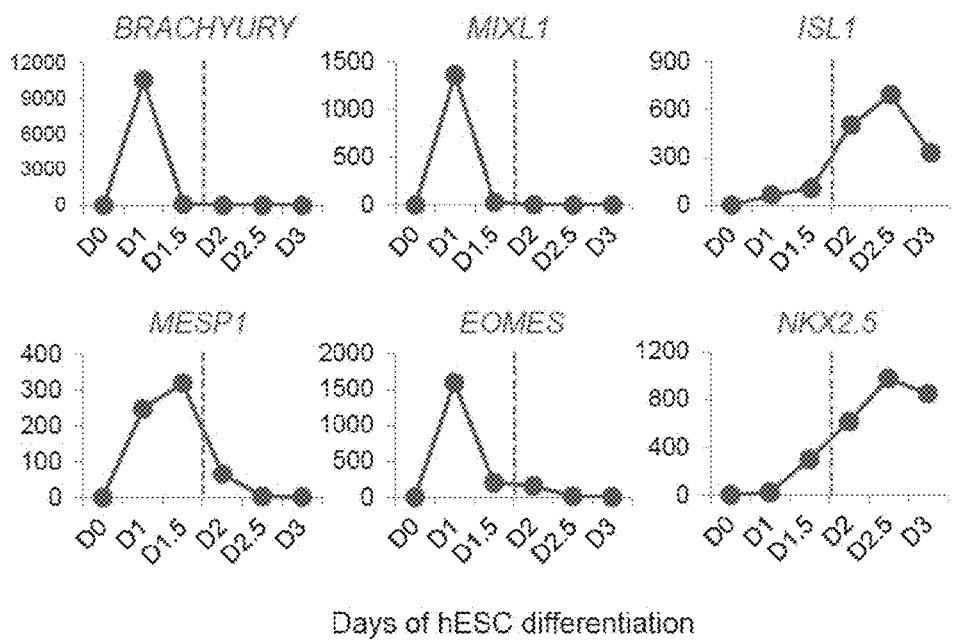

Day 2 lateral mesoderm was was differentiated into day 4 cardiac mesoderm by treating them with 1 µM A8301+30 ng/mL BMP4+1 µM C59+20 ng/mL FGF2 for 48 hrs, or alternatively, with 1 µM A8301+30 ng/mL BMP4+20 ng/mL FGF2 for 24 hrs followed by 25 ng/mL Activin+30 ng/mL BMP4+1 µM C59 for the next 24 hrs (schema in FIG. 5E; positive effect of mid-stage Activin shown in FIG. 12K). Subsequently, day 4 cardiac mesoderm was briefly washed (DMEM/F12) and treated with 30 ng/mL BMP4+1 µM XAV939+200 µg/mL 2-phospho-ascorbic acid (Sigma) for 48-96 hrs to yield day 6-8 cardiomyocyte-containing populations. Spontaneously contracting cardiomyocyte foci were evident from day 8 onwards.

Immunostaining

Adherent cells were fixed with 4% formaldehyde (Electron Microscopy Services, in PBS) for 15 minutes (4° C.) and washed twice (PBS). They were then permeabilized and blocked in perm/blocking buffer (PBS+0.1% Triton X100

(Sigma)+1% donkey serum (Jackson Immunoresearch)) for 1 hour (4° C.) and then stained overnight with primary antibody diluted in perm/blocking buffer. Subsequently, cells were washed twice (perm/blocking buffer) and stained with secondary antibody (diluted in perm/blocking buffer) for 1 hour (4° C.). For nuclear counterstaining, the cells were stained with Hoescht 3342 (1:1000, diluted in perm/blocking buffer) for 5 mins and then washed twice more prior to conducting fluorescent microscopy.

Safranin-O Staining for hPSC-Derived Cartilage hPSC-derived cartilage progeny were stained with safranin-O to assess their production of acidic proteoglycans, which is a key trademark of cartilage phenotypic function. Safranin-O staining was conducted in accord with standard procedures. Namely, hPSC-derived cartilage progeny at day 12 of differentiation (day 6 sclerotome treated with chondrogenic BMP4 for 6 further days) were fixed (with 4% formaldehyde, for 10 minutes at room temperature), washed twice in PBS, briefly treated with 1M acetic acid for 15 seconds, stained with 1% safranin-O solution for 10 minutes, washed with PBS, and wide-field visualization was performed with a dissecting microscope (Leica M205 FA).

High-Throughput Cell-Surface Marker Screening hESCs or their differentiated mesoderm progeny were dissociated (using TrypLE Express) and plated into individual wells of four 96-well plates, each well containing a distinct antibody against a human cell-surface antigen, altogether totaling >300 (i.e. 332) unique cell-surface markers across multiple 96-well plates (LEGENDScreen PE-Conjugated Human Antibody Plates; Biolegend, 700001). For each LEGENDScreen experiment, approximately 10-70 million cells of each lineage were used. High-throughput cell-surface marker staining was largely done as per the manufacturer's recommendations, and cells were stained with a viability dye (DAPI, 1.1 µM; Biolegend) prior to analysis on an LSR Fortessa (Stanford Stem Cell Institute FACS Core). Stained cells were not fixed prior to FACS analysis. Sometimes, after lysophilized antibodies were reconstituted in LEGENDScreen plates they were aliquoted into a separate plate to generate replicates of antibody arrays.

The following cell populations were used for LEGENDScreen analyses (FIG. 6): H7 hESCs ("undifferentiated hESCs"), H7-derived day 2 paraxial mesoderm ("paraxial mesoderm"), H7-derived day 3 early somite progenitors ("early somite"), H7-derived day 5 dermomyotome ("dermomyotome"), H7-derived day 6 sclerotome ("sclerotome"), MIXL1-GFP HES3 hESC-derived day 1 anterior primitive streak ("primitive streak") and finally, NKX2.5-GFP HES3 hESC-derived day 3 cardiac mesoderm ("cardiac mesoderm").

Figure 6B:
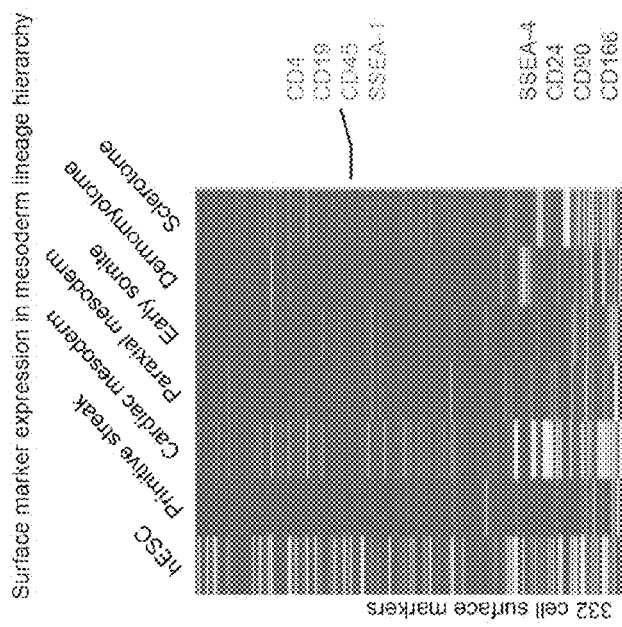
Figure 6A:
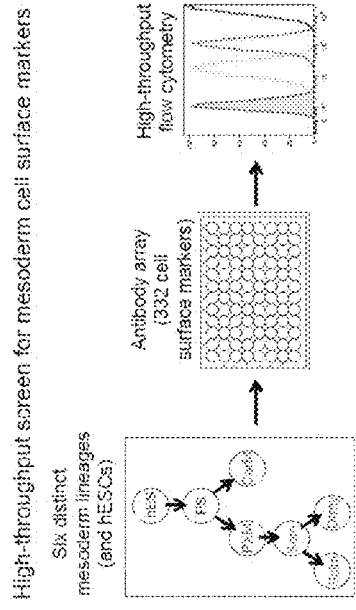
Figure 6C:
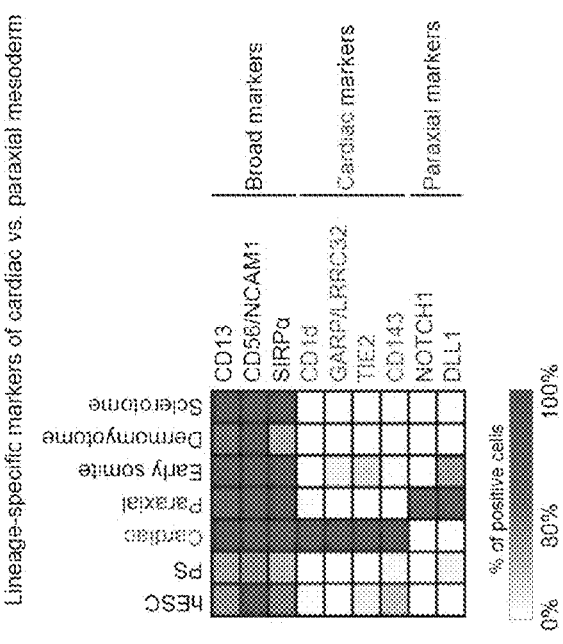

For the data plotted in FIG. 6b and FIG. 6c, cell surface marker analysis of day 1 primitive streak populations was conducted with MIXL1-GFP HES3 hESCs, with pre-gating on the MIXL1-GFP$^+$ fraction before assaying cell-surface marker expression for visualization. Furthermore, cell surface marker analysis of day 3 cardiac mesoderm populations was conducted with NKX2.5-GFP HES3 hESCs, with pre-gating on the NKX2.5-GFP$^+$ fraction before assaying cell-surface marker expression for visualization.

Fluorescence Activated Cell Sorting (FACS) on Cell-Surface Markers

Flow cytometry was conducted largely as previously described, see, e.g., Loh et al., the disclosure of which is incorporated herein by reference in its entirety. hESCs or their differentiated derivatives were dissociated using TrypLE Express, were washed off the plate with FACS buffer (PBS+0.1% BSA fraction V (Gibco)+1 mM EDTA (Gibco)+1% penicillin/streptomycin (Gibco)) and were pelleted through centrifugation (5 mins, 4° C.). (when necessary, in order to optionally decrease clumping at downstream steps, dissociated cells were strained through a 70 µm filter prior to pelleting.) Subsequently, cell pellets were directly resuspended in FACS buffer containing pre-diluted primary antibodies (see Table 1 for antibodies), thoroughly triturated to ensure a single cell suspension, and primary staining was conducted for 30 mins on ice. Afterwards, cells were washed with an excess of FACS buffer and pelleted again, and this was conducted one more time. Finally, washed cell pellets were resuspended in FACS buffer containing 1.1 µM DAPI (Biolegend), and were strained through a 30 µm filter. Flow cytometry and sorting was conducted on a BD FACSAria II (Stanford Stem Cell Institute FACS Core).

Intracellular Flow Cytometry

To quantitatively analyze the expression of SMAα/ACTA2 or TROPONIN/TNNT2 in hPSC-derived smooth muscle-like or hPSC-derived cardiomyocyte-like cells, respectively, intracellular flow cytometry was conducted using the Cytofix/Cytoperm kit (BD Biosciences, 554714) largely as per the manufacturer's instructions. Adherent cell populations were briefly washed with HBSS (lacking $Ca^{2+}$ and $Mg^{2+}$) to remove dead or floating cells, dissociated with TrypLE Express (Gibco), washed off the plate with FACS buffer (composition above), and pelleted. Subsequently, cells were fixed in Cytofix/Cytoperm buffer (20 minutes, on ice), washed twice in 1× Perm/Wash buffer, and directly resuspended in 50-100 µL of 1× Perm/Wash buffer containing staining antibodies (1:10 of α-SMAα PE (R&D Systems) or α-TNNT2 PE (BD Biosciences)). SMAα staining was conducted for 30 mins on ice. TNNT2 staining was conducted for 45 minutes at room temperature. After antibody staining, cells were washed twice (Perm/Wash buffer), and finally resuspended in FACS buffer before straining through a 70 µm filter and flow cytometry was conducted on a BD FACSAria II (Stanford Stem Cell Institute FACS Core).

Construction of BCL2-GFP-Expressing hESC Line

Figure 11A:
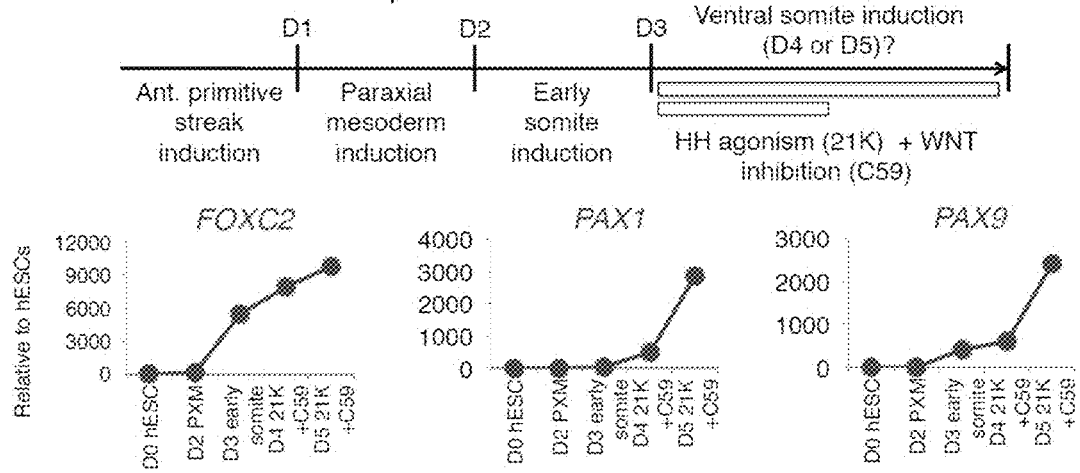
FIG. 11A-11N, depict the signaling logic for differentiation of early somite progenitors into sclerotome and dermomyotome and subsequently their downstream derivatives. Figure descriptions are provided in the Examples section.
Figure 11B:
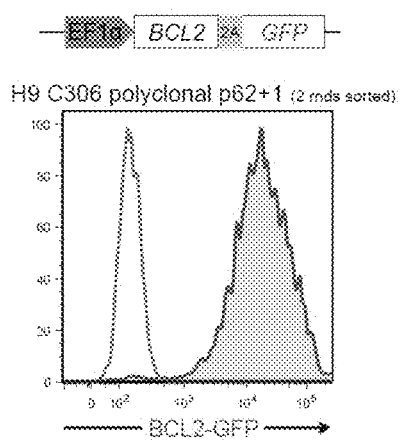

H9 hESCs were passaged with accutase, and 1-2 days post-seeding, were infected in mTeSR1 with a EF1α-BCL2-T2A-GFP lentivirus (C306) in which a constitutive EF1α promoter drives the expression of a BCL2-T2A-GFP cassette. Over the next 2 weeks, transduced populations were FACS sorted twice to enrich for GFP$^+$ cells until a near-homogeneous (>95%) population of GFP$^+$ hESCs was generated (FIG. 11b). BCL2 protein expression was confirmed by intracellular FACS. After sorting for GFP$^+$ hESCs, cells were directly sorted into mTeSR1 in the collection tube and then were subsequently plated in thiazovivin (1 µM) and ciprofloxacin (10 µg/mL) for 2-3 days to enhance recovery at a density of ~1×10$^5$ hPSC/well in a 6-well plate.

In Vivo Transplantation

H9 BCL2-2A-GFP-expressing hESCs (C306) were differentiated towards Day 6 sclerotome in 10-cm dishes, and were harvested by briefly washing with PBS followed by dissociation by TrypLE Express. After centrifugation and pelleting, cells were resuspended in a small volume of cold CDM2 basal medium, counted, and diluted with an equal volume of cold Matrigel (BD Biosciences, 354234), yielding a cell suspension in a 1:1 mixture of CDM2/Matrigel that was kept on ice until transplantation.

Immunodeficient NOD-SCID Il2γ$^{-/-}$ (NSG) mice of 2-3 months of age were used for transplantation and were anesthetized by inhaled isoflurane. For subcutaneous transplantation, the skin along the midline was tented using forceps and approximately 100 μL of cell suspension was injected with care not to puncture the skin at the opposite end of the tent. After the needle was retracted, immediately forceps were used to pinch the site of exit in order to ensure that the cell suspension did not escape. In all, 1.5 million sclerotome cells were transplanted subcutaneously per graft.

All animal experiments were conducted pursuant to experimental protocols approved by the Stanford Administrative Panel on Laboratory Animal Care (APLAC) and the Stem Cell Research Oversight (SCRO) committee.

Histological Analysis of Tissue Grafts

Recipient mice were humanely sacrificed and grafts were retrieved, embedded in paraffin, and sectioned. Staining was performed with either hematoxylin & eosin (as per standard procedures) or with Russell-Movat's Pentachrome (American MasterTech, KTRMPPT).

Other Differentiation Protocols

Paraxial Mesoderm:

FLyB→FLy differentiation was conducted as described previously by Cheung et al. 2012, the disclosure of which is incorporated herein by reference in its entirety, with 1.5 days of FGF2 (20 ng/mL)+BMP4 (10 ng/mL)+LY294002 treatment followed by 1.5 days of FGF2 (20 ng/mL)+LY294002 treatment (until day 3 of differentiation). CF→FR differentiation was conducted as described previously by Mendjan et al., 2014, the disclosure of which is incorporated herein by reference in its entirety, with 1.5 days of CHIR99021 (8 μM)+FGF2 (20 ng/mL) treatment followed by 1.5 days of FGF2 (4 ng/mL)+RA (1 μM) (until day 3 of differentiation) (used in FIG. 3e).

Cardiac Mesoderm:

CHIR→C59 differentiation was conducted as described previously by Burridge et al., 2014, the disclosure of which is incorporated herein by reference in its entirety, with 2 days of CHIR99021 (6 μM) treatment, followed by 2 days of C59 (2 μM) treatment, followed by treatment with basal medium alone. The basal medium used was RPMI1640+0.5 mg/mL albumin+213 μg/mL 2-phospho-L-ascorbic acid (used in FIG. 5f).

RNA Extraction and Reverse Transcription

In general, RNA was extracted from undifferentiated or differentiated hPSC populations plated in 12-well format by lysing them with 350 μL RLT Plus Buffer per well and RNA was extracted with the RNeasy Plus Mini Kit (Qiagen) as per the manufacturer's instructions. 50-200 ng of total RNA was reverse-transcribed with the High Capacity cDNA Reverse Transcription Kit (Applied Biosystems).

Quantitative PCR (qPCR)

Total cDNA was diluted 1:10-1:30 in $H_2O$ and qPCR was performed with the SensiFAST SYBR Lo-ROX Kit (Bioline) with 10 μL qPCR reactions per well in a 384-well plate: 5.0 μL 2× qPCR Master Mix+4.6 μL cDNA (totaling ~120 ng of cDNA)+0.4 μL of 10 μM primer stock (5 μM forward+5 μM reverse primers). In general, gene-specific primer pairs were tested for (1) specificity of amplicon amplification (only one peak on a dissociation curve) and (2) linearity of amplicon amplification (linear detection of gene expression in cDNA samples serially diluted seven times over two orders of magnitude, with 90-110% efficiency of amplification deemed acceptably linear). After qPCR plates were prepared by arraying sample-specific cDNAs and gene-specific primers, they were sealed and briefly centrifuged (5 mins). 384-well qPCR plates and their adhesive sealing sheets were obtained from Thermo (AB1384 and AB0558, respectively). qPCR plates were run on a 7900HT Fast Real-Time PCR System (Applied Biosystems) with the following cycling parameters: initial dissociation (95° C., 2 mins) followed by 40 cycles of amplification and SYBR signal detection (95° C. dissociation, 5 seconds; 60° C. annealing, 10 seconds; followed by 72° C. extension, 30 seconds), with a final series of steps to generate a dissociation curve at the end of each qPCR run. During qPCR data analysis, the fluorescence threshold to determine Ct values was set at the linear phase of amplification; other qPCR data analysis methods including qPCR heatmap generation using the GenePattern platform (Broad Institute) were described previously by Loh et al., 2014, the disclosure of which is incorporated herein by reference in its entirety.

Bulk-Population RNA-Seq Profiling

For bulk-population RNA-seq, RNA was extracted from undifferentiated H7 hESCs (d0), H7-derived anterior primitive streak populations (day 1), H7-derived mid primitive streak populations (day 1), H7-derived lateral mesoderm (day 2), H7-derived FACS-sorted GARP$^+$ cardiac mesoderm (day 3), H7-derived FACS-sorted DLL1$^+$ paraxial mesoderm populations (day 2), H7-derived day 3 early somite progenitor populations (day 3), H7-derived dermomyotome populations (day 5, treated with BMP4+CHIR99021+Vismodegib on days 4-5), H7-derived FACS-sorted PDGFRα$^+$ sclerotome populations (day 6). Subsequently, the integrity of extracted RNA was assayed by on-chip electrophoresis (Agilent Bioanalyzer) and only samples with a high RNA integrity (RIN) value were used for RNA-seq.

Purified total RNA was reverse-transcribed into cDNA using the Ovation RNA-seq System V2 (NuGEN) and cDNA was sheared using the Covaris S2 system (duty cycle 10%, intensity 5, cycle/burst 100, total time 5 min), and sheared cDNA was cleaned up using Agencourt AMPure XP beads (Beckman Coulter). Subsequently, sheared cDNA was ligated to adapters and sequencing libraries were constructed using the NEBNext Ultra DNA Library Prep Kit (New England Biolabs), using barcoded adapters to enable multiplexing of libraries on the same lane. For each RNA-seq library, the effectiveness of adapter ligation and effective library concentration was determined by qPCR prior to loading them in multiplexed fashion onto a Next-Seq 500 (Stanford Stem Cell Institute Genomics Core) to obtain 150 bp paired-end reads.

The ENCODE long RNA-seq pipeline for quantification was followed (www(dot)encodeproject(dot)org/rna-seq/long-rnas/). Specifically, reads were aligned to hg38 using STAR; gene-level expression was then quantified using RSEM. The $\log_2(\text{TPM}+1)$ values were used as starting values for the analyses.

To accurately measure differential expression between cell-types (FIG. 3F), DESeq2 was used to call differentially expressed genes and calculate shrunken fold change estimates. Batch correction for this analysis was also done by DESeq2 via the inclusion of a known batch parameter in the design matrix. Each gene included in FIG. 3F was called as differentially expressed at a False Discovery Rate (FDR) of 0.1.

For global comparisons of gene expression levels across cell types (FIGS. 7B and 7C) all genes where there was a difference of less than 2 (in $\log_2$TPM units, i.e., a 4-fold difference in expression) between the cell types with the highest and lowest expression were first filtered out. Next, ComBat (as implemented through the sva R package) was used to correct for batch effects. This sometimes left small negative values for the expression of some genes, which were set to 0. Finally, for the purposes of visualization, the expression of all genes were normalized such that for each gene, the highest expression was 1.0.

In Vivo Construction of Human Fetal Heart Grafts in the Mouse Ear and Subsequent Transplantation of hESC-Derived Cardiac Populations After isolation, de-identified fetal week 15-17 human fetal hearts were shipped on ice in UW organ cryopreservation solution and used for experiments within several hours of harvesting. For the purposes of this study, only two independent human fetal hearts were obtained under regulatory approval from Stanford University. Using scissors, the atria were removed, and subsequently, the ventricles were dissected into fragments that were up to approximately 2 mm×7 mm in size.

NSG mice of 2-3 months of age were anesthetized by inhaled isoflurane. The ear was shaved to the base of the skull and was disinfected. Using fine-point scissors, a small incision was made on the dorsal side of the ear close to the base where the ear meets the skull. Subsequently a blunt-end forcep was inserted into the incision and then was gently tunneled towards the apex of the ear to create a subcutaneous pocket. Then, a human ventricle fragment was loaded into a trocar. The trocar was custom-produced by fitting a 16-gauge intravenous plastic catheter with a blunted plunger.

The tip of the trocar was slid into the subcutaneous pocket and then the human ventricle fragment was gently implanted using the plunger. Afterwards, the pocket was closed by gently massaging the ear proximal to the graft with a Q-tip in order to remove residual air and close the tunnel.

1 month after implanting the human fetal heart graft, hESC-derived cardiac cells were directly injected into the graft. In brief, mice were anesthetized by isoflurane and then $1.5-2\times10^6$ EF1A-BCL2-2A-GFP; UBC-tdTomato-2A-Luciferase H9-derived day 3 cardiac mesoderm or day 8 cardiomyocytes were directly injected into the subcutaneous graft in a 1:1 mixture of CDM2 and Matrigel using a 31-gauge insulin syringe.

Bioluminescence Imaging

To non-invasively image luciferase$^+$ hESC-derived donor cells after sclerotome or cardiac lineage transplants, bioluminescence imaging was conducted. In brief, mice were injected intraperitoneally with 0.33 mg D-luciferin (in 200 μL volume of PBS) 20 minutes prior to imaging. 5 minutes before imaging, mice were anesthetized by isoflurane and placed in the IVIS Spectrum imaging chamber. A single image was captured using the following settings: autoexposure, small binning and Fstop_2. Data were subsequently analyzed using Living Image software.

Single-Cell RNA-Seq Profiling

Cells were briefly washed (DMEM/F12), dissociated (TrypLE Express), strained (100 μm filter), pelleted and resuspended in DMEM/F12 for counting. Before single-cell capture, two quality control steps were implemented. Firstly, cell size was estimated in order to determine whether cells should be loaded onto C1 capture arrays of either 10-17 μm or 17-25 μM size. Arrays were chosen for each lineage by estimating the median cell size of each given population on a flow cytometer on the basis of the FSC-W signal and choosing an array with an appropriate pore size to accommodate such cells. Secondly, to ensure the high viability of in vitro-differentiated cells prior to commencing single-cell RNA-seq, for each population a separate aliquot of cells was stained with 1.1 μM DAPI and analyzed by flow cytometry; for all cell populations that were used for single-cell RNA-seq, >98% of cells were viable (i.e., DAPI negative).

For single-cell capture, cells were diluted to a concentration of 1000 cells/4, diluted 3:2 in C1 Cell Suspension Reagent, and loaded onto a Fluidigm C1 single-cell capture array (a 10-17 μm array was used for hESCs, day 1 anterior PS, day 2 sorted DLL1$^+$ paraxial mesoderm, day 2.25 somitomeres, day 3 early somites, day 3 sorted GARP$^+$ cardiac mesoderm, day 5 central dermomyotome or day 6 sorted PDGFRA$^+$ sclerotome while a 17-25 μm array was used for day 1 mid PS) for automated capture on a Fluidigm C1 Machine (Stanford Stem Cell Institute Genomics Core).

After cells were loaded onto C1 arrays, single-cell capture was verified on an automated microscope, followed by cell lysis, reverse transcription and cDNA synthesis on the C1 machine using the SMARTer Ultra Low RNA Kit (Clontech, 634833) generally as per the manufacturers' instructions (Fluidigm, PN 100-7168 version 11). Subsequently, the concentration and integrity of single-cell cDNA libraries was assessed by an electrophoresis-based method to assess DNA concentration and fragment size (Fragment Analyzer, Advanced Analytical). Only single-cell cDNA libraries that (1) were not degraded and (2) originated from wells that were microscopically verified to contain a single cell were carried forward for subsequent library construction.

Using a Mosquito high-throughput robotic pipetter (TTP Labtech), single-cell cDNA libraries from all lineages were approximately diluted to a 0.1-0.16 ng/μL concentration range using C1 Harvest Reagent (Fluidigm) in order to normalize sample concentrations and enhance the consistency of subsequent library construction across all lineages. Subsequently, diluted single-cell cDNA libraries were tagmented and barcoded through the use of the Nextera XT DNA Sample Prep Kit (Illumina, FC-131-1096) and then pooled and cleaned up (Agencourt AMPure XP beads) for deep sequencing, as per the manufacturers' instructions (Fluidigm, PN 100-7168 version 11) such that 384 individual single-cell RNA-seq libraries were sequenced in a single sequencing lane.

After deep sequencing (Next-Seq 500) to obtain 150 bp paired-end reads, we quantified single-cell gene expression using the ENCODE long RNA-seq pipeline (described above), with an additional filtering step to ensure that we only kept cells with at least 1 million uniquely mapped reads and with at least 70% of reads uniquely mapping.

Figure 3G:
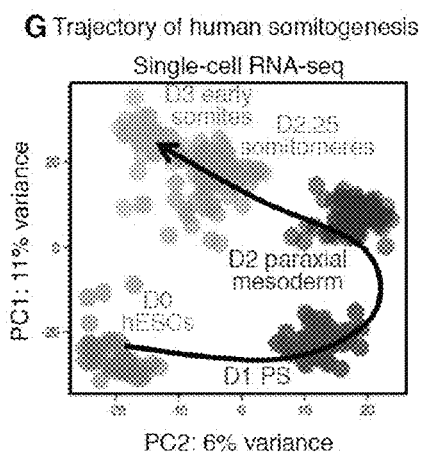
Figure 3H:
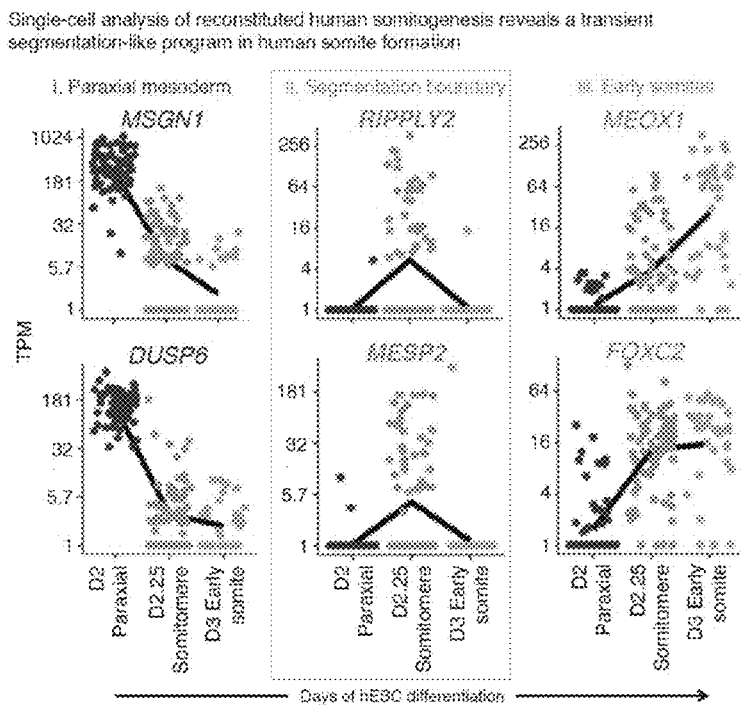
Figure 3I:
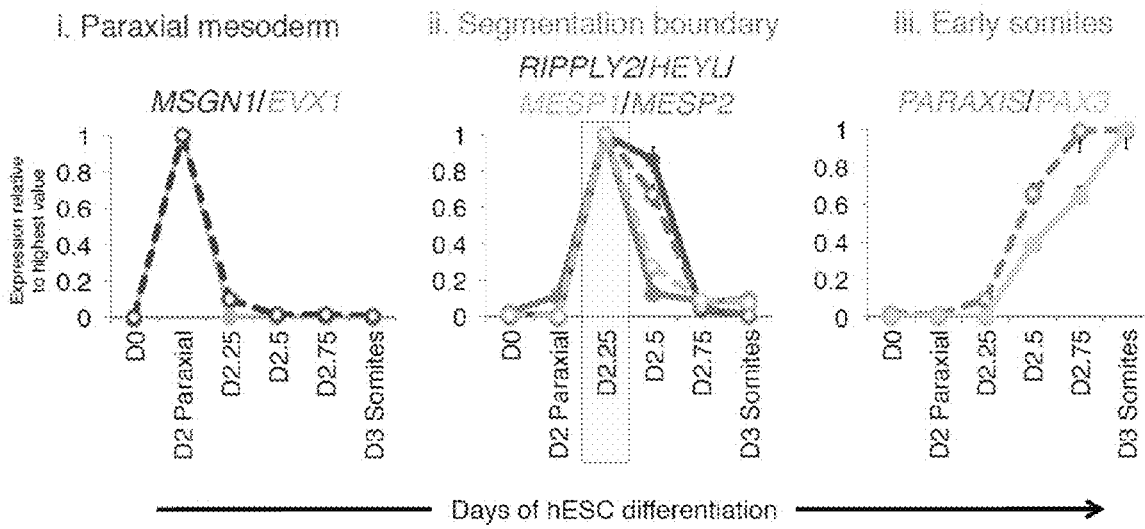

Principal component analysis (PCA) for the purpose of visualization (FIG. 3G and FIG. 4I) was done on the expression values (in $\log_2$ TPM) of the top 500 genes by variance.

Temporal Analysis of Single-Cell RNA-Seq

To study the kinetics of gene expression in single cells progressing through somitogenesis, single cells were ordered from D2 paraxial mesoderm, D2.25 somitomeres, and D3 early somites along a single inferred temporal trajectory. To do this, genes that did not vary in these cell types were first filtered out by computing the average $\log_2$ TPM value of each gene in each of the three cell types and only keeping genes that displayed a difference of at least 2 (in $\log_2$ TPM units, i.e., a 4-fold difference in expression) between the cell type with the highest and lowest expression. PCA of the 1,240 retained genes was conducted (FIG. 10F) and it was observed that the first principal component (PC1) recovered the correct bulk ordering of D2, D2.25, and D3 cells. Indeed, the three genes with the strongest loadings in PC1 were MSGN1, DKK1, and TSPAN7, of which the first two genes were known to be involved in somitogenesis in vivo. Therefore, the projection of each cell along PC1 was used to obtain an inferred temporal ordering of the cells along "pseudotime", as used in FIGS. 16A and 16B.

Given the inferred pseudotemporal ordering, the genes were then clustered by their expression dynamics across pseudotime during reconstituted human somitogenesis. To account for technical dropout and other sources of variation, Loess curve was fitted to the single-cell expression levels of each gene and used that to impute gene expression values for each cell. Next, the expression levels for each gene were individually normalized by dividing by the maximum expression value for that gene over all cells, so that the resulting values would be reflective of the shape of the trajectory and not its absolute value. Finally, we ran k-medoids clustering with k=10 (implemented with the pam method in the R package cluster.

ATAC-Seq

ATAC-seq was performed generally as previously described by Buenrostro et al., 2013 (Nat Methods. 2013 10(12):1213-8, the disclosure of which is incorporated herein by reference in its entirety), with minor modifications. In brief, for each replicate, 50,000 cells were lysed in lysis buffer containing 0.01% IGEPAL CA-630 (Sigma, 18896) to obtain nuclei, which were directly used in the Tn5 transposition reaction (reagents from Nextera DNA Sample Preparation Kit; Illumina, FC-121-1030). Immediately following transposition, DNA fragments were purified (MinElute Kit, Qiagen) and PCR amplified for a total of 12-13 cycles using previously-designed primer sequences that contained library barcodes. Then, libraries were purified (MinElute Kit, Qiagen), pooled and finally concentrations were assessed (Bioanalyzer) prior to next-generation sequencing. The quality of ATAC-seq libraries was confirmed using a MiSeq v3 (Stanford Functional Genomics Facility, 2×75 bp reads) before deep sequencing was performed on a NextSeq 500 (2×75 bp reads). Two replicates were analyzed per cell-type.

ATAC-seq reads were aligned to hg19 ((Bowtie2) and peak-calling was conducted (MACS2), using a relaxed FDR threshold of 0.01). After calling peaks for each individual replicate, a unified peak list was created for each cell-type by selecting only peaks that were reproducible between both replicates. This was done through an irreproducible discovery rate (IDR) analysis. In brief, the IDR method takes in peak calls from a pair of replicates, filters out all peaks that only appear in one replicate, and then uses a copula mixture model to model the remaining peaks as belonging to either a reproducible "signal" population or an irreproducible "noise" population. We used an IDR threshold of 0.02, i.e., only peaks that were deemed to have come from the "signal" population with a probability of more than 0.98 were retained. Finally, all peaks that appeared in a curated blacklist of artifactual regions in hg19 were filtered out.

To obtain a universal list of peaks across all cell-types, BEDtools was used to merge the lists of filtered, reproducible peaks for each cell-type. For each cell-type, its two biological replicates were pooled together and called peaks (MACS2) on the pooled reads. To obtain a single measure of confidence at each peak P in the universal list for each cell-type C, the highest $-\log_{10}$ p-value out of all peaks in the pooled replicates for C that intersected with P were taken.

ATAC-Seq Heatmap and Motif Enrichment Analysis

The pipeline above resulted in a universal list of 87,215 peaks across all cell-types. To account for experimental variation and batch effects between samples, a simple binarization method was adopted in which we only called a peak "active" in a given cell-type if its $-\log_{10}$ p-value was within the top 20% for that cell-type out of all 87,215 peaks in the universal list. The p-value for the threshold was used (instead of the fold enrichment or average signal intensity). All peaks that were not "active" in any of the cell-types were then filtered out, resulting in 51,230 peaks. These 51,230 peaks were visualized in the heatmap in FIG. 7d after running k-medoids clustering (L1 distance; implemented with the clara method in the R package cluster) with k=17. The number of clusters was chosen by silhouette analysis (silhouette from the same cluster package) from k=2 to 20, but the heatmap and subsequent motif enrichment were qualitatively similar for different values of k.

Clustering revealed a large cluster of ubiquitously "active" peaks, as well as many smaller clusters of lineage-specific "active" peaks. To find transcription factor motifs enriched in the latter, HOMER was run using peaks in a given lineage-specific cluster as foreground and all peaks in the remaining 16 clusters as background. All motifs shown in FIG. 7d were within the four most statistically-significant motifs identified for each cluster by HOMER. In many cases, the detected motif matched a broad family of transcription factors; where possible, bulk RNA-seq expression data and known biological connections were used to identify a smaller subset of plausible factors (FIG. 7d,e). To verify these results, we also ran SeqGL on the clusters. In brief, SeqGL is a discriminative motif discovery algorithm that compares peaks to flanking regions and builds a k-mer model that can classify peaks vs. flanks; SeqGL relies on HOMER in the backend to generate motifs for visualization and comparison to known motifs. The results obtained with SeqGL (data not shown) matched with those obtained from direct application of HOMER; thus results from the latter were shown for simplicity.

To identify potential FOX motifs in the two putative MEOX1 enhancers (FIG. 7e), we used PWMscan using the motif from the somite-specific cluster that HOMER had associated with the FOX family. PWMscan identified two potential FOX binding sites, one in each enhancer, at an uncorrected p-value cutoff of 0.001.

TABLE 2

Primers for quantitative PCR

| Gene Name | Forward (SEQ ID NOs: 2-67) | Reverse (SEQ ID NOs: 68-133) |
|---|---|---|
| ACTA1 | CGACATCAGGAAGGACCTGTATGCC | GGCCTCGTCGTACTCCTGCTTGG |
| ACTA2 | CTATGAGGGCTATGCCTTGCC | GCTCAGCAGTAGTAACGAAGGA |
| AGGRECAN | CCCCTGCTATTTCATCGACCC | GACACACGGCTCCACTTGAT |
| ALX4 | ATGAATGCTGAGACTTGCGTC | GGGAAATGCCCTAAAAGGCG |
| BAPX1/NKX3.2 | GA TTTCAGGCCTGCTGGGA | TTTCGCACCCCTTGGTTACA |
| BRACHYURY | TGCTTCCCTGAGACCCAGTT | GATCACTTCTTTCCTTTGCATCAAG |

TABLE 2-continued

Primers for quantitative PCR

| Gene Name | Forward (SEQ ID NOs: 2-67) | Reverse (SEQ ID NOs: 68-133) |
|---|---|---|
| CD144/VECAD | AACGAGCAGGGCGAGTTCACCTTC | TAGGTGACCAGCTGCTCGTGGATC |
| CD31/PECAM1 | AACAGTGTTGACATGAAGAGCC | TGTAAAACAGCACGTCATCCTT |
| CD34 | TGGCTGTCTTGGGCATCACTGG | CTGAATGGCCGTTTCTGGAGGTGG |
| CDX2 | GGGCTCTCTGAGAGGCAGGT | CCTTTGCTCTGCGGTTCTG |
| CNN1 | GTCAACCCAAAATTGGCACCA | ACCTTGTTTCCTTTCGTCTTCG |
| COL2A1 | CCAGATGACCTTCCTACGCC | TTCAGGGCAGTGTACGTGAAC |
| COMP | GATCACGTTCCTGAAAAACACG | GCTCTCCGTCTGGATGCAG |
| DLL1 | ACTCCGCGTTCAGCAACCCCAT | TGGGTTTTCTGTTGCGAGGTCATCAGG |
| EOMES | CAACATAAACGGACTCAATCCCA | ACCACCTCTACGAACACATTGT |
| EPIPHYCAN | AGGAGGAGGAATCTACTCCCA | CAGCGGAGGAATAGCATCAAG |
| EVX1 | AGTGACCAGATGCGTCGTTAC | TGGTTTCCGGCAGGTTTAG |
| FLK1 | TTTTTGCCCTTGTTCTGTCC | TCATTGTTCCCAGCATTTCA |
| FOXA2 | GGGAGCGGTGAAGATGGA | TCATGTTGCTCACGGAGGAGTA |
| FOXC2 | CCTCCTGGTATCTCAACCACA1 | GAGGGTCGAGTTCTCAATCCC |
| FOXF1 | AGCAGCCGTATCTGCACCAGAA | CTCCTTTCGGTCACACATGCTG |
| FZD8 | ATCGGCTACAACTACACCTACA | GTACATGCTGCACAGGAAGAA |
| GATA4 | TCCCTCTTCCCTCCTCAAAT | TCAGCGTGTAAAGGCATCTG |
| GATA6 | CCCACAACACAACCTACAGC | GCGAGACTGACGCCTATGTA |
| GSC | GAGGAGAAAGTGGAGGTCTGGTT | CTCTGATGAGGACCGCTTCTG |
| HAND1 | GTGCGTCCTTTAATCCTCTTC | GTGAGAGCAAGCGGAAAAG |
| HHEX | CACCCGACGCCCTTTTACAT | GAAGGCTGGATGGATCGGC |
| HOXB5 | AACTCCTTCTCGGGGCGTTAT | CATCCCATTGTAATTGTAGCCGT |
| ISL1 | AGATTATATCAGGTTGTACGGGATCA | ACACAGCGGAAACACTCGAT |
| MEF2C | ATGGATGAACGTAACAGACAGGT | CGGCTCGTTGTACTCCGTG |
| MEOX1 | TCTGAGCGCCAGGTCAAAG | CTGAACTTGGAGAGGCTGTGG |
| MEOX2 | GTGGCGGCTACAAGGTCATC | CTGGCGCGGAACATAAACA |
| MESP1 | GAAGTGGTTCCTTGGCAGAC | TCCTGCTTGCCTCAAAGTGT |
| MESP2 | AGCTTGGGTGCCTCCTTATT | TGCTTCCCTGAAAGACATCA |
| MIXL1 | GGTACCCCGACATCCACTTG | TAATCTCCGGCCTAGCCAAA |
| MSGN1 | CGGAATTACCTGCCACCTGT | GGTCTGTGAGTTCCCCGATG |
| MYF5 | GCCTGAAGAAGGTCAACCAG | CCATCAGAGCAGTTGGAGGT |
| MYH3 | CTGGAGGATGAATGCTCAGAGC | CCCAGAGAGTTCCTCAGTAAGG |
| MYH6 | GCCCTTTGACATTCGCACTG | GGTTTCAGCAATGACCTTGCC |
| MYH7 | TCGTGCCTGATGACAAACAGGAGT | ATACTCGGTCTCGGCAGTGACTTT |
| MYL7 | ACATCATCACCCATGGAGACGAGA | GCAACAGAGTTTATTGAGGTGCCC |
| MYOD1 | TGCCACAACGGACGACTT | CGGGTCCAGGCTTCGAA |
| MYOG | AGATGTGTCTGTGGCCTTCC | AGCTGGCTTCCTAGCATCAG |
| NKX2.5 | CAAGTGTGCGTCTGCCTTT | CAGCTCTTTCTTTTCGGCTCTA |

TABLE 2-continued

Primers for quantitative PCR

| Gene Name | Forward (SEQ ID NOs: 2-67) | Reverse (SEQ ID NOs: 68-133) |
|---|---|---|
| NKX3.1 | CCAGCTCAGGTGACAACCAT | CTTGGCCCCTTGTGCTTTTC |
| OCT4/POU5F1 | AGTGAGAGGCAACCTGGAGA | ACACTCGGACCACATCCTTC |
| ODD1 | CAGCTCACCAACTACTCCTTCCTTCA | TGCAACGCGCTGAAACCATACA |
| PARAXIS | GAGCTGAGGAGAGTCCCGT | TGTGCCTCTCTCTAGGTCCA |
| PAX1 | CGCTATGGAGCAGACGTATGGCGA | AATGCGCAAGCGGATGGCGTTG |
| PAX3 | CTCCACGCTCCGGATAGTTC | ATCTTGTGGCGGATGTGGTT |
| PAX6 | GCAGATGCAAAAGTCCAGGTG | CAGGTTGCGAAGAACTCTGTTT |
| PAX7 | TCCAAGATTCTTTGCCGCTAC | GGTCACAGTGCCCATCCTTC |
| PAX9 | TGGTTATGTTGCTGGACATGGGTG | GGAAGCCGTGACAGAATGACTACCT |
| PDGFRB | GGTGGGCACACTACAATTTGC | GGTGGGTAGGCCTCGAACA |
| PRRX1 | TGATGCTTTTGTGCGAGAAGA | AGGGAAGCGTTTTTATTGGCT |
| SOX17 | CGCACGGAATTTGAACAGTA | GGATCAGGGACCTGTCACAC |
| SOX2 | TGGACAGTTACGCGCACAT | CGAGTAGGACATGCTGTAGGT |
| SOX9 | CGTCAACGGCTCCAGCAAGAACAA | GCCGCTTCTCGCTCTCGTTCAGAAGT |
| STMN | CGGCCTGCGCGTGTCTAATCC | CTGTGACCTCCAGCAGCTTCCGAA |
| TAGLN | AGTGCAGTCCAAAATCGAGAAG | CTTGCTCAGAATCACGCCAT |
| TBX20 | GGCGACGGAGAACACAATCAA | CTGGGCACAGGACGACTTC |
| TBX5 | TACCACCACACCCATCAAC | ACACCAAGACAGGGACAGAC |
| TBX6 | AAGTACCAACCCCGCATACA | TAGGCTGTCACGGAGATGAA |
| TNNT2 | GGAGGAGTCCAAACCAAAGCC | TCAAAGTCCACTCTCTCTCCATC |
| TWIST1 | CTGCAGCACCGGCACCGTTT | CCCAACGGCTGGACGCACAC |
| UNCX4.1 | CTATCCCGACGTGTTCATGC | GAACTCGGGACTCGACCAG |

Differentiation into Primitive Streak and Hematopoietic Mesoderm

After overnight plating, hESCs were washed (DMEM/F12) and differentiated towards posterior PS using BMP4 (15-40 ng/mL, R&D Systems), CHIR99021 (6 μM, Tocris), FGF2 (20 ng/mL, Invitrogen) and PIK90 (100 nM, Calbiochem) for 24 hours, with the optional inclusion of Activin (30 ng/mL, R&D Systems) to induce mid PS. Day 1 mid or posterior PS was subsequently washed (DMEM/F12) and further differentiated using BMP4 (40 ng/mL), GDC-0941 (0.25-2.5 μM, Cellagen Technology), Forskolin (10 μM, Tocris), SB-505124 (2 μM, Tocris), VEGF (100 ng/mL, R&D Systems), XAV939 (1 Tocris) and ascorbic acid-2-phosphate (200 μg/mL, Sigma) for 24 hours. Day 2 cultures were further directed into the definitive hematopoietic lineage/hemogenic precursors by Activin A (15 ng/mL), GDC-0941 (0.25-2.5 μM), VEGF (100 ng/mL), XAV939 (1 μM) and ascorbic acid-2-phosphate (200 μg/mL) for 24 hours.

Differentiation into Arterial Endothelial Progenitors

Day 3 definitive hematopoietic mesoderm progenitors were subsequently differentiated into early Runx1lowGfi1low hemogenic intermediates through day 4-5 treatment with BMP4 (50 ng/mL), TTNPB (500 nM), VEGF (100 ng/mL) and XAV939 (1 μM) for 48 hours, supplemented with SB-505124 (2 μM) on day 5.

Differentiation into Hematopoietic Intermediates

Day 5 populations were then dissociated into single cells, counted and reaggregated in individual wells of a low-adhesion V-bottom or U-bottom 96-well plate (e.g., Thermo Fisher, catalog no. 249952) with ~15,000-20,000 cells seeded per well. Aggregates were cultured for 48 additional hours until day 7 in BMP4 (50 ng/mL), TTNPB (500 nM), VEGF (100 ng/mL), XAV939 (1 μM), SB-505124 (2 μM), SCF (25-50 ng/mL, R&D Systems), IL6 (10 ng/mL, R&D Systems) and IL6RA (250-1000 ng/mL, R&D Systems). All differentiation was conducted in serum-free CDM2 fully-defined basal media.

Myeloid and Lymphoid Assays in Stromal Coculture

Day 5 hESC-derived hematopoietic intermediates were dissociated (Accutase) and plated onto largely-confluent OP9 cells to test their myeloid competence. OP9 cells were routinely propagated in OP9 medium (MEMα medium+10% FBS+1% penicillin/streptomycin, with pH adjusted with NaHCO3) for maintenance. hESC-derived hematopoietic intermediates were differentiated towards myeloid fates on OP9 stroma for 4 weeks in OP9 medium+SCF (50 ng/mL)+TPO (50 ng/mL)+IL2 (10 ng/mL)+IL7 (20 ng/mL)+GM-CSF (20 ng/mL)+G-CSF (20 ng/mL)+M-CSF (10 ng/mL), modified from a previous report 26. Cocultures were split every week, and after 4 weeks of myeloid differentiation, both adherent and floating cells were collected for FACS analysis.

Differentiation into Mid-Primitive Streak and Lateral Mesoderm hESCs were differentiated into mid primitive streak for 24 hours (D0-1; 30 ng/mL Activin+40 ng/mL BMP4+6 µM CHIR99021+20 ng/mL FGF2+100 nM PIK90). Mid primitive streak was subsequently differentiated into lateral mesoderm (D1-2; 1 µM A-83-01+30 ng/mL BMP4+1 µM C59), with the inclusion of 50 nM of TTNPB or 2 µM ATRA on D1-2 for trunk lateral mesoderm that was subsequently competent for forelimb differentiation.

Differentiation into Forelimb and Hindlimb Progenitors

Day 2 trunk lateral mesoderm was differentiated into day 3 forelimb progenitors (D2-3; 1 µM A-83-01+1 µM DMH1+3 µM CHIR99021). By contrast, day 2 non-trunk lateral mesoderm was differentiated into day 3 hindlimb progenitors (D2-3; 25 ng/mL Activin+1 µM DMH1+3 µM CHIR99021).

Figure 8H:
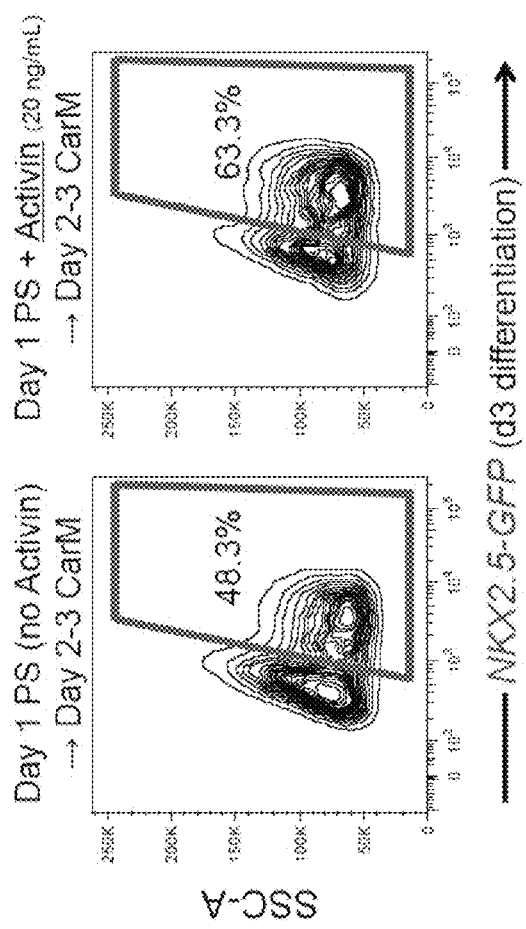

Example 1: BMP and TGFβ Control Anterior-Posterior Patterning of the Primitive Streak in the Context of FGF and WNT Activation Efficient initial induction of the primitive streak (PS) from hPSCs is crucial for downstream mesoderm generation (FIG. 1a). To track PS induction, expression of Mixl1, which is a conserved PS marker in vertebrate embryos, was monitored. A >98% pure MIXL1-GFP$^+$ PS population was efficiently generated within 24 hours of hPSC differentiation by activating FGF and WNT, inhibiting PI3K and providing TGFβ and/or BMP signals (FIG. 1b, FIG. 8b).

However, in vivo, different regions of the PS along the anterior-posterior axis each give rise to distinct mesodermal derivatives (FIG. 1c). Therefore, inducing the desired PS precursor (whether of anterior or posterior character) is be key to subsequently generating specific kinds of mesoderm from hPSCs.

Signaling conditions were established to specify the anterior PS and mid PS, which respectively harbored the potential to subsequently form paraxial mesoderm or cardiac mesoderm in vitro (FIG. 1c). "Anterior PS" induced in the presence of an anteriorizing Activin signal (FIG. 8ei) on day 0-1 of hPSC differentiation had the maximum competence to subsequently form TBX6$^+$ paraxial mesoderm on day 2 of differentiation (FIG. 1d). Conversely, specifying PS in the presence of posteriorizing BMP instead inhibited paraxial mesoderm potential (FIG. 8fi, 8g) and endowed cardiac differentiation potential (FIG. 8fii). Thus, "mid PS" induced in the presence of both posteriorizing BMP (FIG. 8fii) and anteriorizing Activin (FIG. 8eii, 8h) had maximal potential to subsequently form NKX2.5$^+$ cardiac mesoderm.

PS specification in both anterior PS (98.9±0.2% MIXL1$^+$) and mid PS (99.0±0.3% MIXL1$^+$) conditions was highly efficient, as quantified with a MIXL1-GFP knock-in hESC reporter line, which has been previously described in Davis et al., 2008, the disclosure of which is incorporated herein by reference in its entirety (FIG. 1c). In summary, this efficient and synchronous generation of MIXL1$^+$ PS by day 1 of hPSC differentiation provided an ideal platform to study subsequent bifurcation of paraxial versus lateral mesoderm fates (FIG. 2a).

Example 2: Cross-Antagonizing BMP and WNT Signals Respectively Specify Lateral Versus Paraxial Mesoderm from Primitive Streak After PS induction on day 0-1, we found that TGFβ inhibition and FGF/ERK activation broadly promoted differentiation into both paraxial and lateral mesoderm. Continued TGFβ activation on day 1-2 of hPSC differentiation drove day 1 PS towards endoderm (FIG. 9a); therefore we inhibited TGFβ on day 1-2 to repress endoderm and divert differentiation towards mesoderm (FIG. 2b, FIG. 9b-d). Thus while TGFβ is critical to drive hPSCs towards PS, subsequently it must be dynamically inhibited 24 hours later to sharply induce progression into mesoderm while blocking endoderm formation. Furthermore, FGF/ERK supported both paraxial and lateral mesoderm induction on day 1-2 (FIG. 9b, 9e). Since FGF activation together with TGFβ repression created a permissive context for both paraxial and lateral mesoderm formation, we sought signals that distinguished each of these mutually-exclusive mesoderm subtypes on days 1-2 of differentiation.

Countervailing BMP and WNT signals respectively was found to induce lateral versus paraxial mesoderm and each repressed the formation of the mutually-exclusive lineage, driving the bifurcation of these two mesoderm subtypes (summarized in FIG. 2f). Exogenous BMP induced lateral mesoderm and repressed paraxial mesoderm on day 1-2 of hPSC differentiation (FIG. 2c, FIG. 2dii, FIG. 2eii, FIG. 9f). By contrast, inhibiting endogenous BMP signaling abrogated lateral mesoderm and instead expanded paraxial mesoderm (FIG. 2c, FIG. 2dii, FIG. 2eii, FIG. 9c).

Conversely, WNT played an opposing role: it promoted paraxial mesoderm and repressed lateral mesoderm. WNT agonism (by GSK3 inhibition) induced paraxial markers while suppressing lateral/cardiac markers (FIG. 2di, FIG. 2ei). By contrast, WNT antagonists elicited lateral mesoderm while blocking the paraxial fate (FIG. 2di, FIG. 2ei).

In summary, on day 1-2 of hPSC differentiation, BMP agonism and WNT blockade specified lateral mesoderm whereas conversely BMP inhibition and WNT activation induced paraxial mesoderm from the PS within the permissive context of TGFβ inhibition/FGF activation (FIG. 2f). These two distinct signaling conditions enabled us to generate either CDX2$^+$HAND1$^-$ paraxial mesoderm or CDX2$^{lo/-}$HAND1$^+$lateral mesoderm by day 2 of differentiation in a mutually-exclusive fashion (FIG. 2f,g). Immunostaining of day 2 paraxial mesoderm populations induced from the GMP-grade hiPSC line BJC1 revealed that key paraxial mesoderm transcription factors TBX6 and CDX2, described previously by Chapman & Papaioannou, 1998 and Beck et al., 1995, the disclosures of which are herein incorporated by reference in their entirety, were co-expressed in 91.2±0.1% of cells (FIG. 2h).

Example 3: Combined BMP, FGF/ERK, TGFβ and WNT Blockade Drives Paraxial Mesoderm to Early Somites Having established a method to rapidly and efficiently generate paraxial mesoderm by day 2 of hPSC differentiation methods to drive these cells into early somite progenitors was next investigated (FIG. 3a). During embryogenesis, the sheet of paraxial (presomitic) mesoderm is progressively segmented at its anterior edge to generate spherical early somites (FIG. 3a). Within the vertebrate embryo, high posterior levels of FGF/ERK and WNT signals within paraxial mesoderm are thought to maintain uncommitted paraxial mesoderm precursors, whereas lower anterior levels of FGF and WNT lead to exit from self-renewal and consequently somite formation at the "wavefront".

Whereas paraxial mesoderm was specified on day 1-2 by FGF and WNT signaling, it was found that subsequently the inhibition of FGF/ERK and WNT signaling on day 2-3 strongly downregulated paraxial mesoderm genes (e.g., TBX6, MSGN1) and upregulated early somite markers (e.g., FOXC2; FIG. 3b, FIG. 10a). Early somite markers were further upregulated when the TGFβ (FIG. 10b) and BMP pathways (FIG. 10c) were inhibited; therefore quadruple inhibition of these 4 pathways was employed to drive near-complete conversion of day 2 CDX2$^+$ paraxial mesoderm into 96.8±5.7% pure FOXC2$^+$ early somite precursors by day 3 (FIG. 3c).

Therefore, by implementing these dynamic changes in FGF and WNT signaling in the permissive context of BMP/TGFβ inhibition. This protocol (FIG. 3d) to sequentially generate PS, paraxial mesoderm and subsequently early somite progenitors from hPSCs, more robustly and rapidly than was possible with other differentiation protocols (FIG. 3e). Having efficiently generated early somite progenitors from hPSCs, methods to subsequently generate distinct dorsoventral somite derivatives were next investigated (FIG. 4a).

Example 4: Cross-Antagonizing HEDGEHOG and WNT Signals Respectively Induce Ventral and Dorsal Somite Fates Early somites are patterned along their dorsal-ventral axis in vivo to generate sclerotome (ventral somite; precursor to smooth muscle, bone and cartilage) and dermomyotome (dorsal somite; precursor to skeletal muscle, brown fat and dorsal dermis; FIG. 4a).

Starting from day 3 hPSC-derived early somite progenitors, it was found that HEDGEHOG (HH) and WNT respectively induced ventral somite (sclerotome) and dorsal somite (dermomyotome) and each cross-antagonized the effect of the other on days 3-5 of differentiation (summarized in FIG. 4d). HH activation in conjunction with WNT inhibition efficiently induced sclerotome (PAX1, PAX9) and inhibited dermomyotome (FIG. 4b). Conversely, WNT activation together with HH blockade blocked sclerotome markers and instead exclusively specified dermomyotome (FIG. 4b). If HH and WNT were simultaneously activated, neither sclerotome or dermomyotome was elicited (FIG. 4b).

Figure 11C:
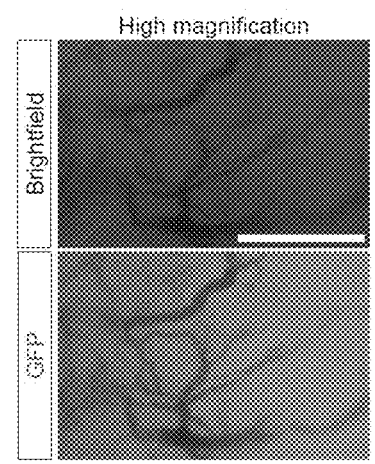
Figure 11D:
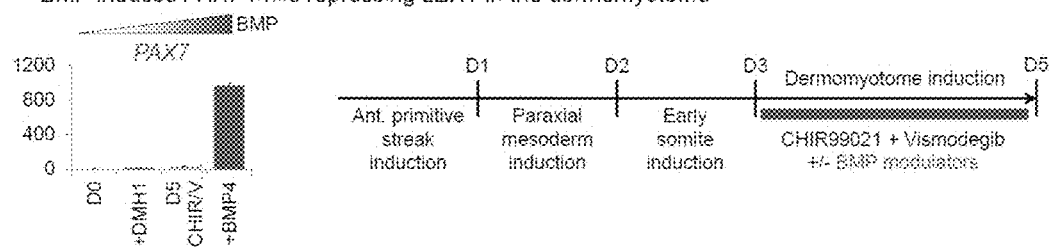
Figure 11F:
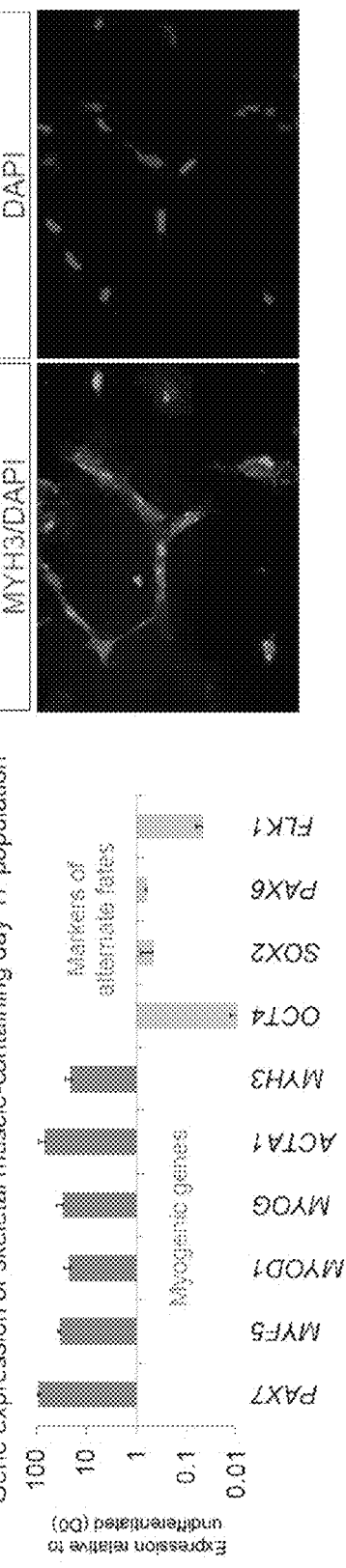

Dermomyotome was induced by treating hPSC-derived day 3 early somite progenitors with a small-molecule WNT activator (CHIR) together with a HH inhibitor (Vismodegib, which is described by Robarge et al., 2009, the disclosure of which is herein incorporated by reference in its entirety), which sustained dorsal somite marker PAX3 while inhibiting the sclerotome fate (FIG. 4c). The addition of BMP also enhanced dermomyotome marker PAX7 (FIG. 11d). The ability of hPSC-derived dermomyotome to differentiate into skeletal muscle was subsequently tested, as this is a key dermomyotome derivative. Upon treatment with empirical, previously-established serum conditions, such as those described by Xu et al., 2013, the disclosure of which is incorporated herein by reference in its entirety, these cells underwent myogenesis, expressing myogenic transcription factors MYOD1, MYF5 and MYOG and skeletal muscle contractile components ACTA1 and MYH3 (FIG. 11f).

Example 5: hPSC-Derived Sclerotome Forms an Ectopic Human Bone In Vivo

Conversely, 2-3 days of combined HH activation and WNT inhibition efficiently induced the sclerotome fate from hPSC-derived day 3 early somite precursors (FIG. 4c, FIG. 11a), which was achieved using the small-molecule Hedgehog agonist 21K and the small-molecule WNT antagonist C59, which is described by Proffitt et al., 2012, the disclosure of which is incorporated by reference herein in its entirety. hPSC-derived sclerotome expressed a broad array of characteristic sclerotome transcription factors, including NKX3.2/BAPX1, FOXC2, SOX9, TWIST1, PAX1 and PAX9 (FIG. 4c). Beyond these molecular markers, the in vivo lineage potential of hESC-derived sclerotome was also assessed.

Upon subcutaneous transplantation into immunodeficient mice, hESC-derived sclerotome strikingly formed ectopic human bone-like structures that contained bone and cartilage (FIG. 4e). Labeling sclerotome with a BCL2-GFP construct (FIG. 11b) prior to transplantation confirmed that the ectopic subcutaneous GFP$^+$ bones (FIG. 4e) were not derived from uncolored resident mouse cells. These ectopic sclerotome-derived human bones had a complex organization and were vascularized by host blood vessels (FIG. 11c).

In summary, our hESC-derived sclerotome harbored robust bone/cartilage progenitor activity in vivo. Moreover this validates that hPSC-derived sclerotome can form the fates expected of embryonic sclerotome.

Figure 11E:
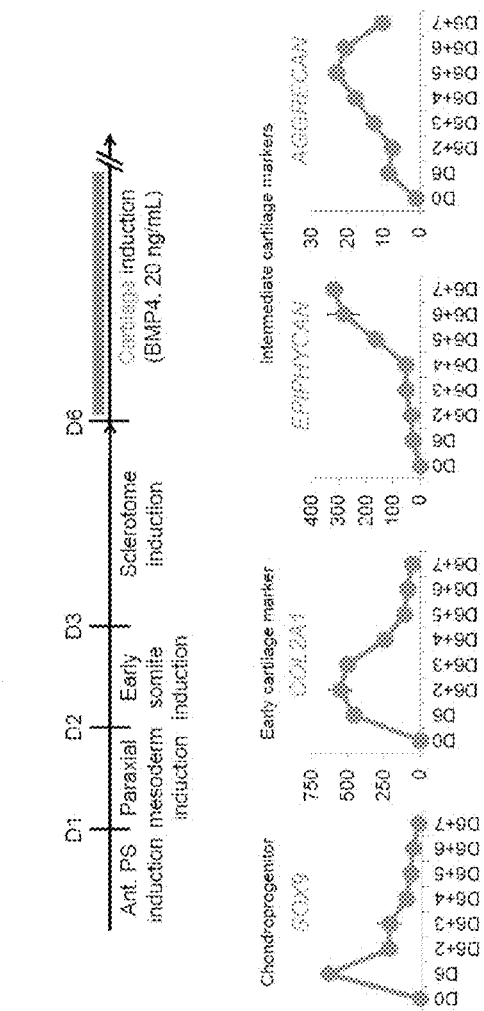
Figure 11G:
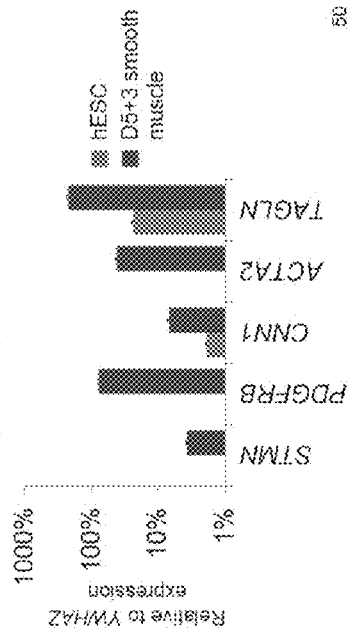
Figure 11H:
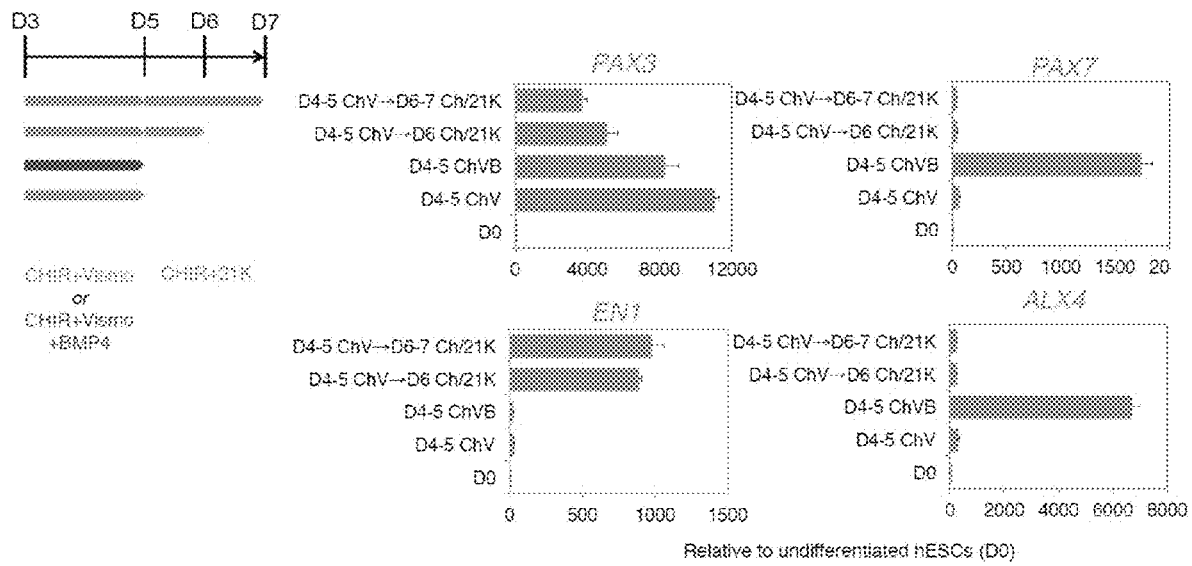
Figure 11I:
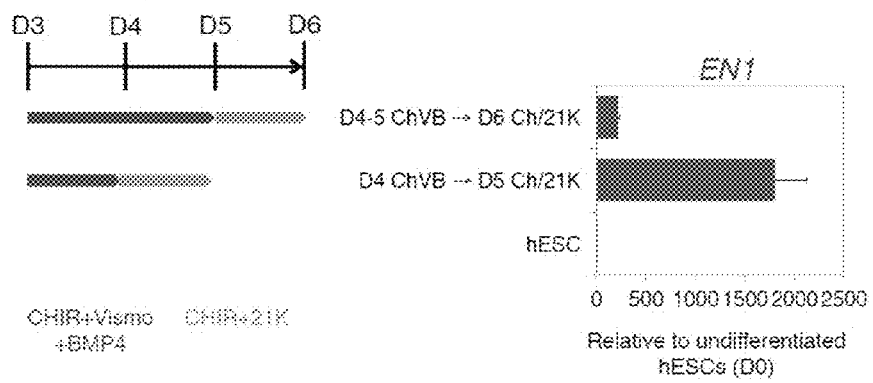
Figure 11J:
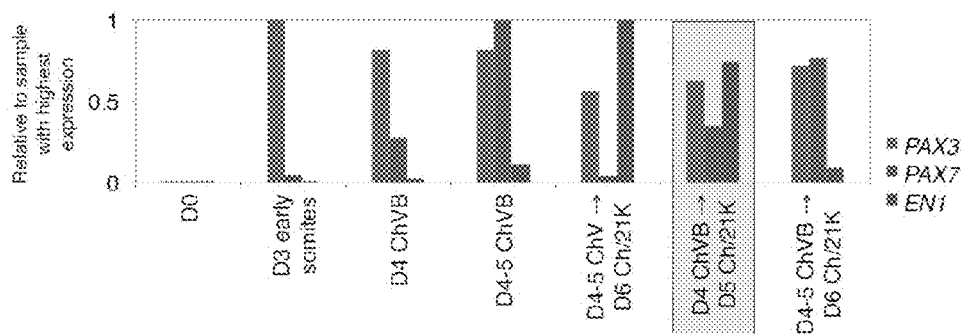

Example 6: Rapid Generation of Smooth Muscle and Cartilage Fates from hPSC-Derived Sclerotome We next sought to further differentiate hPSC-derived sclerotome into downstream smooth muscle and cartilage fates in vitro. By treating day 5 sclerotome with smooth muscle-inductive signals PDGF and TGFβ for 3 further days, a >90% pure SMAα$^{hi}$ smooth muscle-like population was rapidly and efficiently generated after 8 overall days of hESC differentiation (FIG. 4f), in which smooth muscle genes TAGLN, CALPONIN, PDGFRβ, STMN and SMAα were upregulated (FIG. 11g).

Alternatively, by treating day 6 sclerotome with BMP4 for 3 further days, it could be differentiated towards a cartilage fate marked by cartilage structural genes (COL2A1, AGGRECAN, EPIPHYCAN and COMP) after 9 overall days of hESC differentiation (FIG. 4g). hPSC-derived cartilage monolayers were robustly stained by safranin-O (FIG. 4g), indicating that these cells secreted acidic proteoglycans, which is a trademark of differentiated cartilage. Upon BMP treatment, chondroprogenitor genes were silenced and differentiated chondrocyte markers were progressively upregulated (FIG. 11e).

Example 7: FGF and WNT Control Anterior-Posterior Patterning of Lateral Mesoderm, Leading to Cardiac Mesoderm Starting from day 2 hPSC-derived lateral mesoderm, regulators of lateral mesoderm patterning were investigated. After its formation, lateral mesoderm is patterned in vivo along the anterior-posterior axis: Nkx2.5$^+$ anterior lateral mesoderm forms the heart (cardiac mesoderm) whereas Prrx1$^+$ posterior lateral mesoderm generates the limbs amongst other tissues (FIG. 5a).

It was found that a signaling cross-antagonism between FGF and WNT patterned lateral mesoderm, respectively leading to a bifurcation in anterior (cardiac) vs. posterior (limb bud) lateral mesoderm fates (summarized in FIG. 5d). WNT posteriorized lateral mesoderm, inducing limb markers PRRX1 and HOXB5 while suppressing heart field markers NKX2.5 and TBX20 on days 2-3 of hESC differentiation (FIG. 5b, FIG. 12a). Reciprocally, WNT inhibition suppressed posterior lateral mesoderm and instead induced cardiac mesoderm (FIG. 5b, FIG. 12a).

Conversely FGF was critical to anteriorize lateral mesoderm: exogenous FGF enhanced NKX2.5-GFP$^+$ cardiac mesoderm induction by day 3 of hESC differentiation, whereas FGF inhibition abolished the generation of this lineage (FIG. 5c).

Therefore, by activating pro-cardiac FGF signaling and inhibiting pro-limb WNT signaling (in the permissive context of BMP activation and TGFβ inhibition), day 2 lateral mesoderm was efficiently directed towards cardiac mesoderm, as quantified by flow cytometry of an NKX2.5-GFP knock-in hESC line. >80% and >90% NKX2.5-GFP$^+$ cardiac mesoderm was respectively obtained by days 3 and 4 of hPSC differentiation (FIG. 5e), which is twice as rapid as earlier approaches in which NKX2.5 was first expressed by day 7-8 of differentiation. Indeed, generation of NKX2.5-GFP$^+$ cardiac progenitors in our system was more rapid and more robust (FIG. 5f) than when directly compared to another cardiomyocyte differentiation protocol that solely used small molecule WNT modulators.

Example 8: Rapidly Driving Cardiac Mesoderm to Cardiomyocytes by BMP Activation and WNT Inhibition Having rapidly generated a >90% pure NKX2.5$^+$ cardiac mesoderm population by day 4 of hESC differentiation (FIG. 5e,f), methods to drive these progenitors towards cardiomyocytes were next sought.

Figure 12E:
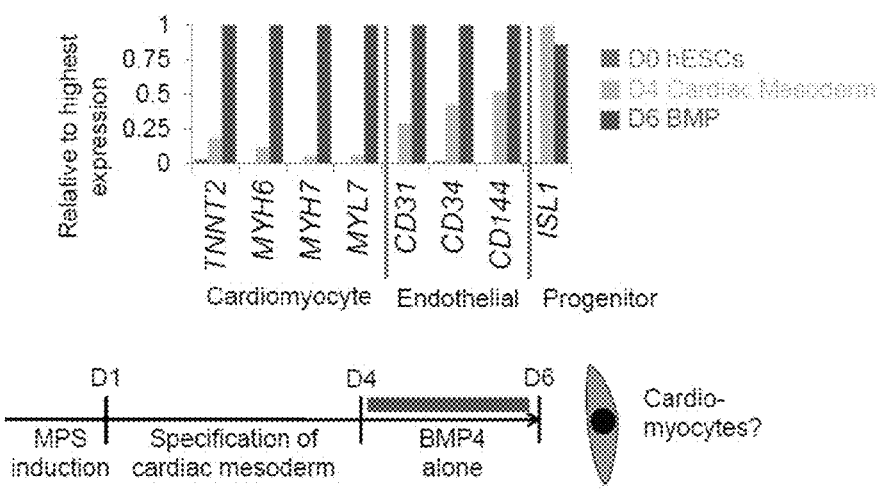
Figure 12F:
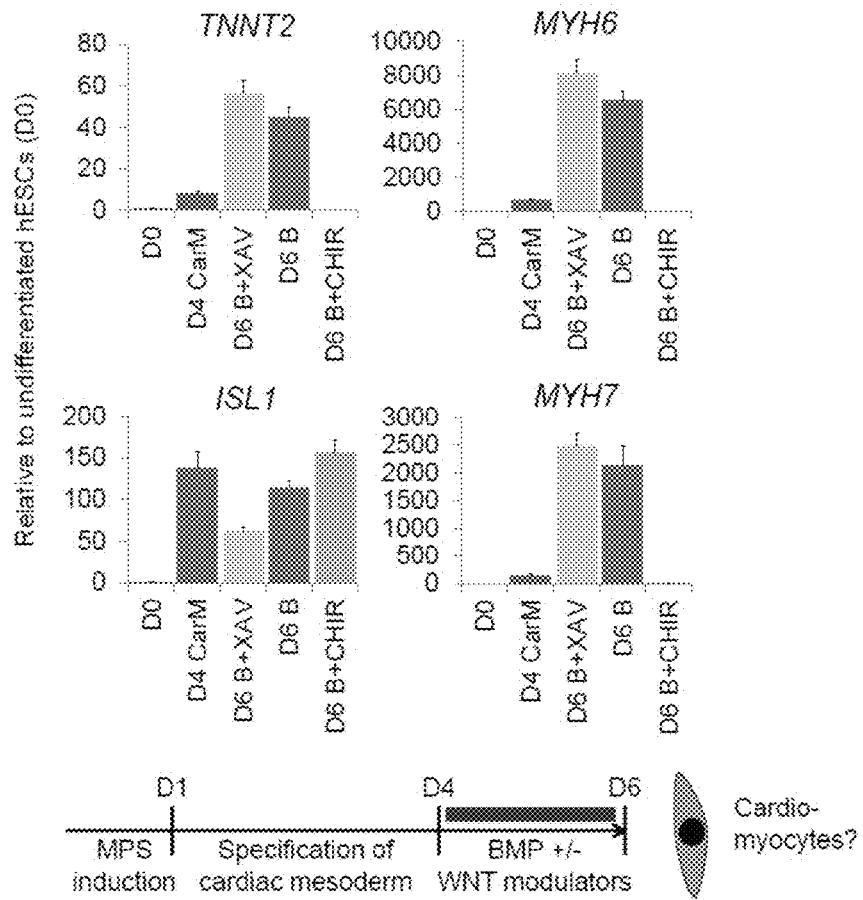
Figure 12G:
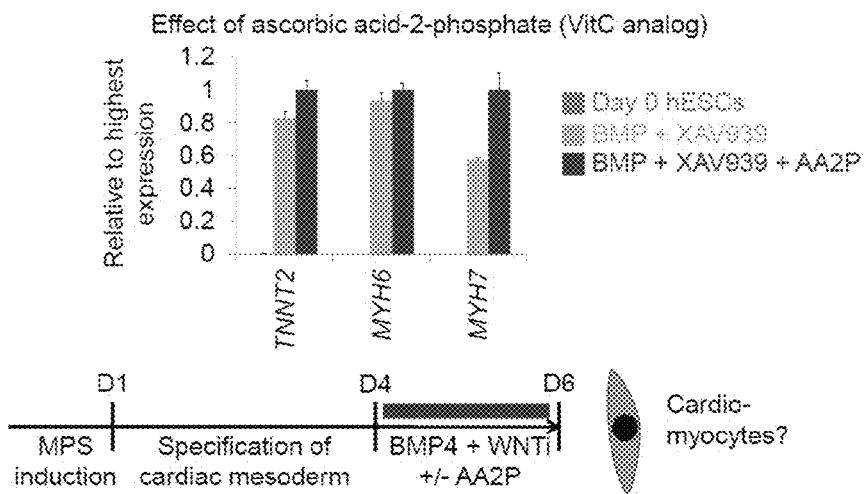
Figure 12I:
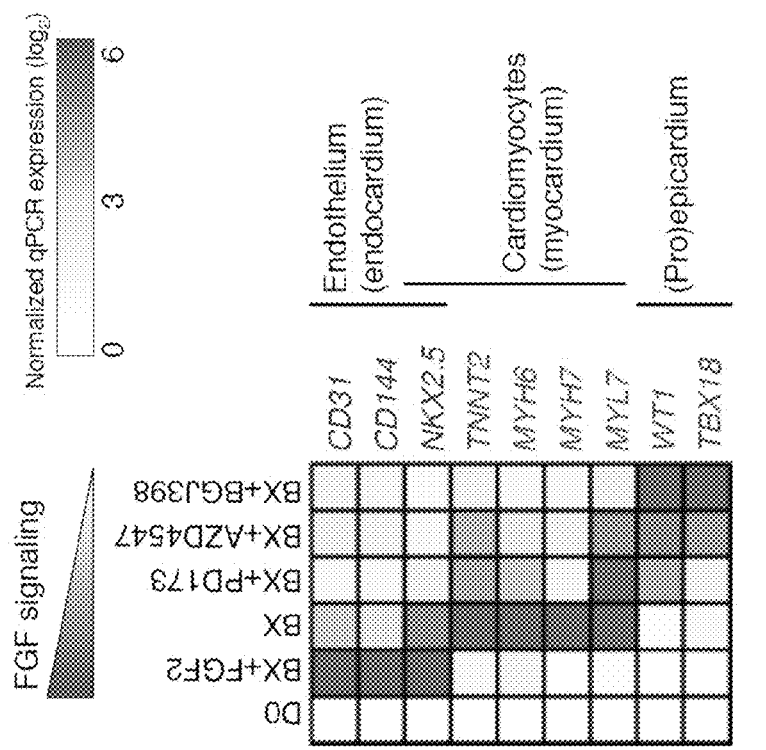
Figure 12H:
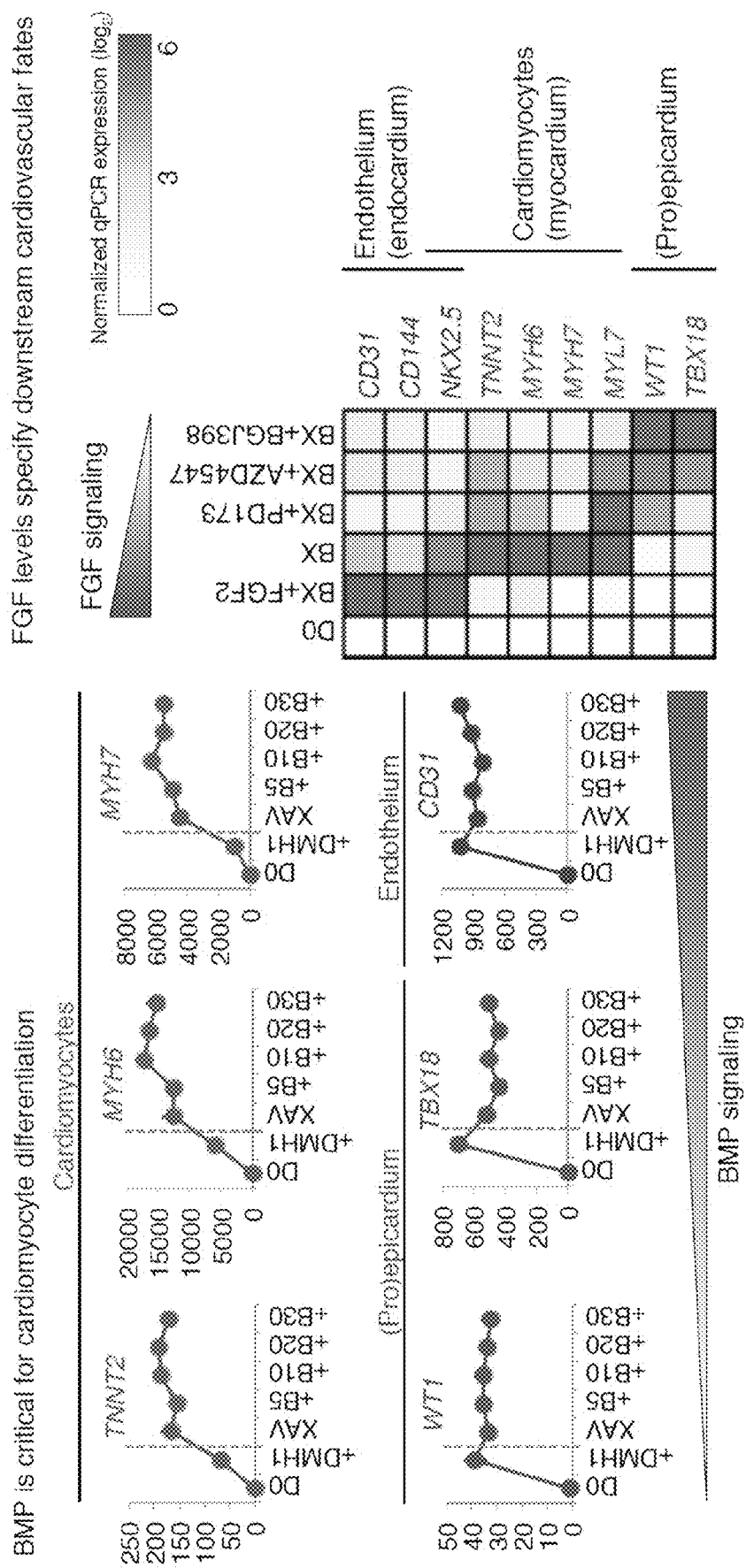

BMP treatment of day 4 cardiac mesoderm induced differentiation into both cardiomyocytes and endocardium (FIG. 12e). WNT activation seemed to sustain undifferentiated cardiac mesoderm progenitors (elevating ISL1 expression) and completely inhibited progression into the cardiomyocyte fate (FIG. 12f). Therefore, WNT blockade in conjunction with BMP activation enhanced cardiomyocyte differentiation (FIG. 12f), which was further enhanced by the inclusion of vitamin C (FIG. 12g). By treating day 4 cardiac mesoderm with these factors, a 54.5±4.7% and a 75.2±1.7% pure TROPONIN$^+$ cardiomyocyte population was rapidly generated by days 6 and 8 of hPSC differentiation, respectively (FIG. 5g) in which cardiomyocyte contractility genes TROPONIN/TNNT2, MYL7, MYH6 and MYH7 were highly expressed (FIG. 5h). Cardiomyocyte contractions were evident on day 8 and onwards, evincing the functionality of such cells.

Example 9: A Mesoderm Developmental Hierarchy Defined by Cell-Surface Markers

Diagnostic cell-surface markers for each mesoderm lineage were sought in order to (i) quantitatively track the diversification of distinct mesoderm progeny from hPSCs by flow cytometry, (ii) enable purification of each mesoderm population for assessment of biological function and fate, and (iii) to allow purification of cells for therapeutic purposes. Therefore a high-throughput screen (FIG. 6a) was conducted to assess expression of 332 cell-surface markers in each mesoderm lineage (PS, cardiac mesoderm, paraxial mesoderm, early somites, sclerotome, dermomyotome and hESCs), yielding >2,300 data-points (FIG. 6b, Table 1, provided in FIG. 15). This screen revealed that mesoderm markers CD56/NCAM1, SIRPα and CD13 were broadly expressed in both paraxial and cardiac mesoderm, and even hESCs to some extent (FIG. 6c), though SIRPα and CD13 levels on hESCs tended to be lower (FIG. 13a).

Novel surface markers GARP and DLL1 were found to respectively mark cardiac mesoderm and paraxial mesoderm in a mutually-exclusive way. The Notch ligand DLL1 was specifically expressed in day 2 paraxial mesoderm but was absent from cardiac mesoderm and hESCs (FIG. 6c,d). Conversely, GARP/LRRC32 marked day 3 NKX2.5-GFP$^+$ cardiac mesoderm but was largely absent from paraxial mesoderm and hESCs (FIG. 6c,d). GARP was uniformly expressed by NKX2.5-GFP$^+$ cardiac mesoderm but was present at lower levels in the NKX2.5-GFP$^-$ lateral mesoderm fraction (FIG. 13b). Therefore these mutually-exclusive markers enabled tracking of a clear bifurcation in mesodermal fates, starting from GARP$^-$DLL1$^-$ hESCs to either GARP$^+$DLL1$^-$ cardiac mesoderm or GARP$^-$DLL1$^+$ paraxial mesoderm (FIG. 6d).

Next, whether these markers of hPSC-derived mesoderm faithfully marked their in vivo counterparts in vertebrate embryos was assessed. GARP/LRRC32 is a LRR-containing transmembrane protein of largely unknown function. Strikingly, it was found that lrrc32 was strongly expressed in the early heart primordium of zebrafish embryos by in situ hybridization (FIG. 6e), therefore indicating that GARP/LRRC32 is a conserved marker of cardiac fate in both human and zebrafish development. DLL1 expression in hPSC-derived paraxial mesoderm was also of interest. We re-confirmed that zebrafish deltaC (the homolog to human DLL1) was indeed expressed in the paraxial mesoderm/tailbud mesoderm (FIG. 13c).

Figure 13D:
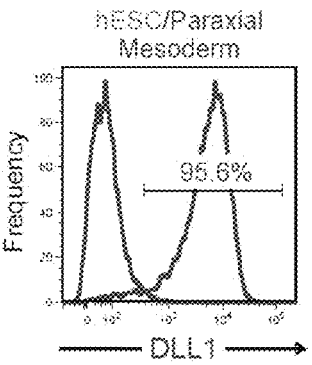
Figure 13E:
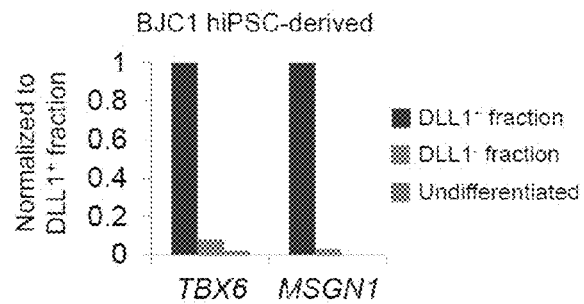

DLL1 was expressed by ~85-95% of the day 2 paraxial mesoderm-containing population, but we noted a DLL1$^-$ subset (FIG. 6f, FIG. 13d). It has been previously described that paraxial mesoderm differentiation yielded a majority of TBX6$^+$CDX2$^+$ paraxial mesoderm cells, though a minority of TBX6$^-$CDX2$^+$ non-paraxial mesoderm was also evident by immunostaining (FIG. 2h). By fractionating on DLL1, it was found that paraxial mesoderm-specific transcription factors (TBX6 and MSGN1) were exclusively expressed by the DLL1$^+$ fraction (FIG. 6f), and these transcription factors were depleted from the DLL1$^-$ subset—though CDX2 was expressed by both DLL1$^+$ and DLL1$^-$ fractions. Sorting DLL1$^+$GARP$^-$ cells consistently enriched for TBX6$^+$ paraxial mesoderm, whether from hESC or hiPSC differentiation (FIG. 13e), thereby highlighting a way to purify paraxial mesoderm from differentiating hPSC cultures.

Figure 13F:
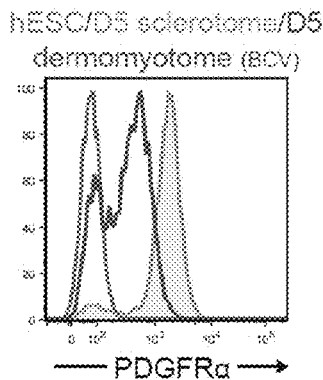
Figure 13G:
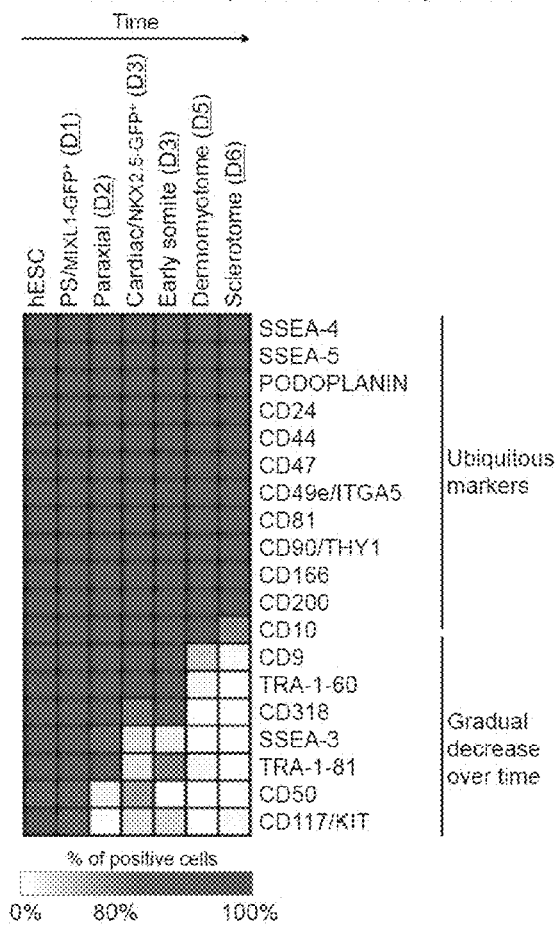

Downstream of paraxial mesoderm during the bifurcation of sclerotome vs. dermomyotome fates, it was also uncovered that PDGFRα enabled the purification of sclerotome. PDGFRα was expressed by ~90-95% of cells in day 5 sclerotome cultures (FIG. 6g). The PDGFRα$^+$ fraction exclusively harbored expression of sclerotome markers (FOXC2, PAX1 and PAX9) compared to the PDGFRα$^-$ subset (FIG. 6g). Therefore, our identification of PDGFRα as a sclerotome marker reaffirms the high purity of sclerotome differentiation and enables the further purification of such cells. It was likewise confirmed by in situ hybridization that pdgfrα was selectively expressed in the sclerotome but not dermomyotome of zebrafish embryos (FIG. 6g). In vitro, PDGFRα was expressed at higher levels in hPSC-derived sclerotome but was decreased in dermomyotome (FIG. 13f), thereby helping to distinguish the ventral from the dorsal somite fate.

In summary, these cell-surface markers define a practical roadmap for mesoderm development (FIG. 7a) by identifying mutually-exclusive types of mesoderm progenitors, thus enabling one to track the products of key developmental branchpoints. These markers are likewise expressed on their counterparts in zebrafish embryos. Through use of these markers to track differentiating hPSCs, we confirmed that differentiation to certain lineages was efficient (FIG. 6), and these markers were subsequently exploited to purify cells.

Example 10: Global Transcriptional Profiling of the Mesoderm Lineage Hierarchy

To chart a molecular roadmap for mesoderm development, global transcriptional dynamics were captured during the commitment of cells to diverging mesodermal fates throughout multiple developmental steps. Therefore, RNA-seq of eight hESC-derived mesoderm lineages (anterior PS, mid PS, NKX2.5-GFP$^+$ cardiac mesoderm, DLL1$^+$ paraxial mesoderm, early somites, PDGFRα$^+$ sclerotome, and dermomyotome) was conducted, using cell-surface markers and intracellular reporters where appropriate to purify mesoderm progenitor populations prior to analysis. Earlier RNA-seq profiling of highly-pure hESC-derived definitive endoderm, as described in Loh et al. 2014, the disclosure of which is incorporated herein by reference in its entirety, was also incorporated to provide insight into the divergence of the endoderm and mesoderm germ layers.

These RNA-seq analyses revealed a clear segregation in developmental fates. Endoderm transcription factor SOX17 was exclusively expressed in hESC-derived definitive endoderm but not paraxial mesoderm or cardiac mesoderm (FIG. 7*bi*). Conversely, TBX6 was activated in hESC-derived day 2 paraxial mesoderm (but not endoderm or cardiac mesoderm), but was promptly shut off within 24 hours of differentiation upon progression to day 3 early somites (FIG. 7*bi*). GARP/LRRC32 expression was largely restricted to cardiac mesoderm (FIG. 7*bi*), consistent with the largely heart-specific expression of lrrc32 in the zebrafish embryo as well as our surface marker profiling of hESC-derived mesoderm lineages (FIG. 6). In summary, these data affirm that definitive endoderm, paraxial mesoderm and cardiac mesoderm fates have been effectively segregated by day 2-3 of hESC differentiation in the described system.

Figures 14A, 14B, 14C, 14D, 14E:
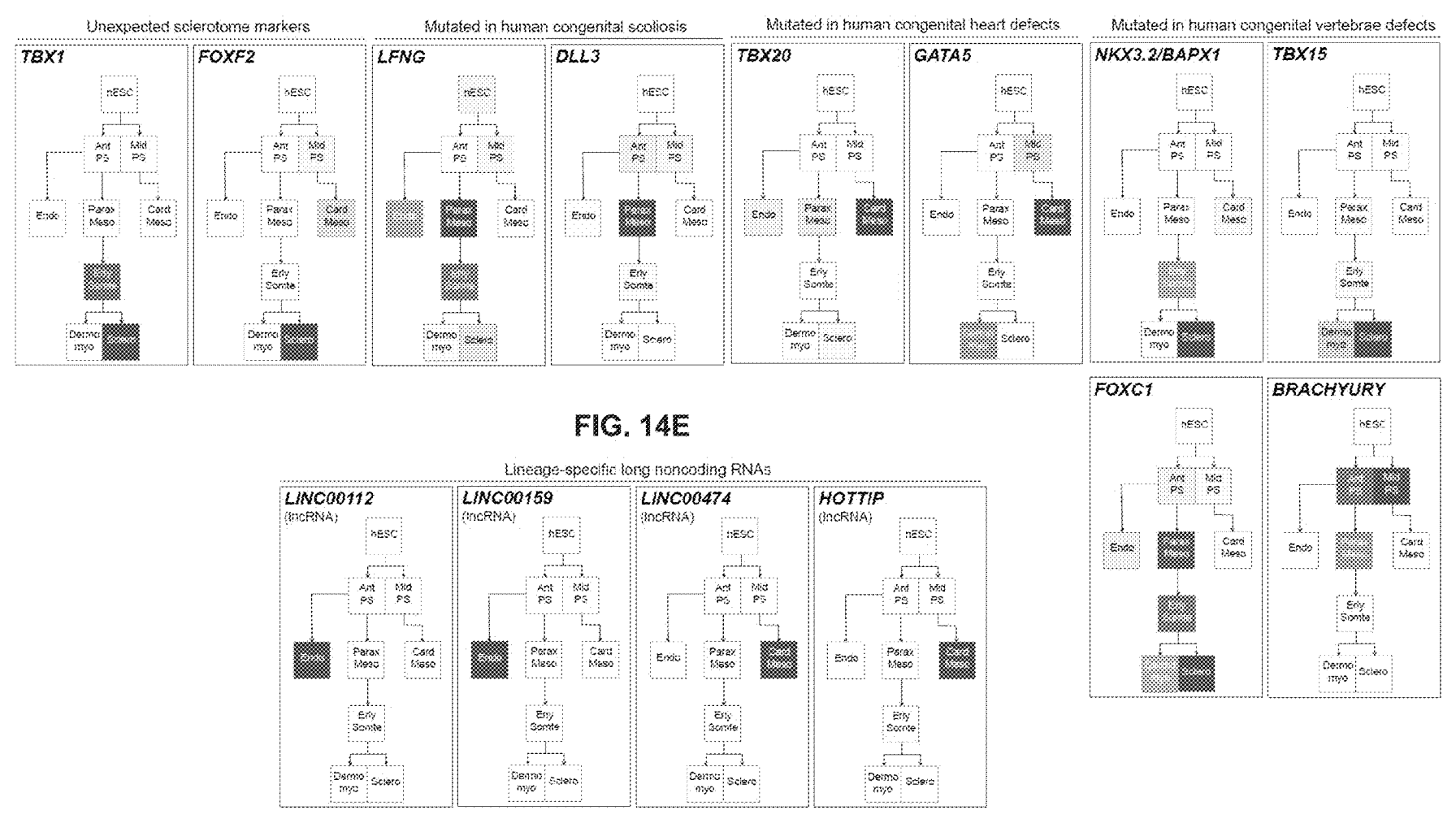

Our profiling also encompassed the bifurcation in sclerotome versus dermomyotome fates. Downstream of paraxial mesoderm, it was found that PAX1 (a sclerotome marker) and PAX3 (a dermomyotome marker) were transiently co-expressed in hESC-derived early somite progenitors, but upon further differentiation, they were subsequently were restricted to either the sclerotome or the dermomyotome, respectively (FIG. 7*bii*). A search for more underappreciated transcription factors that marked this bifurcation yielded TBX1 and FOXF2; these genes were highly expressed in hESC-derived sclerotome but not dermomyotome (FIG. 14*a*). Collectively, these patterns of lineage-specific marker expression lend confidence to the transcriptional dataset.

Next, the relationship between the transcriptional profiles of these human mesoderm tissue progenitors and various human congenital diseases and early developmental defects was assessed. Congenital scoliosis (costovertebral dysplasia) in human patients arises due to an array of spine and rib defects that reflect defective somite segmentation during embryogenesis. This disorder has genetically mapped to mutations in NOTCH pathway genes (DLL3, HES7 and LFNG) in human patients that are thought to alter somitogenesis, though this has remained unproven due to the unavailability of early human embryos to confirm expression of these genes in human paraxial mesoderm. Indeed it was found that DLL3, HES7 and LFNG are robustly expressed in hESC-derived paraxial mesoderm (FIG. 7*biii*, FIG. 14*b*), supporting the notion that mutations in these genes alter human somitogenesis. It was also found that transcription factors mutated in various congenital vertebral disorders (PAX1, NKX3.2, TBX1, TBX15) and congenital heart malformations (GATA5, TBX20) in human patients were respectively expressed in hESC-derived sclerotome (FIG. 7*bii*, FIG. 14*a,d*) and hESC-derived cardiac mesoderm (FIG. 14*c*), suggesting a cell-of-origin for these congenital defects.

Finally, RNA-seq profiling was exploited to interrogate the expression of long noncoding RNAs (lncRNAs). An exemplar of such lncRNAs was FENDRR, which was robustly expressed in hESC-derived cardiac mesoderm (FIG. 7*biii*). Interestingly, Fendrr is likewise expressed in the cardiac mesoderm/lateral mesoderm of the early mouse embryo, and its loss leads to embryonic lethality with decreased expression of E8.5 heart field markers and consequently cardiac malformations. Besides FENDRR, a wide array of lncRNAs with seemingly lineage-specific expression in particular types of mesoderm progenitors was also identified (FIG. 14*e*).

Discussion

A Lineage Bifurcation Roadmap for Mesoderm Development

Figure 7A:
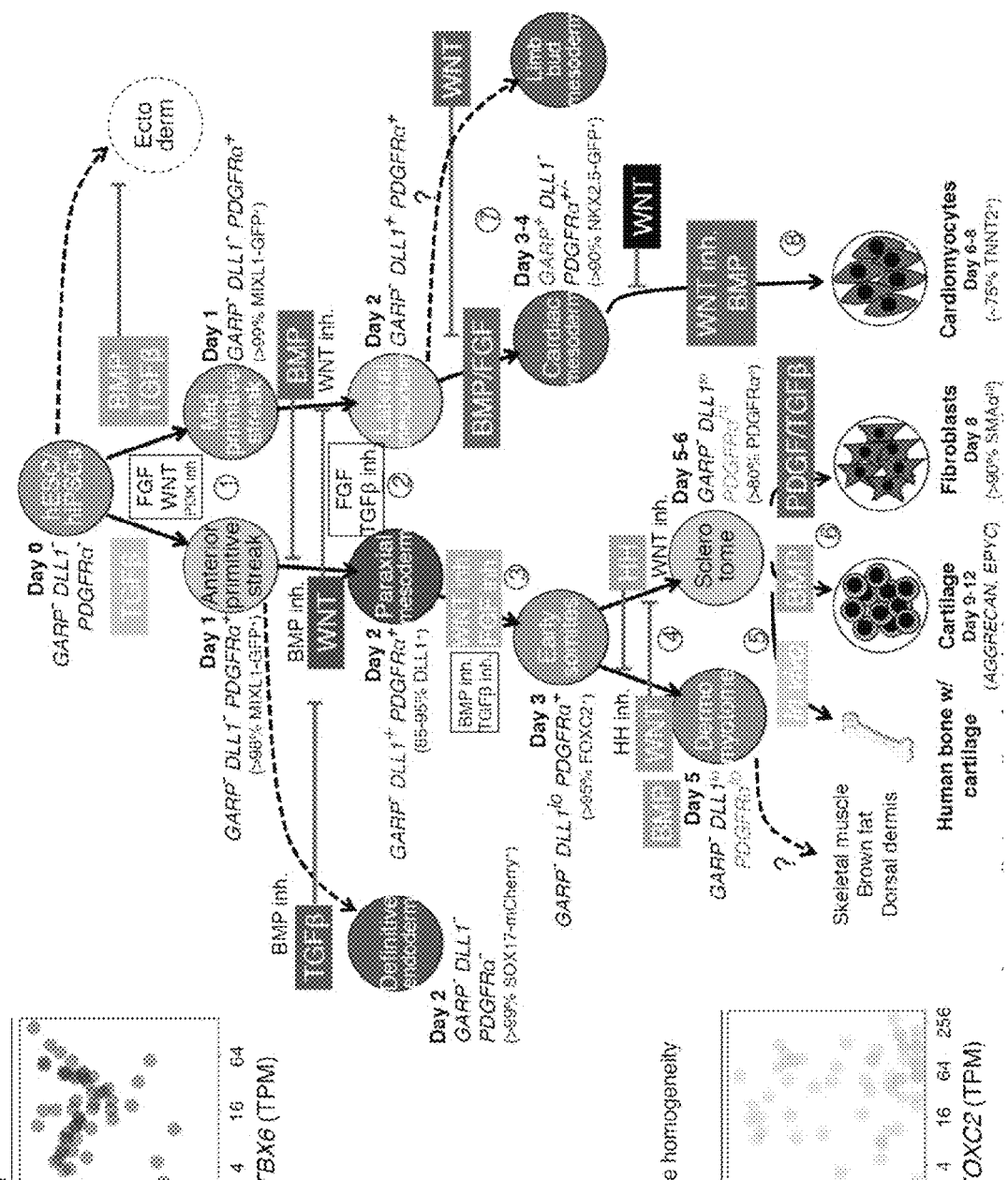
Figure 6H:
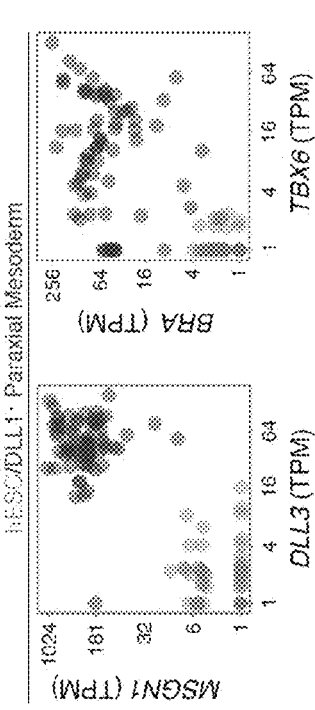
Figure 6I:
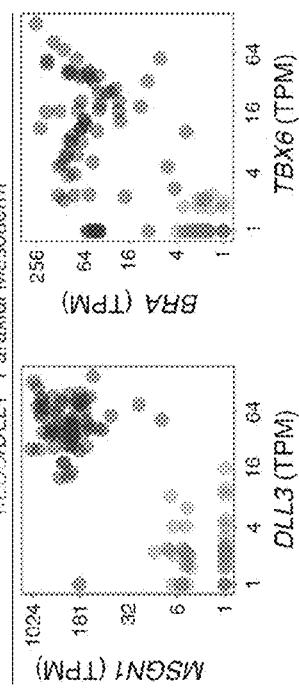
Figure 7E:
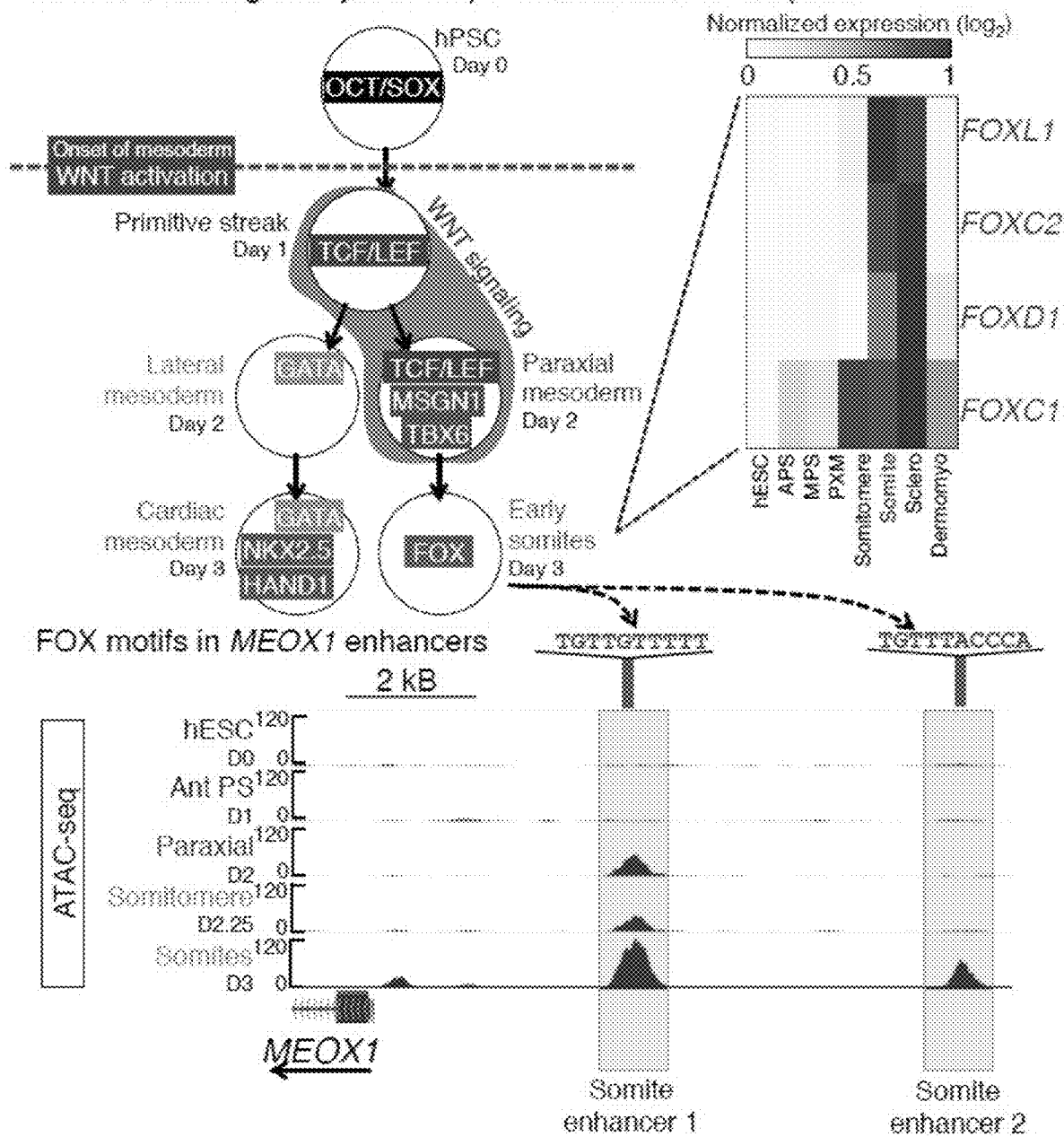

A roadmap has been derived for the patterning of the mesoderm germ layer into diverse derivatives, including bone, cartilage, smooth muscle and heart. This roadmap encompasses a dozen mesoderm progenitors at multiple steps of the developmental hierarchy, starting from human pluripotency and leading towards terminally-differentiated mesoderm fates (FIG. 7*a*). Throughout these consecutive pairwise decisions, aspects have been clearly defined, including: (i) signals inducing mutually-exclusive lineages and (ii) specific cell-surface markers that identify important mesoderm intermediates (FIG. 7*a*). This systematic understanding of lineage bifurcations enables efficient differentiate hPSCs towards one fate or the other at each lineage branchpoint, by providing the relevant positive signal(s) for that lineage while actively inhibiting signal(s) that drive commitment down the other path; thereby enabling unilateral differentiation by inhibiting the alternative fate. Thus, it is possible to rapidly differentiate hPSCs to highly-pure populations of desired mesoderm intermediates (>98% pure MIXL1$^+$ primitive streak; >90% pure NKX2.5-GFP$^+$ cardiac mesoderm; >85% pure DLL1$^+$ paraxial mesoderm), and subsequently into their downstream derivatives. Therefore this roadmap of mesoderm lineage bifurcations enabled the effective generation of a spectrum of mesodermal progeny from hPSCs.

After PS induction, inhibition of pro-endodermal TGFβ signaling during d1-2 of hPSC differentiation shunted differentiation away from endoderm and broadly towards mesoderm. Within this permissive pro-mesodermal context of TGFβ inhibition/FGF activation, it was found that BMP and WNT dueled to respectively induce lateral vs. paraxial mesoderm in a cross-repressive fashion, leading a bifurcation in paraxial (WNT activation/BMP inhibition) and lateral (WNT inhibition/BMP activation) mesoderm fates by the end of d2 of hPSC differentiation.

Subsequently, d2 lateral mesoderm could be efficiently driven to cardiac mesoderm (by d3-4 of hPSC differentiation) through activation of BMP and FGF signaling and simultaneous repression of TGFβ and (pro-limb) WNT signaling. After generating cardiac mesoderm, activation of BMP signaling and inhibition of WNT signaling was important to drive cardiac mesoderm towards cardiomyocytes by d6-8.

Figure 4F:
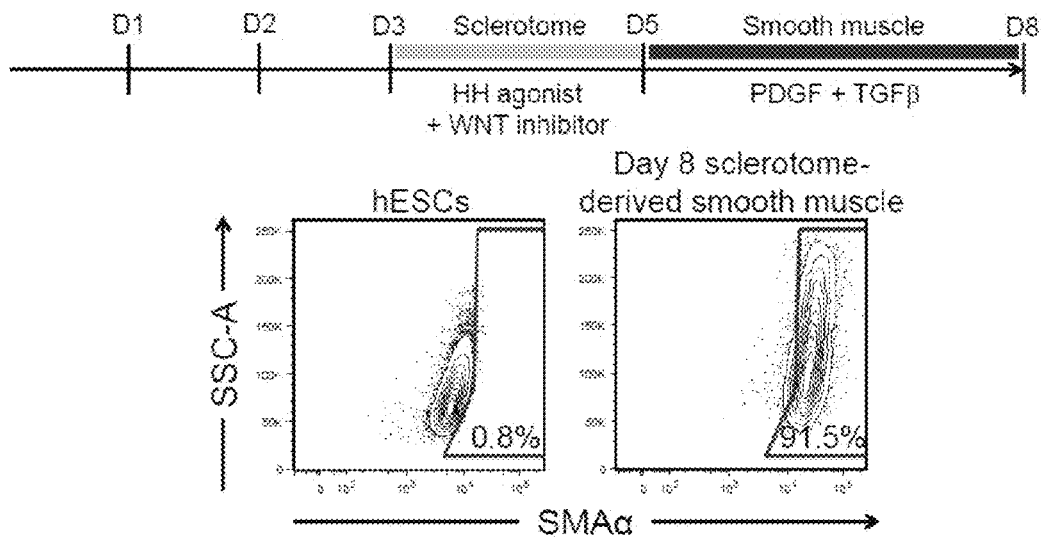
Figure 4G:
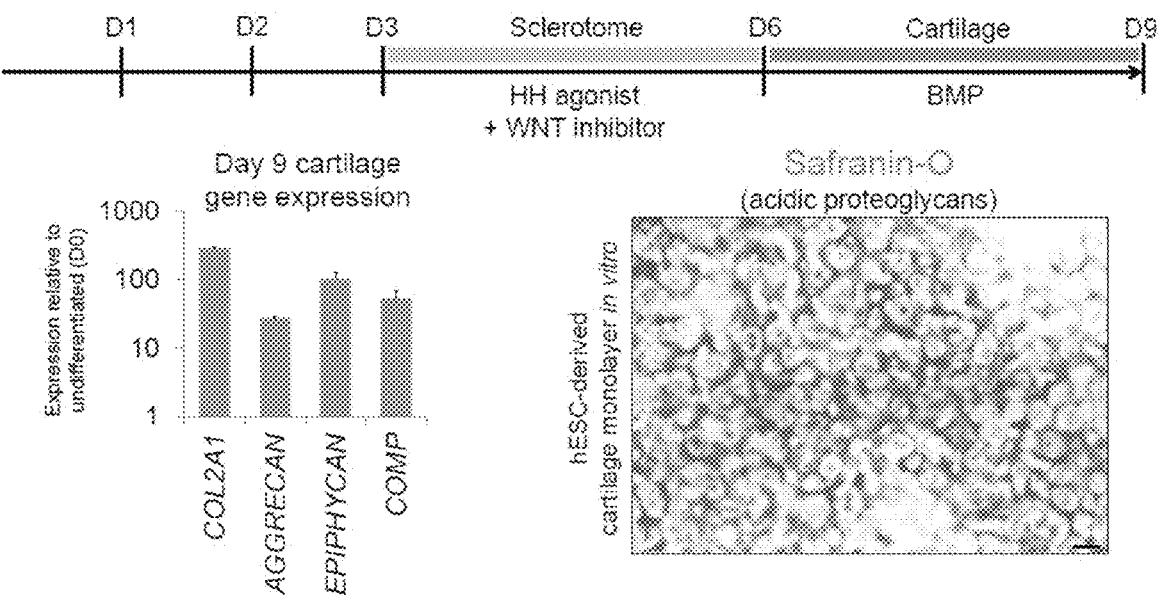
Figure 4H:
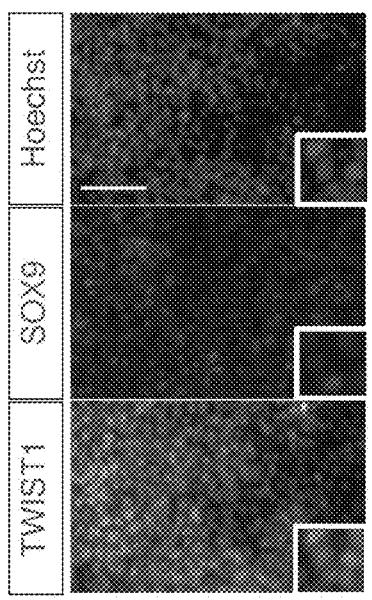
Figure 4I:
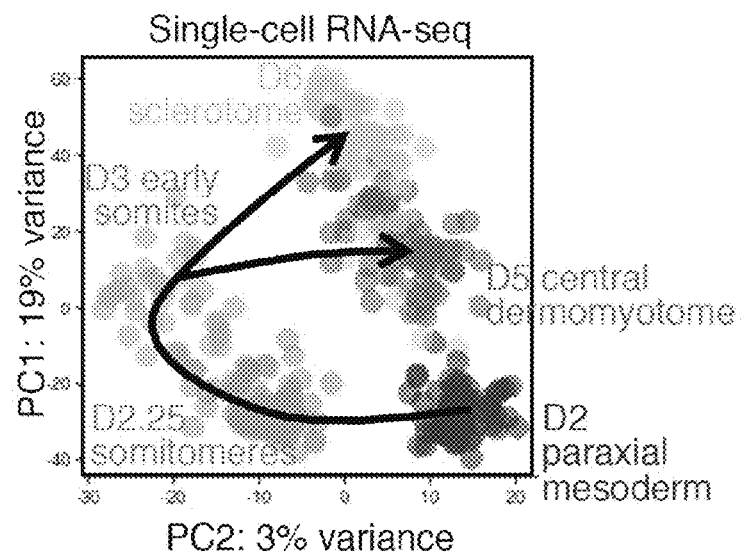
Figure 4J:
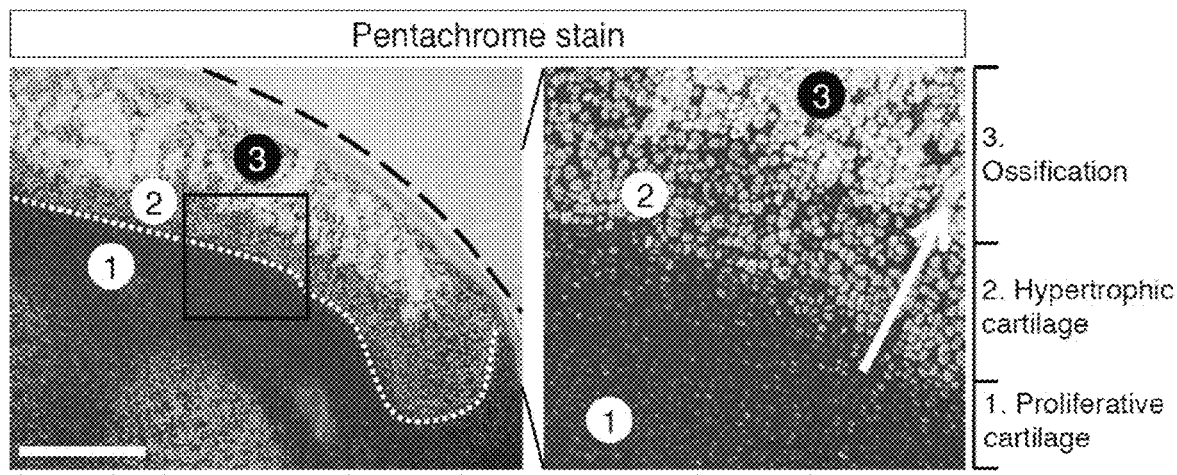

Along a separate developmental route, it was found that d2 paraxial mesoderm could be driven to d3 early somite precursors through the simultaneous inhibition of the BMP, FGF/ERK, TGFβ and WNT pathways. These data emphasize the temporal dynamism of FGF and WNT signaling in somitogenesis: FGF/WNT signaling activated on day 1-2 of differentiation to drive PS towards paraxial mesoderm, but 24 hours later inhibition of these pathways on day 2-3 to generate early somites, all of which occurs in the permissive context of combined BMP/TGFβ inhibition. Subsequently, it was found that cross-antagonizing HH and WNT signals respectively pattern hPSC-derived early somite precursors into sclerotome (ventral somite) or dermomyotome (dorsal somite) on d4-6 of differentiation. This therefore establishes a gateway for the rapid generation of various somite derivatives from hPSCs in vitro, as we show here for smooth muscle and cartilage formation (FIG. 4f,g).

Generating Ectopic Human Bones from hPSCs

Strikingly, it was observed that hPSC-derived sclerotome progenitors robustly formed ectopic human bone-like structures in vivo when subcutaneously transplanted into immunodeficient mice. From the perspective of basic biology, this offers an accessible platform to recreate and decipher human skeletogenesis.

A Lineage Hierarchy for Mesoderm Development with Prospectively-Isolatable Intermediates Importantly, lineage-specific cell-surface markers for major mesoderm subtypes (e.g., DLL1 for paraxial mesoderm and GARP for cardiac mesoderm) were also identified. This enables the prospective isolation of a purified population of a single desired mesoderm subtype which on their own, or from which one can derive tissue stem cells, for therapeutic transplantation. Collectively this work establishes a clear lineage hierarchy for mesoderm development with prospectively-isolatable lineage intermediates at each step which should be key for our understanding of mesoderm development as well as the clinical purification of hPSC-derived progeny for regenerative medicine (FIG. 7a).

Descriptions of Individual Subfigures Presented in FIGS. 8-14

Figure 8I:
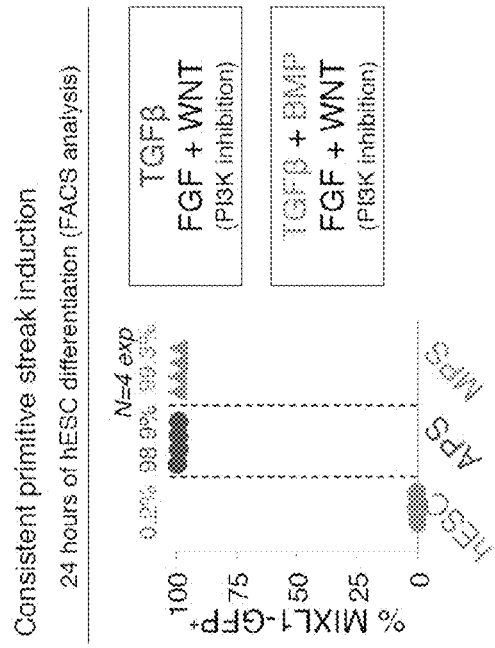
Figure 8J:
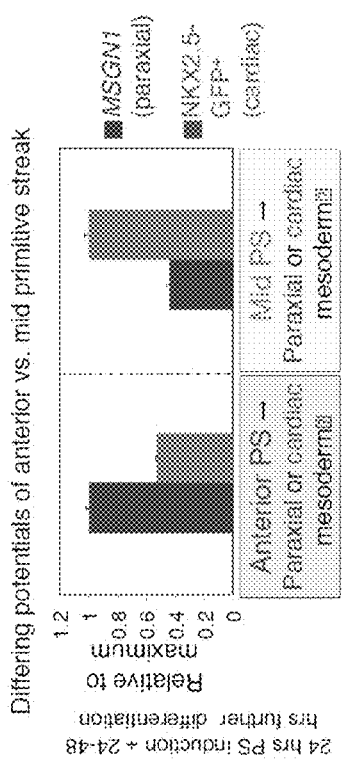

FIG. 8: A) To test the effects of WNT signaling on PS induction, hESCs were differentiated for 24 hours with 3 ng/mL Activin+3 ng/mL BMP4+20 ng/mL FGF2 (A3B3F20) in the presence or absence of a Wnt antagonist (1 μM XAV939) or Wnt agonists (300 ng/mL WNT3A or 0.5-8 μM CHIR99021) and qPCR was conducted; these results showed that WNT activation broadly induces both anterior (TBX6) and mid/posterior (FOXF1, MESP1) PS markers. B) BRACHYURY and MIXL1 immunostaining of hESCs differentiated for 24 hours in mid primitive streak conditions revealed ubiquitous co-expression of both BRACHYURY and MIXL1, evincing the high efficiency of PS differentiation (and corroborated by FACS analysis of a MIXL1-GFP reporter line; see FIG. 1, panel B; nuclear counterstaining by Hoechst dye. C) To test whether TGF signaling was critical for PS induction, hESCs were differentiated towards PS using CHIR99021+20 ng/mL FGF2+ 100 nM PIK90, with or without TGFβR inhibitors (2 μM SB-505124 or 1 μM A-83-01); this revealed that TGF inhibition strongly impairs PS differentiation. D) To assess whether BMP levels patterned the PS along the anterior-posterior axis, hESCs were differentiated towards PS using Activin+CHIR+FGF2+PIK90 (ACFK), in the presence or absence of a BMP antagonist (LDN193189, 250 nM) or increasing doses of BMP4 (3-100 ng/mL); this revealed that whereas BMP inhibition fully abolished PS formation, low (endogenous) levels of BMP supported anterior PS whereas higher levels of exogenous BMP induced posterior PS. E) To assess whether inducing PS in the presence of TGFβ signaling altered its downstream potential to form different kinds of mesoderm, (i) H7 hESCs were differentiated into PS with CHIR99021+FGF2+PIK90 (CFK) for 24 hours in the presence or absence of increasing amounts of Activin (10-100 ng/mL), and then were transferred into paraxial mesoderm induction conditions (A-83-01+CHIR99021+ DM3189+FGF2) for 24 hrs, and qPCR was conducted or (ii) H7 hESCs were differentiated into PS with BMP4 (10 ng/mL)+CHIR99021+FGF2+PIK90 (B10CFK) for 24 hours in the presence or absence of increasing amounts of Activin (10-100 ng/mL), and then were transferred into lateral/ cardiac mesoderm inductions (A-83-01+BMP4+C59) for 24 hours and qPCR was conducted. It was found that inducing PS in the presence of higher Activin doses (e.g., 30 ng/mL) instilled paraxial mesoderm potential, whereas PS induced in lower Activin (e.g., 10 ng/mL) had maximal lateral/ cardiac mesoderm potential. F) To assess whether inducing PS in the presence of BMP signaling altered its downstream potential to form different kinds of mesoderm, H7 hESCs were differentiated into PS with Activin (10 ng/mL)+ CHIR99021+FGF2+PIK90 (A10CFK) for 24 hours in the presence of absence of increasing amounts of BMP4 (1-40 ng/mL), and then were (i) transferred into paraxial mesoderm induction conditions (A-83-01+CHIR99021+ DM3189+FGF2) for 24 hrs, and qPCR was conducted or were (ii) transferred into lateral/cardiac mesoderm inductions (A-83-01+BMP4+C59) for 24 hours and qPCR was conducted. It was found that inducing PS in the presence of BMP4 strongly blocked paraxial mesoderm potential, whereas induction in the presence of high BMP4 (40 ng/mL) maximized lateral/cardiac mesoderm potential. G) H7 hESCs were differentiated into anterior primitive streak (30 ng/mL Activin+4 μM CHIR99021+20 ng/mL FGF2+100 nM PIK90) in the presence or absence of BMP4 (10 ng/mL) for 24 hours, and then transferred into paraxial mesoderm induction conditions for 24 hours before TBX6 immunostaining was conducted. Induction of primitive streak in the presence of BMP4 leads to the subsequent formation of larger numbers of TBX6⁻ clusters of non-paraxial mesoderm cells. H) NKX2.5-GFP hESCs were differentiated into primitive streak with BMP4+CHIR99021+FGF2+PIK90 for 24 hours in the presence or absence of increasing doses of Activin (10-100 ng/mL), and then transferred into suboptimal lateral/cardiac mesoderm induction conditions (A-83-01+BMP4+C59, without FGF2) for 48 hours and FACS was performed after 72 hours of total differentiation to quantify NKX2.5-GFP⁺ cell percentages. The inclusion of low to moderate Activin during PS induction maximizes subsequent differentiation into NKX2.5-GFP⁺ cardiac mesoderm, whereas higher Activin doses (50-100 ng/mL) are less effective. I) Efficient MIXL11⁺ PS specification is highly reproducible in both anterior and mid PS differentiation conditions ("APS" and "MPS", respectively) across 4 independent differentiation experiments, as assayed by a MIXL1-GFP knock-in reporter hESC line. Each circle or triangle represents an individual experiment and the average differentiation efficiency attained across all experiments is indicated. J) Anterior and mid primitive streak populations formed within 24 hours of hESC differentiation have distinct developmental potentials. qPCR of H7 hESC differentiated initially into anterior or mid PS (D0-1), followed by D1-2 paraxial mesoderm induction; qPCR reveals that paraxial mesoderm genes are markedly higher in the APS-derived population (left); day 3 FACS of NKX2.5-GFP hESC differentiated into anterior or mid PS (D0-1), followed by D1-3 lateral/cardiac mesoderm induction; MPS is markedly more competent at generating cardiac progenitors (right).

FIG. 9: A) To assess whether TGFβ agonism drives primitive streak towards definitive endoderm, SOX17-mCherry H9 hESCs were differentiated to anterior primitive streak for 24 hours, after which they were transferred to TGFβ agonism in conjunction with other factors according to Loh et al. 2014, the disclosure of which is incorporated herein by reference in its entirety for 24 hours; FACS was performed on the day 2 population which revealed that >99% of cells were SOX17-mCherry$^+$, indicating their endodermal identity. B) To assess whether FGF/ERK signaling was permissive for both paraxial and lateral/cardiac mesoderm specification, hESCs were differentiated into primitive streak for 24 hours, and then transferred into (i) A-83-01+DM3189 ("AD"; permissive for paraxial mesoderm) or (iii) A-83-01+BMP4+C59 ("AB+C59"; permissive for lateral/cardiac mesoderm) for 24 hours in the presence or absence of a FGF agonist (FGF2, 10-20 ng/mL), an FGFR inhibitor (PD173074, 100 nM) or a MAPK/ERK inhibitor (PD0325901, 500 nM) for 24 hours and qPCR for all experiments was conducted on day 2 (that is, after 48 total hours of hESC differentiation). To assess whether TGFβ signaling altered paraxial, intermediate and lateral/cardiac mesoderm specification, hESCs were differentiated into primitive streak for 24 hours, and then transferred into (ii) DM3189+FGF2 ("DF"; permissive for paraxial mesoderm) or (iv) BMP4+C59 ("B+C59"; permissive for lateral/cardiac mesoderm) for 24 hours in the presence of a TGFβ agonist (Activin, 10-25 ng/mL) or a TGFβR inhibitor (A-83-01, 1 µM) for 24 hours or (v) BMP4 (3 ng/mL)+FGF2 (20 ng/mL) ("B3F20") for 24 hours in the presence of a TGFβ agonist (Activin, 3-25 ng/mL) or a TGFβR inhibitor (A-83-01, 1 µM) and qPCR for all experiments was conducted on day 2 (that is, after 48 total hours of hESC differentiation). C) To demonstrate that blockade of BMP and TGFβ signaling induced paraxial mesoderm, multiple small-molecule inhibitors to these signaling pathways were used to ensure that they phenocopied one another. Therefore, hESCs were differentiated towards primitive streak for 24 hours, and then subsequently transferred into (i) A-83-01+CHIR99021+FGF2 (ACF) in the presence or absence of one of two BMPR inhibitors (DMH1, 1 µM or LDN193189, 250 nM) for 24 hours and qPCR was conducted on day 2. Alternately, hESC-derived PS was transferred into (ii) CHIR99021+DM3189+FGF2 (CDF) for 24 hours in the presence or absence of a TGFβ agonist (25 ng/mL Activin) or one of two TGFβR inhibitors (SB-505124, 2 µM or A-83-01, 1 µM) for 24 hours and qPCR was conducted on day 2. These results affirmed that structurally-distinct inhibitors against the BMP and TGFβ pathways serve to induce paraxial mesoderm. D) NKX2.5-GFP hESCs were differentiated into primitive streak for 24 hours, and then treated with BMP4 (50 ng/mL)+C59 (B50059) for 48 hours in the presence or absence of one of two TGFβR inhibitors (SB-505124, 2 µM or A-83-01, 1 µM) for 48 hours; FACS was conducted on day 3, which confirmed that both TGFβR inhibitors increased NKX2.5-GFP$^+$ cardiac mesoderm induction (**P<0.01). E) To test the role of FGF in lateral mesoderm induction (on day 2 of hESC differentiation), NKX2.5-GFP hESCs were differentiated into mid primitive streak for 24 hours, and then were treated with BMP4+C59+SB505124 in the presence of an FGF agonist (FGF2, 20-50 ng/mL) or a FGFR inhibitor (PD173074, 100 nM) or a MAPK/ERK inhibitor (PD0325901, 500 nM) for 24 hours, and then all cultures were treated with BMP4+C59+SB505124+FGF2 for 24 hours more before being harvested on day 3 for FACS. F) To test the requirement for BMP signaling in lateral mesoderm induction (on day 2 of hESC differentiation), H7 hESCs were differentiated into primitive streak for 24 hours, and then were treated with A8301+C59 for 24 hours in the presence or absence of BMP4 (10-30 ng/mL) and qPCR was conducted; this showed that high amounts of exogenous BMP are required to drive lateral mesoderm specification.

FIG. 10: A) To determine the effects of FGF and WNT signaling on formation of early somite progenitors, BJC1 hiPSCs were differentiated into day 2 paraxial mesoderm, and subsequently were treated with A8301+DM3189 (AD) for 24 hours in the presence or absence of a WNT agonist (CHIR99021, 3 µM), an FGF agonist (FGF2, 20 ng/mL), a WNT inhibitor (C59, 1 µM), a MAPK/ERK inhibitor (PD0325901, 500 nM) or combined WNT and ERK inhibition (C59+PD0325901) (+C+P), which showed that dual WNT and ERK inhibition strongly suppresses paraxial mesoderm genes and enhances early somite marker expression. B) To determine how TGFβ signaling influences early somite progenitor production from paraxial mesoderm, hESC-derived day 2 paraxial mesoderm was exposed to C59+DM3189+PD0325901+RA (CDPR) for 24 hours in the presence or absence of a TGFβ inhibitor (A-83-01, 1 µM) or a TGFβ agonist (Activin, 10-25 ng/mL) and qPCR was conducted on day 3; this revealed that TGFβ inhibition is permissive for expression of early somite markers. C) To determine how BMP signaling influences early somite progenitor production from paraxial mesoderm, hESC-derived day 2 paraxial mesoderm was exposed to C59+PD0325901+RA (CPR) for 24 hours in the presence or absence of a BMP inhibitor (DM3189, 250 nM) or a BMP agonist (BMP4, 5-10 ng/mL) and qPCR was conducted on day 3; for comparison, the gene expression of day 2 paraxial mesoderm was also determined; this revealed that BMP inhibition is permissive for expression of early somite markers. D) To determine whether exogenous retinoic acid is required for early somite progenitor production from paraxial mesoderm, hESC-derived day 2 paraxial mesoderm was exposed to A8301+C59+DM3189+PD0325901 (ACDP) for 24 hours in the presence or absence of increasing concentrations of all-trans retinoic acid (RA, 0.5-2 µM) and qPCR was conducted on day 3 (the gene expression of day 2 paraxial mesoderm was also determined as a control); this revealed that exogenous RA is dispensable for the expression of early somite markers. E) HEYL is transiently expressed during reconstituted human somitogenesis, as shown by single-cell RNA-seq of day 2 paraxial mesoderm, day 2.25 somitomere and day 3 early somite populations; each dot depicts expression in a single cell. Accordingly, HEYL is known to be expressed in mouse somitomeres in vivo. F) Principal component analysis of single-cell RNA-seq data shows the that day 2 paraxial mesoderm, day 2.25 somitomere and day 3 early somite populations progress along a single continuous trajectory; each dot depicts a single cell. Moreover these populations are arranged along their "correct" temporal order (from day 2 to day 2.25 to day 3 of in vitro differentiation) along the PC1 axis. Hence, as in the described methods, the ordering of cells along PC1 was used to infer their progression along developmental "pseudotime" for FIGS. 16A and 16B.

FIG. 11: A) To determine the length of time required for sclerotome differentiation, a qPCR timecourse was performed, encompassing undifferentiated hESCs (D0), day 2 hESC-derived paraxial mesoderm (D2 PXM), day 3 hESC-derived early somite progenitors, and hESC-derived day 3 early somite progenitors that were exposed to sclerotome inductive conditions (5 nM 21K+1 µM C59) for 24 or 48 hours. B) Description of EF1α-BCL2-T2A-GFP lentiviral construct (otherwise known as "C306"; top) and FACS plot of a stably-transduced polyclonal H9 hESC line with near-uniform expression of the BCL2-T2A-GFP transgene (green contour) by comparison to uncolored wild-type hESCs (bottom) (see above methods for details of derivation of the H9 BCL2-T2A-GFP hESC line). C) Higher-magnification picture of BCL2-T2A-GFP hESC-derived sclerotome ectopic bone grafts (originally described above in FIG. 4, panel E), showing that despite the near-ubiquitous expression of GFP throughout the ectopic bone graft (indicating its human provenance), the blood vessels are clearly GFP-negative and therefore presumably derived from the mouse host; scale bar=1 mm. D) Day 3 hESC-derived early somite progenitors were exposed to dermomyotome-inductive conditions (3 μM CHIR99021+150 nM Vismodegib) for 48 hours in the presence or absence of a BMP agonist (BMP4, 10 ng/mL) or a BMPR inhibitor (DMH1, 1 μM); this demonstrated that inducing dermomyotome in the presence of BMP greatly enhances the expression of PAX7. E) Day 6 hESC-derived sclerotome was exposed to pro-chondrogenic BMP4 (20 ng/mL) for varying lengths of time and timecourse qPCR was performed, which showed that SOX9 was rapidly downregulated upon BMP treatment, COL2A1 was already expressed in sclerotome to some extent and become downregulated after several days, and finally that EPIPHYCAN and AGGRECAN were only upregulated after prolonged BMP treatment. F) Day 5 hESC-derived dermomyotome was exposed to 2% horse serum for 12 days to induce myogenic differentiation to some extent (fully described in the above methods), yielding a heterogeneous day 17 population of cells that contained skeletal muscle progeny; qPCR revealed upregulation of myogenic genes whereas markers of alternate fates, including pluripotency (OCT4, SOX2), neuroectoderm (SOX2 and PAX6) and vasculature (FLK1) were minimally expressed (left); immunostaining of the day 17 population revealed expression of skeletal muscle marker MYH3, with nuclear counterstaining by DAPI (right). G) Day 5 hESC-derived sclerotome was differentiated towards smooth muscle-like cells by exposure to PDGF-BB (10 ng/mL)+TGFβ1 (2 ng/mL) for 72 hours; qPCR of the resultant day 8 smooth muscle-like population (brown bars) revealed significant upregulation of smooth muscle-affiliated genes by comparison to the expression of these genes in undifferentiated hESCs (grey bars); y-axis indicates gene expression relative to the expression of reference gene YWHAZ. H) Day 3 hESC-derived early somite progenitors were exposed to dermomyotome-inductive conditions (either CHIR99021+Vismodegib or CHIR99021+Vismodegib+BMP4) for 24 hours, and then were either harvested for qPCR or further transferred into HEDGEHOG-stimulating conditions (CHIR99021+21K, 5 nM) for 24-48 hours; this showed that BMP is important to induce PAX7 in central dermomyotome and that later stage HEDGEHOG activation is important to induce EN1. I) Day 3 hESC-derived early somite progenitors were exposed to dermomyotome-inductive conditions (CHIR99021+Vismodegib+BMP4) for either 24 or 48 hours before being transferred to CHIR99021+21K in order to induce EN1; this showed that only 24 hours of CHIR99021+Vismodegib+BMP4 pre-treatment was optimal for EN1 induction at later stages. J) Combining insights from the data represented in FIG. 11H-11I, it was found that exposure of day 3 hESC-derived early somite progenitors to CHIR99021+Vismodegib+BMP4 from day 3-4 (for 24 hours) followed by exposure to CHIR99021+21K for day 4-5 (for 24 hours) was optimal for the joint upregulation of PAX3, PAX7 and EN1 to induce central dermomyotome-like cells (dashed box). K) Description of pCAG-GFP construct (top); day 6 sclerotome populations derived from pCAG-GFP+H7 hESCs also engrafted when subcutaneously transplanted into NOD-SCID Il2rg$^{-/-}$ mice they formed ectopic bone grafts (bottom), therefore demonstrating that exogenous BCL2 expression is dispensable for sclerotome engraftment and bone formation. L) Description of EF1a-BCL2-T2A-GFP lentiviral construct (otherwise known as "C306"; top) and FACS plot of a stably-transduced polyclonal H9 hESC line with near-uniform expression of the BCL2-T2A-GFP transgene (green contour) by comparison to uncolored wild-type hESCs (bottom) (see the methods described herein for details of derivation of the H9 BCL2-T2A-GFP hESC line). M) Description of UBC-Luciferase-T2A-tdTomato lentiviral construct (top); bioluminescent assay of cultured H9 UBC-Luciferase-T2A-tdTomato hESCs validates that these cells are luciferase-expressing in vitro (bottom). N) Schematically depicts Day 5 to Day 8 fibroblast induction (PDGF-BB+TGFβ1) as demonstrated by fibroblast-like gene expression.

FIG. 12: A) To assess the effects of WNT signaling on lateral mesoderm patterning on day 3 of hESC differentiation, day 2 hESC-derived lateral mesoderm was treated on day 3 with SB-505124 and BMP4 in the presence or absence of a WNT agonist (CHIR99021) or a WNT inhibitor (C59) for 24 hours and qPCR was performed; this revealed that WNT activation specified a posterior lateral mesoderm/forelimb bud fate (PRRX1) whereas its inhibition induced an anterior lateral mesoderm/cardiac mesoderm fate. B) To determine the effects of WNT on lateral mesoderm patterning, D1 PS was differentiated to lateral mesoderm (30 ng/mL BMP4+1 μM C59+2 μM SB505124) for varying lengths of time (until D2, D2.5 or D3) and for the last 12 hrs was treated with C59 or 3 μM CHIR (in addition to BS) and qPCR was conducted; this revealed that pan-lateral mesoderm marker FOXF1 was not markedly changed in response to either WNT activation or inhibition (this panel is an extension of FIG. 5, panel B, above). C) To reveal the possible identity of non-cardiac mesoderm lineages that were contaminating cardiac mesoderm-containing cultures, NKX2.5-GFP hESCs were differentiated towards mid primitive streak (day 1) and were differentiated towards a heterogeneous population containing cardiac mesoderm (day 3) by treatment with SB-505124+BMP4+C59 (without FGF2) on days 2-3 of differentiation. FACS was performed on day 3 to purify either NKX2.5-GFP$^+$ or NKX2.5-GFP$^-$ cells (top subpanels) which were sorted for qPCR (bottom subpanels). Gene expression was normalized to expression of a gene in the NKX2.5-GFP$^+$ fraction (dotted line). D) Timecourse of gene expression in hESCs differentiating towards mid primitive streak and lateral mesoderm, with treatment by SB-505124+BMP4+C59 on days 2-3 of differentiation. Primitive streak markers were transiently expressed on day 1 of hESC differentiation and sharply downregulated, being succeeded by lateral mesoderm markers that were upregulated by day 2. E) Day 4 hESC-derived cardiac mesoderm populations were further treated with BMP4 (30 ng/mL) for 48 hours, which led to the upregulation of both cardiomyocyte (myocardium) and endothelial (presumptive endocardium) genes, suggesting that BMP is permissive for formation of both lineages. F) To assess whether WNT signaling effects the differentiation of cardiac mesoderm into downstream derivatives, day 4 hESC-derived cardiac mesoderm populations (D4 CarM) were exposed to BMP4 (30 ng/mL) in the presence or absence of a WNT agonist (CHIR99021, 3 μM) or a WNT antagonist (XAV939, 1 μM) for 48 hours and qPCR was conducted of day 6 populations; this revealed that WNT activation fully blocked cardiac mesoderm differentiation into cardiomyocytes. G) To assess whether a stabilized vitamin C analog (ascorbic acid-2-phosphate) (AA2P) enhanced cardiac mesoderm differentiation into cardiomyocytes, day 4 hESC-derived cardiac mesoderm was exposed to BMP4 (30 ng/mL)+XAV939 (1 μM) for 48 hours in the presence or absence of 200 μg/mL AA2P and qPCR was conducted of day 6 populations; qPCR data were normalized such that expression values in the highest-expressing sample was normalized=1.0. H) To determine the effects of BMP on downstream differentiation of cardiac mesoderm into various cardiovascular fates, day 4 hESC-derived cardiac mesoderm was treated with XAV939 (1 μM) for 48 hours in presence or absence of BMP4 (5-30 ng/mL) or the BMP receptor antagonist DMH1 (1 μM); this showed that BMP treatment preferentially promotes commitment to cardiomyocyte fate (TNNT2, MYH6, MYH7) without promoting endothelium/endocardium or (pro)epicaridum specification. I) To determine the effects of FGF on downstream differentiation of cardiac mesoderm into various cardiovascular fates, day 4 hESC-derived cardiac mesoderm was treated with $\underline{B}$MP4 (30 ng/mL)+$\underline{X}$AV939 (1 μM) ("BX") for 48 hours in the presence or absence of FGF2 or various FGF receptor antagonists (PD173074, AZD4547 or BGJ398; all at 100 nM); this showed that high FGF signaling promoted endocardium, endogenous FGF levels promoted cardiomyocytes and FGF inhibition promoted (pro)epicardium. J) In the mouse embryo, endocardium (progenitors to heart-affiliated endothelium) are marked by transient coexpression of pan-heart marker Nkx2.5 together with endothelial markers (Ferdous et al., 2009; Stanley et al., 2002). Day 4 cardiac mesoderm derived from NKX2.5-GFP knock-in reporter hESCs was gated on the NKX2.5-GFP$^+$ subset, which was heterogeneous and contained an NKX2.5$^+$CD34$^+$VE-CADHERIN$^+$ putative endocardium-like population and an NKX2.5$^+$CD34$^-$VE-CADHERIN$^-$ non-endocardium population (top). qPCR of these two sorted populations revealed that both expressed pan-heart marker NKX2.5, but only the NKX2.5$^+$CD34$^+$VE-CADHERIN$^+$ endocardium-like population expressed high levels of endothelial markers whereas the NKX2.5$^+$CD34$^-$VE-CADHERIN$^-$ fraction expressed higher levels of HAND1 (bottom). K) Day 3 hESC-derived cardiac mesoderm was treated with BMP4 (30 ng/mL)+C59 (1 μM)+FGF2 (20 ng/mL) for 24 hours in the presence or absence of Activin (25 ng/mL) or the TGFβ inhibitor A-83-01 (1 μM) and then subsequently differentiated into cardiomyocytes for an additional 48 hours in the presence of BMP4+XAV939; this showed that TGFβ activation at the cardiac mesoderm stage enhanced subsequent cardiomyocyte differentiation, potentially consistent with the requirement for TGFβ signaling in zebrafish second heart field development.

FIG. 13: A) After staining for CD13, SIRPα or ROR2, FACS was conducted of undifferentiated NKX2.5-GFP hESCs (grey silhouette) and those that were differentiated in cardiac mesoderm-inducing conditions for 3 days, gating on either NKX2.5-GFP$^+$ cardiac mesoderm (red line) or the NKX2.5-GFP$^-$ non-cardiac fraction (blue line); a fluorescence-minus one (FMO) control was included as a negative control (black line); this revealed that expression levels of CD13, SIRPα or ROR2 in cardiac mesoderm and hESCs were partially overlapping indicating that these markers can partially, but not fully, discriminate between pluripotent and cardiac fates. B) Results from high-throughput cell-surface marker screen of NKX2.5-GFP hESC-derived cardiac mesoderm; gating scheme to identify NKX2.5-GFP$^+$ and NKX2.5-GFP$^-$ populations emerging by day 3 of hESC differentiation (left) and expression of selected markers TIE2, GARP, CD143/ACE and CD1d by FACS (right), showing all 4 markers are uniformly expressed in the NKX2.5-GFP$^+$ cardiac mesoderm lineage by comparison to an isotype control (grey line). C) In situ hybridization for deltaC expression in 18 hpf zebrafish embryos (left; hpf: hours post-fertilization) and a cartoon schematic summarizing the deltaC expression pattern observed, predominately in the U-shaped paraxial mesoderm and to a lesser extent in the posterior halves of the formed somites (right), corroborating earlier studies of deltaC expression in zebrafish embryos. D) Representative example of DLL1 FACS of undifferentiated H7 hESCs (grey) and H7-derived day 2 paraxial mesoderm-containing population (purple); gating reveals that >95% of cells in day 2 cultures highly express DLL1. E) BJC1 hiPSCs were differentiated into day 2 paraxial mesoderm populations, which were sorted into either DLL1$^+$ or DLL1$^-$ fractions and qPCR was conducted of these fractions as well as undifferentiated hiPSCs; this revealed that paraxial mesoderm transcription factors TBX6 and MSGN1 were exclusively expressed in the DLL1$^+$ fraction, reaffirming the validity of DLL1 as a paraxial mesoderm marker. F) PDGFRα FACS of undifferentiated H7 hESCs (grey) or those that were differentiated into day 5 sclerotome (gold) or day 5 dermomyotome (blue), the latter of which was accomplished by treating day 3 early somite progenitors with BMP4+$\underline{C}$HIR+$\underline{V}$ismodegib (BCV) for 48 hours; this revealed that expression of PDGFRα was enriched in sclerotome relative to dermomyotome.

FIG. 14: The panels present RNA-seq profiling of the mesoderm lineage hierarchy, with distinct lineages represented as squares, shades of color in each square indicating gene expression in that lineage, and increasing color intensity denoting higher gene expression (annotated as per FIG. 7). A) Mining RNA-seq data for unexpected transcription factors expressed by the sclerotome but not the dermomyotome yielded TBX1 and FOXF2, reaffirming historical in situ hybridization surveys in mouse embryos that had suggested these transcription factors are also present in sclerotome. B) Congenital scoliosis in human patients (specifically, a condition known as spondylcostal dysostosis) has also been mapped to mutations in NOTCH pathway components LFNG (LUNATIC FRINGE) and DLL3 (DELTA-LIKE 3) (reviewed by Pourquié (2011, Cell 145, 650-663), the disclosure of which is incorporated by reference herein in its entirety), which RNA-seq confirmed are both strongly expressed in hESC-derived day 2 paraxial mesoderm. C) Congenital heart defects have mapped to mutations in a number of developmental genes, including TBX20 and GATA5 (reviewed by Fahed et al. (2013, Circulation Research 112, 707-720), the disclosure of which is incorporated by reference herein in its entirety), which RNA-seq revealed are both highly-expressed in hESC-derived day 4 cardiac mesoderm. D) NKX3.2/BAPX1 mutations lead to vertebral defects in a condition known as spondylo-mega-epiphyseal-metaphyseal dysplasia in human patients, and TBX15 mutations lead to vertebral defects in a condition known as Cousin Syndrome in human patients; RNA-seq revealed that both NKX3.2 and TBX15 are highly-expressed in hESC-derived sclerotome potentially explaining the vertebral defects in these patients. E) Identification of hitherto-cryptic long noncoding RNAs (lncRNAs) expressed exclusively in endoderm or cardiac mesoderm; one of which is HOTTIP (described in, e.g., Wang et al., (2011, Nature 472, 120-124)), the disclosure of which is incorporated by reference herein in its entirety), which is transcribed from the HOXA locus.

Example 11: Efficient Differentiation of Human Pluripotent Stem Cells into Blood Progenitors Along the Definitive Hematopoietic Lineage The signals that drive hESCs into a primitive streak fate (by day 1 of in vitro differentiation), and that subsequently lead to the generation of a highly-homogeneous (>90% pure) CD34+SOX17+ population by day 3 of hESC differentiation have been mapped. These CD34+SOX17+ progenitors, which termed "hemogenic precursors" or "definitive hematopoietic progenitors", express transcription factors and cell-surface markers affiliated with both hematopoietic and endothelial fate. In particular, of endothelial markers, they exclusively express artery markers (but not veins). Therefore the efficient generation of such CD34+ SOX17+ hematopoietic mesoderm represents an ideal starting point for the subsequent generation of terminal blood and blood vessel fates. After 2 days of further differentiation, hematopoietic mesoderm can be differentiated into "hematopoietic intermediates" by day 5 in which expression of blood markers becomes elevated.

The following materials and methods apply to the descriptions of Example 11 provided below.

SOX17$^{mCherry/+}$ H9 hESCs (referred to as SOX17-mCherry hESCs throughout this study) were routinely propagated in mTeSR1 (StemCell Technologies)+1% penicillin/streptomycin. They were passaged ~1:12-1:25 as fine clumps using Accutase (Gibco) onto plates precoated with a Geltrex substratum (Gibco) in mTeSR1 medium supplemented with thiazovivin (2 Tocris; a ROCK inhibitor). After overnight plating, hESCs were washed (DMEM/F12) and differentiated towards posterior PS using BMP4 (15-40 ng/mL, R&D Systems), CHIR99021 (6 Tocris), FGF2 (20 ng/mL, Invitrogen) and PIK90 (100 nM, Calbiochem) for 24 hours, with the optional inclusion of Activin (30 ng/mL, R&D Systems) to induce mid PS. Day 1 mid or posterior PS was subsequently washed (DMEM/F12) and further differentiated using BMP4 (40 ng/mL), GDC-0941 (0.25-2.5 µM, Cellagen Technology), Forskolin (10 µM, Tocris), SB-505124 (2 Tocris), VEGF (100 ng/mL, R&D Systems), XAV939 (1 µM, Tocris) and ascorbic acid-2-phosphate (200 µg/mL, Sigma) for 24 hours. Day 2 cultures were further directed into the definitive hematopoietic lineage/hemogenic precursors by Activin A (15 ng/mL), GDC-0941 (0.25-2.5 µM), VEGF (100 ng/mL), XAV939 (1 µM) and ascorbic acid-2-phosphate (200 µg/mL) for 24 hours. Day 3 definitive hematopoietic progenitors were subsequently differentiated into early Runx1$^{low}$Gfi1$^{low}$ hemogenic intermediates through day 4-5 treatment with BMP4 (50 ng/mL), TTNPB (500 nM), VEGF (100 ng/mL) and XAV939 (1 µM) for 48 hours, supplemented with SB-505124 (2 µM) on day 5. Day 5 populations were then dissociated into single cells, counted and reaggregated in individual wells of a low-adhesion V-bottom or U-bottom 96-well plate (e.g., Thermo Fisher, catalog no. 249952) with ~15,000-20,000 cells seeded per well. Aggregates were cultured for 48 additional hours until day 7 in BMP4 (50 ng/mL), TTNPB (500 nM), VEGF (100 ng/mL), XAV939 (1 µM), SB-505124 (2 µM), SCF (25-50 ng/mL, R&D Systems), IL6 (10 ng/mL, R&D Systems) and IL6RA (250-1000 ng/mL, R&D Systems). All differentiation was conducted in serum-free CDM2 fully-defined basal media.

Myeloid and Lymphoid Assays in Stromal Coculture

Day 5 hESC-derived hematopoietic intermediates were dissociated (Accutase) and plated onto largely-confluent OP9 cells to test their myeloid competence. OP9 cells were routinely propagated in OP9 medium (MEMα medium+ 10% FBS+1% penicillin/streptomycin, with pH adjusted with NaHCO$_3$) for maintenance. hESC-derived hematopoietic intermediates were differentiated towards myeloid fates on OP9 stroma for 4 weeks in OP9 medium+SCF (50 ng/mL)+TPO (50 ng/mL)+IL2 (10 ng/mL)+IL7 (20 ng/mL)+GM-CSF (20 ng/mL)+G-CSF (20 ng/mL)+M-CSF (10 ng/mL. Cocultures were split every week, and after 4 weeks of myeloid differentiation, both adherent and floating cells were collected for FACS analysis.

Basement Membrane Matrices

Geltrex (Gibco) was diluted 1:200 in DMEM/F12 and was used to coat tissue culture plastics for at least 1 hour at 37° C. Recombinant human truncated vitronectin (Gibco, A14700; "VTN-N") was diluted to a 10 µg/mL stock in PBS (lacking Ca$^{2+}$ or Mg$^{2+}$) and was used to coat tissue culture plastics for at least 1 hour at 37° C. For NOTCH activation experiments, VTN-N stock was pre-mixed with 200 nM of a high-affinity mutant DLL4 protein (variant E12) overnight and then the VTN-N/E12 mixture was used to coat tissue culture plastics for at least 1 hour at 37° C. to immobilize the E12 ligand on the plate. Subsequently, coated wells were briefly washed with DMEM/F12 to remove any soluble E12 ligand before plating cells.

Sequential Specification of Primitive Streak and Blood-Island Mesoderm

Figure 20E:
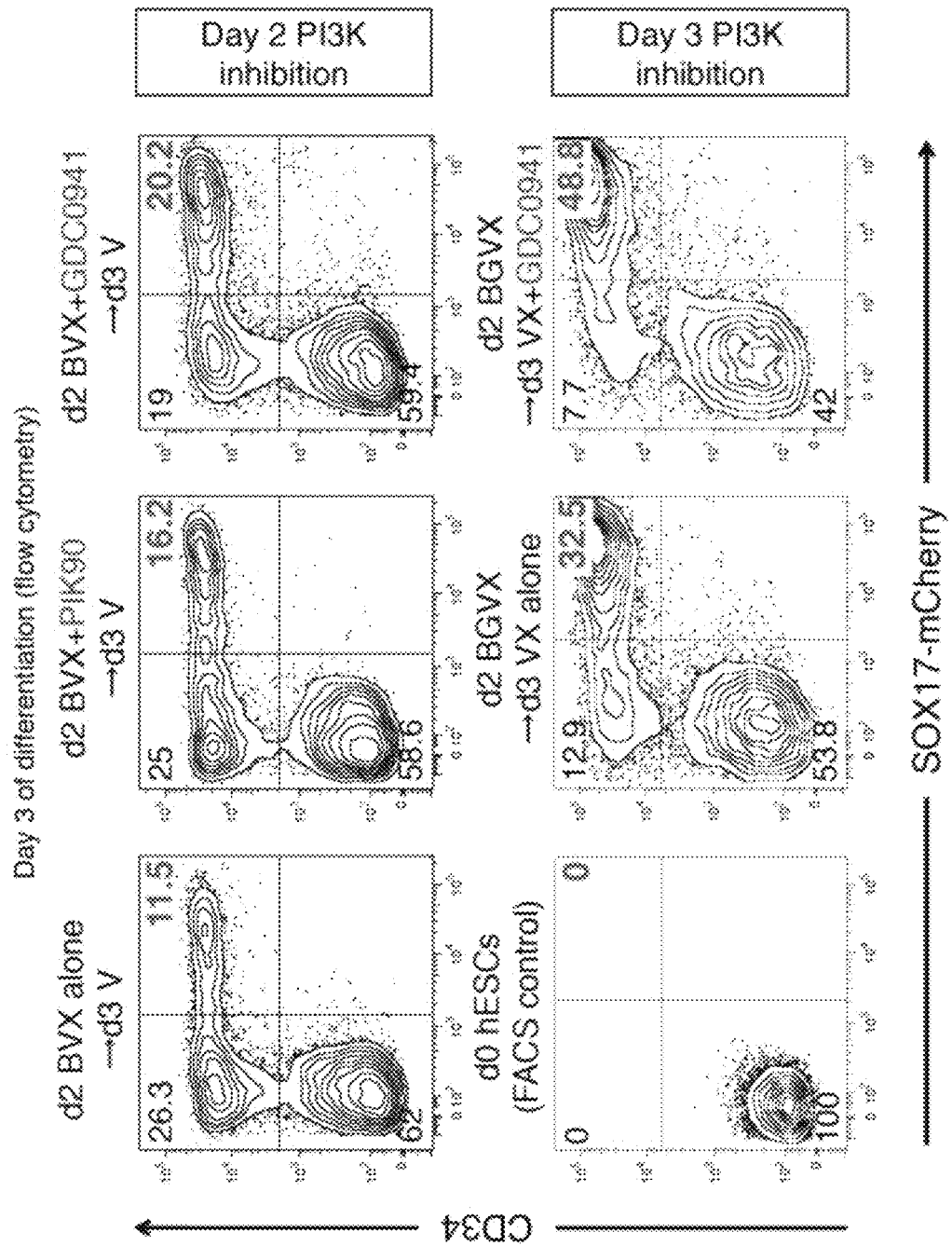

A system to sequentially produce human primitive streak, hemogenic precursors and hematopoietic intermediates from ESCs within several days of serum-free differentiation was developed (summarized in FIG. 18a). Starting from undifferentiated hESCs, specification of posterior primitive streak (PS) combinatorially required the activation of BMP (BMP4, 40 ng/mL), FGF (FGF2, 20 ng/mL) and WNT (CHIR99021, 6 µM) pathways in conjunction with PI3K inhibition (PIK90, 100 nM). Unexpectedly, if PS was induced in the presence of a Activin/TGFβ signal (Activin, 30 ng/mL) to yield a mid PS population, this significantly enhanced the downstream ability of cells to acquire hematopoietic fate (FIG. 20a). Together these signals culminated in the formation of a >97% MIXL1-GFP$^+$ PS population by 24 hours of differentiation (FIG. 18b), as assessed through the use of a MIXL1-GFP knock-in hESC reporter line (Davis, R. P. et al. Blood (2008)111:1876-84). Starting from this highly homogeneous PS population, signals that specify different mesodermal fates including hematopoietic mesoderm were screened for.

Mid and posterior PS collectively develop into several posterior mesoderm lineages, including CDX2$^+$ allantois/chorion, BLIMP1$^+$ primordial germ cells (PGCs) and SCL$^+$ hematopoietic mesoderm in vivo. BMP was found to be commonly required for emergence of all three posterior mesoderm lineages on day 2 of differentiation (FIG. 18c, FIG. 20b), consistent with how Bmp4 is crucial for extra-embryonic mesoderm induction in the mouse embryo. Moreover besides broadly inducing posterior mesoderm fates, BMP activation also suppressed formation of alternative lineages from PS (namely, paraxial mesoderm and definitive endoderm). However, WNT specifically induced allantois/chorion from the PPS and repressed PGC and hematopoietic mesoderm formation (FIG. 18c). Therefore WNT blockade reciprocally expanded PGC and hematopoietic mesoderm (FIG. 18c). Furthermore VEGF signaling was absolutely required for hematopoietic mesoderm formation, mirroring how Vegfr2 is crucial for E7.5 blood island formation in vivo. PKA/cAMP activation (FIG. 20d) and PI3K inhibition (FIG. 20e, top) on day 2 of differentiation further increased blood island specification. Collectively, these findings indicate that collectively activating BMP, PKA/cAMP and VEGF signaling together with simultaneous repression of PI3K, TGFβ and WNT pathways in PS for 24 hours leads to the upregulation of blood-island markers by day 2 of hESC differentiation.

Figure 18D:
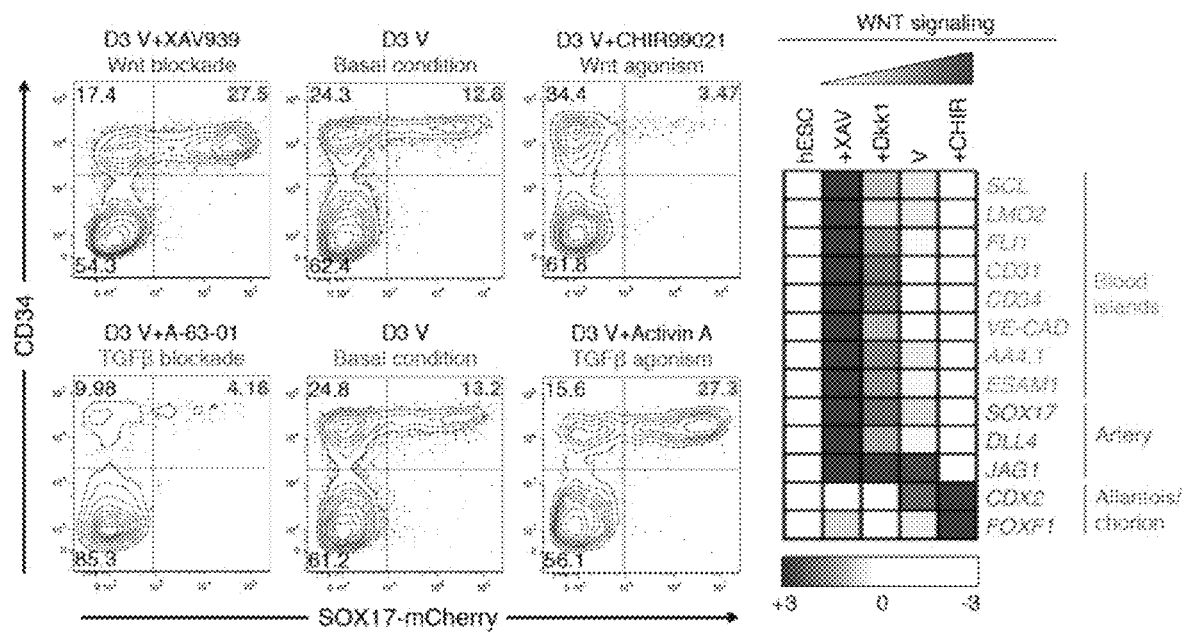
Figure 21A:
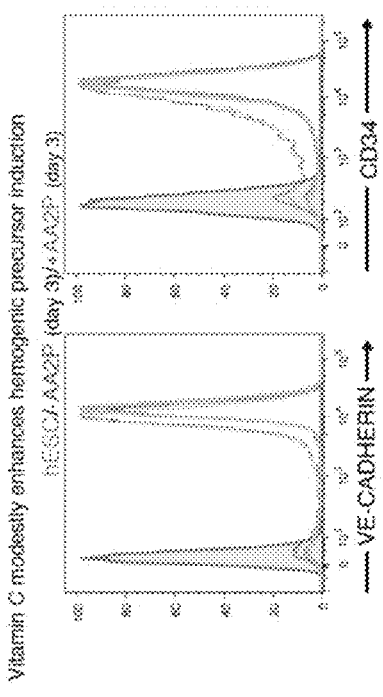
FIG. 21A-21E provide further aspects of further hematopoietic specification of hemogenic precursors according to an embodiment of the instant disclosure.
Figure 21B:
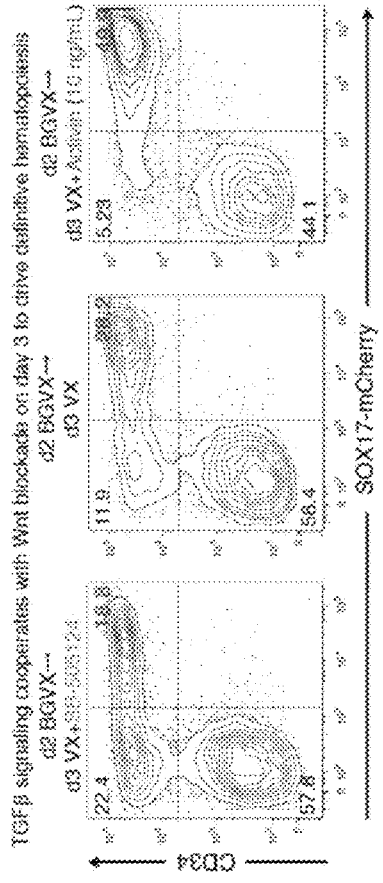
Figure 21C:
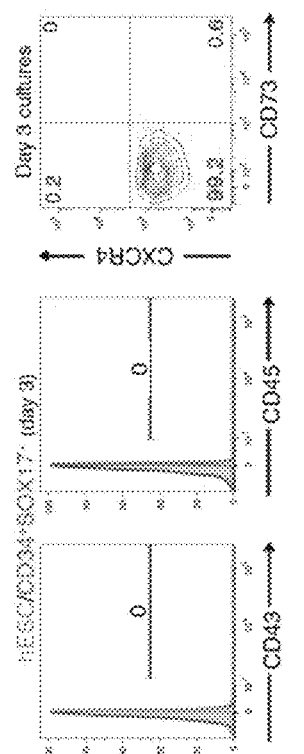

Efficient Generation of SOX17+CD34+Hemogenic Precursors by Day 3 of hESC Differentiation A SOX17-mCherry knock-in hESC reporter line was employed to track the emergence of CD34$^+$SOX17$^+$ hemogenic precursors by day 3 of hESC differentiation. Starting from day 2 differentiated populations, activation of WNT signaling for 24 hours abolished the formation of SOX17$^+$ cells; therefore inhibition of WNT signaling (XAV939) doubled the formation of SOX17$^+$ cells that were formed by day 3 (FIG. 18d, top left and right). Activation of TGFβ signaling (Activin) on day 2-3 also doubled the generation of SOX17$^+$ cells by day 3, whereas TGFβ inhibition was deleterious (FIG. 18d, bottom left and FIG. 21a). Inclusion of a stabilized Vitamin C analog (ascorbic acid-2-phosphate) on days 2 and 3 of differentiation moderately enhanced the efficiency of CD34$^+$ progenitors produced by day 3 (FIG. 21b). Therefore, day 2 differentiated populations were treated with TGFβ and VEGF agonists, together with ascorbic acid-2-phosphate, while simultaneously inhibiting WNT and PI3K signaling (FIG. S20e, bottom) and for 24 hours, which led to the generation of a >90% pure SOX17$^+$CD34$^+$ hemogenic precursor population by day 3 of differentiation in the SOX17-mCherry hESC line (FIG. 18d, left). This method also generated a >90% pure CD34$^+$ hemogenic precursor population from both wild-type H7 and H9 hESC lines within just 3 days of differentiation (FIG. 21c and FIG. 18d, left), attesting to its robustness.

Figure 21D:
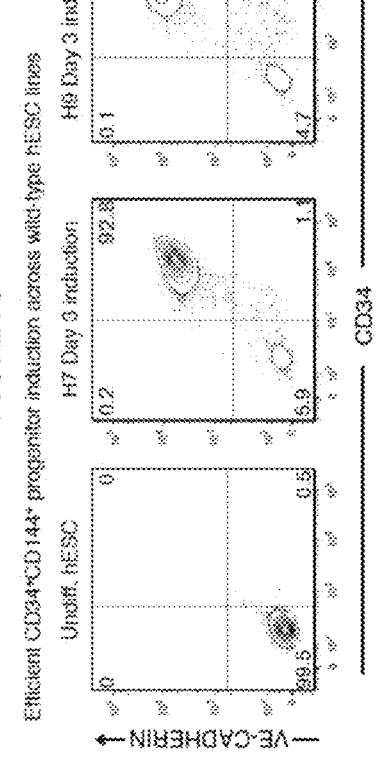
Figure 21E:

Day 3 SOX17$^+$CD34$^+$ hematopoietic mesoderm uniformly expressed other hematopoietic/endothelial-affiliated surface markers (CD31 and CD144/VE-CADHERIN; FIG. 18d, right), indicating these SOX17$^+$ cells were not endodermal. To further probe the identity of these cells, day 3 CD34$^+$SOX17$^+$ hematopoietic mesoderm was FACS-purified and transcriptional profiling was conducted (FIG. 18d, bottom). These cells expressed broad markers of hematopoietic/endothelial identity (SCL, LMO2, FLI1, CD31, CD34, VE-CAD, AA4.1, ESAM1). Particularly they expressed arterial-specific markers SOX17, FOXC1, EFNB2, DLL4, JAG1, NOTCH1 but minimally expressed venous marker NR2F2/COUP-TFII, allantois/chorion markers CDX2 and FOXF1 or pluripotency factors OCT4, SOX2 and NANOG. Moreover CD34$^+$SOX17$^+$ day 3 precursors near-uniformly expressed CD31 and CD144/VE-CADHERIN, yet they lacked markers associated with mature hematopoietic fates (CD43, CD45) indicating they represented uncommitted hemogenic precursors prior to acquisition of a discrete hematopoietic identity (FIG. 21d). Importantly, they did not belong to the primitive hematopoietic lineage (marked by CD235a), as expression of CD235a was mutually exclusive to that of CD34 and SOX17 (FIG. 21e). In summary, day 3 CD34$^+$SOX17$^+$ hemogenic precursors (i) correspond to a population of early blood/blood vessel precursors prior to formation of terminally-differentiated blood cells; (ii) they are committed to a definitive hematopoietic program (as opposed to primitive hematopoiesis); and finally (iii) these hemogenic precursors exist in a arterial-like endothelial state.

Figure 22A:
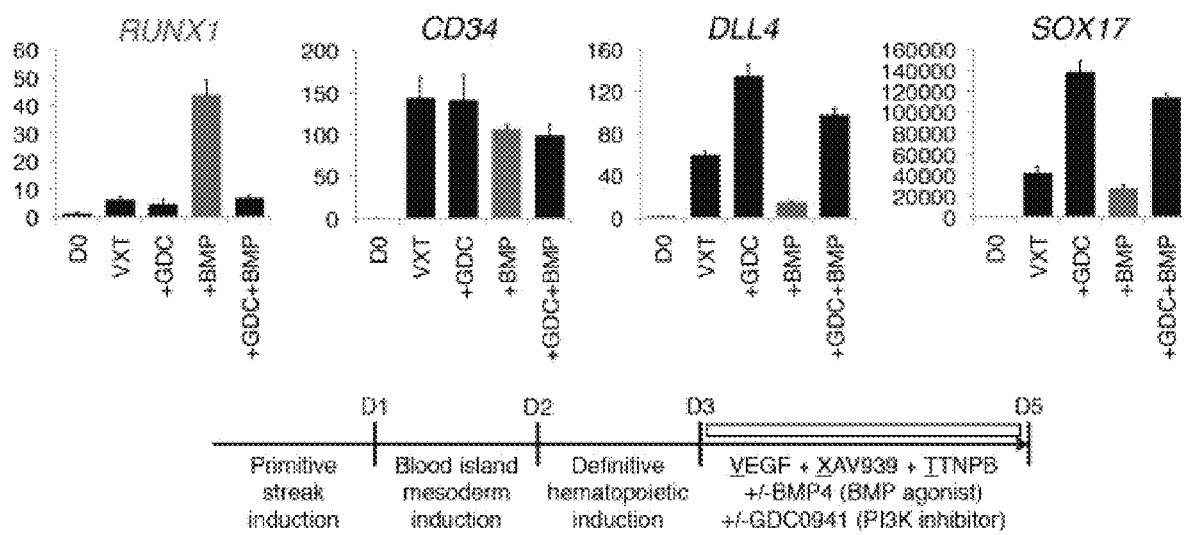
Figure 22B:
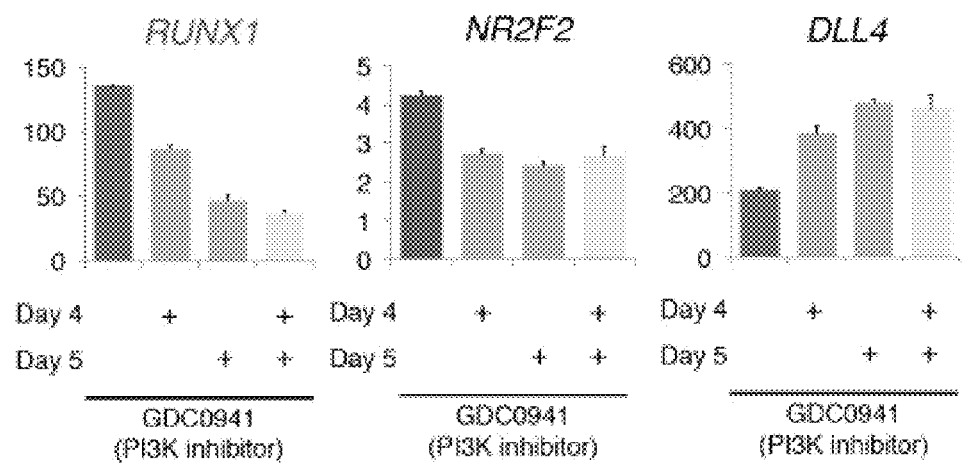

Activating BMP, VEGF and RA while Inhibiting TGFβ and WNT Signaling Drives Hemogenic Precursors into Hematopoietic Intermediates After establishing a homogeneous SOX17$^+$CD34$^+$ arterial-like hemogenic precursor population (FIG. 18e), the signals that subsequently implement a hematopoietic identity were investigated. After the dorsal aorta acquires arterial identity, it is spatially patterned in vivo such that its ventral floor gains hemogenic potential (marked by Runx1) whereas by contrast, its dorsal aspect (marked by Tbx20) lacks hemogenic attributes. a combination of BMP, VEGF, XAV939 (a Wnt antagonist) and TTNPB (a retinoid agonist) were crucial to upregulate RUNX1 in hemogenic precursors by day 5 of differentiation (FIG. 19a). Withdrawal of either BMP or TTNPB crippled RUNX1 expression, indicating their combined necessity (FIG. 19a, FIG. 22a). WNT blockade was pivotal to prevent BMP-induced GATA1 expression and TTNPB was important to downregulate TBX20 expression, thus repressing differentiation towards alternate fates (FIG. 19a). Inhibition of TGFβ signaling also further enhanced the induction of hematopoietic markers RUNX1 and GFI1B (FIG. 22c). Together, this demonstrates that activation of BMP, VEGF and RA together with inhibiting TGFβ and WNT signaling drives day 3 hemogenic precursors into day 5 hematopoietic intermediates.

To test whether day 5 hematopoietic intermediates had the potential to subsequently form differentiated blood fates, they were transferred onto OP9 stromal layers in the presence of hematopoietic growth factors. After 4 weeks of such co-culture, these progenitors differentiated into CD45$^+$ CD33$^+$ myeloid cells, some of which co-expressed monocyte/macrophage marker CD14 (FIG. 19b). Upon further maturation, these hESC-derived myeloid cells were capable of phagocytosing fluorescently-labeled latex beads in a fashion similar to macrophages (not shown). This therefore indicates that day 5 hESC-derived hematopoietic intermediates are competent to subsequently form terminally-differentiated blood cells.

Upregulation of RUNX1 and GFI1B in Continued Aggregate Culture

A screen of signaling modulators identified SCF and IL6 as factors that enhanced hematopoietic transcription factor expression. SCF signaling through the KIT receptor is critical for Runx1 expression in mouse embryos and for embryonic HSC specification. IL6 is closely related to IL11 in the IL6 family of signaling ligands, and the receptor for IL11 is specifically expressed in adult mouse HSCs by comparison to more downstream blood cell-types. To activate IL6 signaling during hESC differentiation, IL6 ligand was provided simultaneously together with soluble IL6 receptor ectodomain (henceforth referred to as IL6RA).

Treating day 5 hematopoietic intermediates with combination of eight factors (BMP4, TTNPB, VEGF, XAV939, SB-505124, SCF, IL6 and IL6RA) continued to strongly upregulate GFI1B and moderately upregulate RUNX1 after 48 hours of continued differentiation (FIG. 19c). Strikingly, differentiation in 3-dimensional aggregates significantly improved GFI1B and RUNX1 expression compared to monolayer differentiation from day 5 onwards (FIG. 19c). Individually withholding each of these 8 factors revealed that GFI1B expression was strongly diminished in the absence of either XAV939, SB-505124, SCF, IL6 or IL6RA (FIG. 19d), indicating (i) the importance of these critical factors and (ii) the reliance of IL6 ligand on the presence of soluble IL6RA receptor ectodomain to potentiate GFI1B expression. Withholding VEGF did not markedly impair GFI1B expression, but was deleterious, as evinced by increased expression of the vein marker NR2F2 (FIG. 19d). By contrast, withdrawal of BMP4 minimally effected hematopoietic or venous gene expression, suggesting it is superfluous (FIG. 19d).

Collectively these findings show that continued differentiation of day 5 hematopoietic intermediates in 3-dimensional aggregates, together with exposure to a number of signaling factors, results in the production of late hematopoietic intermediates by day 7. These late hematopoietic intermediates are marked by fairly high expression of key hematopoietic transcription factors GFI1B and RUNX1.

Discussion

Figure 18E:
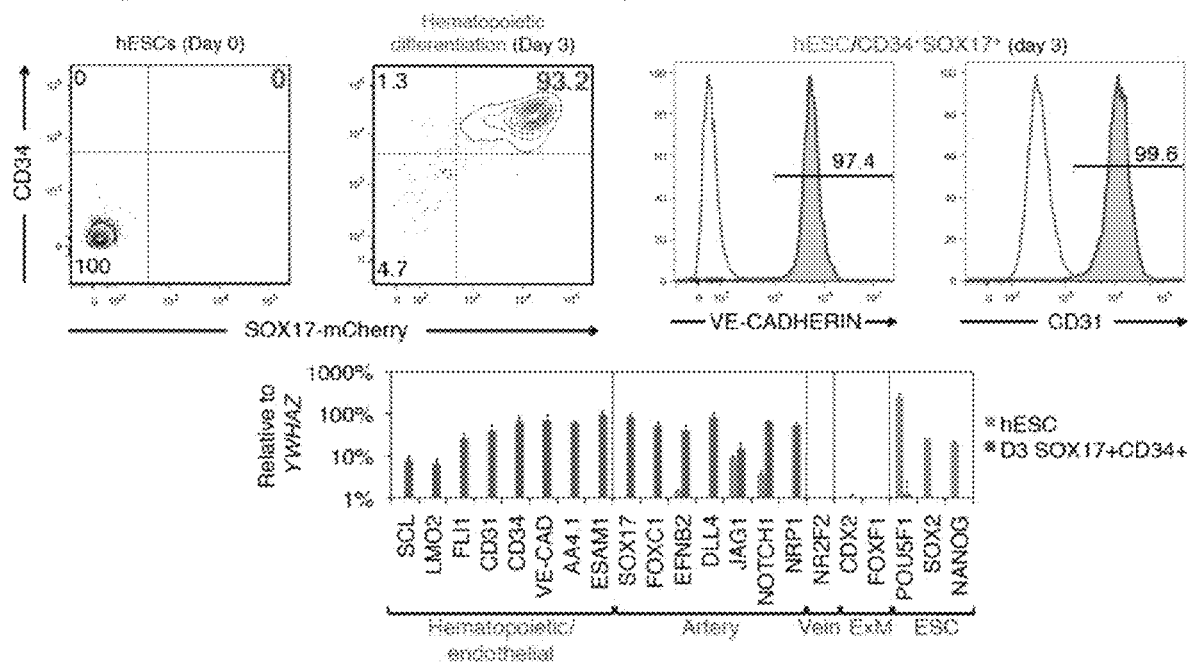

The combinations of inductive and repressive signals that were sufficient to efficiently drive pluripotent cells into hematopoietic mesoderm progenitors along the definitive hematopoietic route were systematically deconvoluted (summarized in FIG. 19a). Availing ourselves of this signaling roadmap, a >97% pure MIXL1$^+$ primitive streak population was generated by 24 hours of hESC differentiation and a >90% pure SOX17$^+$CD34$^+$ hemogenic progenitor population within 72 hours of hESC differentiation (FIG. 18). These day 3 hemogenic progenitors had many characteristics of blood vessel cells (endothelium), as reflected by morphology (not shown) and expression of diagnostic transcription factors and cell-surface markers (FIG. 18e and FIG. 21), and specifically had an artery-like phenotype. Hence, these populations of arterial endothelium-like cells provide a source of cells for neovascularization for regenerative medicine or tissue engineering, among other applications.

Upon progressive differentiation, by day 5 or day 7 these progenitors could mature into hematopoietic intermediates designated by relatively high expression of hematopoietic transcription factors RUNX1 and GFI1B (FIG. 19). The ability of such hematopoietic intermediates to differentiate into CD33$^+$CD14$^+$CD45$^+$ monocyte/macrophage-like cells provided evidence for their hematopoietic developmental potential (FIG. 19b). Hence, these hematopoietic intermediates provide a source of multipotent hematopoietic stem cells for blood and immune system replacement. Alternatively, these hematopoietic intermediates provide progenitors for differentiation into T cells and dendritic cells for cancer immunotherapy, erythroid cells for blood transfusions or megakaryocytes/platelets for clotting disorders. In summary, the newfound capacity to produce fairly homogeneous populations of human blood vessel progenitors and blood progenitors in culture should serve a broad range of applications including regenerative medicine, tissue engineering and cancer therapy.

Example 12: Reconstituting Early Human Limb Bud Progenitors to Interrogate Limb Development and Malformations A reductionist system to study limb formation in a simplified system was developed. Namely, early human limb bud progenitors were efficiently generated in culture from embryonic stem cells and induced pluripotent stem cells. This reductionist system allowed the definition of the key signals that specify limb bud fate from lateral mesoderm; that specify a bifurcation in arm vs. leg fates; and to unravel the sequence with which these signals act. Finally, coupled with single-cell lineage tracing data that shows that limb bud progenitors are multipotent progenitors to bone, cartilage, dermis and other cell-types, our ability to mass-produce human limb bud progenitors in vitro provides a route to robustly generate these downstream cell-types for regenerative medicine and cell replacement therapy.

The following materials and methods apply to those descriptions of Example 12, provided bellow.

Undifferentiated hPSCs (wild-type H7 as well as TBX5-Venus V19-2 H9 hESCs) were maintained in mTeSR1 media on Geltrex-coated plates. As described, they were differentiated into mid primitive streak for 24 hours (D0-1; 30 ng/mL Activin+40 ng/mL BMP4+6 µM CHIR99021+20 ng/mL FGF2+100 nM PIK90) and subsequently differentiated into lateral mesoderm (D1-2; 1 µM A-83-01+30 ng/mL BMP4+1 µM C59), with the inclusion of 50 nM of TTNPB or 2 µM ATRA on D1-2 for trunk lateral mesoderm that was subsequently competent for forelimb differentiation.

Day 2 trunk lateral mesoderm was differentiated into day 3 forelimb progenitors (D2-3; 1 µM A-83-01+1 µM DMH1+3 µM CHIR99021). By contrast, day 2 non-trunk lateral mesoderm was differentiated into day 3 hindlimb progenitors (D2-3; 25 ng/mL Activin+1 µM DMH1+3 µM CHIR99021).

Specification of Forelimb-Biased or Hindlimb-Biased Lateral Mesoderm by Manipulating Retinoid Signaling To reconstitute human limb bud progenitors from pluripotent cells, it is necessary to differentiate pluripotent cells through the sequential mesodermal intermediates that lead to a limb bud fate (FIG. 23a). In the developing embryo, pluripotent epiblast differentiates into mid primitive streak that gives rise to lateral mesoderm, which subsequently becomes diversified into heart, forelimb, hindlimb and other cell-types. A system has been described to produce a >99% pure MIXL1$^+$ mid primitive streak population (day 0-1 [D0-1] of hESC differentiation), followed by activation of BMP signaling and inhibition of TGFβ and WNT for 24 hours to specify a >95% pure HAND1$^+$CDX2$^{lo/-}$ lateral mesoderm population (D1-2 of hESC differentiation) (FIG. 23a).

Using this human lateral mesoderm population, signals that specified limb bud fate were screened for. Unexpectedly, it was found that lateral mesoderm was not a singular lineage, but rather different types of lateral mesoderm were subsequently competent to give rise to forelimb or hindlimb. Activation of retinoic acid (RA) signaling for 24 hours during lateral mesoderm induction (D1-2)—either using all-trans retinoic acid or synthetic agonist TTNPB—was paramount for lateral mesoderm to subsequently express key forelimb transcription factor TBX5 later on D3 of differentiation (FIG. 23b). Hence the data accord a surprisingly early requirement for RA signaling in specifying future forelimb field fate shortly after primitive streak formation. Finally, the data that early lateral mesoderm is exposed to an early RA pulse explains RARE-Cre lineage tracing results that all forelimb cells have at some point experienced RA signaling.

Lateral mesoderm induced in standard conditions or in the presence of retinoid antagonists (BMS493 or AGN193109) was incompetent to subsequently assume a forelimb fate (FIG. 23c). However, lateral mesoderm induced in standard conditions could subsequently differentiate into TBX4$^+$/PITX1$^+$ hindlimb progenitors, though retinoid activation during lateral mesoderm specification decreased such potential (FIG. 23d). This therefore implies that shortly after primitive streak formation, at least two types of lateral mesoderm lineages emerge: one (exposed to RA) competent for forelimb differentiation and the other (not exposed to RA) biased for hindlimb differentiation.

Figure 23E:
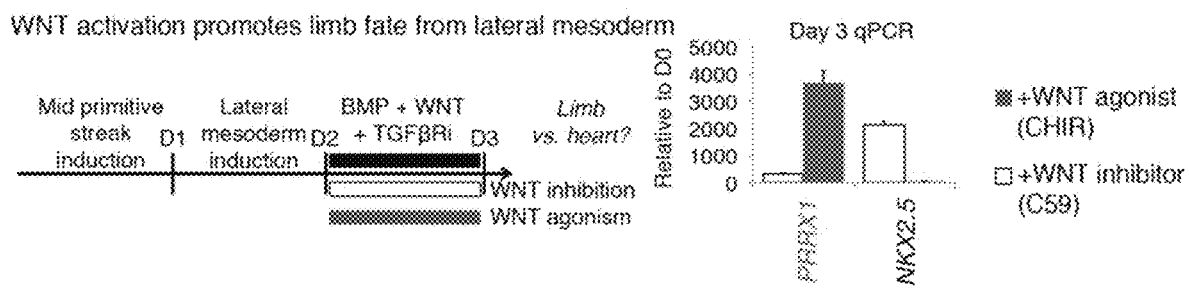

WNT Signaling Specifies Pan-Limb Bud Identity in Conjunction with Differential TGFβ/GDF11 Levels that Program Forelimb Vs. Hindlimb Fate After lateral mesoderm was formed, exposure to WNT on D2-3 specified a PRRX1$^+$ limb bud fate, whereas WNT inhibition induced an NKX2.5$^+$ heart fate (FIG. 23e). Given that WNT was instrumental to induce pan-limb bud progenitors, signals that specified arm (forelimb) vs. leg (hindlimb) fate were screened for.

Figure 23F:
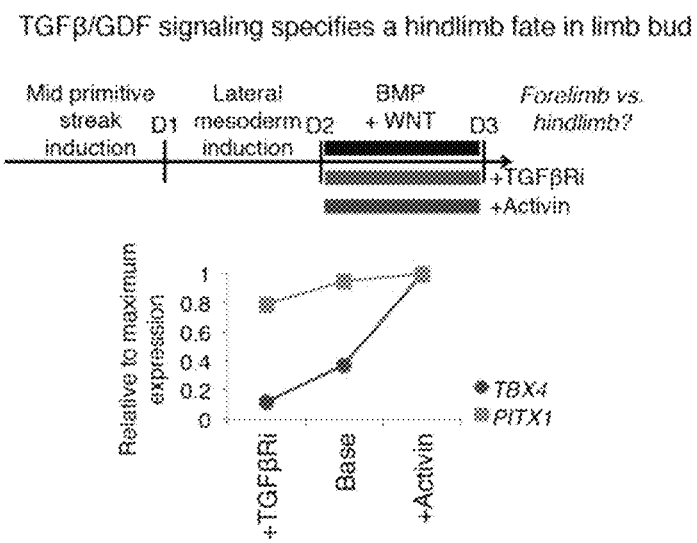

It was found that TGFβ pathway activation was critical to specify hindlimb fate: in the context of BMP and WNT activation on day 2-3, addition of a TGFβ agonist (Activin) strongly induced the hindlimb transcription factors TBX4 and PITX1 whereas TGFβ pathway blockade suppressed the expression of these markers (FIG. 23f). Indeed, TGFβ superfamily ligand Gdf11 is posteriorly expressed in the embryonic tail bud nearby the prospective hindlimbs, and is subsequently expressed in the early hindlimb buds and related ligand Gdf8 is also expressed in the tail bud. Supporting a role for TGFβ/GDF signaling for hindlimb induction in vivo, hindlimb development is progressively more aberrant in Gdf11$^{-/-}$ mouse embryos and Gdf8$^{-/-}$; Gdf11$^{-/-}$ mouse embryos. This therefore indicates that WNT+TGFβ activation is critical to induce the hindlimb program, whereas WNT+TGFβ inhibition specifies a forelimb fate.

Discussion

Figure 23G:
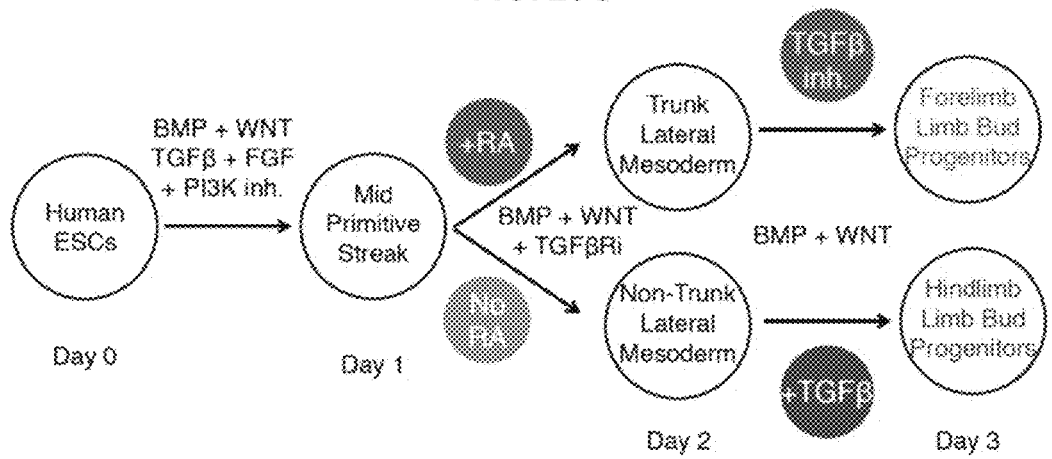

The current data demonstrates that shortly after primitive streak formation on D1, at least two distinct types of lateral mesoderm emerge by D2: RA-exposed trunk lateral mesoderm (forelimb progenitors) or non-trunk lateral mesoderm that is not exposed to early RA (which anteriorly forms heart and posteriorly hindlimb progenitors) (FIG. 23g). This is consistent with in vivo sensor studies that RA levels are high in intermediate regions of the embryo (the trunk) due to Raldh2 expression, whereas RA levels decrease at the anterior and posterior poles of the embryo by virtue of RA-degrading Cyp26 enzyme expression.

Subsequent to lateral mesoderm formation, it was shown that BMP and WNT activation are critical to endow a limb bud fate, which operates in conjunction with high TGFβ/GDF signaling specifies a hindlimb fate, or in parallel with TGFβ inhibition to specify a forelimb fate. This therefore reveals a temporally dynamic and combinatorial logic for forelimb vs. hindlimb specification: exposure to an early RA signal promotes forelimb fate, whereas exposure to a later TGFβ/GDF signal specifies the hindlimb (FIG. 23g).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of producing hematopoietic mesodermal cells, the method comprising:
   a) contacting a population of human pluripotent progenitor cells with a primitive streak induction composition comprising a Wnt pathway activator, a TGF-beta pathway activator, and a BMP pathway activator, and an FGF pathway activator for a time period consisting essentially of 24 hours to generate primitive streak cells;
   b) contacting the primitive streak cells with a first hematopoietic mesoderm induction composition comprising effective amounts of a BMP pathway activator, a VEGF pathway activator, and a Wnt pathway inhibitor for a time period consisting essentially of 24 hours; and
   c) contacting the cells of step b) with a second hematopoietic mesoderm induction composition comprising effective amounts of a TGF-beta pathway activator, a VEGF pathway activator, and a Wnt pathway inhibitor for a time period consisting essentially of 24 hours to generate hematopoietic mesodermal cells.

2. A method of producing arterial endothelial cells, the method comprising:
   a) deriving hematopoietic mesodermal cells according to claim 1; and
   b) contacting hematopoietic mesodermal cells with an arterial endothelial induction composition comprising effective amounts of a BMP pathway activator, a retinoic acid pathway activator and a VEGF pathway activator for a time period consisting essentially of 48 hours to generate arterial endothelial cells.

3. The method of claim 1, wherein the first hematopoietic mesoderm induction composition further comprises a TGF-beta pathway inhibitor, a PKA/cAMP pathway activator, vitamin C/ascorbic acid or an analog thereof, or a combination thereof.

4. The method according to claim 1, wherein the second hematopoietic mesoderm induction composition further comprises a PI3K pathway inhibitor, vitamin C/ascorbic acid or an analog thereof, or a combination thereof.

5. The method of claim 1, wherein the population of hematopoietic mesodermal cells is greater than 90% pure.

6. A method of producing hematopoietic intermediate cells, the method comprising:
   a) deriving arterial endothelial cells according to claim 2; and
   b) contacting arterial endothelial cells with an hematopoietic intermediate induction composition comprising effective amounts of a WNT pathway inhibitor, a TGF-beta pathway inhibitor, a SCF agonist and a gp130/IL6 superfamily agonist for a time period consisting essentially of 48 hours to generate hematopoietic intermediate cells.

7. The method according to claim 2, wherein the arterial endothelial induction composition further comprises a WNT pathway inhibitor, a TGF-beta pathway inhibitor or a combination thereof.

8. The method of claim 2, wherein the population of arterial endothelial cells is greater than 90% pure.

9. The method according to claim 6, wherein the hematopoietic intermediate induction composition further comprises a BMP pathway activator, a retinoic acid pathway activator, a VEGF pathway activator or a combination thereof.

10. The method according to claim 6, wherein the method further comprises culturing the arterial endothelial cells under conditions permissive for aggregation of the cells.

11. The method of claim 6, wherein the population of hematopoietic intermediate cells is greater than 90% pure.

12. A method of producing a substantially pure population of arterial endothelial cells, the method comprising:
   a) contacting a population of human pluripotent progenitor cells with a primitive streak induction composition comprising a Wnt pathway activator, a TGF-beta pathway activator, and a BMP pathway activator, a PI3K inhibitor and an FGF pathway activator for a time period consisting essentially of 24 hours to generate primitive streak cells;
   b) contacting the primitive streak cells with a first hematopoietic mesoderm induction composition comprising effective amounts of a BMP pathway activator, a VEGF pathway activator, and a Wnt pathway inhibitor for a time period consisting essentially of 24 hours;
   c) contacting the cells of step b) with a second hematopoietic mesoderm induction composition comprising effective amounts of a TGF-beta pathway activator, a VEGF pathway activator, and a Wnt pathway inhibitor for a time period consisting essentially of 24 hours to generate hematopoietic mesodermal cells; and
   d) contacting the hematopoietic mesodermal cells with an arterial endothelial induction composition comprising effective amounts of a BMP pathway activator, a retinoic acid pathway activator and a VEGF pathway activator for a time period consisting essentially of 48 hours to generate a substantially pure population comprising greater than 90% arterial endothelial cells.

13. A method of producing a substantially pure population of hematopoietic intermediate cells, the method comprising:
   a) contacting a population of human pluripotent progenitor cells with a primitive streak induction composition comprising a Wnt pathway activator a TGF-beta pathway activator, and a BMP pathway activator, a PI3K inhibitor and an FGF pathway activator for a time period consisting essentially of 24 hours to generate primitive streak cells;
   b) contacting the primitive streak cells with a first hematopoietic mesoderm induction composition comprising effective amounts of a BMP pathway activator, a VEGF pathway activator, and a Wnt pathway inhibitor for a time period consisting essentially of 24 hours;
   c) contacting the cells of step b) with a second hematopoietic mesoderm induction composition comprising effective amounts of a TGF-beta pathway activator, a VEGF pathway activator, and a Wnt pathway inhibitor for a time period consisting essentially of 24 hours to generate hematopoietic mesodermal cells;
   d) contacting the hematopoietic mesodermal cells with an arterial endothelial induction composition comprising effective amounts of a BMP pathway activator, a retinoic acid pathway activator and a VEGF pathway activator for a time period consisting essentially of 48 hours to generate arterial endothelial cells; and
   e) contacting the arterial endothelial cells with an hematopoietic intermediate induction composition comprising effective amounts of a WNT pathway inhibitor, a TGF-beta pathway inhibitor, a SCF agonist and a gp130/IL6 superfamily agonist for a time period consisting essentially of 48 hours to generate a substantially pure population comprising greater than 90% hematopoietic intermediate cells.

14. A method of generating a substantially pure population of hematopoietic intermediate cells, the method comprising:
   contacting arterial endothelial cells with a hematopoietic intermediate induction composition comprising effective amounts of a WNT pathway inhibitor, a TGF-beta pathway inhibitor, a SCF agonist and a gp130/IL6 superfamily agonist for a time period consisting essentially of 48 hours to generate a substantially pure population comprising greater than 90% hematopoietic intermediate cells.

* * * * *

SEQUENCE LISTING

```
<160> NUMBER OF SEQ ID NOS: 133

<210> SEQ ID NO 1
<211> LENGTH: 16
<212> TYPE: PRT
<213> ORGANISM: Artificial sequence
<220> FEATURE:
<223> OTHER INFORMATION: synthetic amino acid sequence

<400> SEQUENCE: 1

Lys Lys His Thr Asp Asp Gly Tyr Met Pro Met Ser Pro Gly Val Ala
1               5                   10                  15

<210> SEQ ID NO 2
<211> LENGTH: 25
<212> TYPE: DNA
<213> ORGANISM: Artificial sequence
<220> FEATURE:
<223> OTHER INFORMATION: synthetic oligonucleotide sequence

<400> SEQUENCE: 2
cgacatcagg aaggacctgt atgcc                                          25

<210> SEQ ID NO 3
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 3
ctatgagggc tatgccttgc c                                              21

<210> SEQ ID NO 4
```

```
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 4
cccctgctat ttcatcgacc c                                        21

<210> SEQ ID NO 5
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 5
atgaatgctg agacttgcgt c                                        21

<210> SEQ ID NO 6
<211> LENGTH: 19
<212> TYPE: DNA
<213> ORGANISM: Artificial sequence
<220> FEATURE:
<223> OTHER INFORMATION: synthetic oligonucleotide sequence

<400> SEQUENCE: 6
gatttcaggc ctgctggga                                           19

<210> SEQ ID NO 7
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 7
tgcttccctg agacccagtt                                          20

<210> SEQ ID NO 8
<211> LENGTH: 24
<212> TYPE: DNA
<213> ORGANISM: Artificial sequence
<220> FEATURE:
<223> OTHER INFORMATION: synthetic oligonucleotide sequence

<400> SEQUENCE: 8
aacgagcagg gcgagttcac cttc                                     24

<210> SEQ ID NO 9
<211> LENGTH: 22
<212> TYPE: DNA
<213> ORGANISM: Artificial sequence
<220> FEATURE:
<223> OTHER INFORMATION: synthetic oligonucleotide sequence

<400> SEQUENCE: 9
aacagtgttg acatgaagag cc                                       22

<210> SEQ ID NO 10
<211> LENGTH: 22
<212> TYPE: DNA
<213> ORGANISM: Artificial sequence
<220> FEATURE:
<223> OTHER INFORMATION: synthetic oligonucleotide sequence

<400> SEQUENCE: 10
```
tggctgtctt gggcatcact gg                                                    22

<210> SEQ ID NO 11
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 11
gggctctctg agaggcaggt                                                       20

<210> SEQ ID NO 12
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 12
gtcaacccaa aattggcacc a                                                     21

<210> SEQ ID NO 13
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 13
ccagatgacc ttcctacgcc                                                       20

<210> SEQ ID NO 14
<211> LENGTH: 22
<212> TYPE: DNA
<213> ORGANISM: Artificial sequence
<220> FEATURE:
<223> OTHER INFORMATION: synthetic oligonucleotide sequence

<400> SEQUENCE: 14
gatcacgttc ctgaaaaaca cg                                                    22

<210> SEQ ID NO 15
<211> LENGTH: 22
<212> TYPE: DNA
<213> ORGANISM: Artificial sequence
<220> FEATURE:
<223> OTHER INFORMATION: synthetic oligonucleotide sequence

<400> SEQUENCE: 15
actccgcgtt cagcaacccc at                                                    22

<210> SEQ ID NO 16
<211> LENGTH: 23
<212> TYPE: DNA
<213> ORGANISM: Artificial sequence
<220> FEATURE:
<223> OTHER INFORMATION: synthetic oligonucleotide sequence

<400> SEQUENCE: 16
caacataaac ggactcaatc cca                                                   23

<210> SEQ ID NO 17
<211> LENGTH: 21
<212> TYPE: DNA

```
<213> ORGANISM: Artificial sequence
<220> FEATURE:
<223> OTHER INFORMATION: synthetic oligonucleotide sequence

<400> SEQUENCE: 17
aggaggagga atctactccc a                                              21

<210> SEQ ID NO 18
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 18
agtgaccaga tgcgtcgtta c                                              21

<210> SEQ ID NO 19
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 19
tttttgccct tgttctgtcc                                                20

<210> SEQ ID NO 20
<211> LENGTH: 18
<212> TYPE: DNA
<213> ORGANISM: Artificial sequence
<220> FEATURE:
<223> OTHER INFORMATION: synthetic oligonucleotide sequence

<400> SEQUENCE: 20
gggagcggtg aagatgga                                                  18

<210> SEQ ID NO 21
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 21
cctcctggta tctcaaccac a                                              21

<210> SEQ ID NO 22
<211> LENGTH: 22
<212> TYPE: DNA
<213> ORGANISM: Artificial sequence
<220> FEATURE:
<223> OTHER INFORMATION: synthetic oligonucleotide sequence

<400> SEQUENCE: 22
agcagccgta tctgcaccag aa                                             22

<210> SEQ ID NO 23
<211> LENGTH: 22
<212> TYPE: DNA
<213> ORGANISM: Artificial sequence
<220> FEATURE:
<223> OTHER INFORMATION: synthetic oligonucleotide sequence

<400> SEQUENCE: 23
atcggctaca actacaccta ca                                             22
```

<210> SEQ ID NO 24
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 24
tccctcttcc ctcctcaaat                                              20

<210> SEQ ID NO 25
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 25
cccacaacac aacctacagc                                              20

<210> SEQ ID NO 26
<211> LENGTH: 23
<212> TYPE: DNA
<213> ORGANISM: Artificial sequence
<220> FEATURE:
<223> OTHER INFORMATION: synthetic oligonucleotide sequence

<400> SEQUENCE: 26
gaggagaaag tggaggtctg gtt                                          23

<210> SEQ ID NO 27
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 27
gtgcgtcctt taatcctctt c                                            21

<210> SEQ ID NO 28
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 28
cacccgacgc ccttttacat                                              20

<210> SEQ ID NO 29
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 29
aactccttct cggggcgtta t                                            21

<210> SEQ ID NO 30
<211> LENGTH: 26
<212> TYPE: DNA
<213> ORGANISM: Artificial sequence
<220> FEATURE:

<223> OTHER INFORMATION: synthetic oligonucleotide sequence

<400> SEQUENCE: 30
agattatatc aggttgtacg ggatca                                        26

<210> SEQ ID NO 31
<211> LENGTH: 23
<212> TYPE: DNA
<213> ORGANISM: Artificial sequence
<220> FEATURE:
<223> OTHER INFORMATION: synthetic oligonucleotide sequence

<400> SEQUENCE: 31
atggatgaac gtaacagaca ggt                                           23

<210> SEQ ID NO 32
<211> LENGTH: 19
<212> TYPE: DNA
<213> ORGANISM: Artificial sequence
<220> FEATURE:
<223> OTHER INFORMATION: synthetic oligonucleotide sequence

<400> SEQUENCE: 32
tctgagcgcc aggtcaaag                                                19

<210> SEQ ID NO 33
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 33
gtggcggcta caaggtcatc                                               20

<210> SEQ ID NO 34
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 34
gaagtggttc cttggcagac                                               20

<210> SEQ ID NO 35
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 35
agcttgggtg cctccttatt                                               20

<210> SEQ ID NO 36
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 36
ggtaccccga catccacttg                                               20

```
<210> SEQ ID NO 37
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 37
cggaattacc tgccacctgt                                              20

<210> SEQ ID NO 38
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 38
gcctgaagaa ggtcaaccag                                              20

<210> SEQ ID NO 39
<211> LENGTH: 22
<212> TYPE: DNA
<213> ORGANISM: Artificial sequence
<220> FEATURE:
<223> OTHER INFORMATION: synthetic oligonucleotide sequence

<400> SEQUENCE: 39
ctggaggatg aatgctcaga gc                                           22

<210> SEQ ID NO 40
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 40 gcccttttgac attcgcactg                                             20

<210> SEQ ID NO 41
<211> LENGTH: 24
<212> TYPE: DNA
<213> ORGANISM: Artificial sequence
<220> FEATURE:
<223> OTHER INFORMATION: synthetic oligonucleotide sequence

<400> SEQUENCE: 41
tcgtgcctga tgacaaacag gagt                                         24

<210> SEQ ID NO 42
<211> LENGTH: 24
<212> TYPE: DNA
<213> ORGANISM: Artificial sequence
<220> FEATURE:
<223> OTHER INFORMATION: synthetic oligonucleotide sequence

<400> SEQUENCE: 42
acatcatcac ccatggagac gaga                                         24

<210> SEQ ID NO 43
<211> LENGTH: 18
<212> TYPE: DNA
<213> ORGANISM: Artificial sequence
<220> FEATURE:
<223> OTHER INFORMATION: synthetic oligonucleotide sequence
```

```
<400> SEQUENCE: 43
tgccacaacg gacgactt                                          18

<210> SEQ ID NO 44
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 44
agatgtgtct gtggccttcc                                        20

<210> SEQ ID NO 45
<211> LENGTH: 19
<212> TYPE: DNA
<213> ORGANISM: Artificial sequence
<220> FEATURE:
<223> OTHER INFORMATION: synthetic oligonucleotide sequence

<400> SEQUENCE: 45
caagtgtgcg tctgcctttt                                        19

<210> SEQ ID NO 46
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 46
ccagctcagg tgacaaccat                                        20

<210> SEQ ID NO 47
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 47
agtgagaggc aacctggaga                                        20

<210> SEQ ID NO 48
<211> LENGTH: 26
<212> TYPE: DNA
<213> ORGANISM: Artificial sequence
<220> FEATURE:
<223> OTHER INFORMATION: synthetic oligonucleotide sequence

<400> SEQUENCE: 48
cagctcacca actactcctt ccttca                                 26

<210> SEQ ID NO 49
<211> LENGTH: 19
<212> TYPE: DNA
<213> ORGANISM: Artificial sequence
<220> FEATURE:
<223> OTHER INFORMATION: synthetic oligonucleotide sequence

<400> SEQUENCE: 49
gagctgagga gagtcccgt                                         19

<210> SEQ ID NO 50
<211> LENGTH: 24
```

```
<212> TYPE: DNA
<213> ORGANISM: Artificial sequence
<220> FEATURE:
<223> OTHER INFORMATION: synthetic oligonucleotide sequence

<400> SEQUENCE: 50
cgctatggag cagacgtatg gcga                                              24

<210> SEQ ID NO 51
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 51
ctccacgctc cggatagttc                                                   20

<210> SEQ ID NO 52
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 52
gcagatgcaa aagtccaggt g                                                 21

<210> SEQ ID NO 53
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 53
tccaagattc tttgccgcta c                                                 21

<210> SEQ ID NO 54
<211> LENGTH: 24
<212> TYPE: DNA
<213> ORGANISM: Artificial sequence
<220> FEATURE:
<223> OTHER INFORMATION: synthetic oligonucleotide sequence

<400> SEQUENCE: 54
tggttatgtt gctggacatg ggtg                                              24

<210> SEQ ID NO 55
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 55
ggtgggcaca ctacaatttg c                                                 21

<210> SEQ ID NO 56
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 56
```
tgatgctttt gtgcgagaag a                                              21

<210> SEQ ID NO 57
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 57
cgcacggaat ttgaacagta                                                20

<210> SEQ ID NO 58
<211> LENGTH: 19
<212> TYPE: DNA
<213> ORGANISM: Artificial sequence
<220> FEATURE:
<223> OTHER INFORMATION: synthetic oligonucleotide sequence

<400> SEQUENCE: 58
tggacagtta cgcgcacat                                                 19

<210> SEQ ID NO 59
<211> LENGTH: 24
<212> TYPE: DNA
<213> ORGANISM: Artificial sequence
<220> FEATURE:
<223> OTHER INFORMATION: synthetic oligonucleotide sequence

<400> SEQUENCE: 59
cgtcaacggc tccagcaaga acaa                                           24

<210> SEQ ID NO 60
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 60
cggcctgcgc gtgtctaatc c                                              21

<210> SEQ ID NO 61
<211> LENGTH: 22
<212> TYPE: DNA
<213> ORGANISM: Artificial sequence
<220> FEATURE:
<223> OTHER INFORMATION: synthetic oligonucleotide sequence

<400> SEQUENCE: 61
agtgcagtcc aaaatcgaga ag                                             22

<210> SEQ ID NO 62
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 62
ggcgacggag aacacaatca a                                              21

<210> SEQ ID NO 63
<211> LENGTH: 19
<212> TYPE: DNA
<213> ORGANISM: Artificial sequence

```
<220> FEATURE:
<223> OTHER INFORMATION: synthetic oligonucleotide sequence

<400> SEQUENCE: 63
taccaccaca cccatcaac                                                   19

<210> SEQ ID NO 64
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 64
aagtaccaac cccgcataca                                                  20

<210> SEQ ID NO 65
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 65
ggaggagtcc aaaccaaagc c                                                21

<210> SEQ ID NO 66
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 66
ctgcagcacc ggcaccgttt                                                  20

<210> SEQ ID NO 67
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 67
ctatcccgac gtgttcatgc                                                  20

<210> SEQ ID NO 68
<211> LENGTH: 23
<212> TYPE: DNA
<213> ORGANISM: Artificial sequence
<220> FEATURE:
<223> OTHER INFORMATION: synthetic oligonucleotide sequence

<400> SEQUENCE: 68
ggcctcgtcg tactcctgct tgg                                              23

<210> SEQ ID NO 69
<211> LENGTH: 22
<212> TYPE: DNA
<213> ORGANISM: Artificial sequence
<220> FEATURE:
<223> OTHER INFORMATION: synthetic oligonucleotide sequence

<400> SEQUENCE: 69
gctcagcagt agtaacgaag ga                                               22
```

<210> SEQ ID NO 70
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 70
gacacacggc tccacttgat                                          20

<210> SEQ ID NO 71
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 71
gggaaatgcc ctaaaaggcg                                          20

<210> SEQ ID NO 72
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 72
tttcgcaccc cttggttaca                                          20

<210> SEQ ID NO 73
<211> LENGTH: 25
<212> TYPE: DNA
<213> ORGANISM: Artificial sequence
<220> FEATURE:
<223> OTHER INFORMATION: synthetic oligonucleotide sequence

<400> SEQUENCE: 73
gatcacttct ttcctttgca tcaag                                    25

<210> SEQ ID NO 74
<211> LENGTH: 24
<212> TYPE: DNA
<213> ORGANISM: Artificial sequence
<220> FEATURE:
<223> OTHER INFORMATION: synthetic oligonucleotide sequence

<400> SEQUENCE: 74
taggtgacca gctgctcgtg gatc                                     24

<210> SEQ ID NO 75
<211> LENGTH: 22
<212> TYPE: DNA
<213> ORGANISM: Artificial sequence
<220> FEATURE:
<223> OTHER INFORMATION: synthetic oligonucleotide sequence

<400> SEQUENCE: 75
tgtaaaacag cacgtcatcc tt                                       22

<210> SEQ ID NO 76
<211> LENGTH: 24
<212> TYPE: DNA
<213> ORGANISM: Artificial sequence
<220> FEATURE:
<223> OTHER INFORMATION: synthetic oligonucleotide sequence

```
<400> SEQUENCE: 76
ctgaatggcc gtttctggag gtgg                                          24

<210> SEQ ID NO 77
<211> LENGTH: 19
<212> TYPE: DNA
<213> ORGANISM: Artificial sequence
<220> FEATURE:
<223> OTHER INFORMATION: synthetic oligonucleotide sequence

<400> SEQUENCE: 77
cctttgctct gcggttctg                                                19

<210> SEQ ID NO 78
<211> LENGTH: 22
<212> TYPE: DNA
<213> ORGANISM: Artificial sequence
<220> FEATURE:
<223> OTHER INFORMATION: synthetic oligonucleotide sequence

<400> SEQUENCE: 78
accttgtttc ctttcgtctt cg                                            22

<210> SEQ ID NO 79
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 79
ttcagggcag tgtacgtgaa c                                             21

<210> SEQ ID NO 80
<211> LENGTH: 19
<212> TYPE: DNA
<213> ORGANISM: Artificial sequence
<220> FEATURE:
<223> OTHER INFORMATION: synthetic oligonucleotide sequence

<400> SEQUENCE: 80
gctctccgtc tggatgcag                                                19

<210> SEQ ID NO 81
<211> LENGTH: 27
<212> TYPE: DNA
<213> ORGANISM: Artificial sequence
<220> FEATURE:
<223> OTHER INFORMATION: synthetic oligonucleotide sequence

<400> SEQUENCE: 81
tgggttttct gttgcgaggt catcagg                                       27

<210> SEQ ID NO 82
<211> LENGTH: 22
<212> TYPE: DNA
<213> ORGANISM: Artificial sequence
<220> FEATURE:
<223> OTHER INFORMATION: synthetic oligonucleotide sequence

<400> SEQUENCE: 82
accacctcta cgaacacatt gt                                            22

<210> SEQ ID NO 83
```

```
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 83
cagcggagga atagcatcaa g                                              21

<210> SEQ ID NO 84
<211> LENGTH: 19
<212> TYPE: DNA
<213> ORGANISM: Artificial sequence
<220> FEATURE:
<223> OTHER INFORMATION: synthetic oligonucleotide sequence

<400> SEQUENCE: 84
tggtttccgg caggtttag                                                 19

<210> SEQ ID NO 85
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 85
tcattgttcc cagcatttca                                                20

<210> SEQ ID NO 86
<211> LENGTH: 22
<212> TYPE: DNA
<213> ORGANISM: Artificial sequence
<220> FEATURE:
<223> OTHER INFORMATION: synthetic oligonucleotide sequence

<400> SEQUENCE: 86
tcatgttgct cacggaggag ta                                             22

<210> SEQ ID NO 87
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 87
gagggtcgag ttctcaatcc c                                              21

<210> SEQ ID NO 88
<211> LENGTH: 22
<212> TYPE: DNA
<213> ORGANISM: Artificial sequence
<220> FEATURE:
<223> OTHER INFORMATION: synthetic oligonucleotide sequence

<400> SEQUENCE: 88
ctcctttcgg tcacacatgc tg                                             22

<210> SEQ ID NO 89
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 89
```
gtacatgctg cacaggaaga a                     21

<210> SEQ ID NO 90
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 90
tcagcgtgta aaggcatctg                       20

<210> SEQ ID NO 91
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 91
gcgagactga cgcctatgta                       20

<210> SEQ ID NO 92
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 92
ctctgatgag gaccgcttct g                     21

<210> SEQ ID NO 93
<211> LENGTH: 19
<212> TYPE: DNA
<213> ORGANISM: Artificial sequence
<220> FEATURE:
<223> OTHER INFORMATION: synthetic oligonucleotide sequence

<400> SEQUENCE: 93
gtgagagcaa gcggaaaag                        19

<210> SEQ ID NO 94
<211> LENGTH: 19
<212> TYPE: DNA
<213> ORGANISM: Artificial sequence
<220> FEATURE:
<223> OTHER INFORMATION: synthetic oligonucleotide sequence

<400> SEQUENCE: 94
gaaggctgga tggatcggc                        19

<210> SEQ ID NO 95
<211> LENGTH: 23
<212> TYPE: DNA
<213> ORGANISM: Artificial sequence
<220> FEATURE:
<223> OTHER INFORMATION: synthetic oligonucleotide sequence

<400> SEQUENCE: 95
catcccattg taattgtagc cgt                   23

<210> SEQ ID NO 96
<211> LENGTH: 20
<212> TYPE: DNA

```
<213> ORGANISM: Artificial sequence
<220> FEATURE:
<223> OTHER INFORMATION: synthetic oligonucleotide sequence

<400> SEQUENCE: 96
acacagcgga aacactcgat                                              20

<210> SEQ ID NO 97
<211> LENGTH: 19
<212> TYPE: DNA
<213> ORGANISM: Artificial sequence
<220> FEATURE:
<223> OTHER INFORMATION: synthetic oligonucleotide sequence

<400> SEQUENCE: 97
cggctcgttg tactccgtg                                               19

<210> SEQ ID NO 98
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 98
ctgaacttgg agaggctgtg g                                            21

<210> SEQ ID NO 99
<211> LENGTH: 19
<212> TYPE: DNA
<213> ORGANISM: Artificial sequence
<220> FEATURE:
<223> OTHER INFORMATION: synthetic oligonucleotide sequence

<400> SEQUENCE: 99
ctggcgcgga acataaaca                                               19

<210> SEQ ID NO 100
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 100
tcctgcttgc ctcaaagtgt                                              20

<210> SEQ ID NO 101
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 101
tgcttccctg aaagacatca                                              20

<210> SEQ ID NO 102
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 102
taatctccgg cctagccaaa                                              20
```

<210> SEQ ID NO 103
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 103
ggtctgtgag ttccccgatg                                          20

<210> SEQ ID NO 104
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 104
ccatcagagc agttggaggt                                          20

<210> SEQ ID NO 105
<211> LENGTH: 22
<212> TYPE: DNA
<213> ORGANISM: Artificial sequence
<220> FEATURE:
<223> OTHER INFORMATION: synthetic oligonucleotide sequence

<400> SEQUENCE: 105
cccagagagt tcctcagtaa gg                                       22

<210> SEQ ID NO 106
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 106
ggtttcagca atgaccttgc c                                        21

<210> SEQ ID NO 107
<211> LENGTH: 24
<212> TYPE: DNA
<213> ORGANISM: Artificial sequence
<220> FEATURE:
<223> OTHER INFORMATION: synthetic oligonucleotide sequence

<400> SEQUENCE: 107
atactcggtc tcggcagtga cttt                                     24

<210> SEQ ID NO 108
<211> LENGTH: 24
<212> TYPE: DNA
<213> ORGANISM: Artificial sequence
<220> FEATURE:
<223> OTHER INFORMATION: synthetic oligonucleotide sequence

<400> SEQUENCE: 108
gcaacagagt ttattgaggt gccc                                     24

<210> SEQ ID NO 109
<211> LENGTH: 17
<212> TYPE: DNA
<213> ORGANISM: Artificial sequence
<220> FEATURE:

```
<223> OTHER INFORMATION: synthetic oligonucleotide sequence

<400> SEQUENCE: 109
cgggtccagg cttcgaa                                                    17

<210> SEQ ID NO 110
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 110
agctggcttc ctagcatcag                                                 20

<210> SEQ ID NO 111
<211> LENGTH: 22
<212> TYPE: DNA
<213> ORGANISM: Artificial sequence
<220> FEATURE:
<223> OTHER INFORMATION: synthetic oligonucleotide sequence

<400> SEQUENCE: 111
cagctctttc ttttcggctc ta                                              22

<210> SEQ ID NO 112
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 112
cttggcccct tgtgcttttc                                                 20

<210> SEQ ID NO 113
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 113
acactcggac cacatccttc                                                 20

<210> SEQ ID NO 114
<211> LENGTH: 22
<212> TYPE: DNA
<213> ORGANISM: Artificial sequence
<220> FEATURE:
<223> OTHER INFORMATION: synthetic oligonucleotide sequence

<400> SEQUENCE: 114
tgcaacgcgc tgaaaccata ca                                              22

<210> SEQ ID NO 115
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 115
tgtgcctctc tctaggtcca                                                 20
```

```
<210> SEQ ID NO 116
<211> LENGTH: 22
<212> TYPE: DNA
<213> ORGANISM: Artificial sequence
<220> FEATURE:
<223> OTHER INFORMATION: synthetic oligonucleotide sequence

<400> SEQUENCE: 116
aatgcgcaag cggatggcgt tg                                          22

<210> SEQ ID NO 117
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 117
atcttgtggc ggatgtggtt                                             20

<210> SEQ ID NO 118
<211> LENGTH: 22
<212> TYPE: DNA
<213> ORGANISM: Artificial sequence
<220> FEATURE:
<223> OTHER INFORMATION: synthetic oligonucleotide sequence

<400> SEQUENCE: 118
caggttgcga agaactctgt tt                                          22

<210> SEQ ID NO 119
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 119
ggtcacagtg cccatccttc                                             20

<210> SEQ ID NO 120
<211> LENGTH: 25
<212> TYPE: DNA
<213> ORGANISM: Artificial sequence
<220> FEATURE:
<223> OTHER INFORMATION: synthetic oligonucleotide sequence

<400> SEQUENCE: 120
ggaagccgtg acagaatgac tacct                                       25

<210> SEQ ID NO 121
<211> LENGTH: 19
<212> TYPE: DNA
<213> ORGANISM: Artificial sequence
<220> FEATURE:
<223> OTHER INFORMATION: synthetic oligonucleotide sequence

<400> SEQUENCE: 121
ggtgggtagg cctcgaaca                                              19

<210> SEQ ID NO 122
<211> LENGTH: 21
<212> TYPE: DNA
<213> ORGANISM: Artificial sequence
<220> FEATURE:
<223> OTHER INFORMATION: synthetic oligonucleotide sequence
```

<400> SEQUENCE: 122
agggaagcgt ttttattggc t                                    21

<210> SEQ ID NO 123
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 123
ggatcaggga cctgtcacac                                      20

<210> SEQ ID NO 124
<211> LENGTH: 21
<212> TYPE: DNA
<213> ORGANISM: Artificial sequence
<220> FEATURE:
<223> OTHER INFORMATION: synthetic oligonucleotide sequence

<400> SEQUENCE: 124
cgagtaggac atgctgtagg t                                    21

<210> SEQ ID NO 125
<211> LENGTH: 26
<212> TYPE: DNA
<213> ORGANISM: Artificial sequence
<220> FEATURE:
<223> OTHER INFORMATION: synthetic oligonucleotide sequence

<400> SEQUENCE: 125
gccgcttctc gctctcgttc agaagt                               26

<210> SEQ ID NO 126
<211> LENGTH: 24
<212> TYPE: DNA
<213> ORGANISM: Artificial sequence
<220> FEATURE:
<223> OTHER INFORMATION: synthetic oligonucleotide sequence

<400> SEQUENCE: 126
ctgtgacctc cagcagcttc cgaa                                 24

<210> SEQ ID NO 127
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 127
cttgctcaga atcacgccat                                      20

<210> SEQ ID NO 128
<211> LENGTH: 19
<212> TYPE: DNA
<213> ORGANISM: Artificial sequence
<220> FEATURE:
<223> OTHER INFORMATION: synthetic oligonucleotide sequence

<400> SEQUENCE: 128
ctgggcacag gacgacttc                                       19

<210> SEQ ID NO 129
<211> LENGTH: 20

```
<212> TYPE: DNA
<213> ORGANISM: Artificial sequence
<220> FEATURE:
<223> OTHER INFORMATION: synthetic oligonucleotide sequence

<400> SEQUENCE: 129
acaccaagac agggacagac                                              20

<210> SEQ ID NO 130
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 130
taggctgtca cggagatgaa                                              20

<210> SEQ ID NO 131
<211> LENGTH: 23
<212> TYPE: DNA
<213> ORGANISM: Artificial sequence
<220> FEATURE:
<223> OTHER INFORMATION: synthetic oligonucleotide sequence

<400> SEQUENCE: 131
tcaaagtcca ctctctctcc atc                                          23

<210> SEQ ID NO 132
<211> LENGTH: 20
<212> TYPE: DNA
<213> ORGANISM: Artificial sequence
<220> FEATURE:
<223> OTHER INFORMATION: synthetic oligonucleotide sequence

<400> SEQUENCE: 132
cccaacggct ggacgcacac                                              20

<210> SEQ ID NO 133
<211> LENGTH: 19
<212> TYPE: DNA
<213> ORGANISM: Artificial sequence
<220> FEATURE:
<223> OTHER INFORMATION: synthetic oligonucleotide sequence

<400> SEQUENCE: 133
gaactcggga ctcgaccag                                               19
```